(12) United States Patent  
Kounde et al.

(10) Patent No.: US 12,012,417 B2
(45) Date of Patent: Jun. 18, 2024

(54) N-SUBSTITUTED TETRAHYDROTHIENOPYRIDINE DERIVATIVES AND USES THEREOF

(71) Applicant: NOVARTIS AG, Basel (CH)

(72) Inventors: Cyrille Kounde, London (GB); Wei Lin Sandra Sim, Singapore (SG); Oliver Simon, Singapore (SG); Gang Wang, Singapore (SG); Hui Quan Yeo, Singapore (SG); Bryan K S Yeung, Seoul (KR); Fumiaki Yokokawa, Dublin, CA (US); Bin Zou, Singapore (SG)

(73) Assignee: NOVARTIS AG, Basel (CH)

( * ) Notice: Subject to any disclaimer, the term of this patent is extended or adjusted under 35 U.S.C. 154(b) by 795 days.

(21) Appl. No.: 17/253,755

(22) PCT Filed: Jun. 18, 2019

(86) PCT No.: PCT/IB2019/055121
§ 371 (c)(1),
(2) Date: Dec. 18, 2020

(87) PCT Pub. No.: WO2019/244047
PCT Pub. Date: Dec. 26, 2019

(65) Prior Publication Data
US 2022/0073535 A1    Mar. 10, 2022

Related U.S. Application Data

(60) Provisional application No. 62/687,068, filed on Jun. 19, 2018.

(51) Int. Cl.
C07D 495/04 (2006.01)
A61K 31/4365 (2006.01)
A61K 45/06 (2006.01)
A61K 47/06 (2006.01)
A61P 31/12 (2006.01)

(52) U.S. Cl.
CPC ............ C07D 495/04 (2013.01); A61K 45/06 (2013.01); A61K 47/06 (2013.01); A61P 31/12 (2018.01)

(58) Field of Classification Search
CPC .... C07D 495/04; A61K 31/4365; A61P 31/12
See application file for complete search history.

(56) References Cited

U.S. PATENT DOCUMENTS

| | | | |
|---|---|---|---|
| 5,807,876 A | 9/1998 | Armistead et al. | |
| 6,054,472 A | 4/2000 | Armistead et al. | |
| 6,344,465 B1 | 2/2002 | Armistead et al. | |
| 6,498,178 B2 | 12/2002 | Stamos et al. | |
| 2003/0232994 A1 | 12/2003 | Lu et al. | |
| 2006/0276533 A1 | 12/2006 | Denis | |
| 2008/0249311 A1 | 10/2008 | Wang | |
| 2009/0163545 A1 | 6/2009 | Goldfarb | |
| 2013/0129677 A1 | 5/2013 | Dai et al. | |

FOREIGN PATENT DOCUMENTS

| | | |
|---|---|---|
| AU | 2012315953 A1 | 4/2014 |
| CN | 108191885 A | 6/2018 |
| CN | 108689987 A | 10/2018 |
| WO | 97/40028 A1 | 10/1997 |
| WO | 98/40381 A1 | 9/1998 |
| WO | 00/56331 A1 | 9/2000 |
| WO | 2002/047762 | 6/2002 |
| WO | 2002/102153 | 12/2002 |
| WO | 2004/024066 | 3/2004 |
| WO | 2004092156 A1 | 10/2004 |
| WO | 2005/044008 | 5/2005 |
| WO | 2005/118071 | 12/2005 |
| WO | 2006/020884 | 2/2006 |
| WO | 2006/084869 | 8/2006 |
| WO | 2006/084904 | 8/2006 |
| WO | 2006/125813 | 11/2006 |
| WO | 2006/125815 | 11/2006 |
| WO | 2008/020024 | 2/2008 |
| WO | 2008/020045 | 2/2008 |
| WO | 2008/067222 | 6/2008 |
| WO | 2010099166 A1 | 9/2010 |
| WO | 2013049407 A3 | 4/2013 |

(Continued)

OTHER PUBLICATIONS

Virgin et al. Cell 2009, 138 (1), 30-50.*
Hrast et al. European Journal of Medicinal Chemistry 2014, 73, 83-96.*
Podvinec et al. J. Med. Chem. 2010, 53, 1483-1495, including Supporting information pp. S1-S11.*
Podvinec, Michael, et al., "Novel Inhibitors of Dengue Virus Methyltransferase: Discovery by in Vitro-Driven Virtual Screening on a Desktop Computer Grid," J. Med. Chem. 2010, 53, 4, 1483-1495.
Mohamed, M., et al., "Anticancer Activities of New N-hetaryl-2-cyanoacetamide Derivatives Incorporating 4,5,6,7-Tetrahydrobenzo[b]thiophene Moiety," Anti-Cancer Agents in Medicinal Chemistry, vol. 17, Issue 8, 2017.

(Continued)

*Primary Examiner* — Irina Neagu

(57) ABSTRACT

A compound of Formula (I) is provided that has been shown to be useful for treating a disease caused by a viral infection: (I) wherein $R^1$, $R^2$, $R^3$, A, L, m, n, p and q are as defined herein.

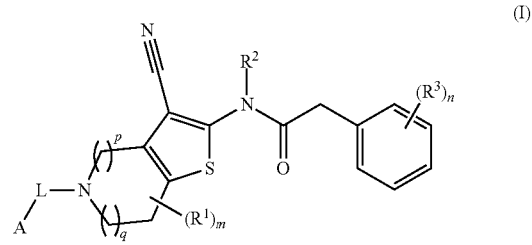

12 Claims, No Drawings

(56) References Cited

FOREIGN PATENT DOCUMENTS

| | | |
|---|---|---|
| WO | 2017011920 A1 | 1/2017 |
| WO | 2018215316 A1 | 11/2018 |
| WO | 2019/024809 A1 | 2/2019 |
| WO | 2019/244047 A1 | 12/2019 |

OTHER PUBLICATIONS

Amr, A., et al., "Anti-Cancer and Kinases Inhibitor Activities of Synthesized Heterocyclic Substituted Thiophene Fused with Cyclohexane Derivative," Journal of Computational and Theoretical Nanoscience, (2017), 14(1), 768-774.
Schul, et al., "A Dengue Fever Viremia Model in Mice Shows Reduction in Viral Replication and Suppression of the Inflammatory Response after Treatment with Antiviral Drugs," 2007. J. Infect. Dis., 195, 665-74.
CAS Registry No. 1330825-05-2; STN Entry Date Sep. 11, 2011; 4-Chloro-N-[3-cyano-4,5,6,7-tetrahydro-6-(phenylmethyl)thieno[2,3-c]pyridin-2-yl]benzeneacetamide.
CAS Registry No. 1330281-70-3; STN Entry Date Sep. 9, 2011; 4-Chloro-N-[3-cyano-4,5,6,7-tetrahydro-6-(phenylmethyl)thieno[2,3-c]pyridin-2-yl]benzeneacetamide hydrochloride.
CAS Registry No. 921877-90-9; STN Entry Date Feb. 19, 2007; N-[3-Cyano-4,5,6,7-tetrahydro-6-(phenylmethyl)thieno[2,3-c]pyridin-2-yl]-2,5-dimethylbenzeneacetamide.
CAS Registry No. 1329926-50-2; STN Entry Date Sep. 8, 2011; N-[3-cyano-4,5,6,7-tetrahydro-6-(phenylmethyl)thieno[2,3-c]pyridin-2-yl]-2,5-dimethylbenzeneacetamide hydrochloride.
CAS Registry No. 921879-09-6; STN Entry Date Feb. 19, 2007; N-[3-Cyano-4,5,6,7-tetrahydro-6-(phenylmethyl)thieno[2,3-c]pyridin-2-yl]-3,4-dimethylbenzeneacetamide.
CAS Registry No. 1329860-80-1; STN Entry Date Sep. 8, 2011; N-[3-cyano-4,5,6,7-tetrahydro-6-(phenylmethyl)thieno[2,3-c]pyridin-2-yl]-3,4-dimethylbenzeneacetamide hydrochloride.
CAS Registry No. 922624-04-2; STN Entry Date Feb. 22, 2007; N-[3-Cyano-4,5,6,7-tetrahydro-6-(phenylmethyl)thieno[2,3-c]pyridin-2-yl]-4-fluorobenzeneacetamide.
CAS Registry No. 1327238-45-8; STN Entry Date Sep. 2, 2011; N-[3-cyano-4,5,6,7-tetrahydro-6-(phenylmethyl)thieno[2,3-c]pyridin-2-yl] 4-fluorobenzeneacetamide hydrochloride.
CAS Registry No. 922822-02-4; STN Entry Date Feb. 23, 2007; N-[3-Cyano-4,5,6,7-tetrahydro-6-(phenylmethyl)thieno[2,3-c]pyridin-2-yl]-2,4-dimethylbenzeneacetamide.
CAS Registry No. 1329919-39-2; STN Entry Date Sep. 8, 2011; N-[3-cyano-4,5,6,7-tetrahydro-6-(phenylmethyl)thieno[2,3-c]pyridin-2-yl]-2,4-dimethylbenzeneacetamide hydrochloride.
CAS Registry No. 1171585-04-8; STN Entry Date Aug. 2, 2009; N-[3-Cyano-4,5,6,7-tetrahydro-6-(phenylmethyl)thieno[2,3-c]pyridin-2-yl]-3-methylbenzeneacetamide.
CAS Registry No. 1172098-87-1; STN Entry Date Aug. 3, 2009; N-[3-Cyano-4,5,6,7-tetrahydro-6-(phenylmethyl)thieno[2,3-c]pyridin-2-yl]-4-[(1-methylethyl)sulfonyl]benzeneacetamide.
CAS Registry No. 1329871-61-5; STN Entry Date Sep. 8, 2011; N-[3-cyano-4,5,6,7-tetrahydro-6-(phenylmethyl)thieno[2,3-c]pyridin-2-yl]-4-[(1-methylethyl)sulfonyl]benzeneacetamide hydrochloride.
CAS Registry No. 1331329-37-3; STN Entry Date Sep. 11, 2011; N-[3-cyano-4,5,6,7-tetrahydro-6-(phenylmethyl)thieno[2,3-c]pyridin-2-yl]-4-methoxybenzeneacetamide hydrochloride.
CAS Registry No. 923415-24-1; STN Entry Date Feb. 28, 2007; N-[3-Cyano-4,5,6,7-tetrahydro-6-(phenylmethyl)thieno[2,3-c]pyridin-2-yl]-4-methoxybenzeneacetamide.
CAS Registry No. 923415-98-9; STN Entry Date Feb. 27, 2007; N-[3-Cyano-4,5,6,7-tetrahydro-6-(phenylmethyl)thieno[2,3-c]pyridin-2-yl]-4-ethoxybenzeneacetamide.
CAS Registry No. 1327596-46-2; STN Entry Date Sep. 4, 2011; N-[3-cyano-4,5,6,7-tetrahydro-6-(phenylmethyl)thieno[2,3-c]pyridin-2-yl]-4-ethoxybenzeneacetamide hydrochloride.
CAS Registry No. 1329480-97-8; STN Entry Date Sep. 7, 2011; N-[3-cyano-4,5,6,7-tetrahydro-6-(phenylmethyl)thieno[2,3-c]pyridin-2-yl]-2,4-dimethoxybenzeneacetamide hydrochloride.
CAS Registry No. 1329745-25-6; STN Entry Date Sep. 8, 2011; N-[3-Cyano-4,5,6,7-tetrahydro-6-(phenylmethyl)thieno[2,3-c]pyridin-2-yl]-2,4-dimethoxybenzeneacetamide.
CAS Registry No. 1216647-16-3; STN Entry Date Apr. 4, 2010; N-[3-cyano-4,5,6,7-tetrahydro-6-(phenylmethyl)thieno[2,3-c]pyridin-2-yl]benzeneacetamide hydrochloride.
CAS Registry No. 380660-31-1; STN Entry Date Jan. 7, 2002; N-[3-Cyano-4,5,6,7-tetrahydro-6-(phenylmethyl)thieno[2,3-c]pyridin-2-yl]benzeneacetamide.
CAS Registry No. 1329872-96-9; STN Entry Date Sep. 8, 2011; N-[3-cyano-4,5,6,7-tetrahydro-6-(phenylmethyl)thieno[2,3-c]pyridin-2-yl]-3-methoxybenzeneacetamide hydrochloride.
CAS Registry No. 1330271-48-1; STN Entry Date Sep. 9, 2011; N-[3-Cyano-4,5,6,7-tetrahydro-6-(phenylmethyl)thieno[2,3-c]pyridin-2-yl]-3-methoxybenzeneacetamide.
CAS Registry No. 1330292-92-6; STN Entry Date Sep. 9, 2011; N-[3-cyano-4,5,6,7-tetrahydro-6-(phenylmethyl)thieno[2,3-c]pyridin-2-yl]-3,4-dimethoxybenzeneacetamide hydrochloride.
CAS Registry No. 1330825-73-4; STN Entry Date Sep. 11, 2011; N-[3-Cyano-4,5,6,7-tetrahydro-6-(phenylmethyl)thieno[2,3-c]pyridin-2-yl]-3,4-dimethoxybenzeneacetamide.
CAS Registry No. 1329482-01-0; STN Entry Date Sep. 7, 2011; N-[3-cyano-4,5,6,7-tetrahydro-6-(phenylmethyl)thieno[2,3-c]pyridin-2-yl]-2-methoxy-5-methylbenzeneacetamide hydrochloride.
CAS Registry No. 1329745-39-2; STN Entry Date Sep. 8, 2011; N-[3-Cyano-4,5,6,7-tetrahydro-6-(phenylmethyl)thieno[2,3-c]pyridin-2-yl]-2-methoxy-5-methylbenzeneacetamide.
Hung et al, "Synthesis of a Potent Pan-Serotype Dengue Virus Inhibitor Having a Tetrahydrothienopyridine Core, Synlett" (2020) Ahead of Print DOI: 10.1055/a-1323-4036 (Novartis journal publication).
Moquin et al, "NITD-688, a pan-serotype inhibitor of the dengue virus NS4B protein, shows favorable pharmacokinetics and efficacy in preclinical animal models," Science Translational Medicine (2021), 13(579), eabb2181 DOI: 10.1126/scitranslmed. abb2181(Novartis journal publication).
Pittala et al, "A facile synthesis of new 2-carboxamido-3-carboxythiophene and 4,5,6,7-tetrahydro-2-carboxamido-3-carboxythieno[2,3-c]pyridine derivatives as potential endothelin receptors ligands," Farmaco (2005), 60(9), 711-720, DOI: Farmaco (2005), 60(9), 711-720 (Universita degli Studi di Catania publication).
Wataru Hakamata et. al.: "Virtual ligand screening of alpha-glucosidase: Identification of a novel potent noncarbohydrate mimetic inhibitor", Bioorganic & Medicinal Chemistry Letters, 22:62-64, 2012.
Mostafam. Ismail, "Synthesis and cyclization reactions of 2-(6-methylquinolin-4-yl)malononitriles and ethyl 2-cyano-2-(6-methylquinolin-4-yl)acetates", J. Serb. Chem. Soc., 71(7):721-732, 2006.
Shirley Louise-May et. al.: "Discovery of novel dialkyl substituted thiophene inhibitors of HCV by in silico screening of the NS5B RdRp", Bioorganic & Medicinal Chemistry Letters, 17:3905-3909, 2007.
Adam J. Wolpaw et. el.: "Modulatory profiling identifies mechanisms of small molecule-induced cell death", PNAS, 108(39):E771-E780, 2011.

* cited by examiner

N-SUBSTITUTED TETRAHYDROTHIENOPYRIDINE DERIVATIVES AND USES THEREOF

FIELD CROSS-REFERENCE TO RELATED APPLICATIONS

This application is the U.S. National Stage of International Application No. PCT/IB2019/055121, filed Jun. 18, 2019, which claims the benefit of priority to U.S. Ser. No. 62/687,068, filed Jun. 19, 2018, the contents of which is incorporated herein by reference.

FIELD

The present invention relates to N-substituted tetrahydrothienopyridine derivatives, pharmaceutical compositions thereof, and their use for the prevention and treatment of viral infections, in particular viral infections caused by dengue virus.

BACKGROUND

Dengue is the most prevalent arthropod-borne viral (arboviral) disease in humans and remains a global health problem. Dengue fever is a febrile disease caused by one of the four dengue virus serotypes DEN-1, DEN-2, DEN-3 and DEN-4, which belong to the family Flaviviridae. The virus is transmitted to humans primarily by *Aedes aegypti*, a mosquito that feeds on humans.

Infections produce a range of clinical manifestations, from milder flu-like symptoms to the more severe and sometimes fatal hemorrhagic disease. Typical symptoms include fever, severe headache, muscle and joint pains and rashes. The more severe forms of the disease are dengue hemorrhagic fever (DHF) and dengue shock syndrome (DSS). According to the WHO, there are four major clinical manifestations of DHF: (1) high fever (2) haemorrhagic phenomena (3) thrombocytopaenia and (4) leakage of plasma. DSS is defined as DHF plus weak rapid pulse, and narrow pulse pressure or hypotension with cold, clammy skin and restlessness. The severity of DHF can be reduced with early detection and intervention, but subjects in shock are at high risk of death.

affects an estimated 390 million people annually, of which 96 million displays clinical signs of the disease. According to the WHO, the number of cases reported increased from 2.2 million in 2010 to 3.2 million in 2015. Before 1970, only 9 countries had experienced severe dengue epidemics. Dengue is now endemic in more than 100 countries in regions monitored by the WHO in Africa, the Americas, the Eastern Mediterranean, South-East Asia and the Western Pacific. The Americas, South-East Asia, and Western Pacific regions remain the most seriously affected. A quarter of the infected individuals will require hospitalization of which 3-6% may progress to dengue hemorrhagic fever or shock syndrome, and represents the fatal manifestation of the disease. The current annual death toll based on WHO estimates were around 12'500 in 2012; however it is believed that this number is severely under representative due to the under-reporting of the majority of cases. The risks to develop lethal forms of dengue and the social costs of dengue justify the discovery and the commercialization of anti-dengue agent to offset hospitalization and inactivity costs Despite regular outbreaks, previously infected people remain susceptible to infection because there are four different serotypes of the dengue virus and infection with one of these serotypes provides immunity to only that serotype. It is believed that DHF is more likely to occur in subjects who have secondary dengue infections. Efficient treatments for dengue fever, DHF and DSS are being sought.

Yellow fever virus (YFV), West Nile virus (WNV), Japanese encephalitis virus (JEV), tick-borne encephalitis virus, Kunjin virus, Murray Valley encephalitis, St Louis encephalitis, Omsk hemorrhagic fever virus, bovine viral diarrhea virus, Zika virus and Hepatitis C virus (HCV) also belong to the family Flaviviridae.

WNV can be asymptomatic, or it can cause flu-like symptoms in some individuals. In some cases it causes neurological disorders, encephalitis, and in severe cases can result in death. WNV is also transmitted by mosquitoes. YFV is also transmitted by mosquitoes, and can cause severe symptoms in infected individuals. JEV is also transmitted by mosquitoes, and is either asymptomatic or causes flu-like symptoms, with some cases developing into encephalitis. The acute encephalitis stage of the disease is characterized by convulsions, neck stiffness and other symptoms. HCV is a blood-borne virus that is transmitted by blood-to-blood contact. In the initial (acute) stage of the disease, most subjects will not show any symptoms. Even during the chronic stage (i.e. where the disease persists for more than 6 months), severity of symptoms can vary from subject to subject. In the long term, some infected persons can progress to cirrhosis and liver cancer. The current treatment for HCV involves a combination of interferon alpha and ribavirin, an anti-viral drug. Efficient treatments for infections caused by these Flaviviridae viruses are being sought as well.

The present invention relates to N-substituted tetrahydrothienopyridine derivatives that are useful for the treatment of viral infections such as those caused by a virus of the family Flaviviridae, especially dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus, and other Flaviviridae viruses as described herein.

SUMMARY

One aspect of the present invention provides compounds of Formula (I) or pharmaceutically acceptable salts thereof:

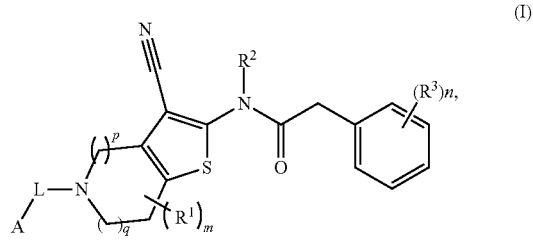

wherein:
  A is phenyl or 3-6 membered cycloalkyl; each of which is optionally substituted with —$C_{1-6}$ alkyl, cyano, —$C_{1-4}$ aminoalkyl, —$C_{1-4}$ alkoxyl, —$C_{1-6}$ haloalkyl, —$C_{1-4}$ haloalkoxyl, and halo;
  L is —$C_{1-6}$ alkylene-;
  each $R^1$ is independently selected from —$C_{1-6}$ alkyl, cyano, —$C_{1-4}$ aminoalkyl, —$C_{1-4}$ alkoxyl, —$C_{1-6}$ haloalkyl, —$C_{1-4}$ haloalkoxyl, and halo;
  each $R^2$ is H or —$C_{1-6}$ alkyl;

$R^3$ is selected from —$C_{1-6}$ alkyl, —ON, —$C_{1-4}$ alkoxyl, —$C_{1-6}$ haloalkyl, —$C_{1-4}$ haloalkoxyl, halogen, —C(O)$R^{3a}$, —C(O)O$R^{3b}$, —C(O)N$R^{3c}R^{3d}$, —P(O)$R^{3e}R^{3f}$, —P(O)(O$R^{3g}$)(O$R^{3h}$), —P(O)(O$R^{3i}$)($R^{3j}$), —S(O)$_2$$R^{3k}$, —S(O)$_2$N$R^{3l}R^{3m}$, —S(O)$R^{3n}$, —N$R^{3o}R^{3p}$, —N$R^{3q}$C(O)$R^{3r}$, —N($R^{3s}$)C(O)O$R^{3t}$ and —N$R^{3u}$S(O)$_2$ $R^{3v}$, wherein each of the —$C_{1-6}$ alkyl, —$C_{1-4}$ alkoxyl, —$C_{1-6}$ haloalkyl, and —$C_{1-4}$ haloalkoxyl is independently optionally substituted by hydroxyl, —N$R^{3w}R^{3x}$, —$C_{1-4}$ alkoxyl, —S(O)$_2$N$R^{3y}R^{3z}$, or —S(O)$_2R^{3a2}$; wherein each of $R^{3w}$, $R^{3x}$, $R^{3y}$, and $R^{3z}$ is independently H, —$C_{1-4}$ alkyl or —$C_{1-6}$ haloalkyl and $R^{3a2}$ is —$C_{1-4}$ alkyl or —$C_{1-6}$ haloalkyl, or any two $R^3$ may combine with one atom to form a 5-6 membered fused heterocycloalkyl, wherein the heterocycloalkyl comprises one or two heteroatoms selected from N and S, and wherein the heterocycloalkyl is independently optionally substituted with one or two groups selected from —$C_{1-6}$ alkyl, —$C_{1-4}$ aminoalkyl —ON, —$C_{1-4}$ alkoxyl, halogen, —$C_{1-6}$ haloalkyl and —$C_{1-4}$haloalkoxyl;

each of $R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, $R^{3n}$, $R^{3o}$, $R^{3p}$, $R^{3q}$, $R^{3r}$, $R^{3s}$, $R^{3t}$, $R^{3u}$, $R^{3v}$ is independently selected from H, —$C_{1-6}$ alkyl and —$C_{1-6}$ haloalkyl;

each of $R^{3l}$ and $R^{3m}$ is independently selected from H, —$C_{1-6}$ alkyl, —$C_{1-6}$ haloalkyl, -aminoalkyl, and -hydroxyalkyl, wherein the —$C_{1-6}$ alkyl is optionally further substituted by 3-6 membered cycloalkyl, and wherein the 3-6 membered cycloalkyl substituent is optionally further substituted by 1-2 halo; or $R^{23}$ and $R^{24}$ may combine with the N to form a 5-6 membered heterocycloalkyl, wherein the 5-6 membered heterocycloalkyl optionally further comprises one hetero atom selected from S and N;

p is 1, 2 or 3; q is 0 or 1; and each of n and m is independently selected from 0, 1 and 2.

The present invention also provides processes and intermediates for making the compounds of the present invention.

The present invention further provides a pharmaceutical composition comprising a therapeutically effective amount of a compound according to Formula (I) or subformulae thereof, or a pharmaceutically acceptable salt thereof, or stereo isomer thereof, and one or more pharmaceutically acceptable carriers.

The present invention provides a combination, in particular a pharmaceutical combination, comprising a therapeutically effective amount of the compound according to Formula I or a sub-formula thereof, or a pharmaceutically acceptable salt thereof, or a stereoisomer thereof, and one or more additional therapeutically active agent.

In another aspect of the present invention, a method is provided for treating a disease caused by a viral infection comprising the step of administering to a subject (in particular, a human) in need thereof, a therapeutically effective amount of a compound of Formula (I) including any of the embodiments described herein. In a particular useful embodiment, the viral infection is caused by a virus selected from the group consisting of dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus. In a more particular useful embodiment, the viral infection is caused by dengue virus. The compound may be administered as a pharmaceutical composition described herein Another aspect of the present invention includes a compound of Formula (I) comprising any one of the embodiments described above, for use as a medicament (e.g., the use of a compound of Formula (I) comprising any one of the embodiments described above in the manufacture of a medicament for treating a disease caused by a viral infection). In a particular useful embodiment, the viral infection is caused by a virus selected from the group consisting of dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus. In a more particular useful embodiment, the viral infection is caused by dengue virus.

DETAILED DESCRIPTION OF THE INVENTION

Definitions

The general terms used hereinbefore and hereinafter preferably have within the context of this invention the following meanings, unless otherwise indicated, where more general terms wherever used may, independently of each other, be replaced by more specific definitions or remain, thus defining more detailed embodiments of the invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The term "a," "an," "the" and similar terms used in the context of the present invention (especially in the context of the claims) are to be construed to cover both the singular and plural unless otherwise indicated herein or clearly contradicted by the context.

As used herein, the term "heteroatoms" refers to nitrogen (N), oxygen (O) or sulfur (S) atoms, in particular nitrogen or oxygen.

Unless otherwise indicated, any heteroatom with unsatisfied valences is assumed to have hydrogen atoms sufficient to satisfy the valences.

As used herein, the term "$C_{1-6}$ alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_{1-4}$ alkyl" is to be construed accordingly. As used herein, the term "n-alkyl" refers to straight chain (un-branched) alkyl radical as defined herein. Examples of $C_{1-8}$ alkyl include, but are not limited to, methyl, ethyl, n-propyl, iso-propyl, n-butyl, isobutyl (—CH-$_2$CH(CH$_3$)$_2$), sec-butyl (—CH(CH$_3$)CH$_2$CH$_3$), t-butyl (—C(CH$_3$)$_3$), n-pentyl, isopentyl (—(CH-2)$_2$CH(CH$_3$)$_2$), neopentyl (—CH$_2$C(CH$_3$)$_3$), tert-pentyl (—C(CH$_3$)$_2$CH$_2$CH$_3$), 2-pentan-yl (—CH(CH$_3$)(CH$_2$)$_2$CH$_3$), n-hexyl, and the like.

The term "alkylene" refers to a divalent alkyl group. For example, the term "$C_1$-$C_6$ alkylene" or "$C_1$ to $C_6$ alkylene" refers to a divalent, straight, or branched aliphatic group containing 1 to 6 carbon atoms (e.g., methylene (—CH$_2$—), ethylene (—CH$_2$CH$_2$—), n-propylene (—CH$_2$CH$_2$CH$_2$—), iso-propylene (—CH(CH$_3$)CH$_2$—), n-butylene, sec-butylene, iso-butylene, tert-butylene, n-pentylene, isopentylene, neopentylene, n-hexylene and the like).

The term "alkoxy" refers to an alkyl linked to an oxygen, which may also be represented as —O—R or —OR, wherein the R represents the alkyl group. "$C_{1-6}$ alkoxy" or "$C_1$ to $C_6$ alkoxy" is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy.

"Amino" as used herein refers to the radical —$NH_2$. When an amino is described as "substituted" or "optionally substituted", the term includes NR'R" wherein each R' and R" is independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl or groups or heteroforms of one of these groups, each of which is optionally substituted with the substituents described herein as suitable for the corresponding group.

The term "amino" also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

Unless indicated otherwise, the compounds of the invention containing amino moieties may include protected derivatives thereof. Suitable protecting groups for amino moieties include acetyl, tert-butoxycarbonyl, benzyloxycarbonyl, and the like.

As used herein, the term "$C_{1-4}$ aminoalkyl" refers to a radical of the formula —$RNH_2$, where R is alkylene as defined above.

"Halogen" or "halo" may be fluorine, chlorine, bromine or iodine (preferred halogens as substituents are fluorine and chlorine).

"Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" represents a haloalkyl group as defined above with the indicated number of carbon atoms attached through an oxygen bridge. For example, "$C_{1-6}$ haloalkoxy" or "$C_1$ to $C_6$ haloalkoxy" is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy.

The term "aryl" refers to 6- to 10-membered aromatic carbocyclic moieties having a single (e.g., phenyl) or a fused ring system (e.g., naphthalene.). A typical aryl group is phenyl group.

"Heterocycloalkyl" means cycloalkyl, as defined in this application, provided that one or more of the ring carbons indicated, are replaced by a moiety selected from —O—, —N═, —NR—, —C(O)—, —S—, —S(O)— and —S(O)$_2$—, wherein R is hydrogen, $C_{1-4}$ alkyl or a nitrogen protecting group (for example, carbobenzyloxy, p-methoxy-benzyl carbonyl, t-butoxycarbonyl, acetyl, benzoyl, benzyl, p-methoxy-benzyl, p-methoxy-phenyl, 3,4-dimethoxybenzyl, and the like). For example, a 3 to 8 membered heterocycloalkyl includes epoxy, aziridinyl, azetidinyl, imidazolidinyl, pyrazolidinyl, tetrahydrofuranyl, tetrahydrothienyl, tetrahydrothienyl 1,1-dioxide, oxazolidinyl, thiazolidinyl, pyrrolidinyl, pyrrolidinyl-2-one, morpholino, piperazinyl, piperidinyl, piperidinylone, pyrazolidinyl, hexahydropyrimidinyl, 1,4-dioxa-8-aza-spiro[4.5]dec-8-yl, thiomorpholino, sulfanomorpholino, sulfonomorpholino, octahydropyrrolo[3,2-b]pyrrolyl, and the like.

The term "heteroaryl" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, isoxazolyl, imidazolyl, triazolyl, tetrazolyl, triazinyl, pyrimidinyl, pyrazinyl, thiazolyl, purinyl, benzimidazolyl, quinolinyl, isoquinolinyl, quinoxalinyl, benzopyranyl, benzothiophenyl, benzoimidazolyl, benzoxazolyl, 1H-benzo[d][1,2,3]triazolyl, and the like.). The heteroaromatic moiety may consist of a single or fused ring system. A typical single heteroaryl ring is a 5- to 6-membered ring containing one to four heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a heteroaryl fused to an aryl (e.g., phenyl).

"Bridging ring" or "bridged rings" as used herein refers to a polycyclic ring system where two ring atoms that are common to two rings are not directly bound to each other. One or more rings of the ring system may include $C_{3-6}$ cycloalkyl or 4- to 6-membered heterocyclic rings comprising heteroatoms selecting from N, O and S as ring atoms. Non-exclusive examples of bridging rings include adamantanyl, azabicyclo[3.2.1]oct-3-en-3-yl,

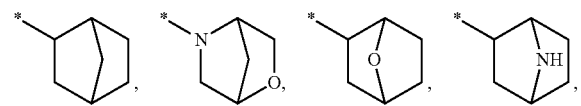

and the like.

As used herein, the term "cyano" means the radical *—C≡N.

The term "cycloalkyl" refers to nonaromatic carbocyclic ring that is a fully hydrogenated ring, including mono-, bi- or poly-cyclic, fused, bridged or spiro, ring systems. "$C_{3-10}$ cycloalkyl" or "$C_3$ to $C_{10}$ cycloalkyl" is intended to include $C_3$, $C_4$, $C_5$, $C_6$, $C_7$, $C_8$, $C_9$ and $C_{10}$ cycloalkyl groups that is 3 to 10 carbon ring members). Example cycloalkyl groups include, but are not limited to, cyclopropyl, cyclobutyl, cyclopentyl, bicyclo[1,1,1]pentanyl, cyclohexyl, norbornyl, and cubanyl.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

The term "hydroxyl" or "hydroxy", as used herein, refers to the radical —OH.

As referred to herein, the term "substituted" means that at least one hydrogen atom is replaced with a non-hydrogen group, provided that normal valencies are maintained and that the substitution results in a stable compound. When a substituent is (i.e. =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with zero to three R, then said group may be unsubstituted or substituted with up to three R, and at each occurrence R is selected independently from the definition of R.

As used herein,

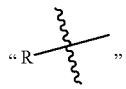

is symbol denoting the point of attachment of R, to other part of the molecule.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" indicates that the substance or composition must be compatible chemically and/or toxicologically, with the other ingredients comprising a formulation, and/or the mammal being treated therewith.

Unless specified otherwise, the term "compounds of the present invention" or "compounds of the present invention" refers to compounds of Formula (I), (IA), (IB) or (IC), as well as isomers, such as stereoisomers (including diastereoisomers, enantiomers and racemates), geometrical isomers, conformational isomers (including rotamers and astropisomers), tautomers, isotopically labeled compounds (including deuterium substitutions), and inherently formed moieties (e.g., polymorphs, solvates and/or hydrates). When a moiety is present that is capable of forming a salt, then salts are included as well, in particular pharmaceutically acceptable salts.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms.

"Enantiomers" are a pair of stereoisomers that are non-superimposable mirror images of each other. A 1:1 mixture of a pair of enantiomers is a "racemic" mixture. The term is used to designate a racemic mixture where appropriate. When designating the stereochemistry for the compounds of the present invention, a single stereoisomer with known relative and absolute configuration of the two chiral centers is designated using the conventional RS system (e.g., (1S, 2S)); a single stereoisomer with known relative configuration but unknown absolute configuration is designated with stars (e.g., (1R*,2R*)); and a racemate with two letters (e.g., (1RS,2RS) as a racemic mixture of (1R,2R) and (1S,2S); (1RS,2SR) as a racemic mixture of (1R,2S) and (1S,2R)).

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (—) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Geometric isomers may occur when a compound contains a double bond or some other feature that gives the molecule a certain amount of structural rigidity. If the compound contains a double bond, the substituent may be E or Z configuration. If the compound contains a disubstituted cycloalkyl, the cycloalkyl substituent may have a cis- or trans-configuration.

Conformational isomers (or conformers) are isomers that can differ by rotations about one or more a bonds. Rotamers are conformers that differ by rotation about only a single a bond.

The term "atropisomer" refers to a structural isomer based on axial or planar chirality resulting from restricted rotation in the molecule.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation).

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; and a mixture of isomeric compounds of the present invention may be separated into the individual isomers.

Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. For example, pharmaceutically acceptable salts include, but are not limited to, acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxymalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate or xinafoate salt form.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like, preferably hydrochloric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns Ito XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy,* 22nd Edition, Pharmaceutical Press, London, UK (2012), the invention of which is hereby incorporated by reference.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, and $^{125}I$ respectively. The present invention includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this present invention can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the present invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

As used herein, the term "patient" encompasses all mammalian species.

As used herein, the term "subject" refers to primates (e.g., humans, male or female, dogs, rabbits, guinea pigs, pigs, rats and mice). In certain embodiments, the subject is a primate. In yet other embodiments, the subject is a human.

As used herein, a subject is "in need of" a treatment if such subject would benefit biologically, medically or in quality of life from such treatment (preferably, a human).

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat', "treating" or "treatment" of any disease/disorder refers to the treatment of the disease/disorder in a mammal, particularly in a human, and includes: (a) ameliorating the disease/disorder, (i.e., slowing or arresting or reducing the development of the disease/disorder, or at least one of the clinical symptoms thereof); (b) relieving or modulating the disease/disorder, (i.e., causing regression of the disease/disorder, either physically, (e.g., stabilization of a discernible symptom), physiologically, (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a mammal, in particular, when such mammal is predisposed to the disease or disorder but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for aqueous, "sat" or "sat'd" for saturated, "MW" for molecular weight, "mw" or "μwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, "ee" for "enantiomeric excess" and "α", "β", "R", "S", "E", and "Z" are stereochemical designations familiar to one skilled in the art.

EMBODIMENTS OF THE INVENTION

Various embodiments of the invention are described herein. It will be recognized that features specified in each embodiment may be combined with other specified features to provide further embodiments. The following enumerated embodiments are representative of the invention.

Embodiment 1. A compound of Formula I, or a pharmaceutically acceptable salt thereof, as described in the Summary of the Invention:

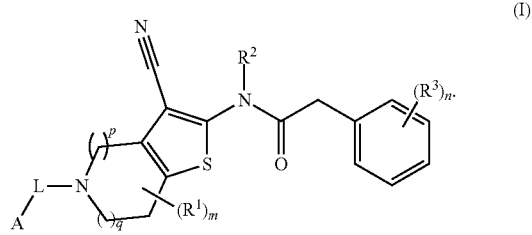

(I)

Embodiment 2a, b, c, d, e and f. The compound of Formula I, or a pharmaceutically acceptable salt thereof, according to Embodiment 1, wherein p is any one of 1, 2 or 3 and q is any one of 0 or 1.

Embodiment 3a and 3b. The compound is of Formula IA or Formula 1B:

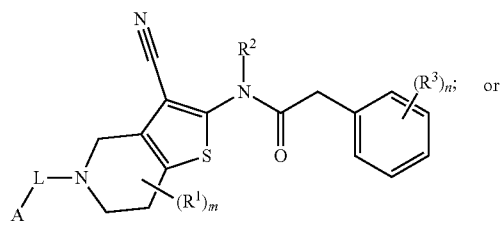

(IA)

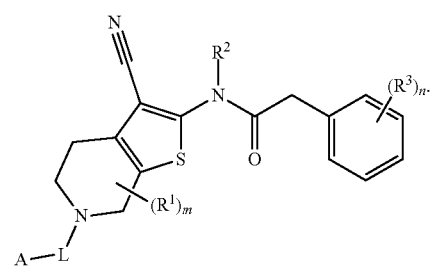

(IB)

Embodiment 4. The compound of Formula I, or a pharmaceutically acceptable salt thereof, according to Embodiment 1-3, wherein the A ring is phenyl.

Embodiment 5. The compound of Formula I, or a pharmaceutically acceptable salt thereof, according to any one of embodiments 1 to 3, wherein A ring is 4-6 membered cycloalkyl.

Embodiment 6. The compound of Formula I, or a pharmaceutically acceptable salt thereof, according to any one of embodiments 1 to 4, wherein L is —$C_{1-4}$ alkyl substituted with phenyl, 3-6 membered cycloalkyl, or 5-7 member bridged cycloalkyl. Each of the phenyl, and 3-6 membered cycloalkyl substituents is independently optionally substituted with 1-3 groups selected from halo, —$C_{1-4}$ alkyl, —$C_{1-4}$ haloalkyl, and —$C_{1-4}$ alkoxyl.

Embodiment 7. The compound of Formula I, or a pharmaceutically acceptable salt thereof, according to any one of embodiments 1 to 5, wherein L-A is selected from

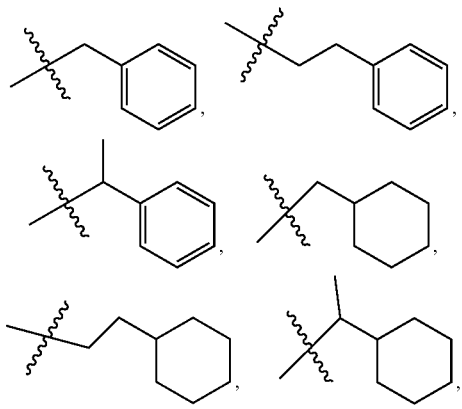

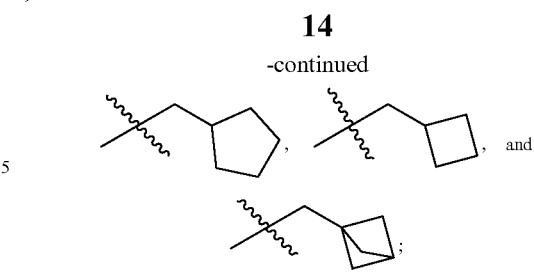

and each of these groups is optionally independently substituted with 1-3 groups selected from halo, —$C_{1-4}$alkyl, —$C_{1-4}$ haloalkyl, and —$C_{1-4}$ alkoxyl.

Embodiment 8. The compound of Formula I, or a pharmaceutically acceptable salt thereof, according to any one of embodiments 1 to 6, wherein L-A is selected from

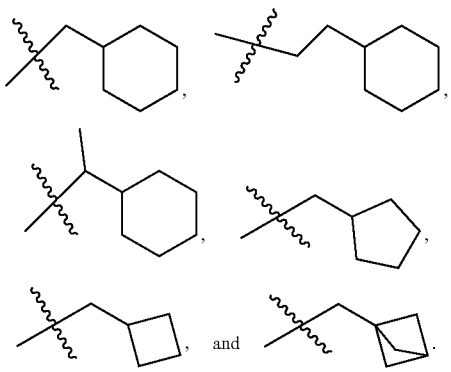

Each of these groups is optionally independently substituted with 1-2 groups selected from halo, —$C_{1-4}$ alkyl, and —$C_{1-4}$ haloalkyl.

Embodiment 9. The compound of Formula I, or a pharmaceutically acceptable salt thereof, according to any one of embodiments 7, wherein L-A is selected from

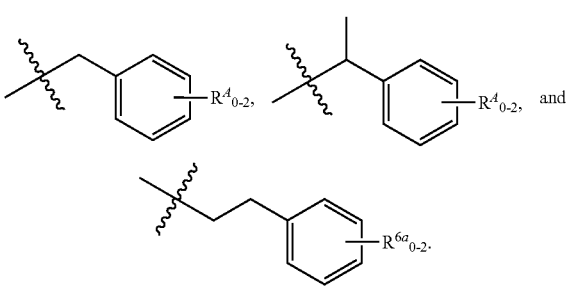

Each of $R^A$ is, at each occurrence, independently selected from halo, —$C_{1-4}$ alkyl, —$C_{1-4}$ haloalkyl, and —$C_{1-4}$ alkoxyl.

Embodiment 10. The compound of Formula I, or a pharmaceutically acceptable salt thereof, according to embodiment 8, wherein each of $R^A$ is independently selected from F, Cl, —$CH_3$, and —$OCH_3$.

Embodiment 11. The compound of Formula I, or a pharmaceutically acceptable salt thereof, according to any one of embodiments 1 to 10, wherein L-A is selected from

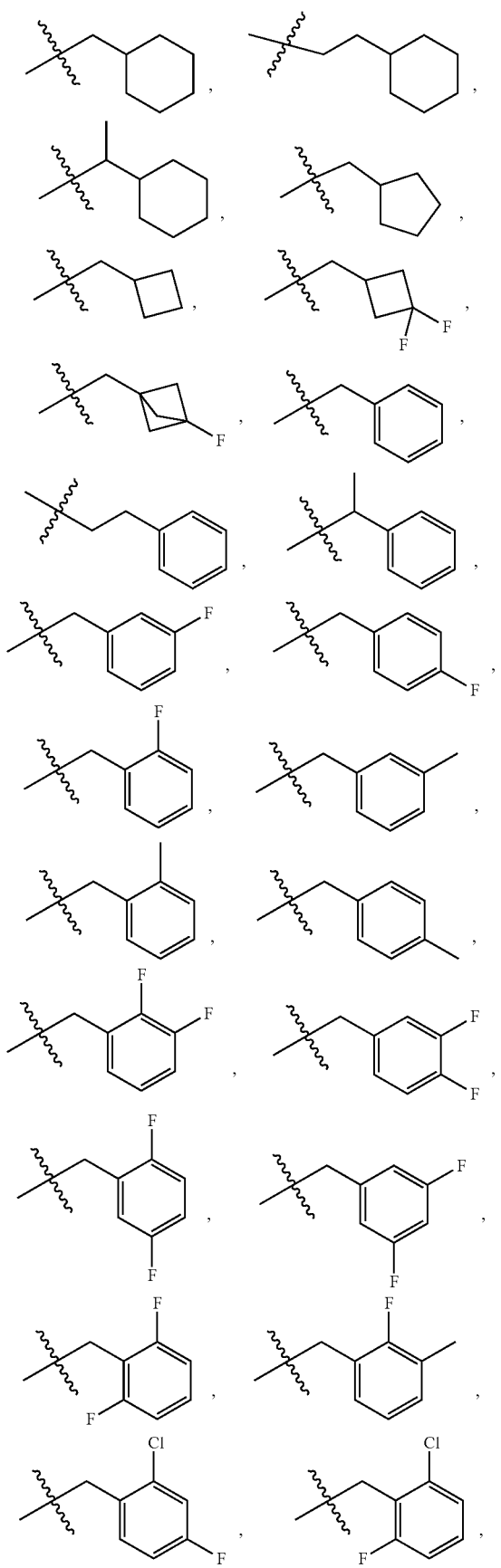

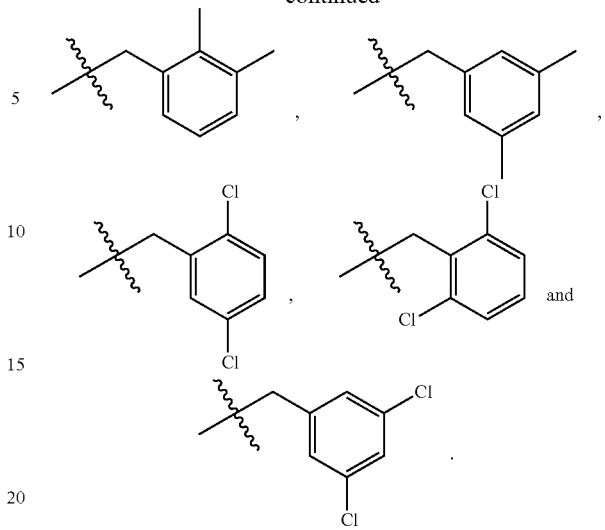

Embodiment 12. The compound of Formula I, or a pharmaceutically acceptable salt thereof, according to any one of embodiments 1-12, wherein each of $R^1$ is independently selected from H, —$C_{1-4}$ alkyl, and —$C_{1-4}$ haloalkyl.

Embodiment 13. The compound of Formula I, or a pharmaceutically acceptable salt thereof, according to any one of embodiments 1-12, wherein at least one of R' is H.

Embodiment 14. The compound of Formula I, or a pharmaceutically acceptable salt thereof, according to any one of embodiments 1-13, wherein both $R^1$ are H.

Embodiment 15. The compound of Formula I, or a pharmaceutically acceptable salt thereof, according to any one of embodiments 1-13, wherein at least one of R' is selected from —$CH_3$, —$CH_2CH_3$, —$CH(CH_3)_2$, —$C(CH_3)_3$, —$CH_2CH_2CH_3$, and $CF_3$.

Embodiment 16. The compound of Formula I, or a pharmaceutically acceptable salt thereof, according to any one of embodiments 1-12, wherein both of R' are —$CH_3$.

Embodiment 17. The compound of Formula I, or a pharmaceutically acceptable salt thereof, according to any one of embodiments 1-16, wherein $R^3$ is selected from —$S(O)_2NH_2$, —$S(O)_2N(CH_3)_2$, —$S(O)_2NHCH_3$, —$S(O)_2NH$—$CH_2$-cyclobutyl, —$S(O)_2NH$—$CH_2$-cyclopentyl, —$S(O)_2NH$—$CH_2$-cyclohexyl, —$S(O)_2NH$—$CH_2$-difluorocyclobutyl, —$S(O)_2CH_3$ and —$S(O)_2CHF_2$.

Embodiment 18. The compound of Formula I, or a pharmaceutically acceptable salt thereof, according to any one of embodiments 1-17, wherein $R^3$ is —$S(O)_2R^4$.

Embodiment 19. The compound of Formula IC, or a pharmaceutically acceptable salt thereof:

(IC)

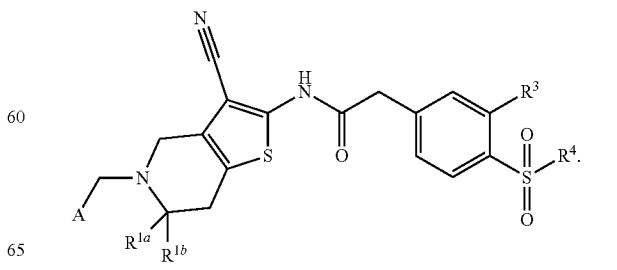

Embodiment 20. The compound of Formula I, or a pharmaceutically acceptable salt thereof, according to any one of embodiments 1-19, wherein $R^3$ is selected from —S(O)$_2$NH$_2$, —S(O)$_2$N(CH$_3$)$_2$, —S(O)CH$_3$, —S(O)$_2$CH$_2$CH$_3$, —N(H)S(O)$_2$CH$_3$, —NC(O)CH$_3$, —CH$_2$S(O)NH$_2$, NH$_2$, and —CONH$_2$.

Embodiment 21. The compound of Formula I, or a pharmaceutically acceptable salt thereof, according to any one of embodiments 1-19 wherein $R^3$ is —S(O)$_2$NH$_2$, or —S(O)$_2$CH$_3$.

Embodiment 22. The compound of Formula I, or a pharmaceutically acceptable salt thereof, according to any one of embodiments 1-16, wherein each $R^3$ is independently selected from halo, CN, and —C$_{1-4}$ alkoxyl.

Embodiment 23. The compound of Formula I, or a pharmaceutically acceptable salt thereof, according to any one of embodiments 1-16, wherein each $R^3$ is independently —C$_{1-4}$alkoxyl.

Embodiment 24. The compound of Formula I, or a pharmaceutically acceptable salt thereof, according to any one of embodiments 1-16, wherein each $R^3$ is independently selected from —OCH$_3$, and —OCH$_2$CH$_3$.

Embodiment 25. The compound of Formula I, or a pharmaceutically acceptable salt thereof, according to any one of embodiments 1-24, wherein m is 0.

Embodiment 26. The compound of Formula I, or a pharmaceutically acceptable salt thereof, according to any one of embodiments 1-24, wherein m is 1.

Embodiment 27. The compound of Formula I, or a pharmaceutically acceptable salt thereof, according to any one of embodiments 1-24, wherein m is 2.

Embodiment 28. The compound of Formula I, or a pharmaceutically acceptable salt thereof, according to any one of embodiments 1-27, wherein n is 0.

Embodiment 29. The compound of Formula I, or a pharmaceutically acceptable salt thereof, according to any one of embodiments 1-27, wherein n is 1.

Embodiment 30. The compound of Formula I, or a pharmaceutically acceptable salt thereof, according to any one of embodiments 1-27, wherein n is 2.

Embodiment 31. The compound of Formula I, or a pharmaceutically acceptable salt thereof, according to embodiment 1, wherein the compound is selected from examples 1-127.

Embodiment 32. A pharmaceutical composition comprising a therapeutically effective amount of a compound of Formula (I), and a pharmaceutically acceptable carrier or excipient.

Embodiment 33. A pharmaceutical composition, comprising a therapeutically effective amount of a compound of Formula (I), any one of embodiments 1 to 31 as an active ingredient, and at least one excipient.

Embodiment 34. The pharmaceutical composition, according to embodiment 32 or 33, comprising a therapeutically effective amount of a compound of Formula (I), and a pharmaceutically acceptable carrier or excipient, further comprising at least one additional pharmaceutical agent.

Embodiment 35. The pharmaceutical composition, according to embodiment 32, wherein the at least one additional pharmaceutical agent is selected from the group consisting of interferons, ribavirin and ribavirin analogs, cyclophilin binder, HCV NS3 protease inhibitors, HCV NS5a inhibitors, P7 inhibitor, entry inhibitor, NS4b inhibitor, alpha-glucosidase inhibitors, host protease inhibitors, immune modulators, symptomatic relief agents, nucleoside and non-nucleoside NS5b inhibitors.

Embodiment 36. A method for treating a disease caused by a viral infection comprising the step of administering to a subject in need thereof a therapeutically effective amount of a compound according to any one of embodiments 1-31.

Embodiment 37. The method of embodiment 36, wherein the viral infection is caused by a virus selected from the group consisting of dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus.

Embodiment 38. The method of embodiment 37, wherein said viral infection is caused by dengue virus.

Embodiment 39. The compound of any one of embodiments 1-31 for use as a medicament.

Embodiment 40. The use of a compound of any one of embodiments 1-31 in the manufacture of a medicament for treating a disease caused by a viral infection.

Embodiment 41. The use of embodiment 40, wherein the viral infection is caused by a virus selected from the group consisting of dengue virus, yellow fever virus, West Nile virus, Japanese encephalitis virus, tick-borne encephalitis virus, Kunjin virus, Murray Valley encephalitis, St Louis encephalitis, Omsk hemorrhagic fever virus, bovine viral diarrhea virus, Zika virus and Hepatitis C virus.

Embodiment 42. The use of embodiment 41, wherein the viral infection is caused by dengue virus.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and
  e) absorbents, colorants, flavors and sweeteners.

Another aspect of the present invention includes a pharmaceutical composition comprising a compound of Formula (I) which comprises any one of embodiments described above, and a pharmaceutically acceptable carrier or excipient. The pharmaceutical composition may further comprise at least one additional pharmaceutical agent described herein below. Examples of the additional pharmaceutical agent include, but are not limited to, interferons, ribavirin and ribavirin analogs, cyclophilin binder, HCV NS3 protease inhibitors, HCV NS5a inhibitors, P7 inhibitor, entry inhibitor, NS4b inhibitor, alpha-glucosidase inhibitors, host protease inhibitors, immune modulators, kinase inhibitors which induce cytokines or chemokines for severe dengue, symptomatic relief agents such as for plasma leakage etc., surface receptors such as CLEC5A and DC-SIGN, nucleoside and non-nucleoside NS5b inhibitors.

Pharmacology and Utility

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques. All tautomeric forms are also intended to be included.

Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Hence the invention further provides co-crystals comprising a compound of the present invention.

The compounds of the present invention are typically used as a pharmaceutical composition (e.g., a compound of the present invention and at least one pharmaceutically acceptable carrier). As used herein, the term "pharmaceutically acceptable carrier" includes generally recognized as safe (GRAS) solvents, dispersion media, surfactants, antioxidants, preservatives (e.g., antibacterial agents, antifungal agents), isotonic agents, salts, preservatives, drug stabilizers, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

In certain instances, it may be advantageous to administer the compound of the present invention in combination with at least one additional pharmaceutical (or therapeutic) agent. The compound of the present invention may be administered either simultaneously with, or before or after, one or more other therapeutic agent(s). Alternatively, the compound of the present invention may be administered separately, by the same or different route of administration, or together in the same pharmaceutical composition as the other agent(s).

Suitable additional pharmaceutical agents include, but not limited to, interferons, ribavirin and ribavirin analogs, cyclophilin binder, HCV NS3 protease inhibitors, HCV NS5a inhibitors, P7 inhibitor, entry inhibitor, NS4b inhibitor, alpha-glucosidase inhibitors, host protease inhibitors, immune modulators, kinase inhibitors which induce cytokines or chemokines for severe dengue, symptomatic relief agents such as for plasma leakage etc., surface receptors such as CLEC5A and DC-SIGN, nucleoside and non-nucleoside NS5b inhibitors.

The compound of the present invention or pharmaceutical composition thereof for use in humans is typically administered orally at a therapeutic dose.

It will be appreciated that the dosage range of a compound of the invention to be employed for treating a viral infection depends upon factors known to the person skilled in the art, including host, nature and severity of the condition to be treated, the mode of administration and the particular substance to be employed.

The daily dosage of the compound of the invention will vary with the compound employed, the mode of administration, the treatment desired and the disease indicated, as well as other factors such as a subject's age, body weight, general health, condition, prior medical history and sex, and like factors known in the medical arts. For example, a compound of the invention is administered at a daily dosage in the range from about 0.5 mg/kg body weight to about 15 mg/kg body weight, e.g. in the range from about 1 mg/kg body weight to about 10 mg/kg body weight. Typically, satisfactory results can be obtained when the compound of the invention is administered at a daily dosage from about 0.001 g to about 10 g, e.g. not exceeding about 1 gram, e.g. from about 0.1 g to about 0.5 g for a 70 kg human, given up to 4 times daily.

Furthermore, several divided dosages, as well as staggered dosages, can be administered daily or sequentially, or the dose can be continuously infused, or can be a bolus injection. Further, the dosages of the compounds of the invention can be proportionally increased or decreased as indicated by the exigencies of the therapeutic or prophylactic situation.

In general, the therapeutically effective dosage of a compound, the pharmaceutical composition, or the combinations thereof, is dependent on the species of the subject, the body weight, age and individual condition, the disorder or disease or the severity thereof being treated. A physician, pharmacist, clinician or veterinarian of ordinary skill can readily determine the effective amount of each of the active ingredients necessary to prevent, treat or inhibit the progress of the disorder or disease.

Another aspect of the invention is a product comprising a compound of the present invention and at least one other therapeutic agent (or pharmaceutical agent) as a combined preparation for simultaneous, separate or sequential use in therapy to treat a subject having a disease caused by viral infection.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent or fixed dose composition); (ii) by the physician themselves (or under the guidance of the physician) shortly before administration; (iii) in the patient themselves, e.g. during sequential administration of the compound of the invention and the other therapeutic agent.

It is especially advantageous to formulate the pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Daily dosages with respect to the other therapeutic agent used will vary depending upon, for example, the compound employed, the host, the mode of administration and the severity of the condition to be treated. Because of the diverse types of the other therapeutic agent that may be used, the amounts can vary greatly, and can be determined by routine experimentation, as described above.

The compound of the invention and at least one other therapeutic (or pharmaceutical) agent may be administered by any conventional route, in particular enterally, e.g. orally, for example in the form of solutions for drinking, tablets or capsules or parenterally, for example in the form of injectable solutions or suspensions.

Combinations include those of a compound of the invention with a non-immunosuppressive cyclophilin-binding cyclosporine, with mycophenolic acid, a salt or a prodrug thereof, and/or with a S1P receptor agonist, e.g. Fingolimod.

In another aspect, this invention provides a method comprising administering a compound of the invention and another anti-viral agent, preferably an anti-Flaviviridae, e.g. and anti-dengue or anti-Hepatitis C virus agent. Such anti-viral agents include, but are not limited to, immunomodulatory agents, such as α, β, and δ interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the Flaviviridae (e.g. dengue virus, Hepatitis C virus) life cycle, including helicase, polymerase, and metalloprotease inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above.

Each component of a combination according to this invention may be administered separately, together, or in any combination thereof. As recognized by skilled practitioners, dosages of interferon are typically measured in IU (e.g., about 4 million IU to about 12 million IU). Each component may be administered in one or more dosage forms. Each dosage form may be administered to the subject in any order.

Preparation of Compounds

The compounds of the present invention can be prepared in a number of ways known to one skilled in the art of organic synthesis in view of the methods, reaction schemes and examples provided herein. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

General Conditions:

Mass spectra were acquired on LC-MS systems using electrospray, chemical and electron impact ionization methods from a range of instruments of the following configurations: SHIMADZU LCMS-2020, Agilent 1200 LC/G1956A MSD and Agilent 1200\G6110A, Agilent 1200 LC & Agilent 6110 MSD Mass Spectrometer [M+H]$^+$ refers to protonated molecular ion of the chemical species.

Chiral HPLC spectra were acquired on SFC systems (Agilent1260 & Berger) using Chiralpak AS-S & AD-S, Chiralcel OD-S & OJ-S.

NMR spectra were run on Bruker 400 MHz spectrometers using ICON-NMR, under TopSpin program control. Spectra were measured at 298 K, unless indicated otherwise, and were referenced relative to the solvent resonance.

Instrumentation:

LC-MS Methods: Using SHIMADZU LCMS-2020, Agilent 1200 LC/G1956A MSD and Agilent 1200\G6110A, Agilent 1200 LC & Agilent 6110 MSD.

Method 1: 5-95CD_R_220&254

| Column | Kinetex EVO C18 2.1 × 30 mm, 5 um |
|---|---|
| Column Temperature | 40° C. |
| Eluents | A: 0.05% $NH_3 \cdot H_2O$ in water (v/v), B: Acetonitrile |
| Flow Rate | 1.5 ml/min |
| Gradient | 5% to 95% B in 0.8 min, 0.4 min 95% B, 95% to 5% B in 0.01 min, 0.29 min 5% B |

| | |
|---|---|
| Ionization source | ESI |
| Drying Gas | N$_2$ |
| Drying Gas Flow | 15(L/min) |
| DL Voltage | 120(V) |
| Qarray DC Voltage | 20(V) |
| MS Polarity | Positive |
| MS Mode | Scan |
| Mass range | 100-1000 |

Method 2: 10-80CD_4MIN_220&254

| | |
|---|---|
| Column | XBridge C18 2.1*50 mm, 5 um |
| Column Temperature | 40° C. |
| Eluents | A: 0.05% NH$_3$•H$_2$O in water (v/v), B: Acetonitrile |
| Flow Rate | 0.8 ml/min |
| Gradient | 10% to 80% B in 3 min, 0.5 min 80% B, 80% to 10% B in 0.01 min, 0.49 min 10% B |
| Ionization source | ESI |
| Drying Gas | N$_2$ |
| Drying Gas Flow | 10 (L/min) |
| Nebulizer Pressure | 35 (psig) |
| Drying Gas Temp | 350 (° C.) |
| Capillary Voltage | 2500 (V) |
| MS Polarity | Positive |
| MS Mode | Scan |
| Mass Range | 100-1000 |

Method 3: 5-95AB_R_220&254

| | |
|---|---|
| Column | Chromolith Flash RP-18e 25*2 mm |
| Column Temperature | 50° C. |
| Eluents | A: 0.0375% TFA in Water (v/v), B: 0.01875% TFA in Acetonitrile (v/v) |
| Flow Rate | 1.5 ml/min |
| Gradient | 0.01 min 5% B; 5% to 95% B in 0.79 min, 0.4 min 95% B, 95% to 5% in 0.01 min, 0.29 min 5% B |
| Ionization source | ESI |
| Drying Gas | N$_2$ |
| Drying Gas Flow | 10 (L/min) |
| Nebulizer Pressure | 60 (psig) |
| Drying Gas Temp | 350 (° C.) |
| Capillary Voltage | 3500 (V) |
| MS Polarity | Positive |
| MS Mode | Scan |
| Mass range | 100-1000 |

Method 4: 5-95AB_4MIN_220&254

| | |
|---|---|
| Column | Chromolith Flash RP-18e 25*2 mm |
| Column Temperature | 50° C. |
| Eluents | A: 0.0375% TFA in Water (v/v), B: 0.01875% TFA in Acetonitrile (v/v) |
| Flow Rate | 0.8 ml/min |
| Gradient | 0.01 min 5% B; 5% to 95% B in 2.99 min, 0.5 min 95% B, 95% to 5% B 0.01 min, 0.49 min 5% B |
| Ionization source | ESI |
| Drying Gas | N$_2$ |
| Drying Gas Flow | 11 (L/min) |
| Nebulizer Pressure | 60 (psig) |
| Drying Gas Temp | 350 (° C.) |
| Capillary Voltage | 3500 (V) |
| MS Polarity | Positive |
| MS Mode | Scan |
| Mass Range | 100-1000 |

Method 5: Using WATERS Acquity UPLC PDA w ZQ2000 Sys (A-I) equipped with WATERS Acquity HSS

| | |
|---|---|
| Column | Acquity HSS T3, 1.8 μm, 2.1 mm × 50 mm |
| Column Temperature | 60° C. |
| Eluents | A: 0.05% formic acid in Water (v/v), B: 0.04% formic acid in Acetonitrile (v/v) |
| Flow Rate | 1.0 ml/min |
| Gradient | From 5 to 98 % B in 1.4 min |
| Ionization source | ESI |
| Drying Gas | N$_2$ |
| MS Polarity | Positive |
| MS Mode | Scan |
| Mass range | 100-1200 |

Method 6: 10-80CD_2MIN_220&254_POS.M

| | |
|---|---|
| Column | XBridge C18 2.1*50 mm, 5 um |
| Column Temperature | 40° C. |
| Eluents | A: 0.05% NH3•H2O in water (v/v), B: Acetonitrile |
| Flow Rate | 1.2 ml/min |
| Gradient | 10% to 80% B in 1.2 min, 0.4 min 80% B, 80% to 10% B in 0.01 min, 0.39 min 10% B |
| Ionization source | ESI |
| Drying Gas | N2 |
| Drying Gas Flow | 10 (L/min) |
| Nebulizer Pressure | 35 (psig) |
| Drying Gas Temp | 350 (° C.) |
| Capillary Voltage | 2500 (V) |
| MS Polarity | Positive |
| MS Mode | Scan |
| Mass range | 100-1000 |

Method 7: Using WATERS Acquity UPLC PDA w ZQ2000 Sys (A-I) equipped with WATERS Acquity CSH

| | |
|---|---|
| Column | Acquity CSH C18, 1.7 μm, 2.1 mm × 50 mm |
| Column Temperature | 60° C. |
| Eluents | A: 0.05% formic acid in Water (v/v), B: 0.04% formic acid in Acetonitrile (v/v) |
| Flow Rate | 1.0 ml/min |
| Gradient | From 5 to 98 % B in 1.4 min |
| Ionization source | ESI |
| Drying Gas | N$_2$ |
| MS Polarity | Positive |
| MS Mode | Scan |
| Mass range | 100-1200 |

| Abbreviations: | |
|---|---|
| AcOH | Acetic acid |
| Boc | tert-Butoxycarbonyl |
| Boc$_2$O | Di-tert-butyl dicarbonate |
| Bn | Benzyl |
| d | doublet |
| dd | doublet of doublets |
| DCM | Dichloromethane |
| DIPEA | Diisopropylethylamine |
| DMAP | 4-Dimethylaminopyridine |
| TFA | Trifluoroacetic Acid |
| DMF | N,N-dimethylformamide |
| DMP | Dess-Martin Periodinane (1,1,1-Triacetoxy-1,1-dihydro-1,2-benziodoxol-3(1H)-one) |
| DMSO | Dimethylsulfoxide |
| Dppf | 1,1'-Bis(diphenylphosphino)ferrocene |
| EtOAc | Ethyl acetate |
| h | hour(s) |
| HATU | 1-[Bis(dimethylamino)methylene]-1H-1,2,3-triazolo[4,5-b]pyridinium 3-oxid hexafluorophosphate |
| HPLC | high pressure liquid chromatography |
| LCMS | liquid chromatography and mass spectrometry |
| MeOH | Methanol |
| MTBE | Methyl tert-butyl ether |

Abbreviations:

| | |
|---|---|
| Ms | Methanesulfonyl |
| MS | Mass spectrometry |
| m | multiplet |
| mg | milligram |
| min | minutes |
| mL | milliliter |
| mmol | millimol |
| m/z | mass to charge ratio |
| NMR | nuclear magnetic resonance |
| ppm | parts per million |
| PE | petroleum ether |
| Rt | retention time |
| S | singlet |
| t | triplet |
| TEA | Triethylamine |
| TLC | Thin-Layer Chromatography |
| Ts (Tos) | p-Toluenesulfonyl |
| TFA | Trifluoroacetic acid |
| $Tf_2O$ | Trifluoromethanesulfonic anhydride |
| THF | Tetrahydrofuran |
| $T_3P$ | 2,4,6-Tripropyl-1,3,5,2,4,6-Trioxatriphosphorinane-2,4,6-Trioxide |

Preparation of Intermediates

Intermediate Core-1a_A 2-amino-5-(3-fluorobenzyl)-4,5,6,7-tetrahydrothieno[3,2-c]pyridine-3-carbonitrile Step 1: tert-butyl 2-amino-3-cyano-6,7-dihydrothieno[3,2-c]pyridine-5(4H)-carboxylate

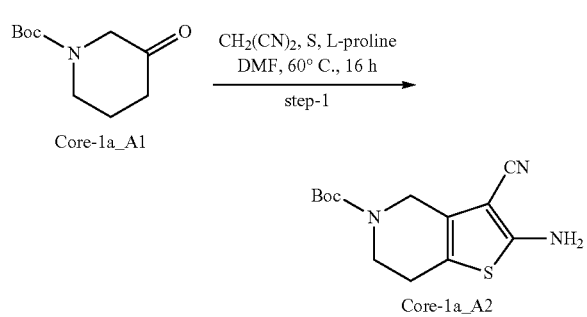

To a solution of tert-butyl 3-oxopiperidine-1-carboxylate Core-1a_A1 (30.00 g, 150 mmol) and $CH_2(CN)_2$ (19.89 g, 300 mmol) in DMF (300.0 mL) was added with sulfur (7.24 g, 225 mmol) and L-proline (3.47 g, 30 mmol). The reaction mixture was stirred at 60° C. for 2 h. The reaction mixture was poured into water (500 mL) and extracted with EtOAc (500 mL×3). The combined organic layers were washed with water (1000 mL) followed by brine (1000 mL), dried over $Na_2SO_4$, filtered and concentrated under reduced pressure. The crude product were washed with EtOAc (50 mL) to afford tert-butyl 2-amino-3-cyano-6,7-dihydrothieno[3,2-c]pyridine-5(4H)-carboxylate Core-1a_A2 (20.50 g, yield 49%); LC-MS Rt 0.92; MS m/z [M+H]$^+$ 223.9, Method 1.

Step 2: 2-amino-4,5,6,7-tetrahydrothieno[3,2-c]pyridine-3-carbonitrile

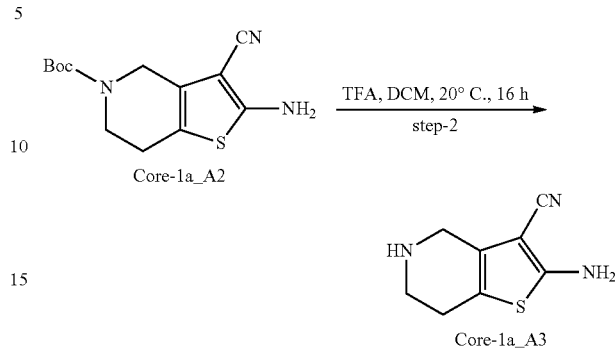

To a solution of tert-butyl 2-amino-3-cyano-6,7-dihydrothieno[3,2-c]pyridine-5(4H)-carboxylate Core-1a_A2 (5.00 g, 17.90 mmol) in DCM (45.0 mL) was added TFA (5.0 mL) at 0° C. The reaction mixture was stirred at 20° C. for 16 h. The reaction mixture was dissolved in water (50 mL) and extracted with DCM (50 mL×2). The aqueous layer was acidified with sat. aqueous $Na_2CO_3$ to pH 8-9 and extracted with DCM (50 mL×3). The combined organic layers were washed with brine (100 mL), dried over anhydrous $Na_2SO_4$ and concentrated to afford 2-amino-4,5,6,7-tetrahydrothieno[3,2-c]pyridine-3-carbonitrile Core-1a_A3 (3.20 g, yield 99%), which was used directly for the next step. LC-MS Rt 0.43 min; MS m/z [M+H]$^+$ 179.9, Method 1.

Step 3: 2-amino-5-(3-fluorobenzyl)-4,5,6,7-tetrahydrothieno[3,2-c]pyridine-3-carbonitrile

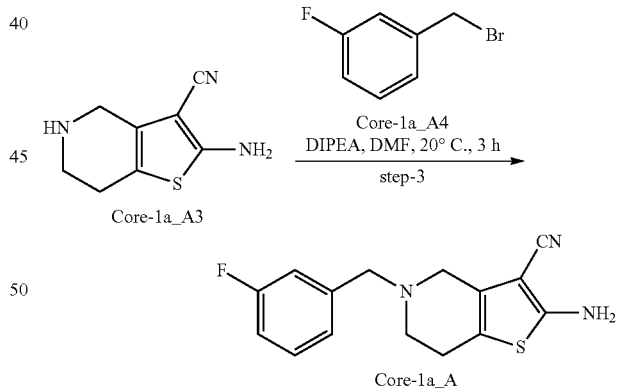

To a stirred solution of 2-amino-4,5,6,7-tetrahydrothieno[3,2-c]pyridine-3-carbonitrile Core-1a_A3 (2.50 g, 13.95 mmol) and 1-(bromomethyl)-3-fluorobenzene Core-1a_A4 (2.64 g, 13.95 mmol) in DMF (20.0 mL) was added DIPEA (3.61 g, 27.90 mmol). The reaction mixture was stirred at 20° C. for 16 h. The reaction mixture was dissolved in water (50 mL) and extracted with EtOAc (50 mL×2). The organic layers were washed with brine solution (100 mL), dried over anhydrous $Na_2SO_4$ and concentrated. The crude product was purified by column chromatography on silica, eluting with PE/EtOAc from 20/1 to 5/1, to afford 2-amino-5-(3-fluorobenzyl)-4,5,6,7-tetrahydrothieno[3,2-c]pyridine-3-carbonitrile Core-1a_A (1.10 g, yield 39%). ¹H NMR (400 MHz, CDCl₃) δ 7.26-7.20 (m, 1H), 7.10-6.98 (m, 2H), 6.95-6.82 (m, 1H), 4.59 (s, 2H), 3.62 (s, 2H), 3.38 (t, J=1.8 Hz, 2H), 2.72-2.65 (m, 2H), 2.59-2.51 (m, 2H); LC-MS Rt 1.40 min; MS m/z [M+H]⁺ 288.1, Method 1.

Intermediate Core-1a_B 2-amino-5-(cyclohexylmethyl)-4,5,6,7-tetrahydrothieno[3,2-c]pyridine-3-carbonitrile Step 1: 2-amino-5-(cyclohexylmethyl)-4,5,6,7-tetrahydrothieno[3,2-c]pyridine-3-carbonitrile

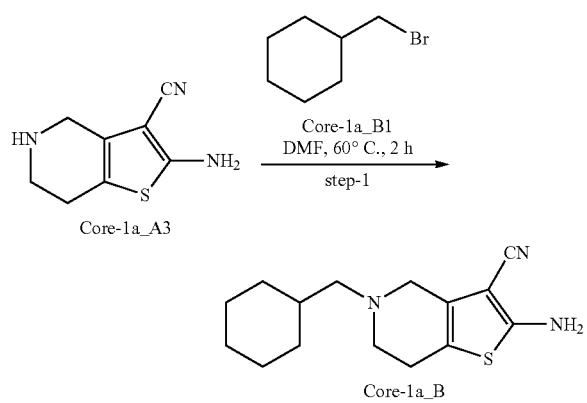

To a solution of 2-amino-4,5,6,7-tetrahydrothieno[3,2-c]pyridine-3-carbonitrile Core-1a_A3 (7.0 g, 39.5 mmol) in DMF (70 mL) was added (bromomethyl)cyclohexane Core-1a_B1 (4.2 g, 23.7 mmol) and DIPEA (10.1 g, 79 mmol), then the reaction mixture was stirred at 60° C. for 2 h. The reaction mixture was poured into water (350 mL), and the aqueous layer was extracted with EtOAc (350 mL×3). The combined organic layers were washed with water (200 mL×2), dried over Na₂SO₄, filtrated and concentrated under reduced pressure. The crude product was purified by column chromatography on silica (9-33% EtOAc in PE) to afford 2-amino-5-(cyclohexylmethyl)-4,5,6,7-tetrahydrothieno[3,2-c]pyridine-3-carbonitrile Core-2a_B (2.1 g, yield 19%) as white solid. ¹H NMR (400 MHz, DMSO-d₆) δ 7.03 (s, 2H), 3.33 (s, 3H), 2.66-2.58 (m, 2H), 2.50-2.44 (m, 2H), 2.51-2.44 (m, 2H), 1.80-1.46 (m, 6H), 1.32-1.06 (m, 3H), 0.95-0.78 (m, 2H); LC-MS Rt 1.03 min; MS m/z [M+H]⁺ 276.0; Method 1.

Intermediate Core-1a_C 2-amino-5-((3,3-difluorocyclobutyl)methyl)-4,5,6,7-tetrahydrothieno[3,2-c]pyridine-3-carbonitrile Step 1: 3,3-difluorocyclobutanecarbaldehyde

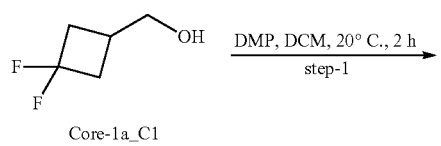

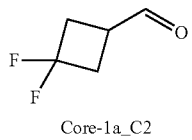

To a solution of (3,3-difluorocyclobutyl)methanol Core-1a_C1 (0.477 g, 3.9 mmol) in DCM (40 mL) was added DMP (1.98 g, 4.68 mmol). The reaction mixture was stirred at 20° C. for 2 h. The reaction mixture was filtered and the filtrate was used for next step directly.

Step 2: 2-amino-5-((3,3-difluorocyclobutyl)methyl)-4,5,6,7-tetrahydrothieno[3,2-c]pyridine-3-carbonitrile

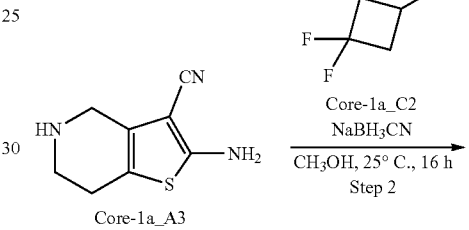

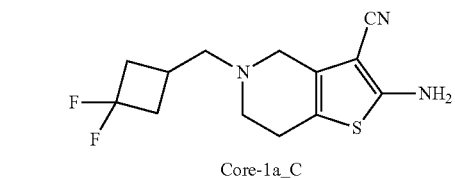

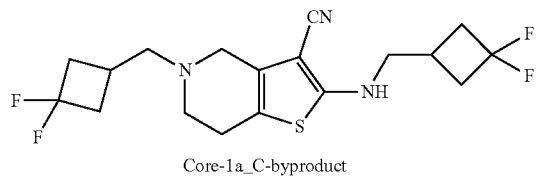

A mixture of 3,3-difluorocyclobutanecarbaldehyde Core-1a_C2 (3.9 mmol, crude), 2-amino-4,5,6,7-tetrahydrothieno[3,2-c]pyridine-3-carbonitrile Core-1a_A3 (1.1 g, 6.5 mmol) in MeOH (1 mL) was stirred at 20° C. for 4 h. After 4 h, the mixture was added NaBH 3 CN (0.5 g, 7.8 mmol). The mixture was stirred at 20° C. for 12 h. The reaction was concentrated to solid and diluted by H₂O (50 mL) and EtOAc (100 mL), the organic layer was concentrated to solid. The crude was purified by reverse column to afford 2-amino-5-((3,3-difluorocyclobutyl)methyl)-4,5,6,7-tetrahydrothieno[3,2-c]pyridine-3-carbonitrile Core-1a_C (0.4 g, yield 35%) as red oil, and by product 5-((3,3-difluorocyclobutyl)methyl)-2-(((3,3-difluorocyclobutyl)methyl)amino)-4,5,6,7-tetrahydrothieno[3,2-c]pyridine-3-carbonitrile Core-1a_C-byproduct (0.2 g, yield 11.5%). LC-MS Rt 0.89 min; MS m/z [M+H]⁺ 284.0; Method 1.

Intermediate Core-1a_D 3-fluorobicyclo[1.1.1]pentane-1-carbaldehyde

Step 1: (3-fluorobicyclo[1.1.1]pentan-1-yl)methanol

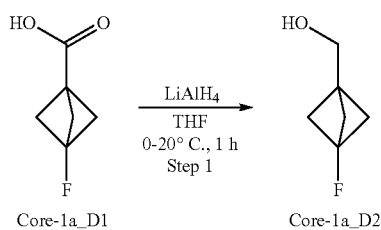

To a solution of 3-fluorobicyclo[1.1.1]pentane-1-carboxylic acid Core-1a_D1 (40 mg, 0.3 mmol) in THF (1 mL) was added LiAlH₄ (17 mg, 0.45 mmol) at 0° C. The mixture was stirred at 0° C. for 10 min, and then warmed to 20° C. and stirred for another 50 min. TLC showed the starting material was consumed and a new spot was formed. The reaction was quenched with MeOH (1 mL). The suspension was filtered, and the filtrate was concentrate to afford the desired Core-1a_D2 (45 mg, crude). The crude product Core-1a_D2 was used in next step without further purification. TLC Rf 0.40 (33% EtOAc in PE).

Step 2: 3-fluorobicyclo[1.1.1]pentane-1-carbaldehyde

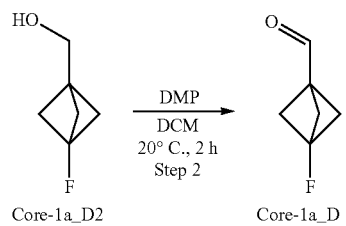 [SMILES: OCC12CC(F)(C1)C2 ; O=CC12CC(F)(C1)C2]

To a solution of (3-fluorobicyclo[1.1.1]pentan-1-yl)methanol Core-1a_D2 (35 mg, 0.3 mmol) in DCM (5 mL) was added DMP (191 mg, 0.45 mmol). The mixture was stirred at 20° C. for 2 h. The reaction solution was filtered. The filtrate was concentrated to remove the most of solvent. The result solution was used in next step directly. TLC Rf 0.70 (33% EtOAc in PE).

Intermediate Core-2a_E 2-(3-methoxy-4-sulfamoylphenyl)acetic acid

Step 1: 2-(2-bromo-5-methoxyphenyl)acetic acid

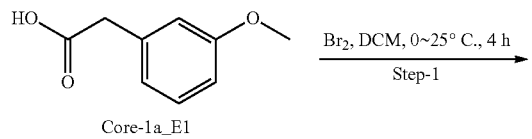

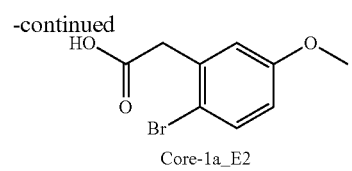

To a solution of 2-(3-methoxyphenyl)acetic acid Core-1a_E1 (7.0 g, 42.12 mmol) in DCM (50 mL) was added Br₂ (8.08 g, 50.55 mmol) at 0° C. The reaction mixture was warmed to 20° C. and stirred for 4 h. TLC (DCM:MeOH (10:1), Rf 0.30) showed that the reaction was complete. The reaction was diluted with DCM (200 mL) and washed aqueous Na₂SO₃ (100 mL). The organic layer was washed with brine, and concentrated to afford Core-1a_E2, (9.0 g, yield 87.2%). ¹H NMR (400 MHz, CDCl₃) δ 7.48 (d, J=8.8 Hz, 1H), 6.87 (d, J=3.0 Hz, 1H), 6.75 (dd, J=3.0, 8.8 Hz, 1H), 3.82 (s, 2H), 3.81 (s, 3H).

Step 2: methyl 2-(2-bromo-5-methoxyphenyl)acetate

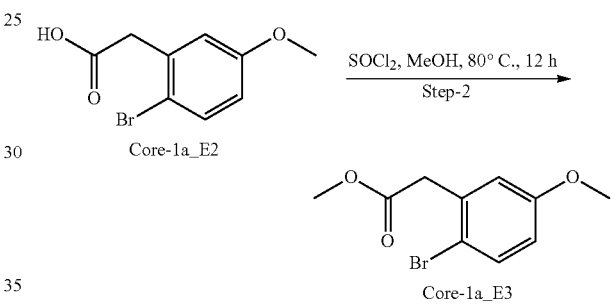

To a solution of 2-(2-bromo-5-methoxyphenyl)acetic acid Core-1a_E2 (9.0 g, 36.72 mmol) in MeOH (50 mL) was added SOCl₂ (26.2 g, 220.35 mmol). The reaction mixture was stirred at 80° C. for 12 h. The reaction mixture was concentrated and the residue was dissolved in EtOAc (200 mL), washed with brine, and concentrated to afford crude Core-1a_E3. (8.0 g, yield 84.0%). The residue was used directly for the next step without further purification.

Step 3: Methyl 2-(2-bromo-4-(chlorosulfonyl)-5-methoxyphenyl)acetate

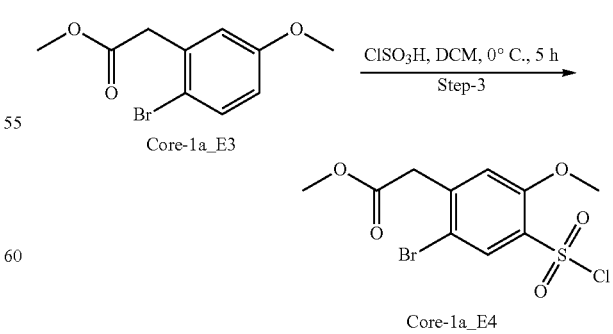

To a stirred solution of methyl 2-((5-methoxy-2-methylphenyl)(2-oxopropyl)amino)acetate Core-1a_E3 (3.00 g, 11.6 mmol) in CH₂C₁₂ (40 mL) was added ClSO₃H (8.11 g, 69.6 mmol) and stirred at 0° C. for 5 h. The reaction mixture was poured into ice-water (500 mL) and extracted with EtOAc (160 mL×3). The combined organic layers were washed with water (300 mL) followed by brine (200 mL×2), dried over $Na_2SO_4$, filtered and concentrated under reduced pressure to afford methyl 2-(2-bromo-4-(chlorosulfonyl)-5-methoxyphenyl)acetate Core-1a_E4 (3.06 g, yield 72.3%), which was used directly for the next step. $^1$H NMR (400 MHz, $CDCl_3$) δ 8.13 (s, 1H), 7.11 (s, 1H), 4.06 (s, 3H), 3.87 (s, 2H), 3.77 (s, 3H).

Step 4: methyl 2-(2-bromo-5-methoxy-4-sulfamoylphenyl)acetate

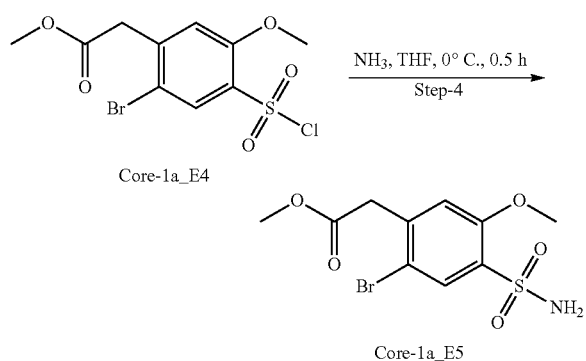

$NH_3$ (gas) was bubbled into a solution of methyl 2-(2-bromo-4-(chlorosulfonyl)-5-methoxyphenyl)acetate Core-1a_E4 (3.00 g, 8.4 mmol) in THF (30 mL) at 0° C. for 0.5 h. The reaction mixture was filtered and the filter cake was washed with EtOAc (10 mL), dried in vacuum to afford methyl 2-(2-bromo-5-methoxy-4-sulfamoylphenyl)acetate Core-1a_E5 (1.60 g, yield 55.9%), which was used directly for the next step. LC-MS Rt 0.76 min; MS m/z [M+H]$^+$ 356.9; Method 1.

Step 5: methyl 2-(3-methoxy-4-sulfamoylphenyl)acetate

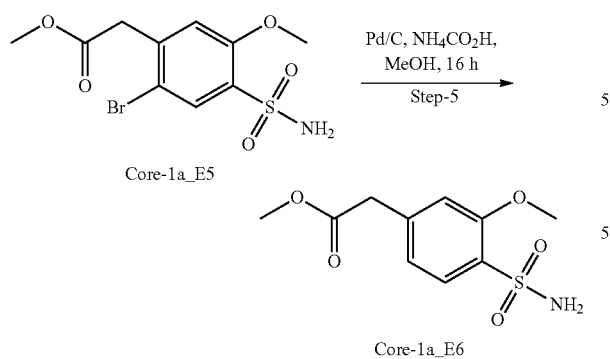

To a solution of methyl 2-(2-bromo-5-methoxy-4-sulfamoylphenyl)acetate Core-1a_E5 (1.57 g, 4.6 mmol) in MeOH (30.0 mL) was added dry Pd/C (0.15 g). The suspension was degassed under vacuum and purged with $H_2$ several times. The reaction mixture was stirred under $H_2$ (50 psi) at 80° C. for 16 h. The reaction mixture was filtered and the filter cake was washed with 30.0 mL of MeOH. The filtrate was dried in vacuum to afford methyl 2-(3-methoxy-4-sulfamoylphenyl)acetate Core-1a_E6 (1.10 g, yield 92.2%), which was used directly for the next step. TLC DCM:MeOH (10:1), Rf 0.3; $^1$H NMR (400 MHz, DMSO-$d_6$) δ 7.66-7.65 (d, J=7.9 Hz, 1H), 7.13 (m, 3H), 6.96-6.94 (d, J=8.0 Hz, 1H), 3.77 (s, 2H), 3.62 (s, 3H).

Step 6: 2-(3-methoxy-4-sulfamoylphenyl)acetic acid

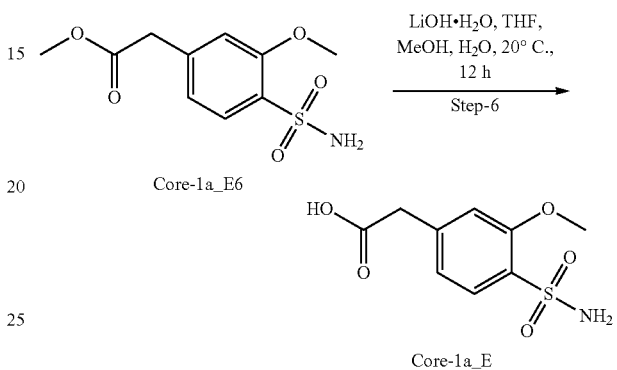

To a solution of methyl 2-(3-methoxy-4-sulfamoylphenyl)acetate Core-1a_E6 (1.07 g, 4.13 mmol) in MeOH (5 mL), THF (10.0 mL) and water (1.4 mL) was added NaOH (0.50 g, 12.5 mmol). The reaction mixture was stirred at 20° C. for 1 h. The reaction mixture was acidified with 2 N HCl to pH 3-4 then concentrated. The crude product was purified by prep-HPLC ($NH_3·H_2O$) to afford 2-(3-methoxy-4-sulfamoylphenyl)acetic acid Core-1a_E1 (0.22 g, yield 21.8%) as white solid. $^1$H NMR (400 MHz, DMSO-$d_6$) δ 12.49 (s, 1H), 7.67-7.66 (d, J=8.0 Hz, 1H), 7.11 (s, 1H), 7.04 (s, 2H), 6.96-6.93 (dd, J=8.0, 1.2 Hz, 1H), 3.88 (s, 3H), 3.66 (s, 2H); LC-MS Rt 0.57 min; MS m/z [M+Na]$^+$ 268.0.

Intermediate Core-1a_F

N-(3-cyano-4,5,6,7-tetrahydrothieno[3,2-c]pyridin-2-yl)-2-(4-sulfamoylphenyl)acetamide Step 1: tert-butyl 3-cyano-2-(2-(4-sulfamoylphenyl)acetamido)-6,7-dihydrothieno[3,2-c]pyridine-5(4H)-carboxylate

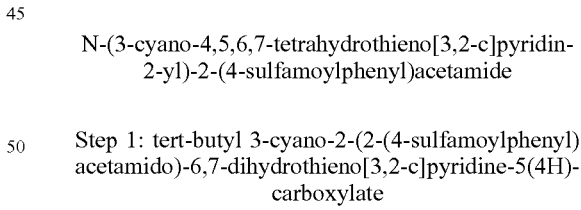

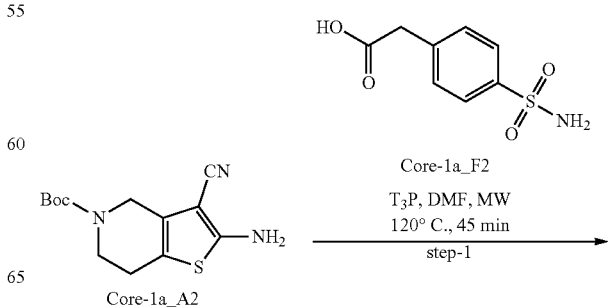

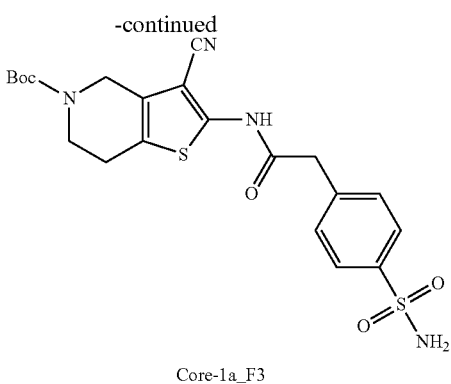
Core-1a_F3

To a stirred solution of tert-butyl 2-amino-3-cyano-6,7-dihydrothieno[3,2-c]pyridine-5(4H)-carboxylate Core-1a_A2 (0.50 g, 1.79 mmol) and 2-(4-sulfamoylphenyl)acetic acid Core-1a_F3 (0.58 g, 2.68 mmol) in DMF (10.0 mL) was added DIPEA (0.46 g, 3.58 mmol) and T$_3$P (50% in EtOAc, 2.28 g, 3.58 mmol). The reaction mixture was stirred at 120° C. under microwave reactor for 45 min. The reaction mixture was poured into water (20 mL) and extracted with EtOAc (20 mL×2). The combined organic layers were washed with water (50 mL) followed by brine (50 mL×4), dried over anhydrous Na$_2$SO$_4$, filtered and concentrated under reduced pressure. The crude product was purified by column chromatography on silica (5-33% EtOAc in PE) to afford tert-butyl 3-cyano-2-(2-(4-sulfamoylphenyl)acetamido)-6,7-dihydrothieno[3,2-c]pyridine-5(4H)-carboxylate Core-1a_F3 (0.53 g, yield 62%). LC-MS Rt 0.84 min; MS m/z [M+H−100]$^+$ 376.9; Method 1.

Step 2: N-(3-cyano-4,5,6,7-tetrahydrothieno[3,2-c]pyridin-2-yl)-2-(4-sulfamoylphenyl)acetamide

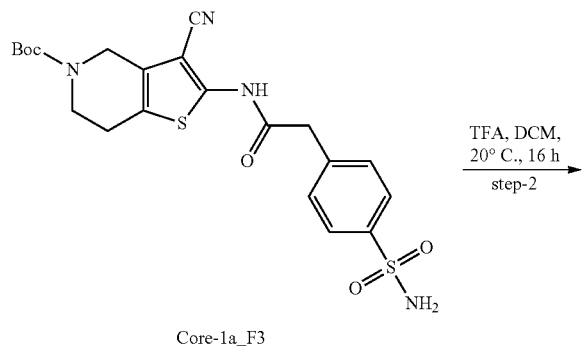

To a stirred solution of tert-butyl 3-cyano-2-(2-(4-sulfamoylphenyl)acetamido)-6,7-dihydrothieno[3,2-c]pyridine-5(4M)-carboxylate Core-1a_F3 (0.53 g, 1.11 mmol) in dry DCM (4.5 mL) was added TFA (0.5 mL). The reaction mixture was stirred at 20° C. for 16 h. The reaction mixture was added water (50 mL) and extracted with DCM (50 mL×2). The aqueous layer was acidified with sat. aqueous Na$_2$CO$_3$ to pH 8-9 and extracted with DCM (50 mL×3). The combined organic layers were washed with brine (100 mL), dried over anhydrous Na$_2$SO$_4$ and concentrated to afford N-(3-cyano-4,5,6,7-tetrahydrothieno[3,2-c]pyridin-2-yl)-2-(4-sulfamoylphenyl)acetamide Core-1a_F (0.31 g, yield 76%). The crude product was used directly for the next step.

Intermediate Core-1a_G: 2-(3-ethoxy-4-sulfamoylphenyl)acetic acid

Step 1: methyl 2-(2-bromo-5-hydroxyphenyl)acetate

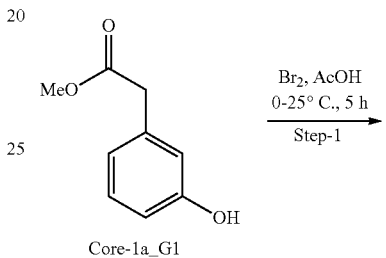

A solution of methyl 2-(3-hydroxyphenyl)acetate Core-1a_G1 (20.0 g, 0.12 mol) in AcOH (150 mL) was cooled down the temperature to 0° C. Then the mixture of Br$_2$ in AcOH (50 mL) was added dropwise. The reaction mixture was stirred at 20° C. for 3 h. The reaction mixture was evaporated under vacuum. H$_2$O (200 mL) and EtOAc (200 mL) were added. The organic phase was separated and the aqueous was further extracted with EtOAc (200 mL×3). The combined organic layers were combined, dried over Na$_2$SO$_4$, and concentrated under reduce pressure to afford methyl 2-(2-bromo-5-hydroxyphenyl)acetate Core-1a_G2 (23.0 g, yield 78%) as yellow solid. LC-MS Rt 0.70 min; MS m/z [M+H]$^+$ 246.9; Method 1.

Step 2: methyl 2-(2-bromo-5-ethoxyphenyl)acetate

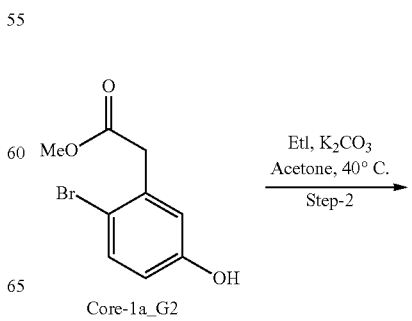

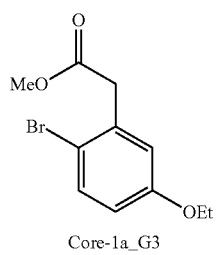

Core-1a_G3

To a solution of methyl 2-(2-bromo-5-hydroxyphenyl)acetate Core-1a_G2 (4.0 g, 16.32 mmol) in acetone (50 mL) was added K$_2$CO$_3$ (2.7 g, 19.59 mmol) and EtI (3.1 g, 19.59 mmol). The reaction mixture was stirred at 50° C. for 16 h and concentrated. The residue was purified by column chromatography on silica gel (2% EtOAc in PE) to afford methyl 2-(2-bromo-5-ethoxyphenyl)acetate Core-1a_G3 (4.0 g, yield 89.7%).

Step 3: 2-(2-bromo-4-(chlorosulfonyl)-5-ethoxyphenyl)acetate

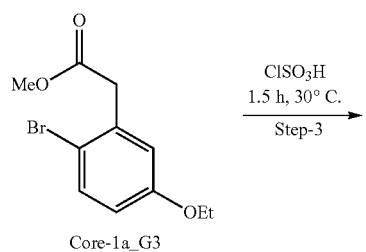

Step 4: methyl 2-(2-bromo-5-ethoxy-4-sulfamoylphenyl)acetate

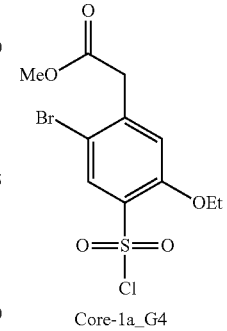 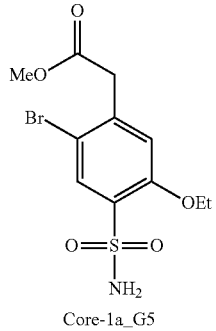

Core-1a_G4      Core-1a_G5

Core-1a_G5 was prepared by a similar method to that of Core-1a_E5 (1.1 g, yield 38.7%). $^1$H NMR (400 MHz, DMSO-d$_6$) δ 7.83 (s, 1H), 7.36 (s, 1H), 7.17 (s, 2H), 4.20 (q, J=6.9 Hz, 2H), 3.89 (s, 2H), 3.65 (s, 3H), 1.38 (t, J=7.0 Hz, 3H); LC-MS Rt 0.95 min; MS m/z [M+H]$^+$ 375.6; Method 3.

Step 5: methyl 2-(3-ethoxy-4-sulfamoylphenyl)acetate

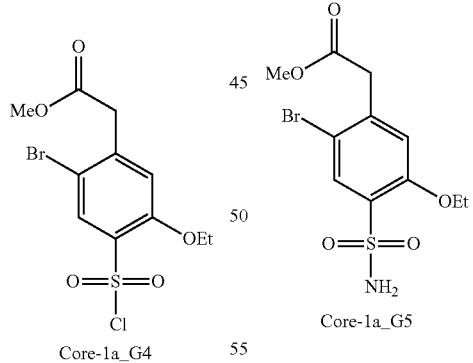 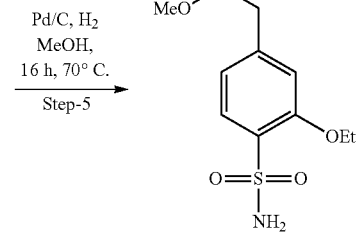

To ClSO$_3$H (30 mL) was added methyl 2-(2-bromo-5-ethoxyphenyl)acetate Core-1a_G3 (4.0 g, 14.62 mmol) at 0° C. The reaction mixture was warmed to 30° C. and stirred for 2 hours. The reaction mixture was poured into ice-water (150 mL) and extracted with DCM (100 mL×2). The combined organic layers were washed with brine (80 mL×2), dried over Na$_2$SO$_4$ and concentrated to afford the methyl 2-(2-bromo-4-(chlorosulfonyl)-5-ethoxyphenyl)acetate Core-1a_G4 (3.0 g, yield 55.1%). The residue was used directly for the next step.

Core-1a_G6 was prepared by a similar method to that of Core-1a_E6 (700.0 mg, yield 90.2%). $^1$H NMR (400 MHz, CDCl$_3$) δ 7.83 (d, J=7.9 Hz, 1H), 7.02-6.90 (m, 2H), 5.08 (s, 2H), 4.26 (q, J=7.0 Hz, 2H), 3.71 (s, 3H), 3.66 (s, 2H), 1.52 (t, J=7.0 Hz, 3H); LC-MS Rt 0.67 min; MS m/z [M+Na]$^+$ 295.6; Method 3.

Step 6: methyl 2-(3-ethoxy-4-sulfamoylphenyl)acetate

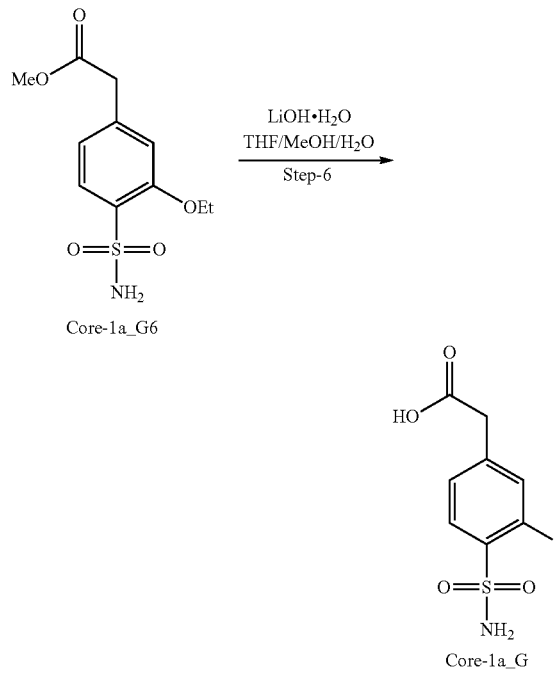

Core-1a_G was prepared by a similar method to that of Core-1a_E (350.0 mg, yield 40.6%). ¹H NMR (400 MHz, DMSO-d$_6$) δ 12.45 (br s, 1H), 7.66 (d, J=8.0 Hz, 1H), 7.12 (s, 1H), 6.93 (d, J=8.0 Hz, 1H), 6.89 (s, 2H), 4.20 (q, J=6.9 Hz, 2H), 3.65 (s, 2H), 1.38 (t, J=7.0 Hz, 3H); LC-MS Rt 0.64 min; MS m/z [M+Na]⁺ 282.0; Method 3.

Intermediate Core-1a_H: 5-(cyclohexylmethyl)-2-(methylamino)-4,5,6,7-tetrahydrothieno[3,2-c]pyridine-3-carbonitrile

Step 1: (E)-methyl N-(3-cyano-5-(cyclohexylmethyl)-4,5,6,7-tetrahydrothieno[3,2-c]pyridin-2-yl)formimidate

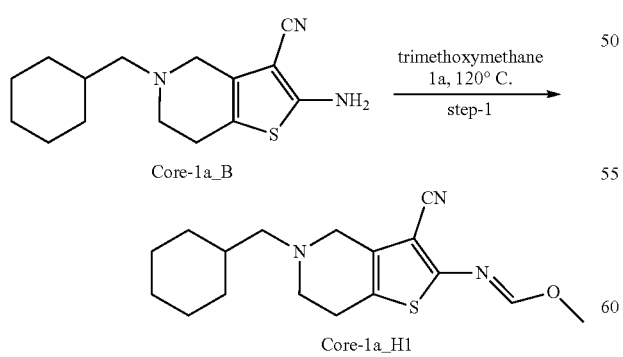

To a flask was added 2-amino-5-(cyclohexylmethyl)-4,5,6,7-tetrahydrothieno[3,2-c]pyridine-3-carbonitrile Core-1a_B (100 mg, 0.36 mmol) in trimethoxymethane (1.5 mL). The reaction mixture was stirred at 120° C. for 16 h. The residual trimethoxymethane was removed under vacuum. The crude Core-1a_H1 (115.0 mg) was used to the next step directly. LC-MS Rt 1.17 min; MS m/z [M+H]⁺ 282.0; Method 1.

Step 2: 5-(cyclohexylmethyl)-2-(methylamino)-4,5,6,7-tetrahydrothieno[3,2-c]pyridine-3-carbonitrile

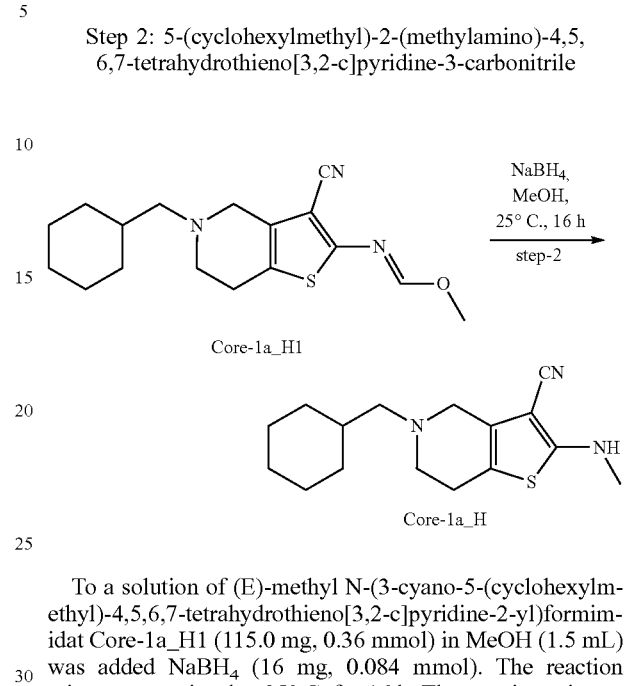

To a solution of (E)-methyl N-(3-cyano-5-(cyclohexylmethyl)-4,5,6,7-tetrahydrothieno[3,2-c]pyridine-2-yl)formimidat Core-1a_H1 (115.0 mg, 0.36 mmol) in MeOH (1.5 mL) was added NaBH$_4$ (16 mg, 0.084 mmol). The reaction mixture was stirred at 25° C. for 16 h. The reaction mixture was poured into H$_2$O (10 mL) and extracted with EtOAc (10 mL×3). The organic layers were combined, dried over Na$_2$SO$_4$, and concentrated under reduce pressure to afford 5-(cyclohexylmethyl)-2-(methylamino)-4,5,6,7-tetrahydrothieno[3,2-c]pyridine-3-carbonitrile Core-1a_H (60.0 mg, yield 57.5%) as yellow solid. LC-MS Rt 1.13 min; MS m/z [M+H]⁺ 290.0; Method 1.

Intermediate Core-1a_I: 2-amino-5-benzyl-4,4-dimethyl-4,5,6,7-tetrahydrothieno[3,2-c]pyridine-3-carbonitrile C-05469-082-P1

Step 1: ethyl 2-(benzylamino)-2-methylpropanoate

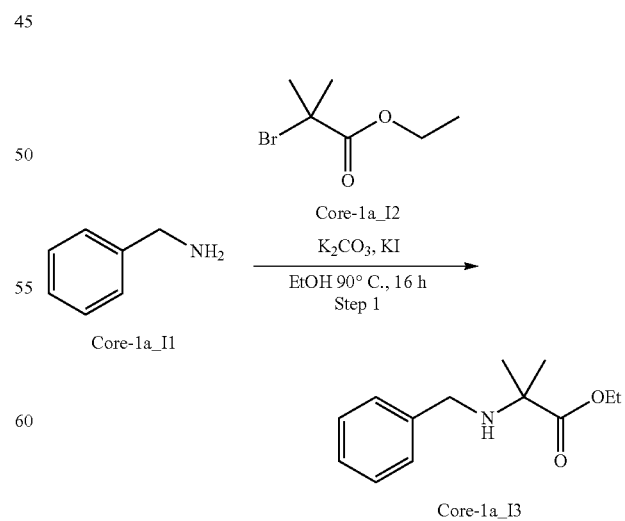

A mixture of phenylmethanamine Core-1a_I1 (6.6 g, 61.4 mmol), ethyl 2-bromo-2-methylpropanoate Core-1a_I2 (10 g, 51.2 mmol), K$_2$CO$_3$ (8.5 g, 61.4 mmol) and KI (100 mg, 0.6 mmol) was stirred at 90° C. for 16 h. The reaction solution was filtered, and the filtrate was concentrated. The residue was purified by column chromatography (10% EtOAc in PE) to afford Core-1a_I3 (1.9 g, yield 17%) as light yellow oil.

Step 2: ethyl 4-(benzyl(1-ethoxy-2-methyl-1-oxopropan-2-yl)amino)butanoate

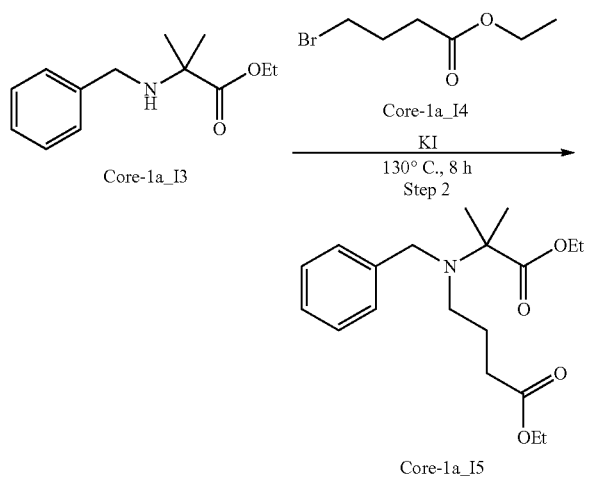

A mixture of ethyl 2-(benzylamino)-2-methylpropanoate Core-1a_I3 (1.9 g, 8.6 mmol), ethyl 4-bromobutanoate Core-1a_I4 (1.9 g, 9.5 mmol) and KI (71 mg, 0.43 mmol) was stirred at 130° C. for 8 h. The reaction mixture was dissolved in water (30 mL) and extracted with EtOAc (15 mL×3). The organic layer was concentrated. The residue was purified by column chromatography (from 5% to 6% EtOAc in PE) to afford the ethyl 4-(benzyl(1-ethoxy-2-methyl-1-oxopropan-2-yl)amino)butanoate Core-1a_I5 (700 mg, yield 24%) as yellow oil.

Step 3: ethyl 1-benzyl-2,2-dimethyl-3-oxopiperidine-4-carboxylate

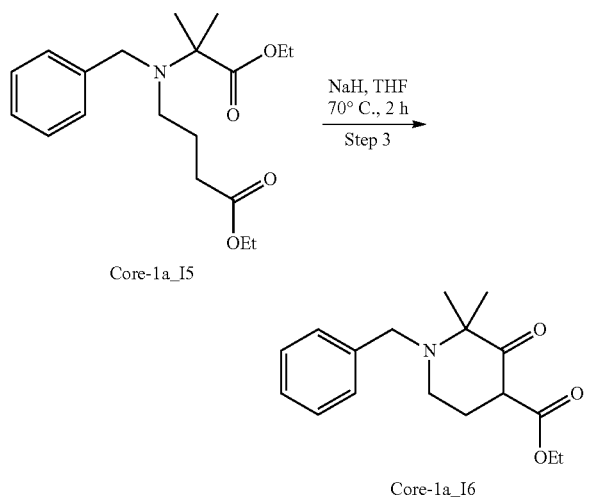

To a solution of ethyl 4-(benzyl(1-ethoxy-2-methyl-1-oxopropan-2-yl)amino)butanoate Core-1a_I5 (700 mg, 2.1 mmol) in THF (30 mL) was added NaH (168 mg, 4.2 mmol). The mixture was stirred at 70° C. for 2 h. The reaction solution was concentrated, and the residue was dissolved in sat. NH$_4$Cl (30 mL) and extracted with EtOAc (20 mL×3). The organic layer was dried over anhydrous Na$_2$SO$_4$, filtered and concentrated to afford ethyl 1-benzyl-2,2-dimethyl-3-oxopiperidine-4-carboxylate Core-1a_I6 (550 mg, yield 90%) as yellow oil. The crude product was used in next step without further purification.

Step 4: 1-benzyl-2,2-dimethylpiperidin-3-one

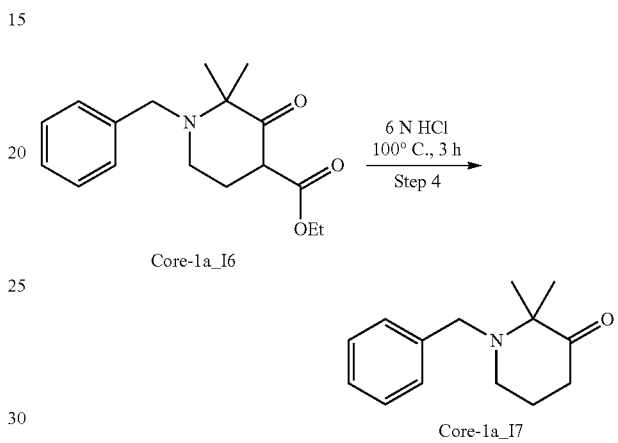

A mixture of ethyl 1-benzyl-2,2-dimethyl-3-oxopiperidine-4-carboxylate Core-1a_I6 (550 mg, 1.9 mmol) in 6 N HCl (15 mL) was stirred at 100° C. for 3 h. The reaction solution was cooled to 20° C. and adjusted pH to 7-7.5 with NaHCO$_3$ solid. The reaction mixture was diluted with water (10 mL) and extracted with EtOAc (20 mL×2). The organic layer was concentrated. The residue was purified by Prep-TLC (9% EtOAc in PE) to afford 1-benzyl-2,2-dimethylpiperidin-3-one Core-1a_I7 (390 mg, yield 94%) as yellow oil.

Step 5: 2-amino-5-benzyl-4,4-dimethyl-4,5,6,7-tetrahydrothieno[3,2-c]pyridine-3-carbonitrile

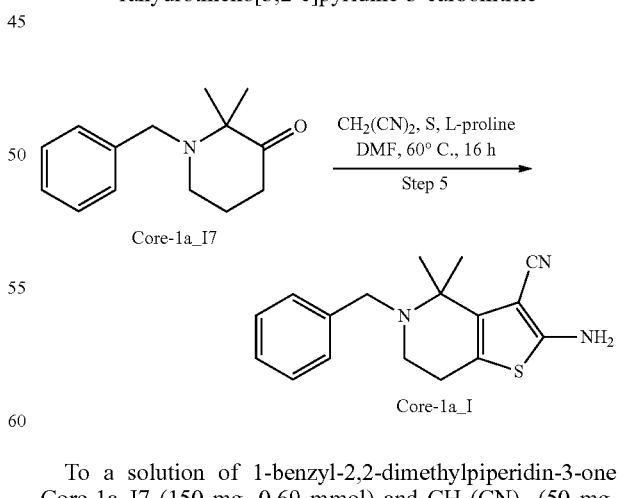

To a solution of 1-benzyl-2,2-dimethylpiperidin-3-one Core-1a_I7 (150 mg, 0.69 mmol) and CH$_2$(CN)$_2$ (50 mg, 0.76 mmol) in DMF (1 mL) was added sulphur (37 mg, 1.14 mmol) and L-proline (8 mg, 0.07 mmol) at 20° C. The mixture was stirred at 20° C. for 30 min followed by heating at 60° C. for 15.5 h. The reaction solution was diluted with water (10 mL) and extracted with EtOAc (10 mL×3). The organic layer was concentrated. The residue was purified by Prep-TLC (33% EtOAc in PE) to afford 2-amino-5-benzyl-4,4-dimethyl-4,5,6,7-tetrahydrothieno[3,2-c]pyridine-3-carbonitrile Core-1a_I (70 mg, yield 33%) as yellow solid. $^1$H NMR (400 MHz, CDCl$_3$) δ 7.34-7.17 (m, 5H), 4.59 (s, 2H), 3.60 (s, 2H), 2.62 (t, J=5.4 Hz, 2H), 2.37 (t, J=5.4 Hz, 2H), 1.48 (s, 6H); LC-MS Rt 0.54 min; MS m/z [M+H]$^+$ 298.0; Method 1.

Intermediate Core-1b_A: tert-butyl 2-amino-3-cyano-6-methyl-6,7-dihydrothieno[3,2-c]pyridine-5(4H)-carboxylate Step 1: 6-methylpiperidin-3-ol acetate

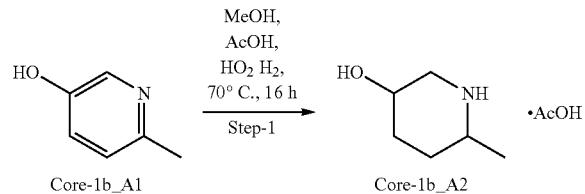

To a solution of 6-methylpyridin-3-ol Core-1b_A1 (5.00 g, 45.8 mmol) in MeOH (50.0 mL) and AcOH (50.0 mL) was added PtO$_2$ (0.50 g). The suspension was degassed under vacuum and purged with H$_2$ several times. The reaction mixture was stirred at 70° C. under H$_2$ (50 psi) for 16 h. The reaction mixture was concentrated. The crude product 6-methylpiperidin-3-ol acetate Core-1b_A2 (6.78 g, crude) was used directly for the next step.

Step 2: tert-butyl 5-hydroxy-2-methylpiperidine-1-carboxylate

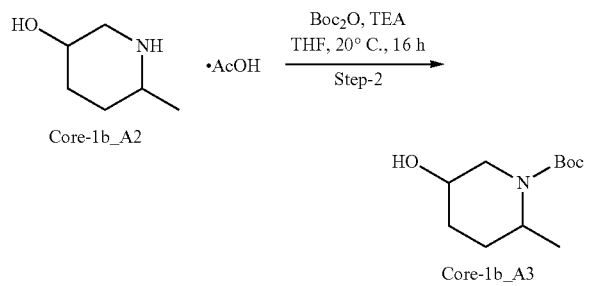

To a solution of 6-methylpiperidin-3-ol acetate Core-1b_A2 (6.00 g, 34.2 mmol) in THF (50.0 mL) was added with TEA (10.38 g, 102.6 mmol), Boc$_2$O (11.20 g, 51.3 mmol) and the reaction mixture was stirred at 20° C. for 16 h. The reaction mixture was poured into water (50 mL) and extracted with EtOAc (50 mL×3). The combined organic layers were washed with water (100 mL) and by brine (100 mL), dried over Na$_2$SO$_4$, filtered and concentrated under reduced pressure. The crude product was purified by column chromatography on silica (9-33% EtOAc in PE) to afford tert-butyl 5-hydroxy-2-methylpiperidine-1-carboxylate Core-1b_A3 (3.82 g, yield 52%); $^1$H NMR (400 MHz, DMSO-d$_6$) δ 4.92-4.49 (m, 1H), 4.23-4.18 (m, 1H), 3.75-3.71 (m, 1H), 3.34-3.26 (m, 1H), 2.90-2.87 (m, 1H), 1.99-1.97 (m, 1H), 1.71-1.68 (m, 1H), 1.55-1.44 (m, 1H), 1.39 (s, 9H), 1.06-1.03 (dd, J=6.9, 2.6 Hz, 3H).

Step 3: tert-butyl 2-methyl-5-oxopiperidine-1-carboxylate

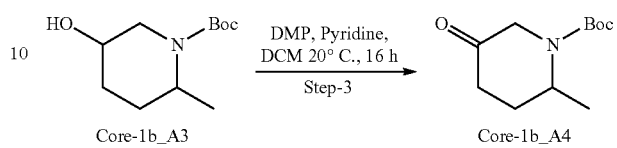

To a solution of tert-butyl 5-hydroxy-2-methylpiperidine-1-carboxylate Core-1b_A3 (3.00 g, 13.9 mmol) in DCM (100.0 mL) was added with pyridine (3.31 g, 41.8 mmol), DMP (17.73 g, 41.8 mmol) and the reaction mixture was stirred at 20° C. for 16 h. The reaction mixture was poured into saturated sodium thiosulfate solution (50 mL) and extracted with DCM (50 mL×3). The combined organic layers were washed with water (100 mL) followed by brine (100 mL), dried over Na$_2$SO$_4$, filtered and concentrated under reduced pressure. The crude product was purified by silica gel chromatography, eluting with PE/EtOAc from 10/1, to afford tert-butyl 2-methyl-5-oxopiperidine-1-carboxylate Core-1b_A4 (2.05 g, yield 69%); $^1$H NMR (400 MHz, CDCl$_3$) δ 4.55-4.30 (m, 2H), 3.61-3.56 (d, J=18.8 Hz, 1H), 2.44-2.41 (m, 2H), 2.24-2.19 (m, 1H), 1.63-1.56 (m, 1H), 1.51-1.46 (m, 9H), 1.25-1.23 (d, J=6.5 Hz, 3H).

Step 4: tert-butyl 2-amino-3-cyano-6-methyl-6,7-dihydrothieno[3,2-c]pyridine-5(4H)-carboxylate

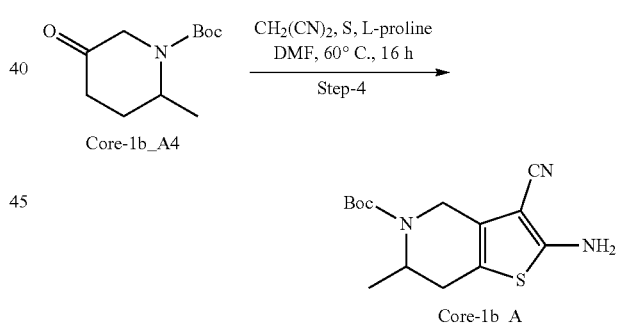

To a solution of tert-butyl 2-methyl-5-oxopiperidine-1-carboxylate Core-1b_A4 (1.50 g, 7.03 mmol) and CH$_2$(CN)$_2$ (1.39 g, 21.09 mmol) in DMF (15.0 mL) was added with sulfur (0.67 g, 21.09 mmol) and L-proline (80.6 mg, 0.70 mmol). The reaction mixture was stirred at 60° C. for 16 h. The reaction mixture was poured into water (30 mL) and extracted with EtOAc (30 mL×3). The combined organic layers were washed with water (50 mL) followed by brine (50 mL), dried over Na$_2$SO$_4$, filtered and concentrated under reduced pressure. The crude product was purified by pre-HPLC (base) to afford tert-butyl 2-amino-3-cyano-6-methyl-6,7-dihydrothieno[3,2-c]pyridine-5(4H)-carboxylate Core-1b_A (0.86 g, yield 42%); $^1$H NMR (400 MHz, CDCl$_3$) δ 4.71 (s, 4H), 3.91-3.80 (m, 1H), 2.87-2.78 (m, 1H), 2.27-2.20 (m, 1H), 1.41 (s, 9H), 1.07 (d, J=7.0 Hz, 3H); LC-MS Rt 1.37 min, MS m/z [M+Na]$^+$ 316.1; Method 2.

Intermediate Core-1 b_B: N-(3-cyano-6-methyl-4,5,6,7-tetrahydrothieno[3,2-c]pyridin-2-yl)-2-(4-sulfamoylphenyl)acetamide Step 1: tert-butyl 3-cyano-6-methyl-2-(2-(4-sulfamoylphenyl)acetamido)-6,7-dihydrothieno[3,2-c]pyridine-5(4H)-carboxylate

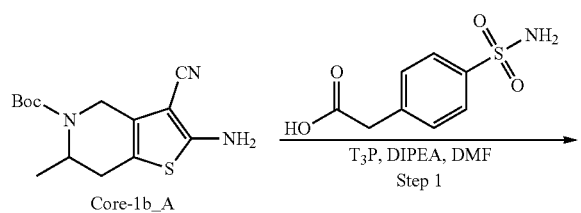

Core-1b_A

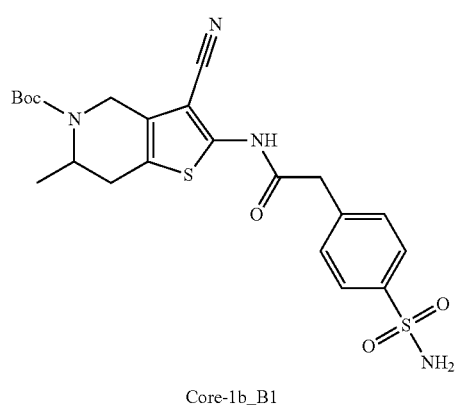

Core-1b_B1

To a solution of tert-butyl 2-amino-3-cyano-6-methyl-6,7-dihydrothieno[3,2-c]pyridine-5(4H)-carboxylate Core-1b_A (500 mg, 1.71 mmol) and 2-(4-sulfamoylphenyl)acetic acid (477 mg, 2.22 mmol) in DMF (6 mL) were added DIPEA (441 mg, 3.36 mmol) and T$_3$P (1.63 mg, 2.57 mmol). The reaction mixture was stirred at 120° C. under microwave for 0.5 h. The reaction mixture poured into H$_2$O (150 mL) and extracted with EtOAc (150 mL×3). The organic layer was washed with brine, dried over Na$_2$SO$_4$ and filtered. The filtrate was concentrated under reduced pressure to get the crude product. Then crude product was purified by silica gel chromatography (PE:EtOAc=20:1-3:1) to afford tert-butyl 3-cyano-6-methyl-2-(2-(4-sulfamoylphenyl)acetamido)-6,7-dihydrothieno[3,2-c]pyridine-5(4H)-carboxylate Core-1b_B1 (1.28 g, yield 48%) as a yellow solid; $^1$H NMR (400 MHz, DMSO-d$_6$) δ 11.99 (s, 1H), 7.78 (d, J=8.2 Hz, 2H), 7.49 (d, J=8.2 Hz, 2H), 7.32 (s, 2H), 4.62 (d, J=17.1 Hz, 2H), 4.09 (d, J=5.0 Hz, 1H), 4.01-3.90 (m, 3H), 2.92-2.77 (m, 1H), 1.43 (s, 9H), 1.03 (d, J=6.7 Hz, 3H); LC-MS Rt 0.89 min, MS m/z [M+H−100]$^+$ 391.0; Method 1.

Step 2: N-(3-cyano-6-methyl-4,5,6,7-tetrahydrothieno[3,2-c]pyridin-2-yl)-2-(4-sulfamoylphenyl)acetamide 2,2,2-trifluoroacetate

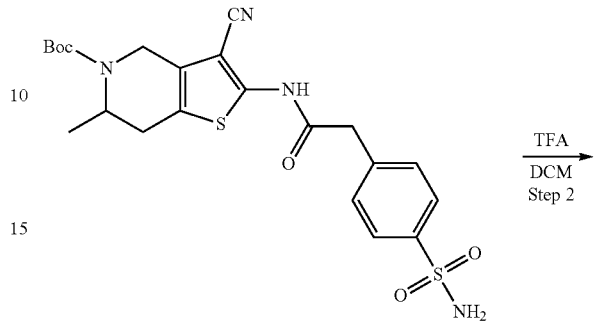

Core-1b_B1

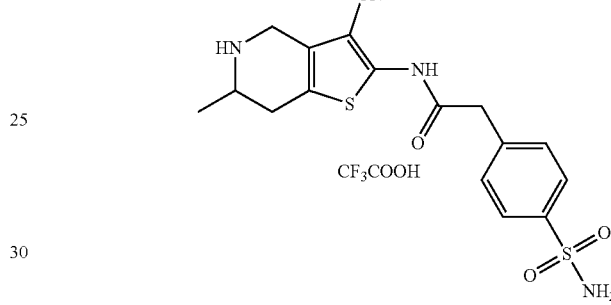

Core-1b_B2

To a solution of tert-butyl 3-cyano-6-methyl-2-(2-(4-sulfamoylphenyl)acetamido)-6,7-dihydrothieno[3,2-c]pyridine-5(4H)-carboxylate Core-1b_B1 (680 mg, 1.43 mmol) in DCM (7.2 mL) was added TFA (0.8 mL), then the reaction mixture was stirred at 20° C. for 4 h. Then the reaction mixture was evaporated under reduce pressure to afford N-(3-cyano-6-methyl-4,5,6,7-tetrahydrothieno[3,2-c]pyridin-2-yl)-2-(4-sulfamoylphenyl)acetamide 2,2,2-trifluoroacetate Core-1b_B2 (563 mg, crude) as dark red solid, and the crude product was used in next step directly.

Step 3: N-(3-cyano-6-methyl-4,5,6,7-tetrahydrothieno[3,2-c]pyridin-2-yl)-2-(4-sulfamoylphenyl)acetamide

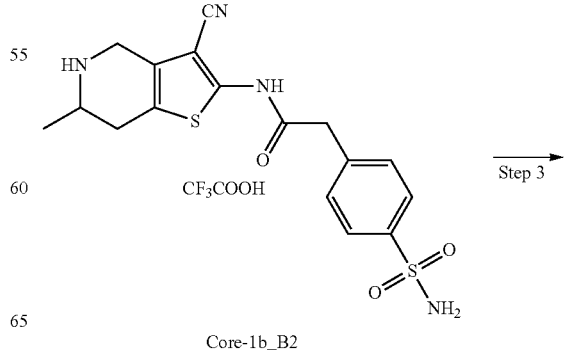

Core-1b_B2

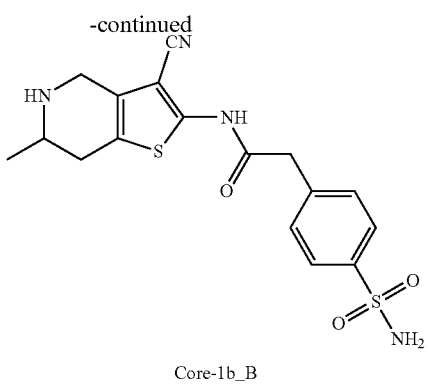

Core-1b_B

To a solution of N-(3-cyano-6-methyl-4,5,6,7-tetrahydrothieno[3,2-c]pyridin-2-yl)-2-(4-sulfamoylphenyl)acetamide 2,2,2-trifluoroacetate Core-1b_B2 (560 mg, 1.15 mmol) in MeOH (3 mL) were added Amberlyst® A-21 ion exchange resin (2 g), then the reaction mixture was stirred at 20° C. for 3 h. Then the reaction mixture was filtered and evaporated under reduce pressures to afford N-(3-cyano-6-methyl-4,5,6,7-tetrahydrothieno[3,2-c]pyridin-2-yl)-2-(4-sulfamoylphenyl)acetamide Core-1b_B (220 mg, 0.56 mmol) as red solid; LC-MS Rt 0.68 min, MS m/z [M+Na]$^+$ 413.0; Method 3.

Intermediate Core-1b_C: tert-butyl 2-amino-3-cyano-6-ethyl-6,7-dihydrothieno[3,2-c]pyridine-5(4H)-carboxylate Step 1: 6-vinylpyridin-3-ol

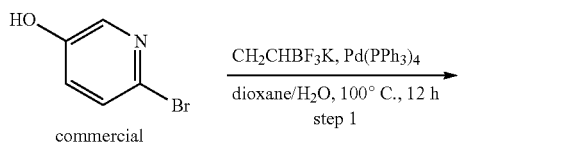

commercial

Core-1b_C1

To a suspension of 6-bromopyridin-3-ol (20.0 g, 114.94 mmol), potassium vinyltrifluoroborate (23.1 g, 174.41 mmol), Pd(PPh$_3$)$_4$ (2.7 g, 2.30 mmol) and K$_2$CO$_3$ (31.8 g, 229.88 mmol) in dioxane/H$_2$O (100/100 mL) was stirred at 100° C. for 12 h. The reaction mixture was adjust with 1 N HCl to pH=5-6, extracted with EtOAc (200 mL×3). The organic layer was dried over anhydrous Na$_2$SO$_4$ and concentrated. The residue was purified by column chromatography on silica gel (PE:EtOAc=20:1-5:1) to afford 6-vinylpyridin-3-ol Core-1b_C1 (10.0 g, crude) as yellow solid; $^1$H NMR (400 MHz, CDCl$_3$) δ 8.17 (d, J=2.8 Hz, 1H), 7.34 (d, J=8.4 Hz, 1H), 7.23 (dd, J=8.4, 2.8 Hz, 1H), 6.77 (dd, J=17.6, 11.2 Hz, 1H), 5.90 (d, J=17.6 Hz, 1H), 5.66-5.47 (m, 1H), 5.34 (d, J=11.2 Hz, 1H).

Step 2: 6-ethylpiperidin-3-ol hydrochloride

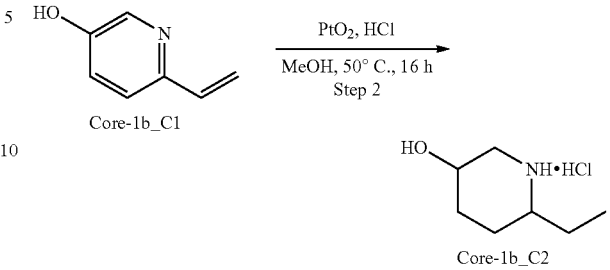

To a solution of 6-vinylpyridin-3-ol Core-1b_C1 (2.5 g, 20.64 mmol) MeOH (25 mL) was added with HCl (1.7 mL, 20.64 mmol) and PtO$_2$ (250.0 mg). The mixture was charged with H$_2$ to 50 psi and stirred at 50° C. for 16 h. The reaction mixture was concentrated to afford 6-ethylpiperidin-3-ol hydrochloride Core-1b_C2 (2.5 g, crude), which was used directly in the next step.

Step 3: tert-butyl 2-ethyl-5-hydroxypiperidine-1-carboxylate

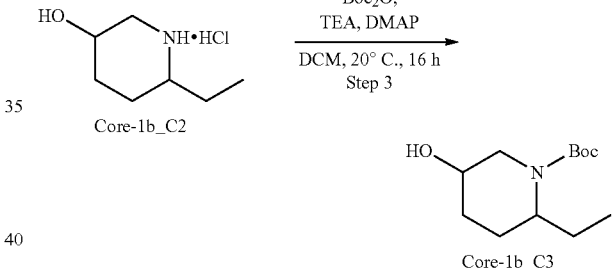

To a suspension of 6-ethylpiperidin-3-ol hydrochloride Core-1b_C2 (5.5 g, 33.20 mmol), TEA (10.1 g, 99.60 mmol) and DMAP (405.6 mg, 3.32 mmol) in DCM (50 mL) was added Boc$_2$O (21.7 g, 99.60 mmol). The mixture was stirred at 20° C. for 16 h. The reaction mixture was diluted with DCM (200 mL), washed with water (50 mL×3), brine (50 mL×3). The organic layer was dried over anhydrous Na$_2$SO$_4$ and concentrated. The residue was purified by column chromatography on solica gel (PE:EtOAc=10:1-2:1) to afford tert-butyl 2-ethyl-5-hydroxypiperidine-1-carboxylate Core-1b_C3 (1.0 g, 70% purity) as colorless oil.

Step 4: tert-butyl 2-ethyl-5-oxopiperidine-1-carboxylate

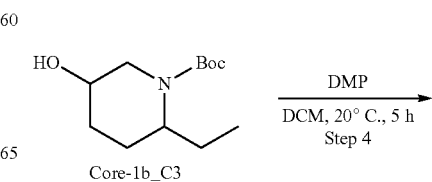

-continued

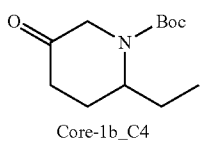

Core-1b_C4

To a suspension of tert-butyl 2-ethyl-5-hydroxypiperidine-1-carboxylate Core-1b_C3 (1.0 g, 4.36 mmol), pyridine (1.0 g, 13.08 mmol) in DCM (10 mL) was added with DMP (5.5 g, 13.08 mmol). The mixture was stirred at 20° C. for 5 h. The reaction was quenched with saturated aqueous $Na_2S_2O_3$ (50 mL), and the mixture was extracted with DCM (100 mL×3). The organic layer was dried over anhydrous $Na_2SO_4$ and concentrated. The crude product was purified by column chromatography on silica gel (PE:EtOAc=10:1-5:1) to afford C tert-butyl 2-ethyl-5-oxopiperidine-1-carboxylate Core-1b_C4 (460.0 mg, crude) as colorless oil, which was used directly in the next step.

Step 5: tert-butyl 2-amino-3-cyano-6-ethyl-6,7-dihydrothieno[3,2-c]pyridine-5(4H)-carboxylate

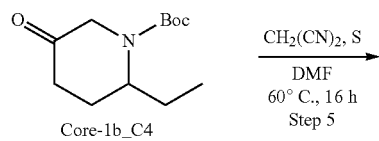

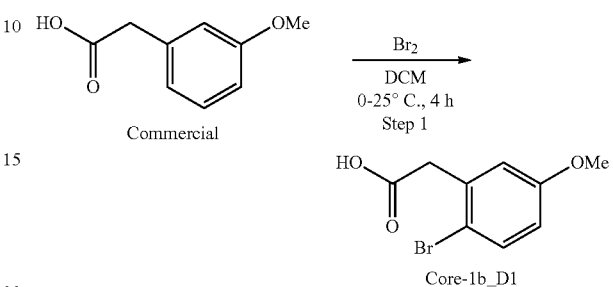

Core-1b_C

To a solution of tert-butyl 2-ethyl-5-oxopiperidine-1-carboxylate (460.0 mg, 2.02 mmol) Core-1b_C4, S (97.3 mg, 3.04 mmol), $CH_2(CN)_2$ (147.1 mg, 2.23 mmol) and L-proline (23.0 mg, 0.20 mmol) in DMF (5 mL) was stirred at 60° C. for 16 h. The reaction mixture was diluted with EtOAc (30 mL), washed with water (10 mL×3). The organic layer was dried over anhydrous $Na_2SO_4$ and concentrated. The residue was purified by prep-TLC (PE:EtOAc=2:1) to afford tert-butyl 2-amino-3-cyano-6-ethyl-6,7-dihydrothieno[3,2-c]pyridine-5(4H)-carboxylate Core-1b_C (90.0 mg, yield 14%) as yellow solid; $^1$H NMR (400 MHz, $CD_3OD$) δ 4.65-4.47 (m, 2H), 3.81 (s, 1H), 2.80 (dd, J=2.4, 13.2 Hz, 1H), 2.43 (d, J=16.1 Hz, 1H), 1.66-1.55 (m, 1H), 1.50 (s, 9H), 1.47-1.41 (m, 1H), 0.91 (t, J=7.4 Hz, 3H); LC-MS Rt 1.45 min, MS m/z $[M+Na]^+$ 330.0; Method 2.

Intermediate Core-1b_D: tert-butyl 3-cyano-2-(2-(3-methoxy-4-sulfamoylphenyl)acetamido)-6-methyl-6,7-dihydrothieno[3,2-c]pyridine-5(4H)-carboxylate Step 1: 2-(2-bromo-5-methoxyphenyl)acetic acid

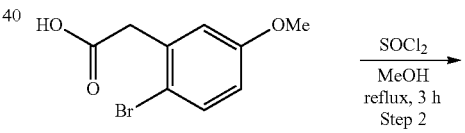

To a solution of 2-(3-methoxyphenyl) acetic acid (3.0 g, 18.05 mmol) in DCM (30 mL) was added with $Br_2$ (4.3 g, 27.08 mmol) at 0° C. After addition, the reaction mixture was warmed to 20° C. and stirred for 4 h. The reaction mixture was diluted with DCM (100 mL), washed with saturated $Na_2SO_3$ (30 mL×3) and brine (30 mL×3). The organic layer was dried over anhydrous $Na_2SO_4$ and concentrated to afford 2-(2-bromo-5-methoxyphenyl)acetic acid Core-1b_D1 (4.2 g), which was used directly in the next step; LC-MS Rt 0.64 min, MS m/z $[M+H]^+$ 246.9; Method 3.

Step 2: methyl 2-(2-bromo-5-methoxyphenyl)acetate

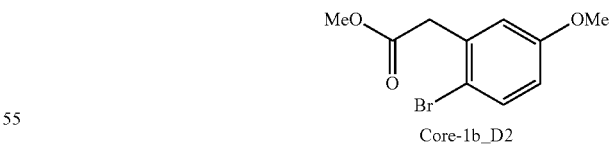

To a solution of 2-(2-bromo-5-methoxyphenyl) acetic acid Core-1b_D1 (4.2 g, 17.14 mmol) in MeOH (50 mL) was added with $SOCl_2$ (12.2 g, 102.83 mmol) at 0° C. After addition, the reaction mixture was warmed to 80° C. and stirred for 4 h. The reaction mixture was concentrated to dryness. The residue was diluted with EtOAc (100 mL), washed with brine (30 mL×3). The organic layer was dried over anhydrous $Na_2SO_4$ to afford 4.5 g of crude product, which was used directly in the next step.

Step 3: methyl 2-(2-bromo-4-(chlorosulfonyl)-5-methoxyphenyl)acetate

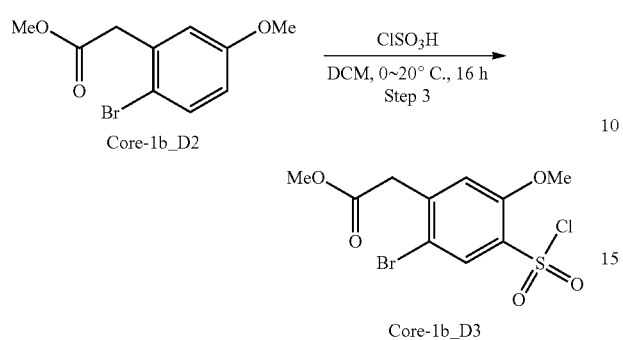

Methyl 2-(2-bromo-5-methoxyphenyl) acetate Core-1b_D2 (7.0 g, 27.02 mmol) was added to ClDO$_3$H (20 mL) at 0° C. After addition, the reaction mixture was warmed to 20° C. and stirred for 16 h. The reaction mixture was poured into ice water (500 mL) and extracted with EtOAc (100 mL×3). The combined organic layers were washed with brine (50 mL×3), dried over anhydrous Na$_2$SO$_4$ and concentrated to afford the crude product (6.0 g), which was used directly in the next step; $^1$H NMR (400 MHz, CDCl$_3$) δ 8.13 (s, 1H), 7.10 (s, 1H), 4.06 (s, 3H), 3.87 (s, 2H), 3.77 (s, 3H).

Step 4: methyl 2-(2-bromo-5-methoxy-4-sulfamoylphenyl)acetate

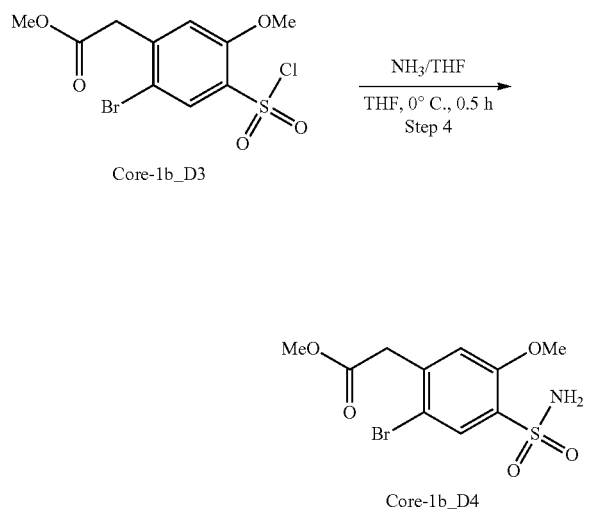

NH$_3$ was bubbled into a solution of methyl 2-(2-bromo-4-(chlorosulfonyl)-5-methoxyphenyl)acetate Core-1b_D3 (6.0 g, 16.78 mmol) in THF (100 mL) at 0° C. for 0.5 h. The reaction mixture was filtered and the filter cake was washed with 20 mL THF, and dried in vacuum. The crude product was washed with PE:EtOAc=3:1 (200 mL) to afford methyl 2-(2-bromo-5-methoxy-4-sulfamoylphenyl)acetate Core-1b_D4 (2.6 g, yield 46%) as yellow solid. LC-MS Rt 0.78 min, MS m/z [M+Na]$^+$ 361.9; Method 1.

Step 5: methyl 2-(3-methoxy-4-sulfamoylphenyl)acetate

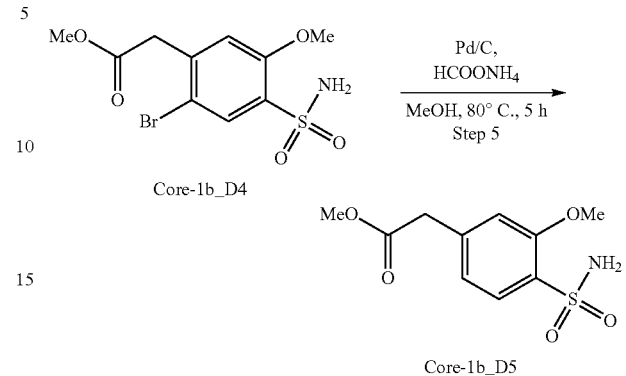

To a solution of methyl 2-(2-bromo-5-methoxy-4-sulfamoylphenyl)acetate Core-1b_D4 (2.6 g, 7.69 mmol), HCOONH$_4$ (533.3 mg, 8.46 mmol) in MeOH (30 mL) was added Pd/C (300.0 mg). The mixture was stirred at 80° C. for 5 h. The reaction mixture was filtered and the filter cake was washed with 20 mL MeOH, and dried in vacuum. The crude product was washed with PE:EtOAc=3:1 (20 mL) to afford methyl 2-(3-methoxy-4-sulfamoylphenyl)acetate Core-1b_D5 (1.8 g, yield 46%) as yellow solid; $^1$H NMR (400 MHz, DMSO-d$_6$) δ 7.66 (d, J=1.6, 8.0 Hz, 1H), 7.19-6.89 (m, 4H), 3.88 (d, J=1.6 Hz, 3H), 3.77 (s, 2H), 3.63 (d, J=2.4 Hz, 3H).

Step 6: 2-(3-methoxy-4-sulfamoylphenyl)acetic acid

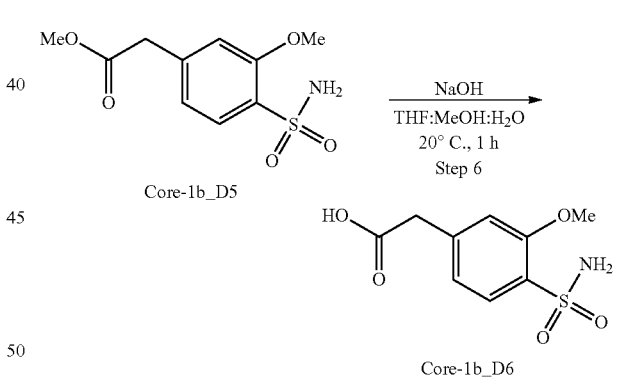

To a solution of methyl 2-(3-methoxy-4-sulfamoylphenyl) acetate Core-1b_D5 (1.3 g, 5.01 mmol) in THF/MeOH/H$_2$O (18/9/9 mL) was added with NaOH (401.1 mg, 10.03 mmol). The mixture was stirred at 20° C. for 1 h. The reaction mixture was concentrated to remove THF and MeOH, then acidified with 6 N HCl to pH=1, extracted with EtOAc (50 mL×3). The organic layer was dried over anhydrous Na$_2$SO$_4$ and concentrated. The residue was washed with DCM (20 mL×3) to afford 2-(3-methoxy-4-sulfamoylphenyl)acetic acid Core-1b_D6 (1.1 g, yield 89%) as white solid; $^1$H NMR (400 MHz, DMSO-d$_6$), δ 7.65 (d, J=8.0 Hz, 1H), 7.11 (s, 1H), 7.03 (s, 2H), 6.94 (d, J=8.0 Hz, 1H), 3.88 (s, 3H), 3.68-3.62 (m, 2H); LC-MS Rt 0.46 min, MS m/z [M+H]$^+$ 246.0.

Step 7: tert-butyl 3-cyano-2-(2-(3-methoxy-4-sulfamoylphenyl)acetamido)-6-methyl-6,7-dihydrothieno[3,2-c]pyridine-5(4H)-carboxylate

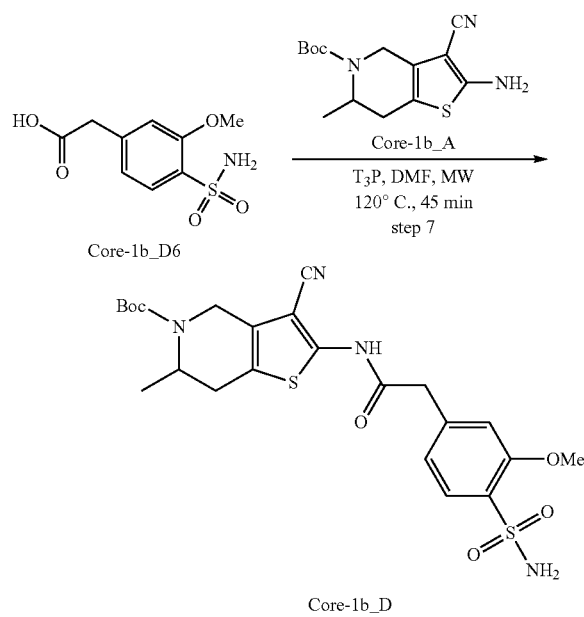

To a solution of 2-(3-methoxy-4-sulfamoylphenyl)acetic acid Core-1b_D6 (250.0 mg, 1.02 mmol), tert-butyl 2-amino-3-cyano-6-methyl-6,7-dihydrothieno[3,2-c]pyridine-5(4H)-carboxylate Core-1b_A (598.2 mg, 2.04 mmol), T$_3$P (486.8 mg, 1.53 mmol) and DIPEA (395.5 mg, 3.06 mmol) in DMF (5 mL) was stirred at 120° C. under microwave for 0.5 h. The reaction mixture was diluted with 50 mL EtOAc, washed with water (10 mL×3) and brine (10 mL×3). The organic layer was dried over anhydrous Na$_2$SO$_4$, and concentrated. The residue was purified by reverse phase column (NH$_3$H$_2$O) to afford tert-butyl 3-cyano-2-(2-(3-methoxy-4-sulfamoylphenyl) acetamido)-6-methyl-6,7-dihydrothieno[3,2-c]pyridine-5(4H)-carboxylate Core-1b_D (152.0 mg, yield 29%) as white solid; $^1$H NMR (400 MHz, DMSO-d$_6$), δ 7.66 (d, J=8.0 Hz, 1H), 7.18 (s, 1H), 7.03 (s, 2H), 6.97 (d, J=8.0 Hz, 1H), 4.60 (d, J=17.2 Hz, 2H), 3.99 (s, 1H), 3.89 (s, 5H), 2.90-2.79 (m, 1H), 2.53 (s, 1H), 1.43 (s, 9H), 1.03 (d, J=6.8 Hz, 3H); LC-MS Rt 0.87 min, MS m/z [M+H−100]$^+$ 421.1; Method 1.

Intermediate Core-1b_E: tert-butyl 3-cyano-6-methyl-2-(2-(4-(methylsulfinyl)phenyl)acetamido)-6,7-dihydrothieno[3,2-c]pyridine-5(4H)-carboxylate

Step 1: 2-(4-(methylsulfinyl)phenyl)acetic acid

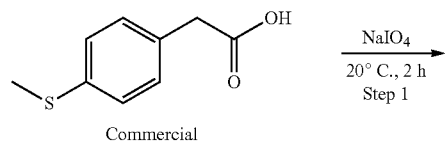

Commercial

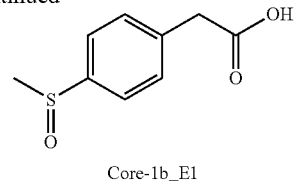

Core-1b_E1

To a solution of 2-(4-(methylthio) phenyl) acetic acid (1.0 g, 5.49 mmol) in MeOH (10 mL) was added with NaIO$_4$ (1.3 g, 6.04 mmol) in H$_2$O (10 mL) at 0° C. After addition, the mixture was stirred at 20° C. for 2 h. The reaction mixture was filtered, concentrated to afford 2-(4-(methylsulfinyl)phenyl) acetic acid Core-1b_E1 (0.9 g, yield 82%) as white solid, which was used directly in the next step; LC-MS Rt 0.204 min, MS m/z [M+H]$^+$ 199.0; Method 3.

Step 2: tert-butyl 3-cyano-6-methyl-2-(2-(4-(methylsulfinyl)phenyl)acetamido)-6,7-dihydrothieno[3,2-c]pyridine-5(4H)-carboxylate

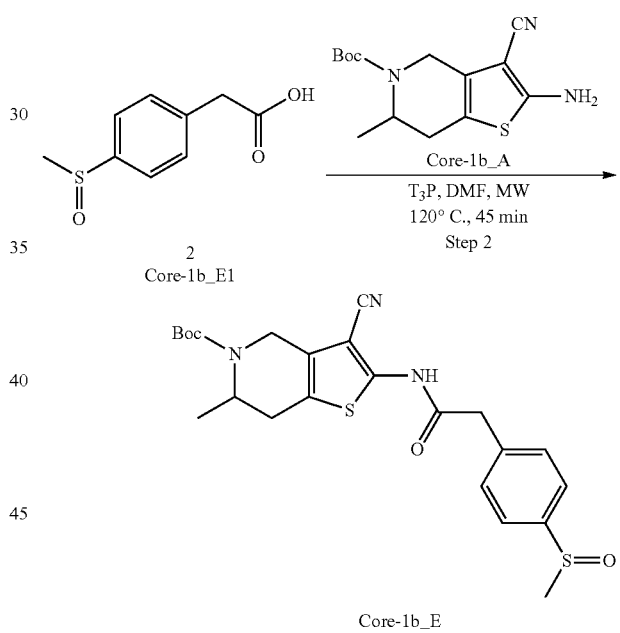

To a solution of tert-butyl 2-amino-3-cyano-6-methyl-6,7-dihydrothieno[3,2-c]pyridine-5(4H)-carboxylate Core-1b_A (100.0 mg, 0.17 mmol), 2-(4-(methylsulfinyl)phenyl) acetic acid Core-1b_E1 (67.6 mg, 0.34 mmol), T$_3$P (81.1 mg, 0.26 mmol) and DIPEA (65.9 mg, 0.51 mmol) in DMF (1 mL) was stirred under microwave at 120° C. for 0.5 h. The reaction mixture was diluted with 20 mL EtOAc, washed with water (10 mL×3), and brine (10 mL×3). The organic layer was dried over anhydrous Na$_2$SO$_4$ and concentrated. The residue was purified by reverse phase column (NH$_3$·H$_2$O) to afford tert-butyl 3-cyano-6-methyl-2-(2-(4-(methylsulfinyl)phenyl)acetamido)-6,7-dihydrothieno[3,2-c]pyridine-5(4H)-carboxylate Core-1b_E (47 mg, yield 29%) as white solid; $^1$H NMR (400 MHz, DMSO-d$_6$) δ 7.65 (d, J=8.4 Hz, 2H), 7.52 (d, J=8.4 Hz, 2H), 4.61 (d, J=17.6 Hz, 2H), 4.06-3.96 (m, 1H), 3.94 (s, 2H), 2.88-2.79 (m, 1H), 2.73 (s, 3H), 2.55 (s, 1H), 1.43 (s, 9H), 1.03 (d, J=6.8 Hz, 3H); LC-MS Rt 0.91 min, MS m/z [M+H−100]+ 374.0; Method 1.

Intermediate Core-1 b F: 4-(2-((3-cyano-6-methyl-4,5,6,7-tetrahydrothieno[3,2-c]pyridin-2-yl)amino)-2-oxoethyl)benzamide Step 1: 2-(4-carbamoylphenyl)acetic acid

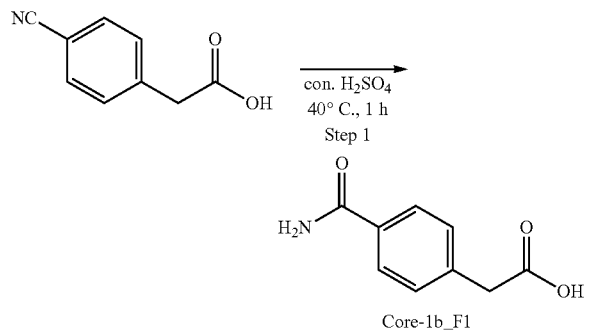

2-(4-cyanophenyl)acetic acid (400 mg, 2.5 mmol) was added to conc·H₂SO₄ (4 mL). The mixture was stirred at 40° C. for 1 h. The reaction was cooled to 20° C., and then poured into water (8 mL). The suspension was filtered, and the filter cake was collected to afford 2-(4-carbamoylphenyl) acetic acid Core-1b F1 (300 mg, yield 67%) as white solid. The product was used in next step without further purification; ¹H NMR (400 MHz, DMSO-d₆) δ 7.81 (d, J=8 Hz, 2H), 7.33 (d, J=8 Hz, 2H), 3.64 (s, 2H).

Step 2: tert-butyl 2-(2-(4-carbamoylphenyl)acetamido)-3-cyano-6-methyl-6,7-dihydrothieno[3,2-c]pyridine-5(4H)-carboxylate

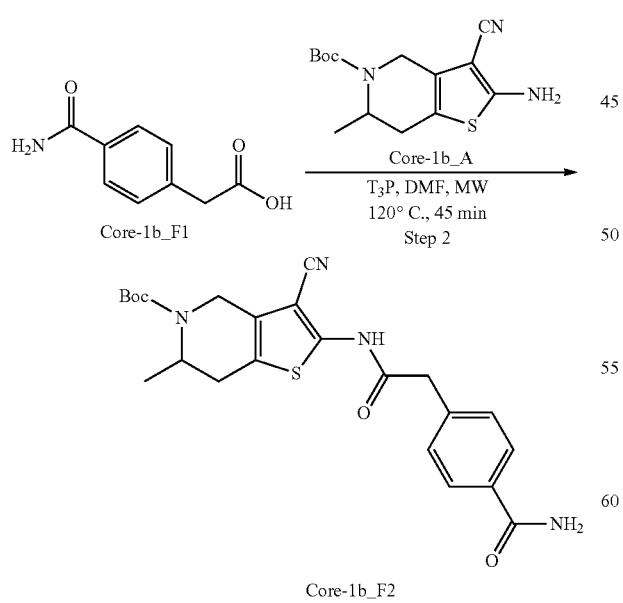

2-Amino-3-cyano-6-methyl-6,7-dihydrothieno[3,2-c]pyridine-5(4H)-carboxylate Core-1b_A (394 mg, 1.34 mmol), 2-(4-carbamoylphenyl)acetic acid Core-1b F1 (200 mg, 1.12 mmol), a solution of T₃P in EtOAc (1.43 g, 2.24 mmol, w/w=50%) and DIPEA (290 mg, 2.24 mmol) was stirred at 120° C. for 45 min under microwave. LC-MS showed the desired mass was detected. The solution was diluted with water (30 mL) and extracted with EtOAc (20 mL×3). The organic layer was concentrated. The residue was purified by Prep-TLC (9% MeOH in DCM) to afford tert-butyl 2-(2-(4-carbamoylphenyl)acetamido)-3-cyano-6-methyl-6,7-dihydrothieno[3,2-c]pyridine-5(4H)-carboxylate Core-1b F2 (66 mg, yield 13%) as yellow solid; LC-MS Rt 0.85 min, MS m/z [M+H−100]+ 355.0; Method 3.

Step 3: 4-(2-((3-cyano-6-methyl-4,5,6,7-tetrahydrothieno[3,2-c]pyridin-2-yl)amino)-2-oxoethyl)benzamide

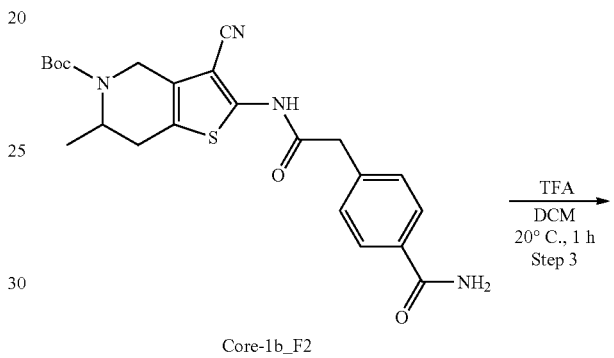

To a solution of tert-butyl 2-(2-(4-carbamoylphenyl)acetamido)-3-cyano-6-methyl-6,7-dihydrothieno[3,2-c]pyridine-5(4H)-carboxylate Core-1b F2 (100 mg, 0.22 mmol) in DCM (5 mL) was added TFA (0.5 mL). The mixture was stirred at 20° C. for 1 h. The reaction solution was concentrated. The crude product was used in next step without further purification; LC-MS Rt 1.26 min, MS m/z [M+H]+ 355.0; Method 5.

Intermediate Core-1b G: tert-butyl 3-cyano-6-methyl-2-(2-(4-(methylsulfonyl)phenyl)acetamido)-6,7-dihydrothieno[3,2-c]pyridine-5(4H)-carboxylate Step 1: tert-butyl 3-cyano-6-methyl-2-(2-(4-(methylsulfonyl)phenyl)acetamido)-6,7-dihydrothieno[3,2-c]pyridine-5(4H)-carboxylate

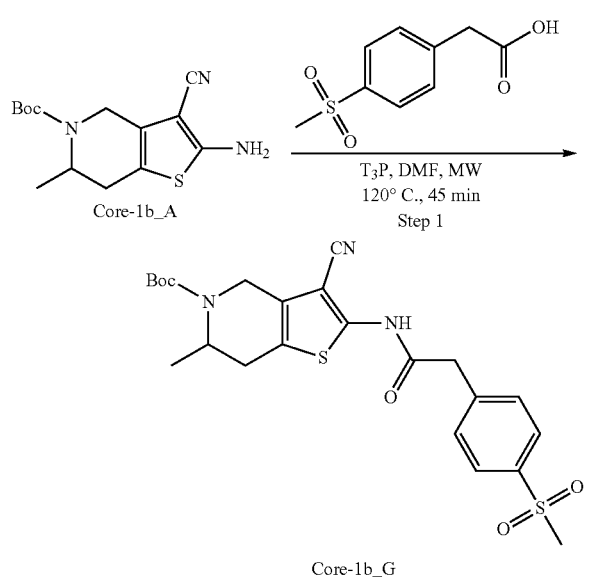

To a solution of tert-butyl 2-amino-3-cyano-6-methyl-6,7-dihydrothieno[3,2-c]pyridine-5(4H)-carboxylate (1 g, 3.41 mmol) Core-1b_A and 2-(4-(methylsulfonyl)phenyl) acetic acid (1.1 g, 5.11 mmol) in DMF (10 mL) were added DIPEA (879.3 mg, 6.82 mmol) and T₃P (3.21 g, 5.11 mmol). The reaction mixture was stirred at 120° C. under microwave for 50 min. The reaction mixture was poured into H₂O (50 mL) and extracted with EtOAc (50 mL×3), then the organic layer was dried over Na₂SO₄, and concentrated under reduced pressure to get the crude product, which was purified by column chromatography (PE:EtOAc=10:1-1:1) to afford the desired product (612 mg, yield 37%); ¹H NMR (400 MHz, CDCl₃) δ 8.91 (s, 1H), 7.98 (d, J=8.0 Hz, 2H), 7.57 (d, J=8.4 Hz, 2H), 4.85 (s, 2H), 4.04-4.00 (m, 1H), 3.94 (s, 2H), 3.07 (s, 3H), 3.00-2.96 (m, 1H), 2.48 (d, J=16 Hz, 1H), 1.49 (s, 9H), 1.12 (d, J=7.2 Hz, 3H); LC-MS Rt 0.92 min, MS m/z [M+H−100]⁺ 390.1; Method 1.

Intermediate Core-1b_I & Core-1b_J:tert-butyl 2-amino-3-cyano-6-methyl-6,7-dihydrothieno[3,2-c] pyridine-5(4H)-carboxylate (Enantiomers)

Step 1: tert-butyl 2-amino-3-cyano-6-methyl-6,7-dihydrothieno[3,2-c]pyridine-5(4H)-carboxylate

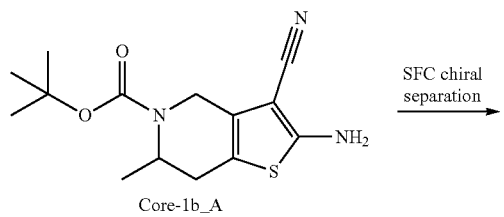

-continued

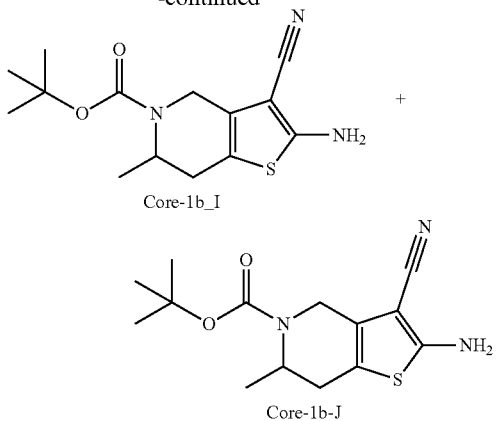

An enantiomer of tert-butyl 2-amino-3-cyano-6-methyl-6,7-dihydrothieno[3,2-c]pyridine-5(4H)-carboxylate Core-1b_A (500 mg) was submitted for chiral SFC to afford Core-1b_I (131 mg, 96% ee) and Core-1b_J (156 mg, 98% ee).

Chiral SFC separation Column: OJ-3 100×4.6 mm I.D., 3 um; Mobile Phase: A for CO₂, B for MeOH (0.05% DEA); Isocratic: 5% to 40% Phase B; Total Flow: 3 mL/min; Back Pressure: 100 Bar; UV: 220 nm; Instrument: SFC 80.

Core-1b_I: ¹H NMR (400 MHz, DMSO-d₆) δ 7.18 (s, 1H), 4.60 (s, 1H), 4.44 (d, J=17.2 Hz, 2H), 4.01 (s, 1H), 2.71-2.51 (m, 1H), 2.25 (d, J=16 Hz, 2H), 1.50-1.39 (m, 9H), 1.16-1.05 (m, 3H); LC-MS: Rt=0.95 MS m/z [M+H-56]+ 238.0; Method 1.

Core-1b_J: ¹H NMR (400 MHz, DMSO-d₆) δ 7.17 (s, 1H), 4.60 (s, 1H), 4.44 (d, J=17.2 Hz, 2H), 4.01 (s, 1H), 2.75-2.71 (m, 1H), 2.50-2.30 (d, J=16 Hz, 2H), 1.48-1.35 (m, 9H), 1.16-1.05 (m, 3H); LC-MS Rt 0.95 MS m/z [M+H-56]+238.0; Method 1.

Intermediate Core-1c_A: 2-amino-5-(cyclohexylmethyl)-6,6-dimethyl-4,5,6,7-tetrahydrothieno[3,2-c] pyridine-3-carbonitrile Step 1: (5-oxotetrahydrofuran-2-yl)methyl formate

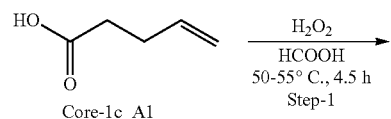

To a stirring solution of 30% hydrogen peroxide (74 mL, 650 mmol) in 85% aqueous formic acid (200 mL) was added a solution of pent-4-enoic acid Core-1c_A1 (50 g, 500 mmol) in 85% aqueous formic acid (100 mL) over 2.5 h at 50-55° C. The solution was maintained at this temperature for 2 h. The reaction was quenched with saturated aqueous of Na₂SO₃ (100 mL). The reaction mixture was concentrated to remove the most of formic acid. The residue was basified by saturated aqueous NaHCO₃ to pH 6.5-7. The solution was extracted with EtOAc (100 mL×3). The combined organic layers were dried over anhydrous Na₂SO₄, filtered and concentrated to afford (5-oxotetrahydrofuran-2-yl)methyl formate Core-1c_A2 (28 g, yield 39%) as colorless oil. The product was used in next step without further purification.

Step 2: 5-(hydroxymethyl)dihydrofuran-2(3H)-one

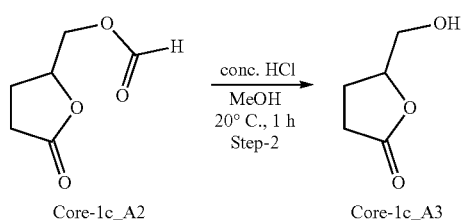 [SMILES: O=COCC1CCC(=O)O1 ; O=C1CCC(CO)O1]

To a solution of (5-oxotetrahydrofuran-2-yl)methyl formate Core-1c_A2 (28 g, 194 mmol) in MeOH (100 mL) was added conc. HCl (2 mL). The mixture was stirred at 20° C. for 1 h. The reaction solution was concentrated to afford 5-(hydroxymethyl)dihydrofuran-2(3H)-one Core-1c_A3 (23 g, yield 100%) as colorless oil; ¹H NMR (400 MHz, CDCl₃) δ 4.64-4.60 (m, 1H), 3.87-3.84 (d, J=12.4 Hz, 1H), 3.64-3.60 (dd, J=12.8 Hz, 4.4 Hz, 1H), 3.25 (s, 1H), 2.60-2.45 (m, 2H), 2.30-2.25 (m, 1H), 2.18-2.06 (m, 1H).

Step 3: (5-oxotetrahydrofuran-2-yl)methyl methanesulfonate

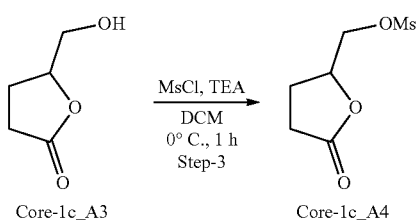 [SMILES: O=C1CCC(CO)O1 ; CS(=O)(=O)OCC1CCC(=O)O1]

To a solution of 5-(hydroxymethyl)dihydrofuran-2(3H)-one Core-1c_A3 (37.9 g, 344 mmol) in DCM (500 mL) at 0° C. was added TEA (69 g, 688 mmol) and MsCl (59 g, 516 mmol). The mixture was stirred at 0° C. for 1 h. The reaction was quenched with water (300 mL) and extracted with DCM (200 mL×3). The combined organic layers were dried over anhydrous Na₂SO₄, filtered and concentrated to afford (5-oxotetrahydrofuran-2-yl)methyl methanesulfonate Core-1c_A4 (65 g, yield 100%). The crude product was used in next step without further purification.

Step 4: 5-(azidomethyl)dihydrofuran-2(3H)-one

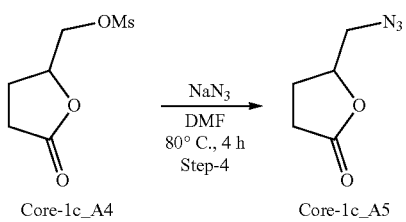 [SMILES: CS(=O)(=O)OCC1CCC(=O)O1 ; [N-]=[N+]=NCC1CCC(=O)O1 ; "NaN3"]

To a solution of (5-oxotetrahydrofuran-2-yl)methyl methanesulfonate Core-1c_A4 (65 g, 335 mmol) in DMF (600 mL) was added NaN 3 (24.5 g, 378 mmol). The mixture was stirred at 80° C. for 4 h. The reaction solution was diluted with water (1.5 L) and extracted with EtOAc (500 mL×5). The combined organic layers were concentrated. The residue was purified by column chromatography on silica (9% to 25% EtOAc in PE) to afford 5-(azidomethyl)dihydrofuran-2(3H)-one Core-1c_A5 (32 g, yield 68%) as colorless oil; ¹H NMR (400 MHz, CDCl₃) δ 4.65-4.61 (m, 1H), 3.59-3.55 (m, 1H), 3.44-3.40 (m, 1H), 2.57-2.45 (m, 2H), 2.31-2.28 (m, 1H), 2.15-1.99 (m, 1H).

Step 5: 5-hydroxypiperidin-2-one

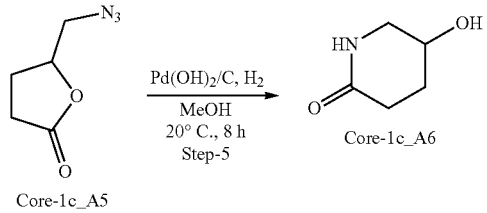

A mixture of 5-(azidomethyl)dihydrofuran-2(3H)-one Core-1c_A5 (32 g, 227 mmol) and Pd(OH)₂/C (3 g, cat.) in MeOH (600 mL) was hydrogenated at 20° C. under H₂ (15 psi) for 4 h. The reaction solution was filtered, and the filtrate was concentrated. The residue was purified by column chromatography on silica (50% EtOAc in PE to 9% MeOH in DCM) to afford 5-hydroxypiperidin-2-one Core-1c_A6 (0.93 g, 3.5%) as white solid and unknown intermediate (37 g, crude). The unknown intermediate was divided into 4 batches for hydrogenation. Each batch of crude intermediate was dissolved in MeOH (500 mL) and added Pd(OH)₂/C (1 g). The mixture was hydrogenated at 20° C. under H₂ (15 psi) for 4 h. The reaction solution was filtered. The filtrate was concentrated to afford the 5-hydroxypiperidin-2-one Core-1c_A6 (25 g, yield 95%) as white solid. The product was used in next step without further purification.

Step 6: 1-benzyl-5-(benzyloxy)piperidin-2-one

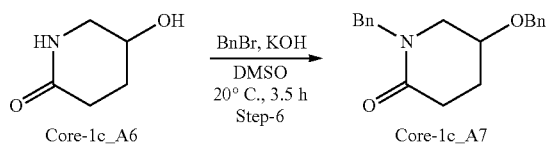

A solution of KOH (48.5 g, 864 mmol) in DMSO (250 mL) was stirred at 20° C. for 30 min under $N_2$. And then a solution of 5-hydroxypiperidin-2-one Core-1c_A6 (12.5 g, 108 mmol) in DMSO (50 mL) was added. After stirring at 20° C. for 1 h, BnBr (74.0 g, 432 mmol) was added. The mixture was stirred for another 2 h. The reaction solution was filtered. The filtrate was diluted with water (1.5 L) and extracted with EtOAc (400 mL×5). The combined organic layers were washed with brine, dried over anhydrous $Na_2SO_4$, filtered and concentrated. The residue was purified by column chromatography on silica (9% to 33% EtOAc in PE) to afford 1-benzyl-5-(benzyloxy)piperidin-2-one Core-1c_A7 (21.5 g, yield 67%) as light yellow oil; $^1$H NMR (400 MHz, $CDCl_3$) δ 7.35-7.27 (m, 10H), 4.68 (d, J=14.8 Hz, 1H), 4.56-4.42 (m, 3H), 3.83-3.80 (m, 1H), 3.34-3.33 (m, 2H), 2.74-2.71 (m, 1H), 2.49-2.44 (m, 1H), 2.08-1.98 (m, 2H).

Step 7: 1-benzyl-5-(benzyloxy)-2,2-dimethylpiperidine

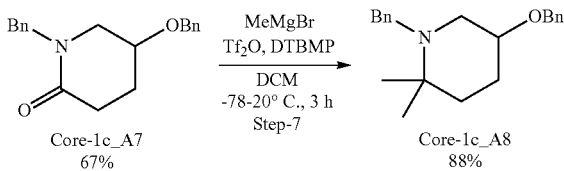 [SMILES: O=C1CCC(OCc2ccccc2)CN1Cc1ccccc1 ; CC1(C)CCC(OCc2ccccc2)CN1Cc1ccccc1]

To a solution of 1-benzyl-5-(benzyloxy)piperidin-2-one Core-1c_A7 (5.0 g, 16.9 mmol) and 2,6-di-tert-butyl-4-methylpyridine (DTBMP) (4.2 g, 20.3 mmol) in DCM (300 mL) at −78° C. was added dropwise $Tf_2O$ (5.7 g, 20.3 mmol) under $N_2$. The mixture was stirred at −78° C. for 1 h. Then a solution of MeMgBr in $Et_2O$ (16.9 mL, 50.7 mmol) was added dropwise. The reaction mixture was warmed to 20° C. and stirred for another 2 h. The reaction was quenched with saturated aqueous $NH_4Cl$ (50 mL), diluted with water (200 mL) and extracted with DCM (80 mL×3). The organic layer was concentrated. The residue was purified by column chromatography (9% EtOAc in PE) to afford 1-benzyl-5-(benzyloxy)-2,2-dimethylpiperidine Core-1c_A8 (4.6 g, yield 88%) as colorless oil; $^1$H NMR (400 MHz, $CDCl_3$) δ 7.42-7.29 (m, 10H), 4.47 (s, 2H), 3.93 (d, J=14 Hz, 1H), 3.47-3.45 (m, 1H), 3.22 (d, J=14 Hz, 1H), 2.80-2.79 (m, 1H), 2.34-2.29 (m, 1H), 1.98-1.96 (m, 1H), 1.66-1.58 (m, 3H), 1.25 (s, 3H), 1.13 (s, 3H).

Step 8: tert-butyl 5-(benzyloxy)-2,2-dimethylpiperidine-1-carboxylate

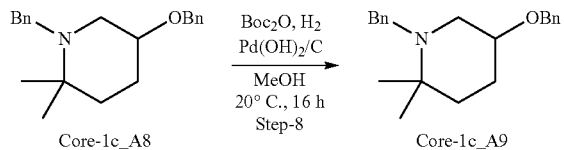 [SMILES: CC1(C)CCC(OCc2ccccc2)CN1Cc1ccccc1 ; CC1(C)CCC(OCc2ccccc2)CN1Cc1ccccc1]

A mixture of 1-benzyl-5-(benzyloxy)-2,2-dimethylpiperidine Core-1c_A8 (4.6 g, 14.8 mmol), $Boc_2O$ (6.5 g, 29.6 mmol) and $Pd(OH)_2/C$ (1.0 g, cat.) in MeOH (100 mL) was hydrogenated at 20° C. under $H_2$ (50 psi) for 16 h. The reaction solution was filtered, and the filtrate was concentrated to afford the desired product (8 g, crude). The crude product was further hydrogenated without purification; LC-MS Rt 0.99 min; MS m/z [M+H]$^+$ 320.1; Method 3.

Step 9: tert-butyl 5-hydroxy-2,2-dimethylpiperidine-1-carboxylate

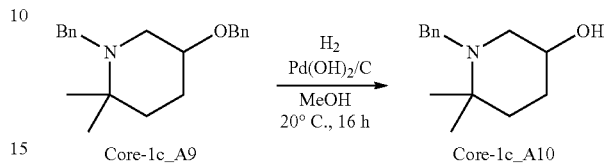

A mixture of tert-butyl 5-(benzyloxy)-2,2-dimethylpiperidine-1-carboxylate Core-1c_A9 (8 g, crude) and $Pd(OH)_2/C$ (1 g, cat.) in MeOH (100 mL) was hydrogenated at 20° C. under $H_2$ (50 psi) for 16 h. The reaction solution was filtered, and the filtrate was concentrated. The residue was purified by column chromatography (9% to 20% EtOAc in PE) to afford tert-butyl 5-hydroxy-2,2-dimethylpiperidine-1-carboxylate Core-1c_A10 (3 g, yield 88%, 2 steps) as white solid; $^1$H NMR (400 MHz, $CDCl_3$) δ 3.93-3.88 (m, 1H), 3.67-3.63 (dd, J=13.6, 4.4 Hz, 1H), 3.31-3.26 (m, 1H), 1.94-1.92 (m, 1H), 1.75-1.65 (m, 1H), 1.60-1.45 (m, 11H), 1.42 (d, J=3.6 Hz, 6H).

Step 10: tert-butyl 2,2-dimethyl-5-oxopiperidine-1-carboxylate

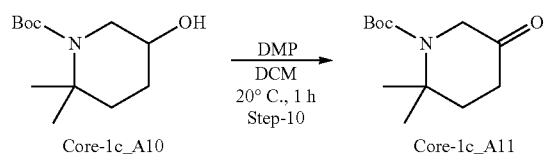 [SMILES: CC(C)(C)OC(=O)N1CC(O)CCC1(C)C ; CC(C)(C)OC(=O)N1CC(=O)CCC1(C)C]

To a solution of tert-butyl 5-hydroxy-2,2-dimethylpiperidine-1-carboxylate Core-1c_A10 (3 g, 13 mmol) in DCM (60 mL) was added DMP (8.3 g, 19.5 mmol). The mixture was stirred at 20° C. for 1 h. The reaction solution was filtered, and the filtrate was concentrated. The residue was purified by column chromatography on silica (20% EtOAc in PE) to afford tert-butyl 2,2-dimethyl-5-oxopiperidine-1-carboxylate Core-1c_A11 (2.8 g, yield 95%) as white solid; $^1$H NMR (400 MHz, $CDCl_3$) δ 4.04 (s, 2H), 2.47 (t, J=6.4 Hz, 2H), 1.90 (t, J=6.4 Hz, 2H), 1.53 (s, 6H), 1.47 (s, 9H).

Step 11: tert-butyl 2-amino-3-cyano-6,6-dimethyl-6,7-dihydrothieno[3,2-c]pyridine-5(4H)-carboxylate

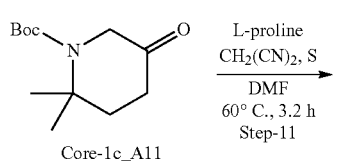

-continued

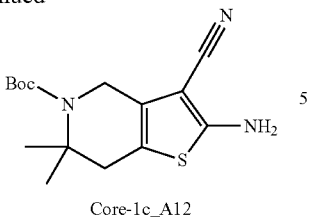

Core-1c_A12

To a solution of tert-butyl 2,2-dimethyl-5-oxopiperidine-1-carboxylate Core-1c_A11 (1.4 g, 6.1 mmol) and CH$_2$(CN)$_2$ (443 mg, 6.7 mmol) in DMF (30 mL) at 20° C. was added sulphur (295 mg, 9.2 mmol) and L-proline (70 mg, 0.61 mmol). The reaction mixture was stirred at 20° C. for 10 min followed by heating at 60° C. for 3 h. The reaction mixture was diluted with water (100 mL) and extracted with EtOAc (50 mL×3). The organic layer was concentrated. The residue was purified by column chromatography on silica (9% to 17% EtOAc in PE) to afford tert-butyl 2-amino-3-cyano-6,6-dimethyl-6,7-dihydrothieno[3,2-c]pyridine-5(4H)-carboxylate Core-1c_A12 (0.55 g, yield 29%) as yellow solid; LC-MS Rt 0.84 min; MS m/z [M+Na]$^+$ 330.0; Method 3; 1 H NMR (400 MHz, CDCl$_3$) δ 4.71 (s, 2H), 4.37 (d, J=1.2 Hz, 2H), 2.58 (s, 2H), 1.49 (s, 6H), 1.48 (s, 9H).

Step 12: 2-amino-6,6-dimethyl-4,5,6,7-tetrahydrothieno[3,2-c]pyridine-3-carbonitrile

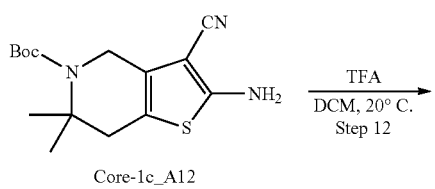

Core-1c_A12

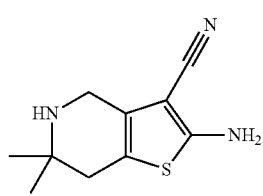

Core-1c_A13

To a solution of tert-butyl 2-amino-3-cyano-6,6-dimethyl-6,7-dihydrothieno[3,2-c]pyridine-5(4H)-carboxylate Core-1c_A12 (4 g, 13 mmol) in DCM (30 mL) was added TFA (3 mL). The reaction solution was concentrated, and the residue was basified by ion exchange resin and filtered. The filtrate was concentrated to afford 2-amino-6,6-dimethyl-4,5,6,7-tetrahydrothieno[3,2-c]pyridine-3-carbonitrile Core-1c_A13 (3 g, crude). The crude product was used in next step without further purification; LC-MS Rt 0.76 min; MS m/z [M+H]$^+$ 330.0; Method 1.

Step 13: 2-amino-5-(cyclohexylmethyl)-6,6-dimethyl-4,5,6,7-tetrahydrothieno[3,2-c]pyridine-3-carbonitrile

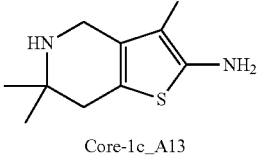 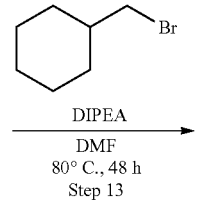

Core-1c_A13

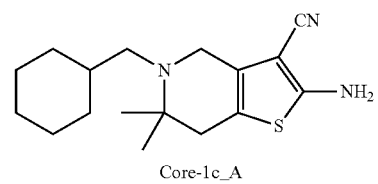

Core-1c_A

To a solution of 2-amino-6,6-dimethyl-4,5,6,7-tetrahydrothieno[3,2-c]pyridine-3-carbonitrile Core-1c_A12 (2.0 g, 12 mmol) in DMF (20 mL) was added DIPEA (3.1 g, 24 mmol) and (bromomethyl)cyclohexane (2.1 g, 12 mmol). The mixture was stirred at 80° C. for 16 h. Another batch of (bromomethyl)cyclohexane (2.1 g, 12 mmol) was added, and the mixture was stirred at 80° C. for an additional 16 h. A third batch of (bromomethyl)cyclohexane (1.1 g, 6 mmol) was added, and then the reaction mixture was stirred at 80° C. for another 16 h. The reaction was quenched with water (80 mL) and extracted with EtOAc (40 mL×3). The organic layer was concentrated. The residue was purified by column chromatography on silica (17% EtOAc in PE) to afford 2-amino-5-(cyclohexylmethyl)-6,6-dimethyl-4,5,6,7-tetrahydrothieno[3,2-c]pyridine-3-carbonitrile Core-1c_A (418.5 mg, yield 11.5%) as yellow solid; LC-MS Rt 1.14 min; MS m/z [M+H]$^+$ 304.1; Method 1; 1 H NMR (400 MHz, DMSO-d$_6$) δ 7.00 (s, 2H), 3.30 (s, 2H), 2.29 (s, 2H), 2.20 (d, J=6.8 Hz, 2H), 1.75-1.60 (m, 5H), 1.40-1.30 (m, 1H), 1.21-1.13 (m, 3H), 1.00 (s, 6H), 0.80-0.77 (m, 2H).

Step 14: N-(3-cyano-6,6-dimethyl-4,5,6,7-tetrahydrothieno[3,2-c]pyridin-2-yl)-2-(3-methoxy-4-sulfamoylphenyl)acetamide Core-1c_A14

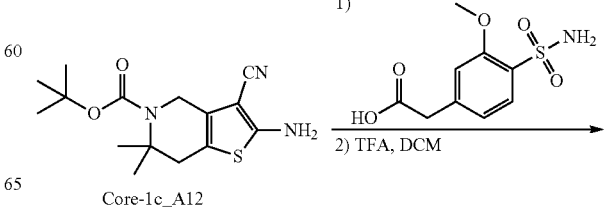

Core-1c_A12

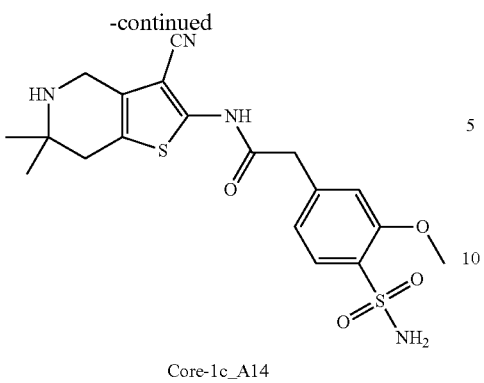

Core-1c_A14

A mixture of tert-butyl 2-amino-3-cyano-6,6-dimethyl-6,7-dihydrothieno[3,2-c]pyridine-5(4H)-carboxylate Core-1c_A12 (100 mg, 0.325 mmol), 2-(3-methoxy-4-sulfamoylphenyl)acetic acid (80 mg, 0.325 mmol) and TEA (91 μL, 0.653 mmol) in DMF (2.5 mL), was added 2,4,6-tripropyl-1,3,5,2,4,6-trioxatriphosphinane 2,4,6-trioxide (50% in DMF) (0.25 mL, 0.423 mmol) under argon. The reaction was stirred at room temperature for 16 h. The reaction was quenched with water (20 mL) and product was extracted with EtOAc (3×50 mL). The combined organic layer was then washed with brine (20 mL) and dried over anhydrous Na$_2$SO$_4$, filtered and concentrated under reduced pressure to its crude, which was purified by normal phase chromatography on (eluent: c-Hexane/EtOAc) to get tert-butyl 3-cyano-2-(2-(3-methoxy-4-sulfamoylphenyl)acetamido)-6,6-dimethyl-6,7-dihydrothieno[3,2-c]pyridine-5(4H)-carboxylate. (49 mg, yield 28%); LC-MS Rt 1.1 min, MS m/z [M+H]$^+$ 535.2; Method 5.

To a solution of tert-butyl 3-cyano-2-(2-(3-methoxy-4-sulfamoylphenyl)acetamido)-6,6-dimethyl-6,7-dihydrothieno[3,2-c]pyridine-5(4H)-carboxylate (63 mg, 0.118 mmol) in DCM 1.5 mL), was added TFA (0.1 mL, 1.298 mmol). The reaction was stirred at room temperature for 16 h. The reaction was then concentrated under vacuum (co-evaporate few times with DCM) to get N-(3-cyano-6,6-dimethyl-4,5,6,7-tetrahydrothieno[3,2-c]pyridin-2-yl)-2-(3-methoxy-4-sulfamoylphenyl)acetamide (60 mg, crude), which was used directly for next step.

Intermediate Core-1c_B: 2-amino-5-((3,3-difluorocyclobutyl)methyl)-6,6-dimethyl-4,5,6,7-tetrahydrothieno[3,2-c]pyridine-3-carbonitrile Step 1: (3,3-difluorocyclobutyl)methyl 4-methylbenzenesulfonate

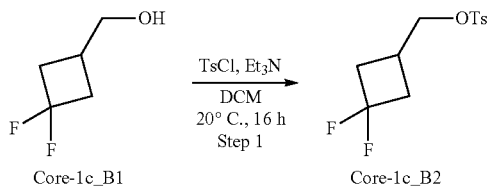

To a solution of (3,3-difluorocyclobutyl)methanol Core-1c_B1 (4 g, 32.7 mmol) in DCM (60 mL) was added TEA (6.6 g, 65.4 mmol) and TsCl (7.5 g, 39.2 mmol). The mixture was stirred at 20° C. for 16 h. The reaction solution was concentrated. The residue was purified by column chromatography on silica (17% EtOAc in PE) to afford Core-1c_B2 (4.8 g, yield 53%) as colorless oil.

Step 2: 2-amino-5-((3,3-difluorocyclobutyl)methyl)-6,6-dimethyl-4,5,6,7-tetrahydrothieno[3,2-c]pyridine-3-carbonitrile

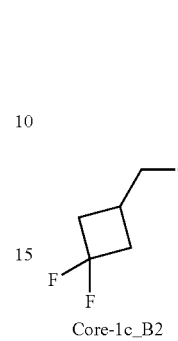

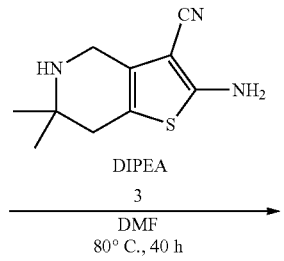

Core-1c_B3

To a solution of 2-amino-6,6-dimethyl-4,5,6,7-tetrahydrothieno[3,2-c]pyridine-3-carbonitrile Core-1c_B2 (2.0 g, 9.6 mmol) in DMF (30 mL) was added DIPEA (2.5 g, 19.2 mmol) and (3,3-difluorocyclobutyl)methyl 4-methylbenzenesulfonate (2.7 g, 9.6 mmol). The mixture was stirred at 80° C. for 16 h. A second batch of (3,3-difluorocyclobutyl)methyl 4-methylbenzenesulfonate (2.1 g, 7.8 mmol) was added, and the mixture was stirred at 80° C. for 24 h. The reaction was quenched with water (80 mL) and extracted with EtOAc (40 mL×3). The organic layer was concentrated. The residue was purified by column chromatography on silica (17% EtOAc in PE) to afford 2-amino-5-((3,3-difluorocyclobutyl)methyl)-6,6-dimethyl-4,5,6,7-tetrahydrothieno[3,2-c]pyridine-3-carbonitrile Core-1c_B3 (148 mg, yield 5%) as yellow solid; LC-MS Rt 0.95 min; MS m/z [M+H]$^+$ 312.0; Method 1; 1 H NMR (400 MHz, DMSO-d$_6$) δ 7.03 (s, 2H), 3.34 (s, 2H), 2.66-2.61 (m, 2H), 2.52-2.51 (m, 2H), 2.32-2.18 (m, 5H), 1.05 (s, 6H).

Intermediate Core-1c_C: 2-amino-5-(3-fluorobenzyl)-6,6-dimethyl-4,5,6,7-tetrahydrothieno[3,2-c]pyridine-3-carbonitrile Step 1: 2-amino-5-(3-fluorobenzyl)-6,6-dimethyl-4,5,6,7-tetrahydrothieno[3,2-c]pyridine-3-carbonitrile

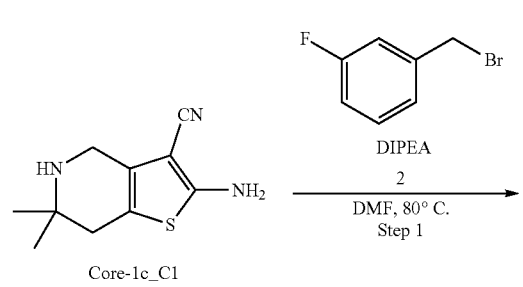

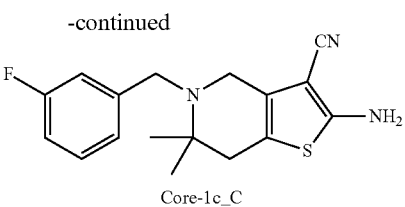

Core-1c_C

To a solution of 2-amino-6,6-dimethyl-4,5,6,7-tetrahydrothieno[3,2-c]pyridine-3-carbonitrile Core-1c_C1 (500 mg, 2.41 mmol) in DMF (5 mL) was added DIPEA (623 mg, 4.82 mmol) and 1-(bromomethyl)-3-fluorobenzene (501 mg, 2.65 mmol). The mixture was stirred at 80° C. for 16 h. The reaction solution was diluted with water (30 mL) and extracted with EtOAc (15 mL×3). The organic layer was concentrated. The residue was purified by column chromatography (PE:EtOAc=10:1-8:1) to afford 2-amino-5-(3-fluorobenzyl)-6,6-dimethyl-4,5,6,7-tetrahydrothieno[3,2-c]pyridine-3-carbonitrile Core-1c_C (350 mg, yield 46%) as yellow solid.

Preparation of Intermediates

Intermediate Core-2a_A: N-(3-cyano-4,5,6,7-tetrahydrothieno[2,3-c]pyridin-2-yl)-2-(4-sulfamoylphenyl)acetamide

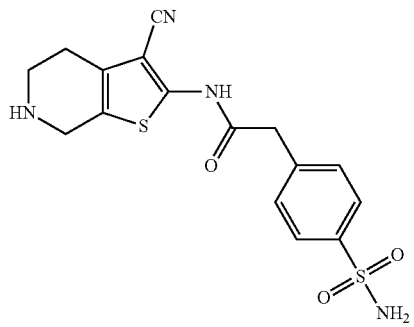 [SMILES: N#Cc1c(NC(=O)Cc2ccc(S(N)(=O)=O)cc2)sc2c1CCNC2]

Step 1: Tert-butyl-2-amino-3-cyano-4,5-dihydrothieno[2,3-c]pyridine-6(7H)-carboxylate

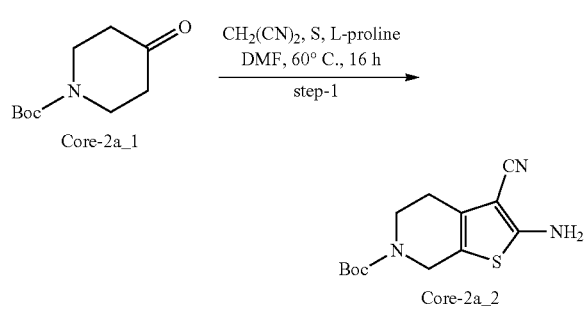

To a solution of tert-butyl-4-oxopiperidine-1-carboxylate Core-2a_1 (14.00 g, 70.3 mmol) and CH$_2$(CN)$_2$ (13.93 g, 210.8 mmol) in DMF (150 mL) was added with sulfur (6.76 g, 210.8 mmol) and L-proline (1.62 g, 14.1 mmol). The reaction mixture was stirred at 60° C. for 16 h. The reaction mixture was poured into water (500 mL) and extracted with EA (500 mL×2). The combined organic layers were washed with water (700 mL) and brine (700 mL), dried over anhydrous Na$_2$SO$_4$, filtered and concentrated under reduced pressure to afford a crude product, which was purified by silica gel chromatography, eluted with PE/EtOAc from 10/1 to 2/1, to afford tert-butyl-2-amino-3-cyano-4,5-dihydrothieno[2,3-c]pyridine-6(7H)-carboxylate Core-2a_2 (17.52 g, yield 89%); LC-MS Rt 0.905 min; MS m/z [M+H−56]+ 221.9; Method 1.

Step 2: Tert-butyl-3-cyano-2-(2-(4-sulfamoylphenyl)acetamido)-4,5-dihydrothieno[2,3-c]pyridine-6-(7H-1)-carboxylate 4

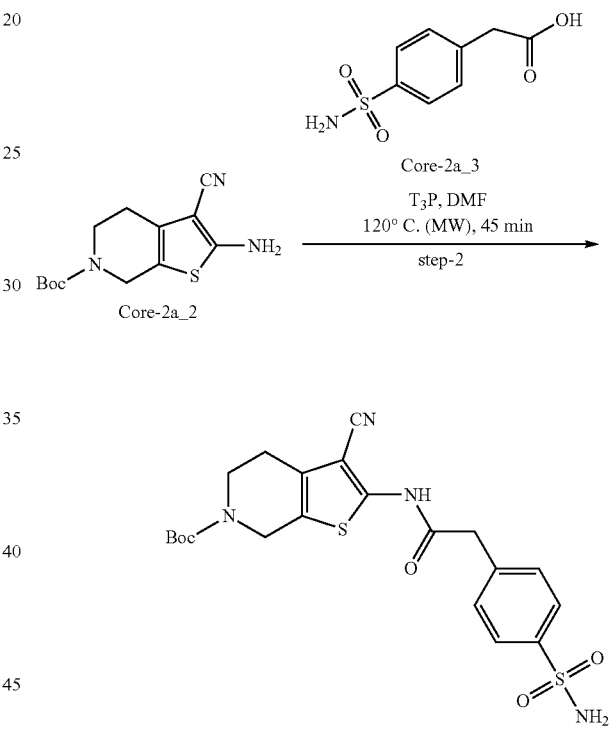

To a stirred solution of tert-butyl-2-amino-3-cyano-4,5-dihydrothieno-[2,3-c]pyridine-6(7H)-carboxylate Core-2a_2 (0.90 g, 3.22 mmol) and 2-(4-sulfamoylphenyl)acetic acid Core-2a_3 (1.04 g, 4.83 mmol) in DMF (10 mL) was added DIPEA (0.83 g, 6.44 mmol) and T$_3$P (50% in EtOAc, 4.10 g, 6.44 mmol). The reaction mixture was stirred at 120° C. under microwave reactor for 45 min. The reaction mixture were poured into water (200 mL) and extracted with EA (200 mL×2). The combined organic layers were washed with water (500 mL), followed by brine (500 mL×4), dried over anhydrous Na$_2$SO$_4$, filtered and concentrated under reduced pressure to afford a crude product, which was purified by silica gel chromatography, eluted with PE/EA from 10/1 to 1/1, to afford tert-butyl-3-cyano-2-(2-(4-sulfamoylphenyl)acetamido)-4,5-dihydrothieno[2,3-c]pyridine-6 (7H)-carboxylate Core-2a_4 (3.21 g, yield 75%); LC-MS Rt 0.84 min; MS m/z [M+H−100]+ 377.0, Method 1.

Step 3: N-(3-cyano-4,5,6,7-tetrahydrothieno[2,3-c]pyridin-2-yl)-2-(4-sulfamoylphenyl)acetamide

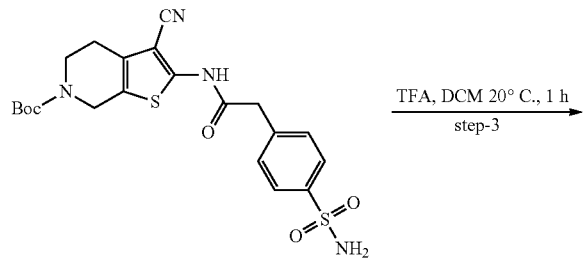

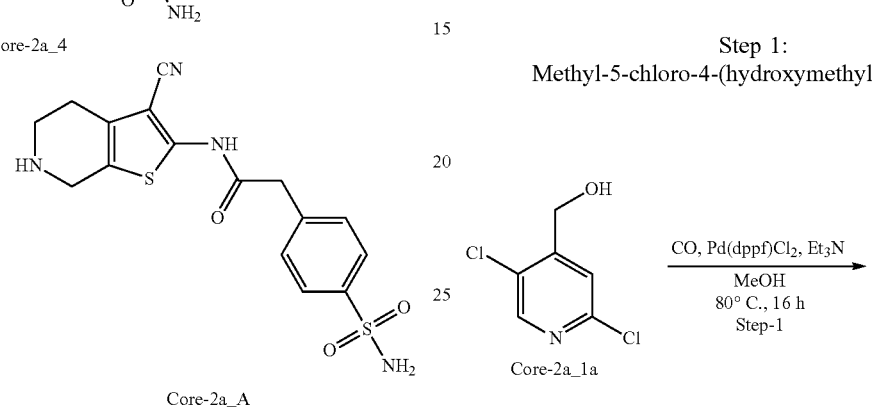

To a stirred solution of tert-butyl-3-cyano-2-(2-(4-sulfamoylphenyl)acetamido)-4,5-dihydrothieno[2,3-c]pyridine-6(7H)-carboxylate Core-2a_4 (2.21 g, 4.64 mmol) in dry DCM (27 mL) was added TFA (3 mL). The reaction mixture was stirred at 20° C. for 1 h. The reaction mixture was concentrated under reduced pressure to remove organic solvent to afford a crude product (1.60 g, yield 91%), which was used directly for the next step; $^1$H NMR (400 MHz, DMSO-$d_6$) δ 11.96 (1H, s), 7.22 (4H, m), 7.09 (4H, m), 5.95 (1H, s), 4.12 (2H, m), 4.10 (3H, s), 2.29 (3H, s), 2.29 (3H, s), 2.15 (2H, t), 1.75 (2H, m), 1.46 (2H, m), 1.35-1.23 (4H, m); LC-MS Rt 0.584 min; MS m/z [M+H]$^+$ 377.0; Method 1.

Intermediate Core-2a_B: (2,5-dichloropyridin-4-yl)methyl-4-methylbenzenesulfonate

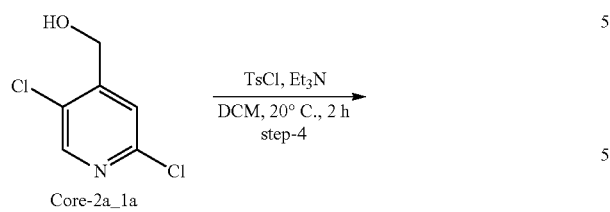

To a solution of (2,5-dichloropyridin-4-yl)methanol Core-2a_1a (100 mg, 0.56 mmol) in DCM (2 mL) was added TsCl (128 mg, 0.67 mmol) and Et 3 N (113 mg, 1.18 mmol). The reaction mixture was stirred for 2 h at 20° C. The reaction mixture was purified by prep-TLC (PE/EtOAc=10/1) directly to afford (2,5-dichloropyridin-4-yl)-methyl-4-methylbenzenesulfonate Core-2a_B as a white solid (70 mg, yield 37%); LC-MS Rt 0.919 min; MS m/z [M+H]$^+$ 332.0; Method 3.

Intermediate Core-2a_C: Methyl-5-chloro-4-((tosyloxy)methyl)picolinate

Step 1: Methyl-5-chloro-4-(hydroxymethyl)picolinate

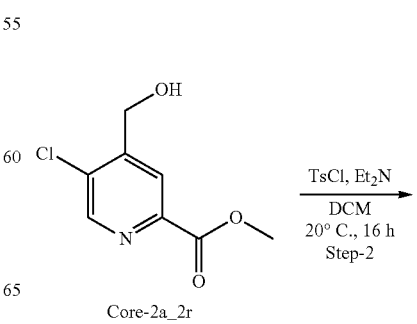

A mixture of (2,5-dichloropyridin-4-yl)methanol Core-2a 1a (200 mg, 1.12 mmol), Pd(dppf)Cl$_2$ (80 mg, 0.11 mmol) and Et 3 N (227 mg, 2.24 mmol) in MeOH (30 mL) was stirred at 80° C. under CO (50 psi) for 16 h. The reaction solution was filtered, and the filtrate was concentrated to afford a residue. The residue was purified by prep-TLC (PE:EtOAc=2:1) to afford methyl-5-chloro-4-(hydroxymethyl)picolinate Core-2a_2r (200 mg, yield: 88%) as a white solid; $^1$H NMR (400 MHz, CDCl$_3$) δ 8.62 (s, 1H), 8.38 (s, 1H), 4.88 (s, 2H), 4.02 (s, 3H).

Step 2: Methyl-5-chloro-4-((tosyloxy)methyl)picolinate

-continued

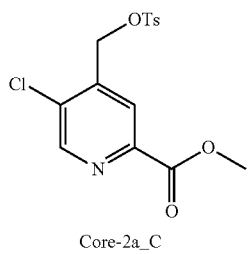

Core-2a_C

To a solution of methyl-5-chloro-4-(hydroxymethyl)picolinate Core-2a_2r (100 mg, 0.50 mmol) in DCM (10 mL) was added Et 3 N (101 mg, 1.00 mmol) and TsCl (143 mg, 0.75 mmol). The mixture was stirred at 20° C. for 16 h. The reaction mixture was concentrated to afford a residue. The residue was purified by column chromatography (PE:EtOAc=4:1) to afford methyl-5-chloro-4-((tosyloxy)methyl) picolinate Core-2a_C (50 mg, yield 28%) as a white solid; LC-MS: Rt=0.841 min; MS m/z [M+H]$^+$ 355.9; Method 3.

Intermediate Core-2a_D: 2-amino-6-(2,2,2-trifluoro-1-phenylethyl)-4,5,6,7-tetrahydrothieno[2,3-c]pyridine-3-carbonitrile Step 1: 8-(2,2,2-trifluoro-1-phenylethyl)-1,4-dioxa-8-azaspiro[4.5]decane

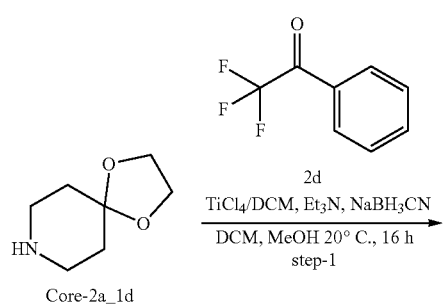

Step 2: 1-(2,2,2-trifluoro-1-phenylethyl)piperidin-4-one

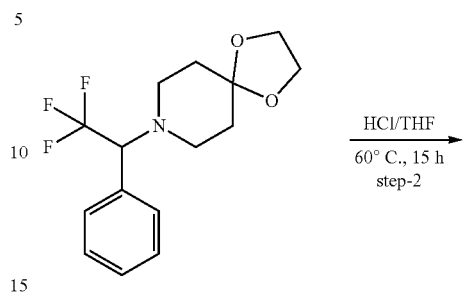

To a solution of 8-(2,2,2-trifluoro-1-phenylethyl)-1,4-dioxa-8-azaspiro[4.5]decane Core-2a 3d (270 mg, 0.89 mmol) in THF (1 mL) was added aq. HCl (4 N, 9 mL, 36 mmol). The reaction was stirred at 60° C. for 16 h. The reaction was diluted by water (5 mL) and washed by MTBE (2×10 mL). The aqueous layer was basified by aq. NaOH (2 N) to pH 9-10. The mixture was extracted by EtOAc (2×20 mL). The organic layers were combined, washed with brine, dried over Na$_2$SO$_4$, and filtered. The filtrate was concentrated to afford 1-(2,2,2-trifluoro-1-phenylethyl)piperidin-4-one Core-2a 4d (130 mg, yield: 56%) as oil; LC-MS Rt 0.956 min; MS m/z [M+H]$^+$ 258.0; Method 1.

Step 3: 2-amino-6-(2,2,2-trifluoro-1-phenylethyl)-4,5,6,7-tetrahydrothieno[2,3-c]pyridine-3-carbonitrile

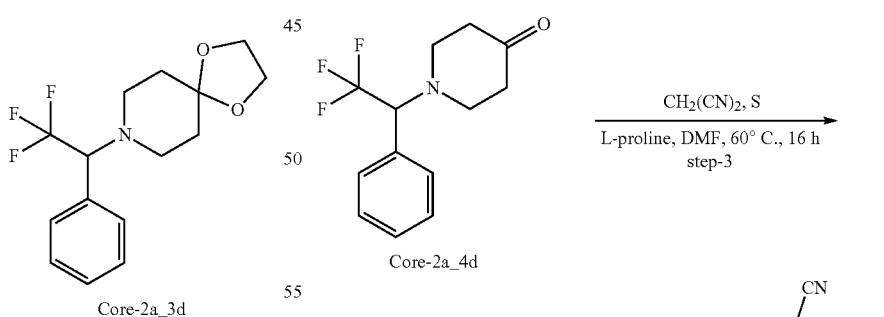

To a solution of (2,5-dichloropyridin-4-yl)methanol Core-2a_1d (100 mg, 0.56 mmol) in DCM (2 mL) was added TsCl (128 mg, 0.67 mmol) and Et 3 N (113 mg, 1.18 mmol). The reaction mixture was stirred for 2 h at 20° C. The reaction mixture was purified by prep-TLC (PE/EtOAc=10/1) directly to afford (2,5-dichloropyridin-4-yl)-methyl-4-methylbenzenesulfonate Core-2a 3d as a white solid (70 mg, yield 37%); LC-MS Rt 0.849 min; MS m/z [M+H]$^+$ 302.1; Method 3.

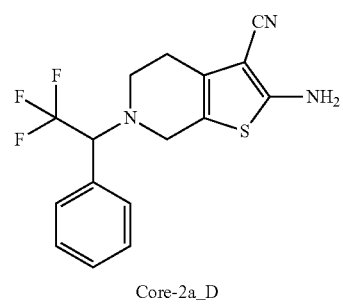

Core-2a_D

To a solution of 1-(2,2,2-trifluoro-1-phenylethyl)piperidin-4-one Core-2a_4d (130 mg, 0.5 mmol) and CH$_2$(ON)$_2$ (40 mg, 0.6 mmol) in DMF (10 mL) was added sulphur (24 mg, 0.75 mmol) and L-proline (10 mg, 0.087 mmol) at 20° C. The mixture was heating at 60° C. for 6 h. The reaction was concentrated, diluted by water (10 mL), and extracted with EtOAc (3×10 mL). The combined organic layers were washed brine and concentrated. The residue was purified by Prep-TLC to afford 2-amino-6-(2,2,2-trifluoro-1-phenylethyl)-4,5,6,7-tetrahydrothieno[2,3-c]pyridine-3-carbonitrile Core-2a_D (100 mg, yield 60%) as yellow solid; LC-MS Rt 0.854 min MS m/z [M+H]$^+$ 338.0; Method 3.

Intermediate Core-2b_A: (R)-tert-butyl 2-amino-3-cyano-5-methyl-4,5-dihydrothieno[2,3-c]pyridine-6(7H)-carboxylate Step 1: (E)-N-methoxy-N-methylbut-2-enamide

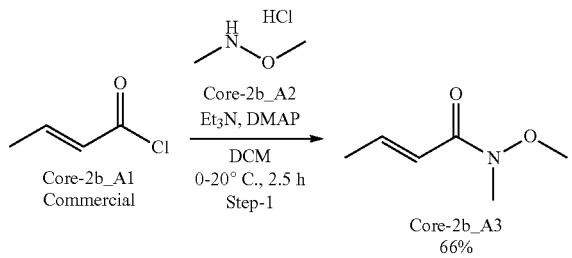

To a solution of N,O-dimethylhydroxylamine hydrochloride Core-2b_A2 (4.7 g, 47.8 mmol) in DCM (200 mL) at 0° C. was added a solution of Et 3 N (11.1 g, 110 mmol) and DMAP (584 mg, 4.78 mmol) in DCM (30 mL). After 30 min, a solution of crotonyl chloride Core-2b_A1 (5.0 g, 47.8 mmol) in DCM (20 mL) was added at 0° C. The mixture was stirred at 20° C. for 2 h. The reaction was quenched with water (200 mL) and extracted with DCM (100 mL×3). The organic layer was dried over anhydrous Na$_2$SO$_4$, filtered and concentrated. The residue was purified by column chromatography (9% ethyl acetate/petroleum ether) to afford (E)-N-methoxy-N-methylbut-2-enamide Core-2b_A3 (4.1 g, yield 66%) as yellow oil; $^1$H NMR (400 MHz, CDCl$_3$) δ 6.97-6.88 (m, 1H), 6.37 (d, J=16 Hz, 1H), 3.65 (s, 3H), 3.18 (s, 3H), 1.86 (d, J=8 Hz, 3H).

Step 2: (R)-2-methyl-1-((S)-1-phenylethyl)piperidin-4-one 6a & (S)-2-methyl-1-((S)-1-phenylethyl)piperidin-4-one

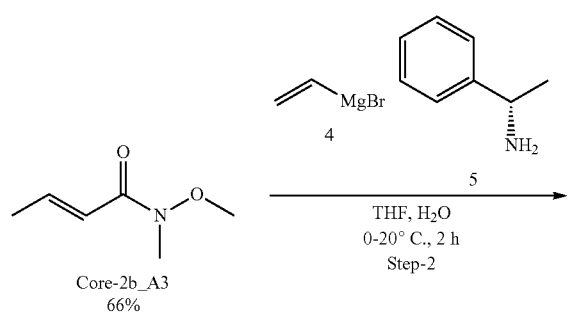

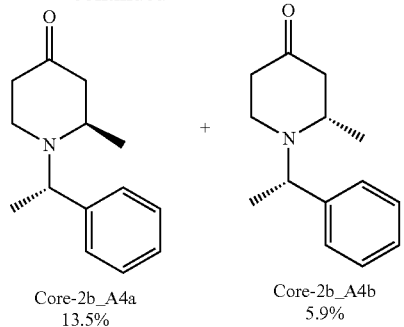

To a solution of Core-2b_A3 (2.0 g, 15.5 mmol) in THF (40 mL) at 0° C. was added dropwise vinylmagnesium bromide (17 mL, 17.0 mmol, 1 N solution in THF) under N$_2$. The reaction was warmed to 20° C. After stirring for 1 h, (S)-1-phenylethanamine (3.8 g, 31.0 mmol) and water (4 mL) was added. The system was stirred for another 1 h. The reaction solution was diluted with water (60 mL), concentrated to remove THF and extracted with DCM (50 mL×3). The organic layers were combined and concentrated. The residue was purified by column chromatography on silica (PE:EtOAc=10:1) to afford Core-2b_A4a (450 mg, yield 13.5%) as yellow solid and Core-2b_A4b (200 mg, yield 5.9%) as yellow solid; Core-2b_A4a, $^1$H NMR (400 MHz, CDCl$_3$) δ 7.47-7.45 (m, 2H), 7.37-7.33 (m, 2H), 7.28-7.26 (m, 1H), 4.05-4.00 (m, 1H), 3.42-3.39 (m, 1H), 2.77-2.67 (m, 3H), 2.28-2.27 (m, 1H), 2.25-2.23 (m, 2H), 1.35 (d, J=6.8 Hz, 3H), 1.15 (d, J=6.8 Hz, 3H); Core-2b_A4b, $^1$H NMR (400 MHz, CDCl$_3$) δ 7.38-7.31 (m, 4H), 7.28-7.27 (m, 1H), 3.96-3.93 (m, 1H), 3.19-3.17 (m, 1H), 2.99-2.95 (m, 2H), 2.60-2.55 (m, 2H), 2.36-2.30 (m, 1H), 2.15-2.10 (m, 1H), 1.44 (d, J=6.8 Hz, 3H), 1.06 (d, J=6.8 Hz, 3H).

Step 3: (R)-tert-butyl 2-methyl-4-oxopiperidine-1-carboxylate

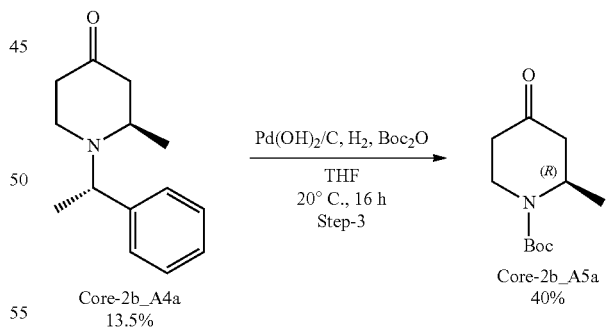

A mixture of Core-2b_A4a (450 mg, 2.1 mmol), Boc$_2$O (698 mg, 3.2 mmol) and Pd(OH)$_2$/C (50 mg, cat.) in THF (40 mL) at 20° C. was hydrogenated under H$_2$ (50 psi) for 16 h. The reaction mixture was filtered, and the filtrate was concentrated. The residue was purified by column chromatography on silica (20% EtOAc/PE) to afford Core-2b_A5a (180 mg, yield 40%) as white solid; $^1$H NMR (400 MHz, CDCl$_3$) δ 4.72 (brs, 1H), 4.27-4.22 (m, 1H), 3.36-3.32 (m, 1H), 2.72-2.66 (m, 1H), 2.58-2.42 (m, 1H), 2.37-2.25 (m, 2H), 1.50 (s, 9H), 1.19 (d, J=8 Hz, 3H).

Step 4: (R)-tert-butyl 2-amino-3-cyano-5-methyl-4,5-dihydrothieno[2,3-c]pyridine-6(7H)-carboxylate & (R)-tert-butyl 2-amino-3-cyano-7-methyl-4,5-dihydrothieno[2,3-c]pyridine-6(7H)-carboxylate

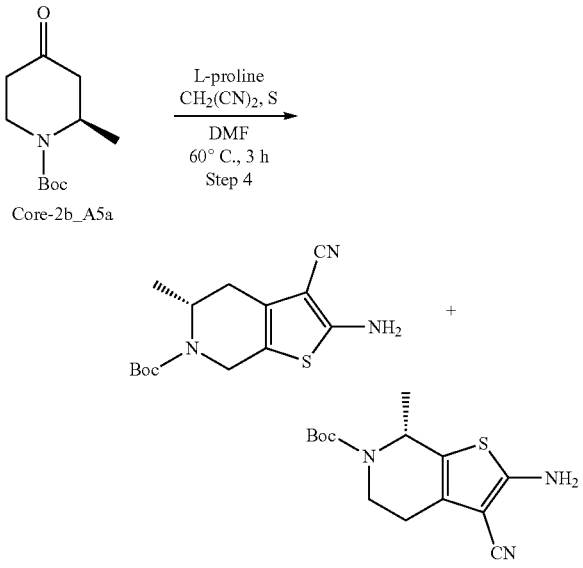

To a solution of (R)-tert-butyl 2-methyl-4-oxopiperidine-1-carboxylate Core-2b_A5a (180 mg, 0.84 mmol) and CH$_2$(ON)$_2$ (61 mg, 0.93 mmol) in DMF (6 mL) at 20° C. was added sulphur (40 mg, 1.26 mmol) and L-proline (10 mg, 0.084 mmol). The mixture was stirred at 20° C. for 10 min followed by heating at 60° C. for 3 h. The reaction solution was diluted with water (20 mL) and extracted with EtOAc (15 mL×3). The organic layer was concentrated. The residue was purified by column chromatography on silica (PE: EtOAc=4:1) to afford a mixture of (R)-tert-butyl 2-amino-3-cyano-5-methyl-4,5-dihydrothieno[2,3-c]pyridine-6(7H)-carboxylate and (R)-tert-butyl 2-amino-3-cyano-7-methyl-4,5-dihydrothieno[2,3-c]pyridine-6(7H)-carboxylate (190 mg) as yellow solid; LC-MS Rt 0.81 min; MS m/z [M+H]$^+$ 294.10; Method 3.

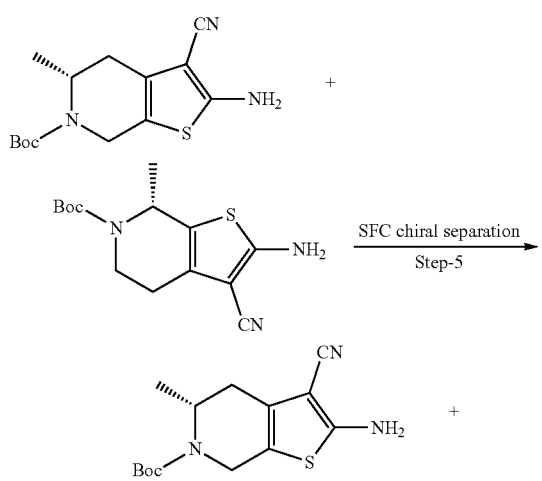

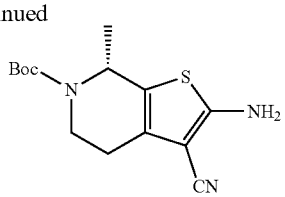

Procedure: The mixture of regioisomers (190 mg) was submitted for chiral SFC to afford (R)-tert-butyl 2-amino-3-cyano-5-methyl-4,5-dihydrothieno[2,3-c]pyridine-6(7H)-carboxylate (86.9 mg, 96% ee) and (R)-tert-butyl 2-amino-3-cyano-7-methyl-4,5-dihydrothieno[2,3-c]pyridine-6(7H)-carboxylate (44.6 mg, 100% ee).

Chiral SFC separation (condition a: Column: OJ-10 urn, 250 mm*30 mm, I.D, 5 um; Mobile Phase: A for CO$_2$, B for EtOH (0.1% Ammonia); Isocratic: 25% Phase B; Total Flow: 55 mL/min; Back Pressure: 100 Bar; UV: 220 nm; Instrument: SFC 80.

(R)-tert-butyl 2-amino-3-cyano-5-methyl-4,5-dihydrothieno[2,3-c]pyridine-6(7H)-carboxylate: $^1$H NMR (400 MHz, DMSO-d$_6$) δ 7.16 (s, 2H), 4.56-4.52 (m, 2H), 3.87-3.83 (m, 1H), 2.65-2.61 (m, 1H), 2.27-2.22 (m, 1H), 1.42 (s, 9H), 1.06 (d, J=6.4 Hz, 3H).

(R)-tert-butyl 2-amino-3-cyano-7-methyl-4,5-dihydrothieno[2,3-c]pyridine-6(7H)-carboxylate: $^1$H NMR (400 MHz, DMSO-d$_6$) δ 7.17 (s, 2H), 4.90-4.84 (m, 1H), 4.11-4.08 (m, 1H), 3.03-2.92 (m, 1H), 2.40-2.36 (m, 2H), 1.42 (s, 9H), 1.26 (d, J=6.4 Hz, 3H).

Intermediate Core-2b_B: (R)-tert-butyl 2-amino-3-cyano-5-methyl-4,5-dihydrothieno[2,3-c]pyridine-6(7H)-carboxylate

Step 1: (S)-tert-butyl 2-methyl-4-oxopiperidine-1-carboxylate

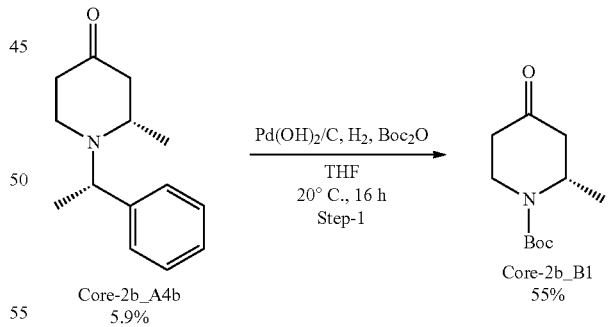

A mixture of Core-2b_A4b (200 mg, 0.92 mmol), Boc$_2$O (301 mg, 1.38 mmol) and Pd(OH)$_2$/C (50 mg, cat.) in THF (30 mL) was hydrogenated at 20° C. under H$_2$ (50 psi) for 16 h. The reaction was filtered, and the filtrate was concentrated. The residue was purified by column chromatography (PE:EtOAc=4:1) to afford Core-2b_B1 (110 mg, yield 55%) as white solid; $^1$H NMR (400 MHz, CDCl$_3$) δ 4.64 (brs, 1H), 4.19-4.14 (m, 1H), 3.28-3.25 (m, 1H), 2.63-2.58 (m, 1H), 2.41-2.39 (m, 1H), 2.29-2.25 (m, 1H), 2.20-2.16 (m, 1H), 1.48 (s, 9H), 1.11 (d, J=8 Hz, 3H).

Step 2: (S)-tert-butyl 2-amino-3-cyano-5-methyl-4,5-dihydrothieno[2,3-c]pyridine-6(7H)-carboxylate & (S)-tert-butyl 2-amino-3-cyano-7-methyl-4,5-dihydrothieno[2,3-c]pyridine-6(7H)-carboxylate

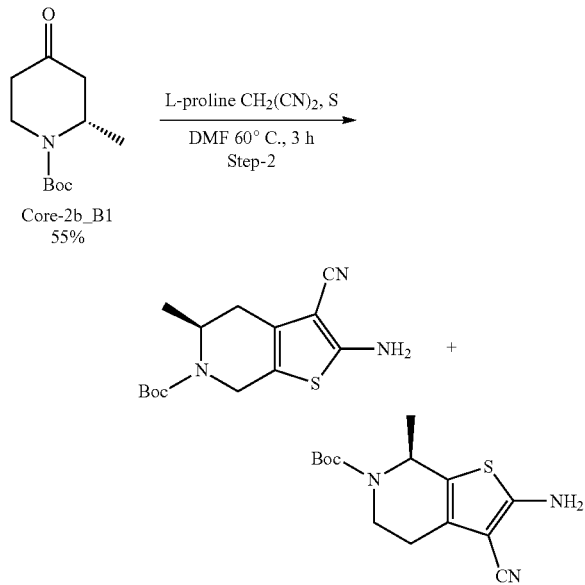

To a solution of Core-2b_B1 (110 mg, 0.52 mmol) and CH₂(ON)₂ (38 mg, 0.57 mmol) in DMF (3 mL) at 20° C. was added sulphur (25 mg, 0.78 mmol) and L-proline (6 mg, 0.052 mmol). The mixture was stirred at 20° C. for 10 min followed by heating at 60° C. for 3 h. The reaction solution was diluted with water (20 mL) and extracted with EtOAc (15 mL×3). The organic layer was concentrated. The residue was purified by column chromatography on silica (20% ethyl acetate/petroleum ether) to afford a mixture (130 mg) of (S)-tert-butyl 2-amino-3-cyano-5-methyl-4,5-dihydrothieno[2,3-c]pyridine-6(7H)-carboxylate and (S)-tert-butyl 2-amino-3-cyano-7-methyl-4,5-dihydrothieno[2,3-c]pyridine-6(7H)-carboxylate (130 mg) as yellow solid; LC-MS Rt 0.81 min; MS m/z [M+H]⁺ 294.10; Method 3.

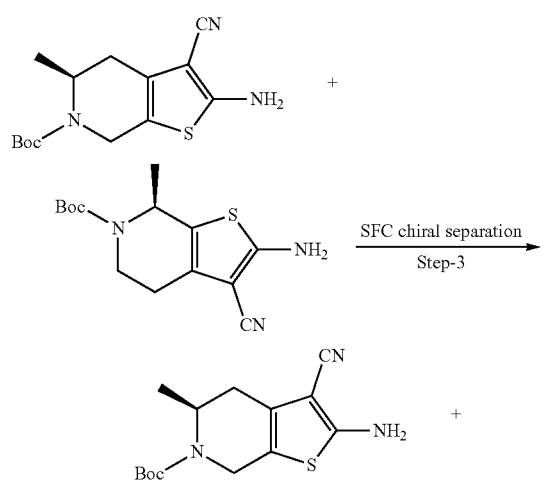

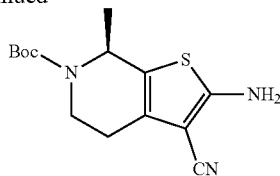

Procedure: A mixture (130 mg) of (S)-tert-butyl 2-amino-3-cyano-5-methyl-4,5-dihydrothieno[2,3-c]pyridine-6(7H)-carboxylate and (S)-tert-butyl 2-amino-3-cyano-7-methyl-4,5-dihydrothieno[2,3-c]pyridine-6(7H)-carboxylate was submitted for chiral SFC to afford (S)-tert-butyl 2-amino-3-cyano-5-methyl-4,5-dihydrothieno[2,3-c]pyridine-6(7H)-carboxylate (57.2 mg, 100% ee) and (S)-tert-butyl 2-amino-3-cyano-7-methyl-4,5-dihydrothieno[2,3-c]pyridine-6(7H)-carboxylate (32.2 mg, 100% ee); LC-MS Rt 0.84 min; MS m/z [M−55]⁺ 238.0; Method 3.

Chiral SFC separation (condition a: Column: OJ-10 um, 250 mm*30 mm, I.D, 5 um; Mobile Phase: A for CO₂, B for EtOH (0.1% Ammonia); Isocratic: 20% Phase B; Total Flow: 55 mL/min; Back Pressure: 100 Bar; UV: 220 nm; Instrument: SFC 80.

(S)-tert-butyl 2-amino-3-cyano-5-methyl-4,5-dihydrothieno[2,3-c]pyridine-6(7H)-carboxylate: ¹H NMR (400 MHz, DMSO-d₆) δ 7.16 (s, 2H), 4.59-4.52 (m, 2H), 3.87-3.83 (m, 1H), 2.66-2.61 (m, 1H), 2.27-2.22 (m, 1H), 1.42 (s, 9H), 1.06 (d, J=6.4 Hz, 3H).

(S)-tert-butyl 2-amino-3-cyano-7-methyl-4,5-dihydrothieno[2,3-c]pyridine-6(7H)-carboxylate: ¹H NMR (400 MHz, DMSO-d₆) δ 7.18 (s, 2H), 4.89-4.84 (m, 1H), 4.11-4.08 (m, 1H), 3.03-2.92 (m, 1H), 2.40-2.36 (m, 2H), 1.42 (s, 9H), 1.26 (d, J=6.4 Hz, 3H).

Intermediates Core-8_A and Core-9_B: 2-amino-5,6,7,8-tetrahydro-4H-thieno[2,3-d]azepine-3-carbonitrile & 2-amino-5,6,7,8-tetrahydro-4H-thieno[2,3-c]azepine-3-carbonitrile Step 1: tert-butyl-2-amino-3-cyano-7,8-dihydro-4H-thieno[2,3-d]azepine-6(5H)-carboxylate & tert-butyl-2-amino-3-cyano-5,6-dihydro-4H-thieno[2,3-c]azepine-7(8H)-carboxylate

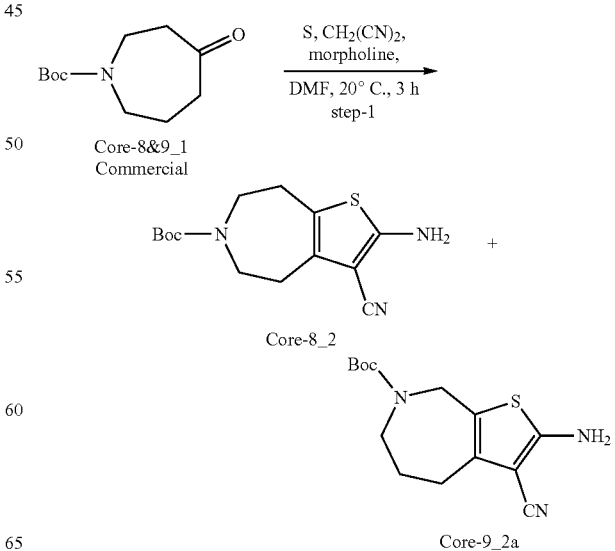

To a solution of tert-butyl-4-oxoazepane-1-carboxylate Core-8&9_1 (5.00 g, 23.4 mmol) and CH₂(CN)₂ (3.10 g, 46.8 mmol) in DMF (50 mL) were added with sulfur (1.50 g, 23.4 mmol) and morpholine (1.02 g, 11.7 mmol). The reaction mixture was stirred at 20° C. for 3 h. The reaction mixture was poured into water (100 mL) and extracted with EtOAc (100 mL×3). The combined organic layers were washed with water (300 mL) and brine (300 mL×3), dried over Na₂SO₄, filtered and concentrated under reduced pressure. The residue was purified by column chromatography on silica gel (PE:EtOAc=10:1 to 2:1) to give a mixture of tert-butyl-2-amino-3-cyano-7,8-dihydro-4H-thieno[2,3-d]azepine-6(5H)-carboxylate Core-8_2 & tert-butyl-2-amino-3-cyano-5,6-dihydro-4H-thieno[2,3-c]azepine-7(8H)-carboxylate Core-9_2a (3.02 g, yield 44%); LC-MS Rt 0.93 min; MS m/z [M+H-56]+237.9; Method 1.

Step 2: 2-amino-5,6,7,8-tetrahydro-4H-thieno[2,3-d]azepine-3-carbonitrile & 2-amino-5,6,7,8-tetrahydro-4H-thieno[2,3-c]azepine-3-carbonitrile

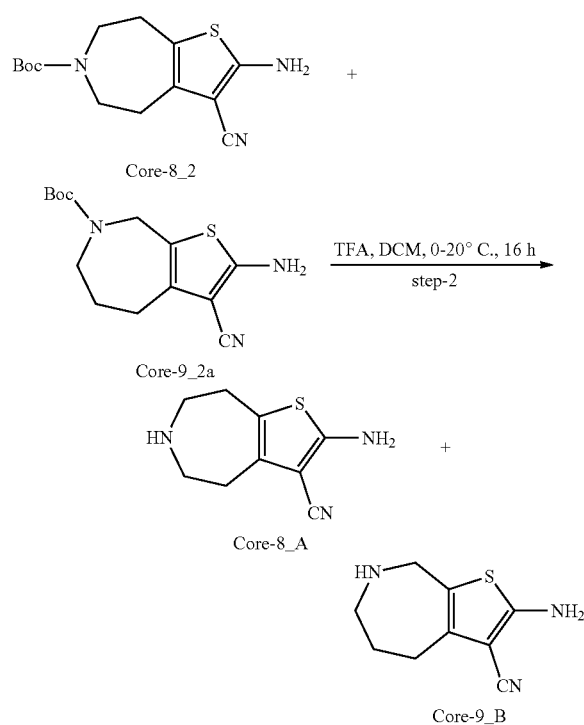

To a solution of tert-butyl-2-amino-3-cyano-7,8-dihydro-4H-thieno[2,3-d]azepine-6(5H)-carboxylate Core-8_2 & tert-butyl-2-amino-3-cyano-5,6-dihydro-4H-thieno[2,3-c]azepine-7(8H)-carboxylate Core-9_2a (3.00 g, 10.23 mmol) in DCM (27 mL) was added TFA (3.0 mL) at 0° C. The reaction mixture was stirred at 20° C. for 16 h. The reaction mixture was dissolved in water (50 mL) and extracted with DCM (50 mL×2). The aqueous layer was adjusted pH to 8-9 with sat. Na₂CO₃ and extracted with DCM (50 mL×3). The organic layers were combined, washed with brine (100 mL), dried over anhydrous Na₂SO₄ and concentrated to give a mixture 2-amino-5,6,7,8-tetrahydro-4H-thieno[2,3-d]azepine-3-carbonitrile Core-8_A & 2-amino-5,6,7,8-tetrahydro-4H-thieno[2,3-c]azepine-3-carbonitrile Core-8_B (2.23 g, crude), which was used directly for the next step; LC-MS Rt 0.66 & 0.71 min; MS m/z [M+H]⁺ 193.9 & [M+H-17]+176.9, Method 1.

2-Amino-6-(3-fluorobenzyl)-5,6,7,8-tetrahydro-4H-thieno[2,3-d]azepine-3-carbonitrile & 2-amino-7-(3-fluorobenzyl)-5,6,7,8-tetrahydro-4H-thieno[2,3-c]azepine-3-carbonitrile

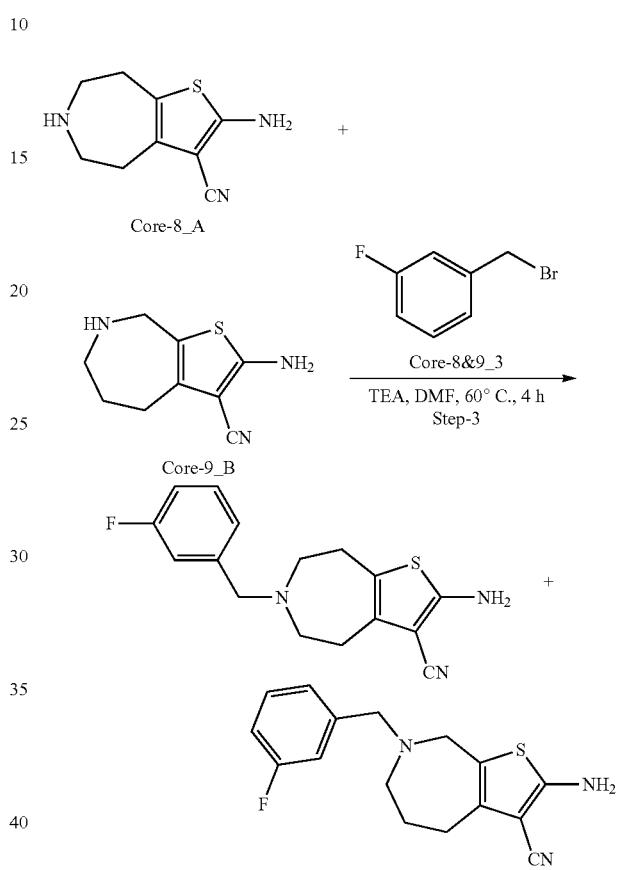

To a solution of 2-amino-5,6,7,8-tetrahydro-4H-thieno[2,3-d]azepine-3-carbonitrile Core-8_A and 2-amino-5,6,7,8-tetrahydro-4H-thieno[2,3-c]azepine-3-carbonitrile Core-9_B (400.0 mg, 2.07 mmol) in DMF (10 mL) were added 1-(bromomethyl)-3-fluorobenzene Core-8&9_3 (470 mg, 2.48 mmoL) and DIPEA (535 mg, 4.14 mmol). The reaction mixture was stirred at 60° C. for 4 h. The reaction mixture was poured into water (50 mL) and extracted with EtOAc (50 mL×3). The combined organic layers were washed with brine (50 mL×2), dried over Na₂SO₄ and concentrated. The residue was purified by column chromatography on silica gel (PE:EtOAc=10:1) to give the crude product (400 mg), which was further purified by prep-TLC (PE:EtOAc=5:1) to afford a mixture of product (350 mg, yield 56.11%). Then the mixture was purified by SFC to give 2-amino-6-(3-fluorobenzyl)-5,6,7,8-tetrahydro-4H-thieno[2,3-d]azepine-3-carbonitrile (125 mg, peak 2.; ¹H NMR (400 MHz, CDCl₃) δ 7.31-7.27 (m, 1H), 7.12 (d, J=7.6 Hz, 2H), 6.98-6.94 (m, 1H), 4.54 (br s, 2H), 3.73 (s, 2H), 2.79-2.63 (m, 8H).; LC-MS: Rt=0.98 min, MS m/z [M+H]⁺ 302.0; Method 1) and 2-amino-7-(3-fluorobenzyl)-5,6,7,8-tetrahydro-4H-thieno[2,3-c]azepine-3-carbonitrile (105 mg, peak 1; 1 H NMR (400 MHz, CDCl₃) δ 7.31-7.27 (m, 1H), 7.09-7.05 (m, 2H), 6.96 (dt, J=8.4, 1.9 Hz, 1H), 4.59 (br s, 2H), 3.66 (s, 2H), 3.63 (s, 2H), 3.20-3.17 (m, 2H), 2.78-2.75 (m, 2H), 1.78-1.73 (m, 2H); LC-MS Rt 0.979 min, MS m/z [M+H]+ 302.0; Method 1.

2-Amino-6-(cyclohexylmethyl)-5,6,7,8-tetrahydro-4H-thieno[2,3-d]azepine-3-carbonitrile & 2-amino-7-(cyclohexylmethyl)-5,6,7,8-tetrahydro-4H-thieno[2,3-c]azepine-3-carbo-nitrile

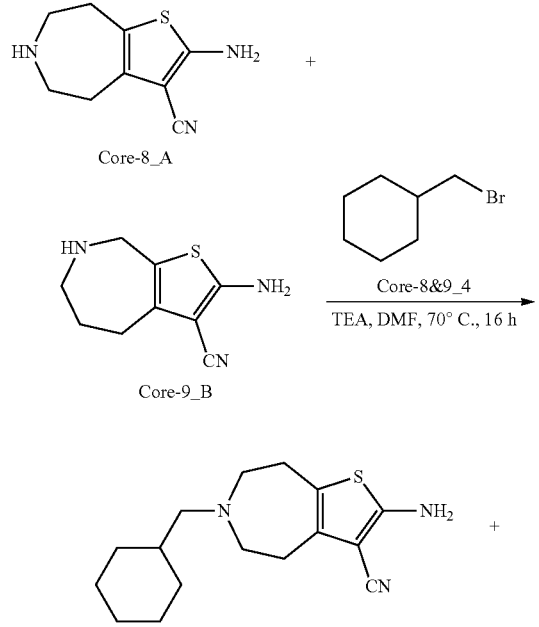

The title compound was prepared by a method similar to that of Example 1 by replacing 1-(bromomethyl)-3-fluorobenzene 5 (Example 1 step 3) with the mixture of 2-amino-5,6,7,8-tetrahydro-4H-thieno[2,3-d]azepine-3-carbonitrile (Intermediate Core-8_A) and 2-amino-5,6,7,8-tetrahydro-4H-thieno[2,3-c]azepine-3-carbonitrile (Intermediate Core-9_B) in DMF for 16 h; 2-Amino-6-(cyclohexylmethyl)-5,6,7,8-tetrahydro-4H-thieno[2,3-d]azepine-3-carbonitrile (145.0 mg, yield 7%; (400 MHz, CDCl$_3$) δ 4.54 (br s, 2H), 2.81-2.70 (m, 8H), 2.38 (d, J=6.8 Hz, 2H), 1.82-1.71 (m, 5H), 1.61-1.48 (m, 1H), 1.28-1.19 (m, 3H), 0.94-0.87 (m, 2H); LC-MS Rt 1.08 min, MS m/z [M+H]+ 290.0; Method 1) and 2-amino-7-(cyclohexylmethyl)-5,6,7,8-tetrahydro-4H-thieno[2,3-c]azepine-3-carbonitrile (110.0 mg, yield 6%; $^1$H NMR ((400 MHz, CDCl$_3$) δ 4.49 (br s, 2H), 3.62 (s, 2H), 3.04-2.99 (m, 2H), 2.65-2.62 (m, 2H), 2.17 (d, J=7.2 Hz, 2H), 1.65-1.57 (m, 7H), 1.41-1.24 (m, 1H), 1.17-1.09 (m, 3H), 0.79-0.74 (m, 2H); LC-MS Rt 0.61 min, MS m/z [M+H]+ 290.2; Method 2).

Preparation of Examples

Example 1: N-(3-cyano-5-((3-fluorobicyclo[1.1.1]pentan-1-yl)methyl)-4,5,6,7-tetrahydrothieno[3,2-c]pyridin-2-yl)-2-(4-sulfamoylphenyl)acetamide

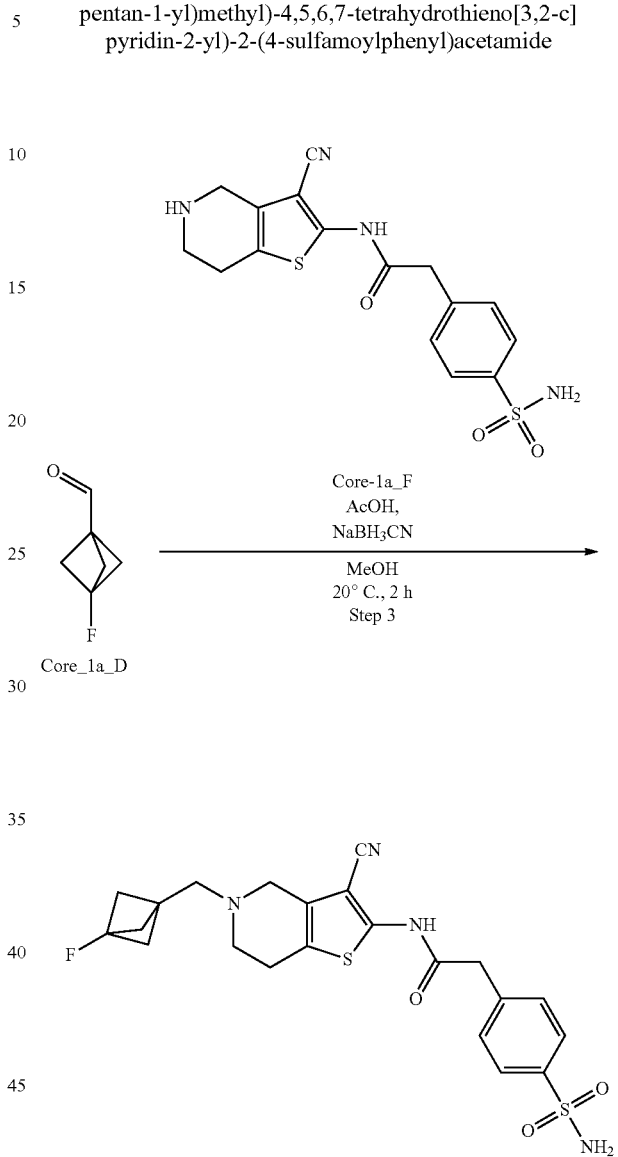

To a solution of N-(3-cyano-4,5,6,7-tetrahydrothieno[3,2-c]pyridin-2-yl)-2-(4-sulfamoylphenyl)acetamide Core-1a_F (20 mg, 0.05 mmol) in MeOH (2 mL) was added AcOH (0.02 mL, cat.) and a solution of 3-fluorobicyclo[1.1.1]pentane-1-carbaldehyde Core 1a_D (crude) in DCM (1 mL). The mixture was stirred at 20° C. for 1 h. NaBH$_3$CN (10 mg, 0.15 mmol) was added. The mixture was stirred at 20° C. for another 1 h. The reaction mixture was purified by prep-TLC (11% MeOH in DCM) to afford the desired product (10 mg, crude) as white solid. The crude product was mixed with another batch and further purified by Prep-TLC (11% MeOH in DCM) to afford the title compound (5.6 mg) as white solid. $^1$H NMR (400 MHz, CD$_3$OD) δ 7.89 (d, J=8.4 Hz, 2H), 7.53 (d, J=8.4 Hz, 2H), 3.97 (s, 2H), 3.60 (s, 2H), 2.95 (s, 2H), 2.90-2.88 (m, 2H), 2.80-2.78 (m, 2H), 2.08 (d, J=2.4 Hz, 6H). LC-MS Rt 1.51 min; MS m/z [M+H]+ 475.1; Method 1.

Example 2: N-(3-cyano-5-((3,3-difluorocyclobutyl)methyl)-4,5,6,7-tetrahydrothieno[3,2-c]pyridin-2-yl)-2-(4-sulfamoylphenyl)acetamide

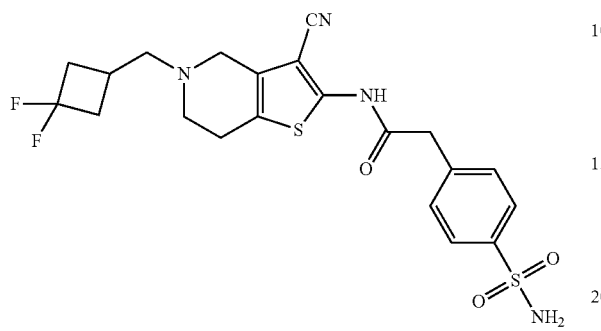

Example 2 was prepared by a method similar to that of Example 1 by using N-(3-cyano-4,5,6,7-tetrahydrothieno[3,2-c]pyridin-2-yl)-2-(4-sulfamoylphenyl)acetamide with the appropriate aldehyde derivative (either commercially available or preparations described hereinabove). $^1$H NMR (400 MHz, DMSO-d$_6$) δ 11.89 (s, 1H), 7.77 (d, J=8.3 Hz, 2H), 7.48 (d, J=8.4 Hz, 2H), 7.31 (s, 2H), 3.90 (s, 2H), 3.41 (s, 2H), 2.78-2.59 (m, 8H), 2.41 (d, J=6.7 Hz, 1H), 2.35-2.19 (m, 2H); LC-MS Rt 0.85 min; MS m/z [M+H]$^+$ 481.0; Method 1.

Example 3: N-(3-cyano-5-(1-cyclohexylethyl)-4,5,6,7-tetrahydrothieno[3,2-c]pyridin-2-yl)-2-(4-sulfamoylphenyl)acetamide

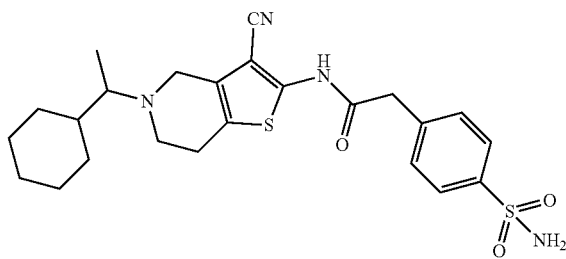 [SMILES: CC(C1CCCCC1)N1CCc2sc(NC(=O)Cc3ccc(S(N)(=O)=O)cc3)c(C#N)c2C1]

Example 3 was prepared by a method similar to that of Example 1 by using N-(3-cyano-4,5,6,7-tetrahydrothieno[3,2-c]pyridin-2-yl)-2-(4-sulfamoylphenyl)acetamide (Core-1a_F) with the appropriate aldehyde derivative (either commercially available or preparations described hereinabove). $^1$H NMR (400 MHz, DMSO-d$_6$) δ 8.36 (s, 1H), 7.75 (d, J=8.4 Hz, 2H), 7.47 (d, J=8.4 Hz, 2H), 7.28 (s, 2H), 3.83 (s, 2H), 3.50 (d, J=14.6 Hz, 2H), 2.82 (d, J=5.2 Hz, 1H), 2.42 (d, J=8.6 Hz, 1H), 2.04-1.92 (m, 3H), 1.76-1.57 (m, 4H), 1.12 (d, J=23.3 Hz, 3H), 0.95 (d, J=6.6 Hz, 3H), 0.92-0.82 (m, 3H); LC-MS Rt 0.66 min, MS m/z [M+H]$^+$ 487.1; Method 5.

Example 4: N-(3-cyano-5-(cyclopentylmethyl)-4,5,6,7-tetrahydrothieno[3,2-c]pyridin-2-yl)-2-(4-sulfamoylphenyl)acetamide

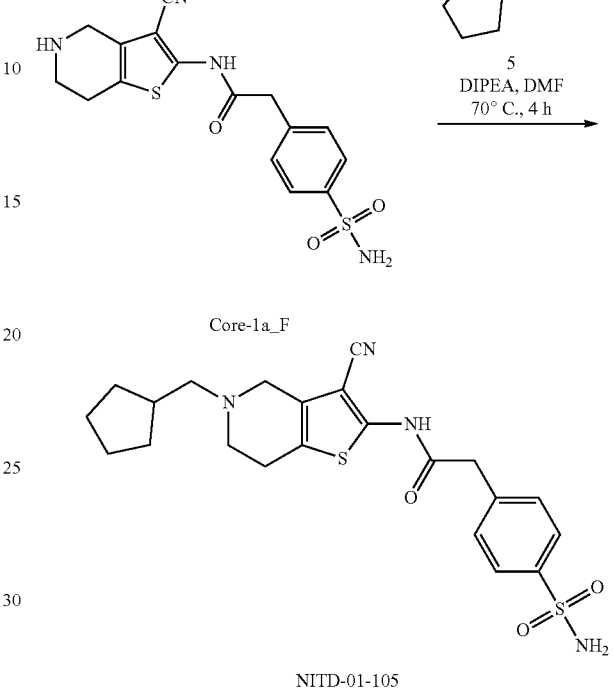

To a stirred solution of N-(3-cyano-4,5,6,7-tetrahydrothieno[3,2-c]pyridin-2-yl)-2-(4-sulfamoylphenyl)acetamide Core-1a_F (100.0 mg, 0.26 mmol) and (bromomethyl)cyclopentane 5 (52.0 mg, 0.32 mmol) in DMF (2.0 mL) was added DIPEA (68.7 mg, 0.52 mmol). The reaction mixture was stirred at 70° C. for 4 h. The reaction mixture was purified by prep-HPLC (NH$_3$H$_2$O) to afford N-(3-cyano-5-(cyclopentylmethyl)-4,5,6,7-tetrahydrothieno[3,2-c]pyridin-2-yl)-2-(4-sulfamoylphenyl)acetamide (24.0 mg, yield 20%). $^1$H NMR (400 MHz, DMSO-d$_6$) δ 11.88 (s, 1H), 7.78 (d, J=8.2 Hz, 2H), 7.49 (d, J=8.2 Hz, 2H), 7.33 (s, 2H), 3.95 (s, 2H), 3.40 (s, 2H), 2.75-2.61 (m, 4H), 2.40 (d, J=7.4 Hz, 2H), 2.21-2.06 (m, 1H), 1.71 (d, J=6.7 Hz, 2H), 1.61-1.44 (m, 4H), 1.26-1.16 (m, 2H); LC-MS Rt 0.93 min; MS m/z [M+H]$^+$ 459.1; Method 1.

Example 5: N-(3-cyano-5-(3-fluorobenzyl)-4,5,6,7-tetrahydrothieno[3,2-c]pyridin-2-yl)-2-(4-sulfamoylphenyl)acetamide

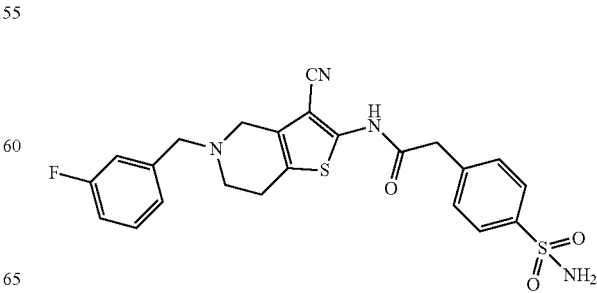

Example 5 was prepared by a similar method to that of Core 2a (K$_2$CO$_3$, rt., 16 h) by using N-(3-cyano-4,5,6,7-tetrahydrothieno[3,2-c]pyridin-2-yl)-2-(4-sulfamoylphenyl)acetamide (00040E) with the appropriate halide derivative (either commercially available or preparations described hereinabove). $^1$H NMR (400 MHz, DMSO-d$_6$) δ 11.89 (s, 1H), 7.79-7.75 (m, 2H), 7.50-7.45 (m, 2H), 7.43-7.36 (m, 1H), 7.31 (s, 2H), 7.19 (t, J=9.4 Hz, 2H), 7.10 (td, J=8.7, 8.3, 2.7 Hz, 1H), 3.95 (s, 2H), 3.72 (s, 2H), 3.42 (s, 2H), 2.77-2.69 (m, 3H), 2.67 (s, 2H); LC-MS Rt 0.61 min, MS m/z [M+H]$^+$ 485.1; Method 5.

Example 6: N-(3-cyano-5-(cyclohexylmethyl)-4,5,6,7-tetrahydrothieno[3,2-c]pyridin-2-yl)-2-(4-sulfamoylphenyl)acetamide

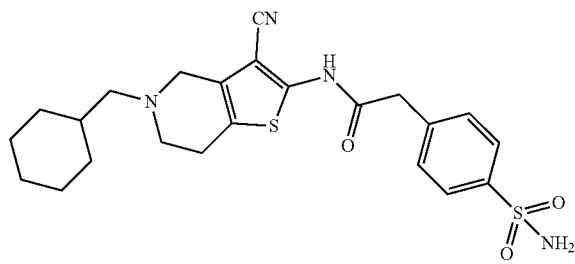 [SMILES: N#Cc1c(NC(=O)Cc2ccc(S(N)(=O)=O)cc2)sc2c1CN(CC1CCCCC1)CC2]

$^1$H NMR (400 MHz, DMSO-d$_6$) δ 7.80-7.75 (m, 2H), 7.48 (d, J=8.4 Hz, 2H), 7.31 (s, 2H), 3.95 (s, 2H), 3.36 (s, 2H), 2.66 (d, J=3.7 Hz, 4H), 2.30 (d, J=7.2 Hz, 2H), 1.79-1.50 (m, 6H), 1.29-1.11 (m, 3H), 0.93-0.80 (m, 2H); LC-MS Rt 0.62 min, MS m/z [M+H]$^+$ 473.0: Method 5.

Example 7: N-(3-cyano-5-(cyclohexylmethyl)-4,5,6,7-tetrahydrothieno[3,2-c]pyridin-2-yl)-2-(3-methoxy-4-sulfamoylphenyl)acetamide

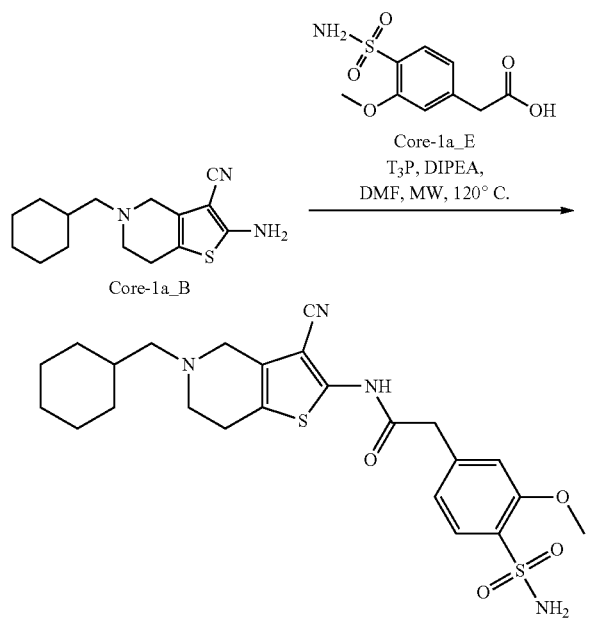

To a solution of 2-amino-5-(cyclohexylmethyl)-4,5,6,7-tetrahydrothieno[3,2-c]pyridine-3-carbonitrile core-1a_B (600 mg, 2.2 mmol) and 2-(3-methoxy-4-sulfamoylphenyl)acetic acid Core-1a_E (809 mg, 3.3 mmol) in DMF (6 mL) were added DIPEA (568 mg, 4.4 mmol) and T$_3$P (2.1 g, 3.3 mmol). The reaction mixture was stirred at 120° C. under microwave for 45 min. Then the reaction mixture was poured into water (60 mL) and Na$_2$CO$_3$ was added to adjusted pH to 8-9. The mixture was extracted with EtOAc (60 mL×3) and the organic layers were combined, dried over Na$_2$SO$_4$, and concentrated. The crude product was washed by MeOH to afford N-(3-cyano-5-(cyclohexylmethyl)-4,5,6,7-tetrahydrothieno[3,2-c]pyridin-2-yl)-2-(3-methoxy-4-sulfamoylphenyl)acetamide (315.0 mg, 16%) as white solid, and the mother liquor was purified by pre-HPLC (NH$_3$·H$_2$O) to afford another batch (232.0 mg, 12%). $^1$H NMR (400 MHz, DMSO-d$_6$) δ 11.87 (s, 1H), 7.67 (d, J=8.0 Hz, 1H), 7.16 (s, 1H), 7.03 (s, 2H), 6.97 (d, J=8.0 Hz, 1H), 3.93 (s, 2H), 3.89 (s, 3H), 3.34 (s, 2H), 2.65 (s, 4H), 2.29 (d, J=7.0 Hz, 2H), 1.75-1.72 (m, 6H), 1.27-1.09 (m, 3H), 0.90-0.81 (m, 2H); LC-MS Rt 0.67 min; MS m/z [M+H]$^+$ 503.1; Method 3.

Examples 8 to 20 were prepared by a similar method to that of Example 3 by using 2-amino-5-(cyclohexylmethyl)-4,5,6,7-tetrahydrothieno[3,2-c]pyridine-3-carbonitrile core-1a_B with the appropriate acid derivatives (either commercially available or preparations described hereinabove).

Example 8: N-(3-cyano-5-(cyclohexylmethyl)-4,5,6,7-tetrahydrothieno[3,2-c]pyridin-2-yl)-2-(4-(1,1,1-trifluoro-2-hydroxypropan-2-yl)phenyl)acetamide

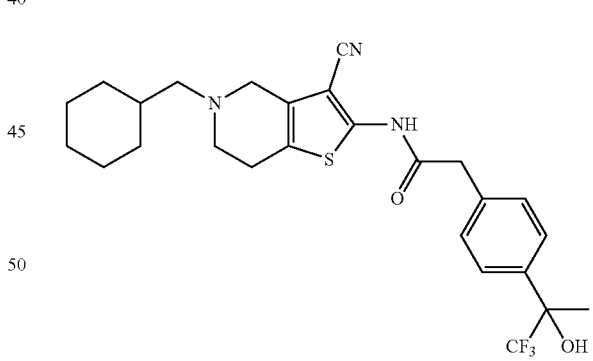

$^1$H NMR (400 MHz, DMSO-d$_6$) δ 11.84 (s, 1H), 7.54 (d, J=8.3 Hz, 2H), 7.35-7.27 (m, 2H), 6.54 (s, 1H), 3.86 (s, 2H), 3.36-3.35 (m, 2H), 2.66 (q, J=4.5, 3.6 Hz, 4H), 2.30 (d, J=7.2 Hz, 2H), 1.74 (d, J=13.3 Hz, 2H), 1.65 (d, J=9.8 Hz, 6H), 1.55 (tt, J=7.3, 3.6 Hz, 1H), 1.29-1.11 (m, 3H), 0.86 (q, J=13.4, 12.7 Hz, 2H); LC-MS Rt 0.79 min, MS m/z [M+H]$^+$ 506.2; Method 5.

Example 9: N-(3-cyano-5-(cyclohexylmethyl)-4,5,6,7-tetrahydrothieno[3,2-c]pyridin-2-yl)-2-(3-fluoro-4-sulfamoylphenyl)acetamide

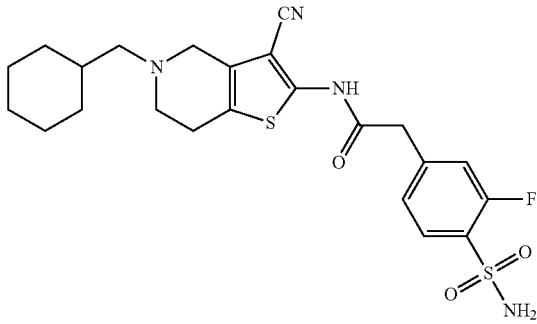 [SMILES: N#Cc1c(NC(=O)Cc2ccc(S(N)(=O)=O)c(F)c2)sc2c1CN(CC1CCCCC1)CC2]

$^1$H NMR (400 MHz, DMSO-d$_6$) δ 7.74 (t, J=7.9 Hz, 1H), 7.61 (s, 2H), 7.36 (d, J=11.3 Hz, 1H), 7.27 (dd, J=8.1, 1.3 Hz, 1H), 3.94 (s, 2H), 3.35 (s, 2H), 2.65 (d, J=3.9 Hz, 4H), 2.30 (d, J=7.2 Hz, 2H), 1.80-1.50 (m, 6H), 1.20 (dq, J=23.6, 11.5, 10.9 Hz, 3H), 0.86 (q, J=13.5, 12.6 Hz, 2H); LC-MS Rt 0.60 min, MS m/z [M+H]$^+$ 491.1; Method 5.

Example 10: N-(3-cyano-5-(cyclohexylmethyl)-4,5,6,7-tetrahydrothieno[3,2-c]pyridin-2-yl)-2-(3-methoxy-4-(methylsulfonyl)phenyl)acetamide

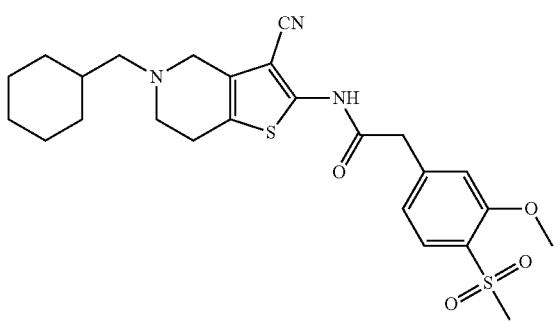 [SMILES: COc1cc(CC(=O)Nc2sc3c(c2C#N)CN(CC2CCCCC2)CC3)ccc1S(C)(=O)=O]

$^1$H NMR (400 MHz, DMSO-d$_6$) δ 7.75 (d, J=8.0 Hz, 1H), 7.27 (d, J=1.4 Hz, 1H), 7.08 (dd, J=8.1, 1.5 Hz, 1H), 3.96 (d, J=6.4 Hz, 5H), 3.36 (s, 2H), 3.22 (s, 3H), 2.66 (d, J=4.1 Hz, 4H), 2.30 (d, J=7.2 Hz, 2H), 1.74 (d, J=13.0 Hz, 2H), 1.66 (d, J=12.8 Hz, 3H), 1.55 (tt, J=7.2, 3.5 Hz, 1H), 1.19 (dq, J=23.7, 11.7, 11.2 Hz, 3H), 0.86 (q, J=11.8 Hz, 2H); LC-MS Rt 0.65 min, MS m/z [M+H]$^+$ 502.1; Method 5.

Example 11: N-(3-cyano-5-(cyclohexylmethyl)-4,5,6,7-tetrahydrothieno[3,2-c]pyridin-2-yl)-2-(4-(((difluoromethyl)sulfonyl)phenyl)acetamide

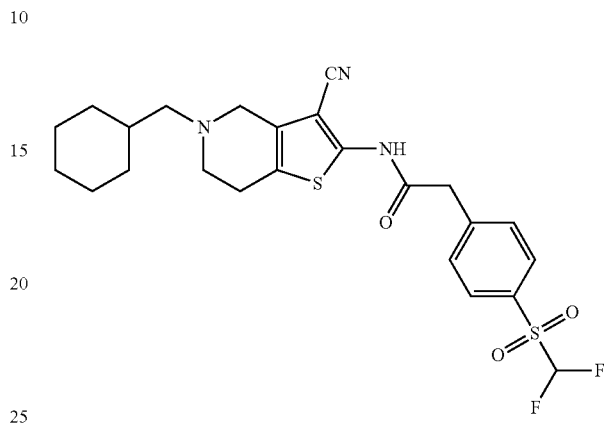

$^1$H NMR (400 MHz, DMSO-d$_6$) δ 7.98-7.90 (m, 2H), 7.75-7.66 (m, 2H), 7.29 (t, J=52.1 Hz, 1H), 4.03 (s, 2H), 3.34 (s, 2H), 2.64 (dt, J=9.7, 4.0 Hz, 4H), 2.29 (d, J=7.2 Hz, 2H), 1.74 (d, J=12.7 Hz, 2H), 1.70-1.50 (m, 4H), 1.26-1.11 (m, 3H), 0.93-0.79 (m, 2H); LC-MS Rt 0.77 min, MS m/z [M+H]$^+$ 508.1; Method 5.

Example 12: N-(3-cyano-5-(cyclohexylmethyl)-4,5,6,7-tetrahydrothieno[3,2-c]pyridin-2-yl)-2-(3-ethoxy-4-sulfamoylphenyl)acetamide

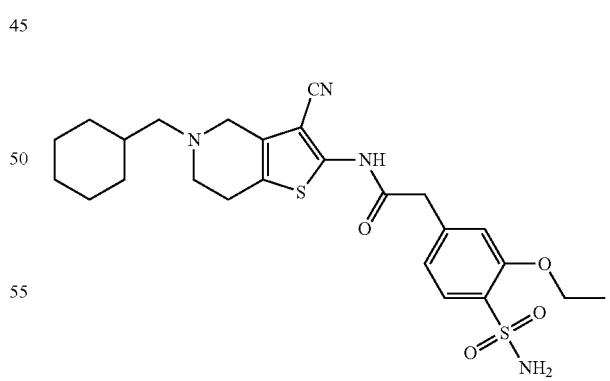

$^1$H NMR (400 MHz, DMSO-d$_6$) δ 7.67 (d, J=8.0 Hz, 1H), 7.17 (d, J=1.2 Hz, 1H), 6.96 (dd, J=8.0, 1.3 Hz, 1H), 6.88 (s, 2H), 4.20 (q, J=7.0 Hz, 2H), 3.91 (s, 2H), 3.36 (s, 2H), 2.66 (d, J=3.5 Hz, 4H), 2.30 (d, J=7.2 Hz, 2H), 1.79-1.51 (m, 6H), 1.38 (t, J=7.0 Hz, 3H), 1.29-1.08 (m, 3H), 0.86 (q, J=11.6 Hz, 2H); LC-MS Rt 0.65 min, MS m/z [M+H]$^+$ 517.2; Method 5.

Example 13: N-(3-cyano-5-(cyclohexylmethyl)-4,5,6,7-tetrahydrothieno[3,2-c]pyridin-2-yl)-2-(4-(methylsulfonamido)phenyl)acetamide

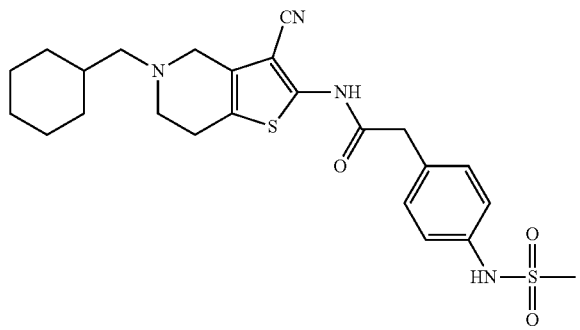 [SMILES: CS(=O)(=O)Nc1ccc(CC(=O)Nc2sc3c(c2C#N)CN(CC2CCCCC2)CC3)cc1]

$^1$H NMR (400 MHz, DMSO-d$_6$) δ 9.68 (s, 1H), 7.27 (d, J=8.6 Hz, 2H), 7.21-7.12 (m, 2H), 3.80 (s, 2H), 3.35 (s, 2H), 2.96 (s, 3H), 2.65 (d, J=3.6 Hz, 4H), 2.29 (d, J=7.2 Hz, 2H), 1.74 (d, J=12.5 Hz, 2H), 1.70-1.50 (m, 4H), 1.30-1.07 (m, 3H), 0.86 (q, J=11.0, 9.9 Hz, 2H); LC-MS Rt 0.65 min, MS m/z [M+H]$^+$ 487.2; Method 5.

Example 14: N-(3-cyano-5-(cyclohexylmethyl)-4,5,6,7-tetrahydrothieno[3,2-c]pyridin-2-yl)-2-(4-(N,N-dimethylsulfamoyl)phenyl)acetamide

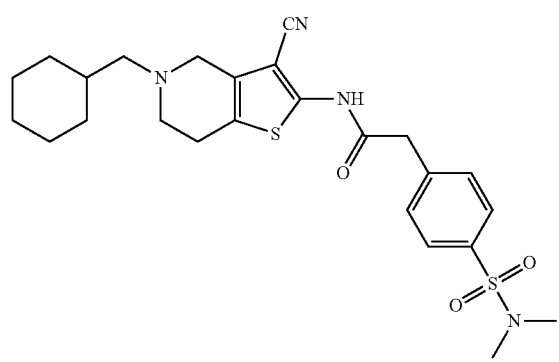 [SMILES: CN(C)S(=O)(=O)c1ccc(CC(=O)Nc2sc3c(c2C#N)CN(CC2CCCCC2)CC3)cc1]

$^1$H NMR (400 MHz, DMSO-d$_6$) δ 11.91 (s, 1H), 7.77-7.68 (m, 2H), 7.58 (d, J=8.4 Hz, 2H), 4.01 (s, 2H), 3.37 (s, 2H), 2.66 (s, 4H), 2.61 (s, 6H), 2.30 (d, J=7.1 Hz, 2H), 1.79-1.50 (m, 6H), 1.30-1.08 (m, 3H), 0.86 (q, J=10.7, 9.7 Hz, 2H); LC-MS Rt 0.71 min, MS m/z [M+H]$^+$ 501.2; Method 5.

Example 15: N-(3-cyano-5-(cyclohexylmethyl)-4,5,6,7-tetrahydrothieno[3,2-c]pyridin-2-yl)-2-(3-(2-methoxyethoxy)phenyl)acetamide

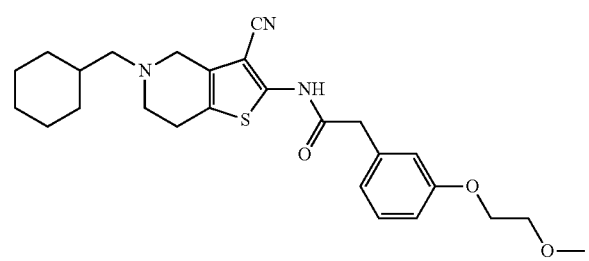 [SMILES: COCCOc1cccc(CC(=O)Nc2sc3c(c2C#N)CN(CC2CCCCC2)CC3)c1]

$^1$H NMR (400 MHz, DMSO-d$_6$) δ 7.22 (t, J=7.9 Hz, 1H), 6.93-6.80 (m, 3H), 4.06 (dd, J=5.4, 3.8 Hz, 2H), 3.80 (s, 2H), 3.65 (dd, J=5.4, 3.8 Hz, 2H), 3.35 (s, 2H), 3.30 (s, 3H), 2.64 (s, 4H), 2.29 (d, J=7.2 Hz, 2H), 1.80-1.47 (m, 6H), 1.31-1.07 (m, 3H), 0.85 (q, J=10.9, 10.3 Hz, 2H); LC-MS Rt 0.70 min, MS m/z [M+H]$^+$ 468.2; Method 5.

Example 16: N-(3-cyano-5-(cyclohexylmethyl)-4,5,6,7-tetrahydrothieno[3,2-c]pyridin-2-yl)-2-(1,1-dioxido-2,3-dihydrobenzo[d]isothiazol-5-yl)acetamide

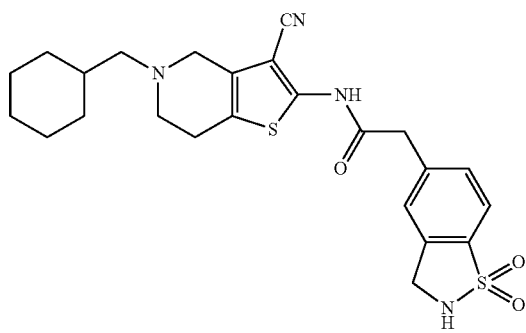 [SMILES: N#Cc1c(NC(=O)Cc2ccc3c(c2)CNS3(=O)=O)sc2c1CN(CC1CCCCC1)CC2]

$^1$H NMR (400 MHz, DMSO-d$_6$) δ 7.80-7.73 (m, 2H), 7.52-7.45 (m, 2H), 4.39 (d, J=4.7 Hz, 2H), 4.00 (s, 2H), 3.36 (s, 2H), 2.66 (d, J=3.7 Hz, 4H), 2.30 (d, J=7.2 Hz, 2H), 1.80-1.49 (m, 6H), 1.20 (dq, J=23.4, 12.0, 11.5 Hz, 3H), 0.86 (q, J=10.8, 10.0 Hz, 2H); LC-MS Rt 0.59 min, MS m/z [M+H]$^+$ 485.2; Method 5.

Example 17: N-(3-cyano-5-(cyclohexylmethyl)-4,5,6,7-tetrahydrothieno[3,2-c]pyridin-2-yl)-2-(4-(sulfamoylmethyl)phenyl)acetamide

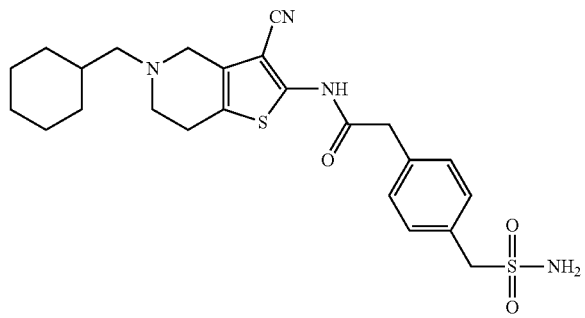 [SMILES: N#Cc1c(NC(=O)Cc2ccc(CS(N)(=O)=O)cc2)sc2c1CN(CC1CCCCC1)CC2]

$^1$H NMR (400 MHz, DMSO-$d_6$) δ 7.36-7.22 (m, 4H), 6.84 (s, 2H), 4.24 (s, 2H), 3.85 (s, 2H), 3.35 (s, 2H), 2.69-2.60 (m, 4H), 2.30 (d, J=7.2 Hz, 2H), 1.74 (d, J=13.0 Hz, 2H), 1.66 (d, J=12.9 Hz, 3H), 1.56 (d, J=3.9 Hz, 1H), 1.27-1.11 (m, 3H), 0.86 (q, J=11.9 Hz, 2H); LC-MS Rt 0.63 min, MS m/z [M+H]$^+$ 487.1; Method 5.

Example 18: N-(3-cyano-5-(cyclohexylmethyl)-4,5,6,7-tetrahydrothieno[3,2-c]pyridin-2-yl)-2-(1,1-dioxido-2,3-dihydrobenzo[b]thiophen-5-yl)acetamide

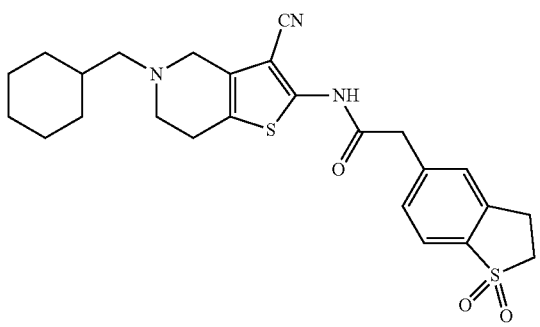 [SMILES: N#Cc1c(NC(=O)Cc2ccc3c(c2)CCS3(=O)=O)sc2c1CN(CC1CCCCC1)CC2]

$^1$H NMR (400 MHz, DMSO-$d_6$) δ 7.72-7.67 (m, 1H), 7.46 (d, J=7.0 Hz, 2H), 3.97 (s, 2H), 3.57 (dd, J=7.5, 6.3 Hz, 2H), 3.36 (s, 2H), 3.34 (s, 2H), 2.69-2.61 (m, 4H), 2.30 (d, J=7.2 Hz, 2H), 1.74 (d, J=13.0 Hz, 2H), 1.66 (d, J=12.7 Hz, 3H), 1.55 (tt, J=7.2, 3.5 Hz, 1H), 1.29-1.11 (m, 3H), 0.86 (q, J=11.6 Hz, 2H); LC-MS Rt 0.63 min, MS m/z [M+H]$^+$ 484.1

Example 19: N-(3-cyano-5-(cyclohexylmethyl)-4,5,6,7-tetrahydrothieno[3,2-c]pyridin-2-yl)-2-(2-methoxy-4-sulfamoylphenyl)acetamide

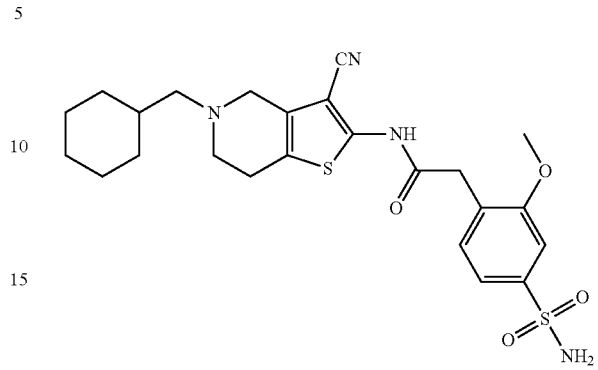

$^1$H NMR (400 MHz, DMSO-$d_6$) δ 11.80 (s, 1H), 7.42-7.36 (m, 3H), 7.32 (s, 2H), 3.89 (s, 2H), 3.81 (s, 3H), 3.37 (s, 2H), 2.66 (d, J=6.0 Hz, 4H), 2.30 (d, J=7.1 Hz, 2H), 1.75 (d, J=13.1 Hz, 2H), 1.66 (d, J=12.9 Hz, 3H), 1.59-1.51 (m, 1H), 1.26-1.15 (m, 3H), 0.87 (q, J=11.5 Hz, 2H); LC-MS Rt 0.63 min, MS m/z [M+H]$^+$ 503.2; Method 5.

Example 20: N-(3-cyano-5-(cyclohexylmethyl)-4,5,6,7-tetrahydrothieno[3,2-c]pyridin-2-yl)-2-(isoindolin-5-yl)acetamide

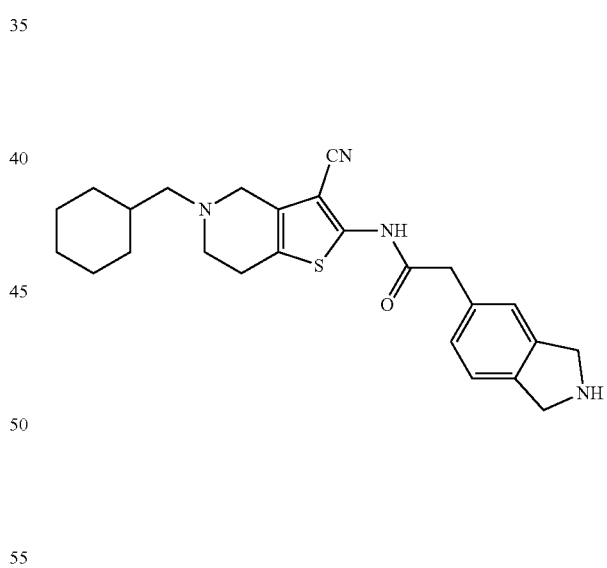

$^1$H NMR (400 MHz, DMSO-$d_6$) δ 7.30 (d, J=11.4 Hz, 2H), 7.23 (d, J=7.6 Hz, 1H), 4.33 (s, 2H), 3.86 (s, 2H), 2.69-2.57 (m, 4H), 2.30 (d, J=7.2 Hz, 2H), 1.79-1.60 (m, 5H), 1.50 (d, J=41.0 Hz, 3H), 1.28-1.09 (m, 4H), 0.89 (d, J=9.9 Hz, 4H); LC-MS Rt 0.46 min, MS m/z [M+H]$^+$ 435.2; Method 5.

Examples 21 to 49 were prepared by a similar method by replacing 2-amino-5-(3-fluorobenzyl)-4,5,6,7-tetrahydrothieno[3,2-c]pyridine-3-carbonitril Core-1a_A with the appropriate acid derivatives (either commercially available or preparations described hereinabove).

Example 21: N-(3-cyano-5-(3-fluorobenzyl)-4,5,6,7-tetrahydrothieno[3,2-c]pyridin-2-yl)-2-(3-ethoxy-4-sulfamoylphenyl)acetamide

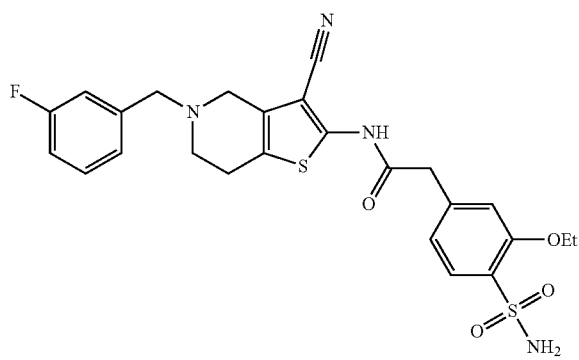 [SMILES: CCOc1cc(CC(=O)Nc2sc3c(c2C#N)CN(Cc2cccc(F)c2)CC3)ccc1S(N)(=O)=O]

Yield 30%; $^1$H NMR (400 MHz, DMSO-d$_6$) δ 7.67 (d, J=8.0 Hz, 1H), 7.44-7.35 (m, 1H), 7.23-7.15 (m, 3H), 7.14-7.06 (m, 1H), 6.96 (d, J=7.9 Hz, 1H), 6.90 (s, 2H), 4.20 (q, J=6.9 Hz, 2H), 3.90 (s, 2H), 3.72 (s, 2H), 2.76-2.63 (m, 4H), 1.38 (t, J=7.0 Hz, 3H); LC-MS Rt 0.94 min; MS m/z [M+H]$^+$ 529.1; Method 3.

Example 22: N-(3-cyano-5-(3-fluorobenzyl)-4,5,6,7-tetrahydrothieno[3,2-c]pyridin-2-yl)-2-(3-methoxy-4-sulfamoylphenyl)acetamide

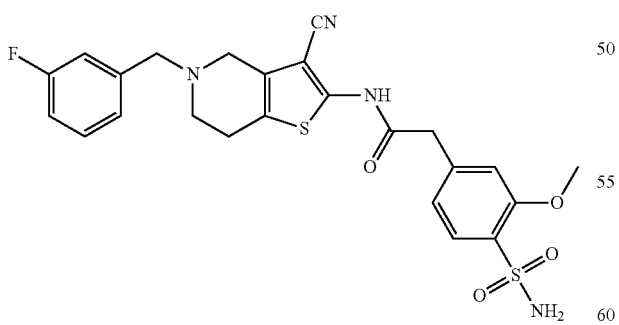

Yield 76%; $^1$H NMR (400 MHz, DMSO-d$_6$) δ 11.86 (s, 1H) 7.69-7.66 (d, J=8.03 Hz, 1H) 7.44-7.34 (m, 1H) 7.25-7.23 (m, 1H) 7.24-6.92 (m, 6H) 3.97-3.86 (m, 5H) 3.72 (s, 2H) 3.46-3.40 (m, 2H) 3.47-3.37 (m, 1H) 2.65-2.80 (m, 4H); LC-MS Rt 0.90 min; MS m/z [M+H]$^+$ 515.1; Method 1.

Example 23: N-(3-cyano-5-(3-fluorobenzyl)-4,5,6,7-tetrahydrothieno[3,2-c]pyridin-2-yl)-2-(1,1-dioxido-2,3-dihydrobenzo[d]isothiazol-5-yl)acetamide

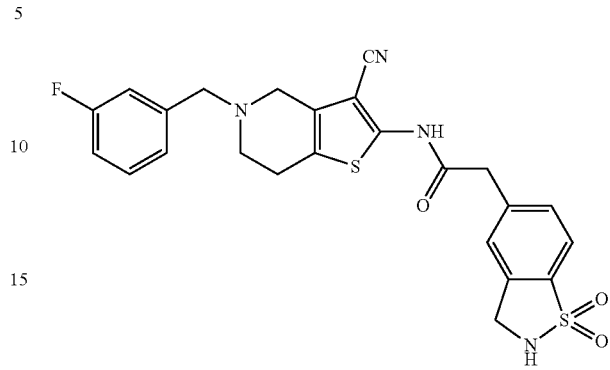

Yield 16%; $^1$H NMR (400 MHz, DMSO-d$_6$) δ 7.73 (d, J=8.0 Hz, 2H), 7.48-7.38 (m, 3H), 7.20-7.10 (m, 2H), 4.38 (s, 2H), 3.86 (s, 2H), 3.70 (s, 2H), 3.48 (s, 2H), 2.71 (m, 2H), 2.61 (m, 2H); LC-MS Rt 0.91 min; MS m/z [M+H]$^+$ 497.13; Method 1.

Example 24: N-(3-cyano-5-(3-fluorobenzyl)-4,5,6,7-tetrahydrothieno[3,2-c]pyridin-2-yl)-2-(2-methoxy-4-sulfamoylphenyl)acetamide

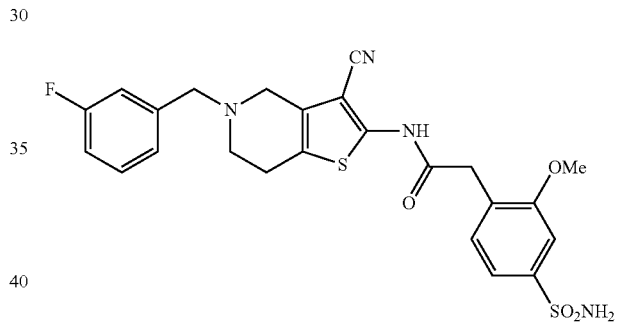

Yield 24%; $^1$H NMR (400 MHz, DMSO-d$_6$) δ 7.42-7.33 (m, 6H), 7.21-7.10 (m, 3H), 3.88 (s, 2H), 3.81 (s, 3H), 3.73 (s, 2H), 3.42 (s, 2H), 2.91-2.72 (m, 4H); LC-MS Rt 0.95 min; MS m/z [M+H]$^+$ 515.1; Method 1.

Example 25: N-(3-cyano-5-(3-fluorobenzyl)-4,5,6,7-tetrahydrothieno[3,2-c]pyridin-2-yl)-2-(1,1-dioxido-2,3-dihydrobenzo[d]isothiazol-6-yl)acetamide

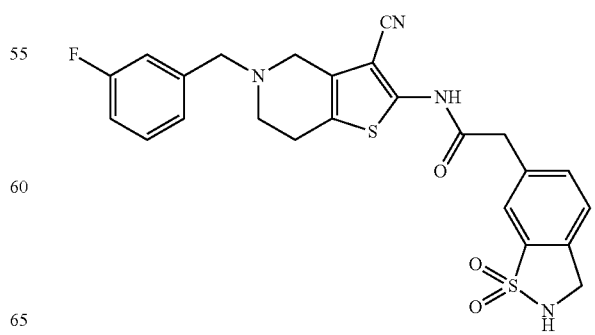

Yield 24%; ¹H NMR (400 MHz, DMSO-d₆) δ 12.16 (s, 1H), 11.39 (s, 1H), 7.85-7.34 (m, 7H), 4.49-4.22 (m, 6H), 4.04 (s, 2H), 3.08-3.00 (m, 2H), 2.59-2.55 (m, 2H); LC-MS Rt 0.63 min; MS m/z [M+H]⁺ 497.0; Method 3.

Example 26: N-(3-cyano-5-(3-fluorobenzyl)-4,5,6,7-tetrahydrothieno[3,2-c]pyridin-2-yl)-2-(isoindolin-5-yl)acetamide

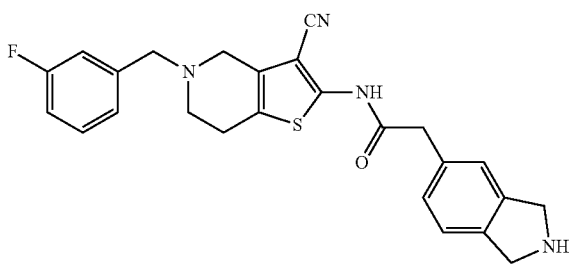 [SMILES: N#Cc1c(NC(=O)Cc2ccc3c(c2)CNC3)sc2c1CN(Cc1cccc(F)c1)CC2]

Yield 11%; ¹H NMR (400 MHz, CD₃OD) δ 7.35-7.24 (m, 1H) 7.23-7.10 (m, 5H) 7.02-6.98 (m, 1H) 4.15-4.14 (d, J=3.42 Hz, 4H) 3.80 (s, 2H) 3.74 (s, 2H) 3.48 (s, 2H) 3.35-3.34 (m, 2H) 2.82-2.72 (m, 4H); LC-MS Rt 1.01 min; m/z [M+H]⁺ 447.1; Method 1.

Example 27: 2-(3-cyano-4-(methylsulfonyl)phenyl)-N-(3-cyano-5-(3-fluorobenzyl)-4,5,6,7-tetrahydrothieno[3,2-c]pyridin-2-yl)acetamide

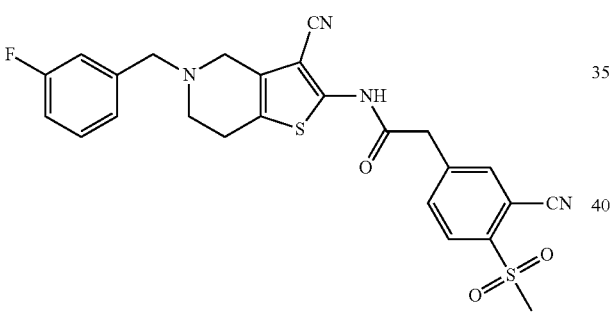

Yield 31%; ¹H NMR (400 MHz, DMSO-d₆) δ 11.98 (s, 1H), 11.39 (s, 1H), 8.13-8.09 (m, 2H), 7.91-7.89 (m, 1H), 7.39-7.10 (m, 4H), 4.07 (s, 2H), 3.72 (s, 2H), 3.41 (s, 2H), 3.38 (s, 3H), 2.67-2.66 (m, 4H); LC-MS Rt 0.94 min; MS m/z [M+H]⁺ 509.2; Method 1.

Example 28: N-(3-cyano-5-(3-fluorobenzyl)-4,5,6,7-tetrahydrothieno[3,2-c]pyridin-2-yl)-2-(2-(N-methylsulfamoyl)phenyl)acetamide

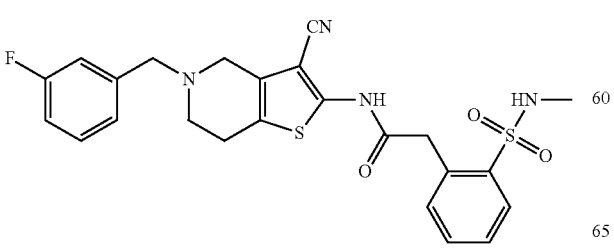

Yield 7.8%; ¹H NMR: (400 MHz, DMSO-d₆) δ 11.91 (s, 1H), 7.76 (s, 1H), 7.75-7.64 (m, 1H), 7.60-7.54 (m, 2H), 7.49-7.35 (m, 2H), 7.24-7.15 (m, 2H), 7.14-7.07 (m, 1H), 3.99 (s, 2H), 3.73 (s, 2H), 3.43 (s, 2H), 2.80-2.64 (m, 4H), 2.43 (d, J=5.01 Hz, 3H); LC-MS Rt 1.38 min; MS m/z [M+H]⁺ 499.1; Method 6.

Example 29: N-(3-cyano-5-(3-fluorobenzyl)-4,5,6,7-tetrahydrothieno[3,2-c]pyridin-2-yl)-2-(4-(N-methylsulfamoyl)phenyl)acetamide

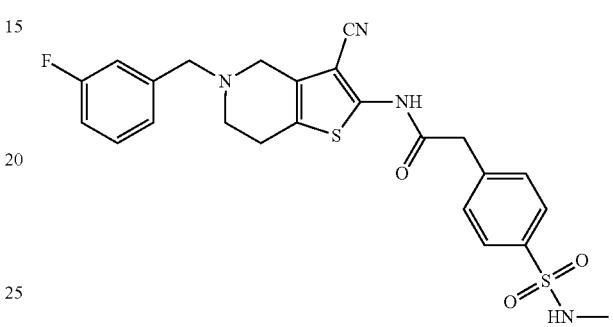

Yield 9.2%; ¹H NMR (400 MHz, DMSO-d₆) δ 11.92 (s, 1H), 7.74 (d, J=8.19 Hz, 2H), 7.53 (d, J=8.31 Hz, 2H), 7.46-7.35 (m, 2H), 7.23-7.15 (m, 2H), 7.11 (td, J=8.56, 2.32 Hz, 1H), 3.98 (s, 2H), 3.73 (s, 2H), 3.43 (s, 1H), 2.73 (d, J=5.01 Hz, 2H), 2.41 (d, J=5.01 Hz, 3H), 2.68 (d, J=4.89 Hz, 2H); LC-MS Rt 0.94 min; MS m/z [M+H]⁺ 499.1; Method 1.

Example 30: N-(3-cyano-5-(3-fluorobenzyl)-4,5,6,7-tetrahydrothieno[3,2-c]pyridin-2-yl)-2-(3-methoxy-4-(methylsulfonyl)phenyl)acetamide

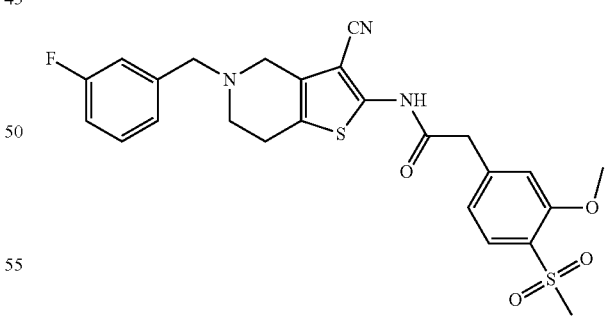

Yield 20.6%; ¹H NMR (400 MHz, DMSO-d₆) δ 12.60-11.22 (m, 1H), 7.73 (d, J=8.03 Hz, 1H), 7.45-7.34 (m, 1H), 7.30-7.23 (m, 1H), 7.22-7.14 (m, 2H), 7.13-7.05 (m, 2H), 3.98-3.87 (m, 5H), 3.71 (s, 2H), 3.50-3.48 (m, 2H), 3.21 (s, 3H), 2.76-2.69 (m, 2H), 2.66 (d, J=4.64 Hz, 2H); LC-MS Rt 0.93 min, MS m/z [M+H]⁺ 514.1; Method 1.

Example 31: N-(3-cyano-5-(3-fluorobenzyl)-4,5,6,7-tetrahydrothieno[3,2-c]pyridin-2-yl)-2-(3-(2-methoxyethoxy)phenyl)acetamide

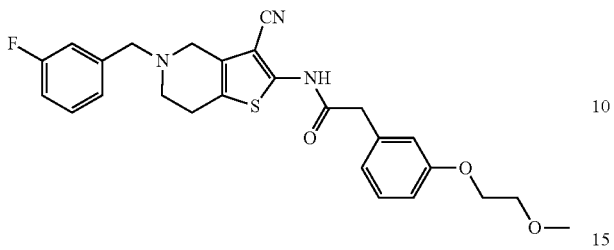

Yield 17.6%; $^1$H NMR (400 MHz, DMSO-$d_6$) δ 11.81 (s, 1H), 7.44-7.35 (m, 1H), 7.26-7.15 (m, 3H), 7.13-7.04 (m, 1H), 6.91-6.81 (m, 3H), 4.11-4.03 (m, 2H), 3.80 (s, 2H), 3.72 (s, 2H), 3.67-3.61 (m, 2H), 3.42 (s, 2H), 3.30 (s, 3H), 2.72 (d, J=4.89 Hz, 2H), 2.67 (s, 2H); LC-MS Rt 1.04 min; MS m/z [M+H]$^+$ 480.2; Method 1.

Example 32: N-(3-cyano-5-(3-fluorobenzyl)-4,5,6,7-tetrahydrothieno[3,2-c]pyridin-2-yl)-2-(4-((methylsulfonyl)methyl)phenyl)acetamide

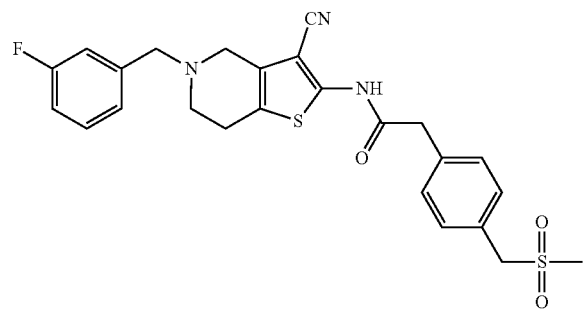 [SMILES: CS(=O)(=O)Cc1ccc(CC(=O)Nc2sc3c(c2C#N)CN(Cc2cccc(F)c2)CC3)cc1]

Yield 6.4%; $^1$H NMR: (400 MHz, DMSO-$d_6$) δ 11.83 (s, 1H), 7.42-7.37 (m, 1H), 7.37-7.30 (m, 4H), 7.22-7.14 (m, 2H), 7.13-7.05 (m, 1H), 4.44 (s, 2H), 3.80 (s, 2H), 3.71 (s, 2H), 2.88 (s, 3H), 2.74-2.69 (m, 2H), 2.64 (d, J=4.8 Hz, 2H); LC-MS Rt 0.94 min; MS m/z [M+H]$^+$ 498.1; Method 1.

Example 33: N-(3-cyano-5-(3-fluorobenzyl)-4,5,6,7-tetrahydrothieno[3,2-c]pyridin-2-yl)-2-(1,1-dioxido-2,3-dihydrobenzo[b]thiophen-5-yl)acetamide

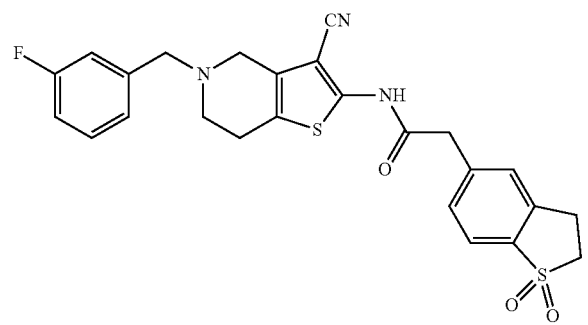 [SMILES: N#Cc1c(NC(=O)Cc2ccc3c(c2)CCS3(=O)=O)sc2c1CN(Cc1cccc(F)c1)CC2]

Yield 6.4%; $^1$H NMR (400 MHz, CDCl$_3$) δ 9.12-8.68 (m, 1H), 7.74 (d, J=7.9 Hz, 1H), 7.49-7.37 (m, 2H), 7.33-7.28 (m, 1H), 7.18-7.05 (m, 2H), 6.97 (dt, J=2.2, 8.3 Hz, 1H), 3.88 (s, 2H), 3.72 (s, 2H), 3.58-3.47 (m, 4H), 3.44-3.34 (m, 2H), 2.78 (dd, J=4.5, 11.5 Hz, 4H). LC-MS Rt 0.93 min, MS m/z [M+H]$^+$ 496.1; Method 1.

Example 34: N-(3-cyano-5-(3-fluorobenzyl)-4,5,6,7-tetrahydrothieno[3,2-c]pyridin-2-yl)-2-(2,3-dimethoxyphenyl)acetamide

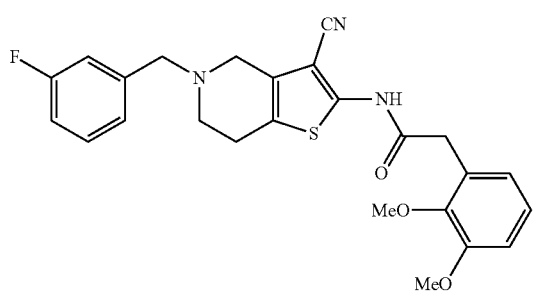 [SMILES: COc1cccc(CC(=O)Nc2sc3c(c2C#N)CN(Cc2cccc(F)c2)CC3)c1OC]

Yield 61%; $^1$H NMR (400 MHz, DMSO-$d_6$) δ 11.81 (s, 1H), 7.44-7.36 (m, 1H), 7.21-7.10 (m, 3H), 7.01-6.97 (m, 2H), 6.83-6.81 (dd, J=7.15, 1.65 Hz, 1H), 3.82 (s, 2H), 3.79 (s, 3H), 3.72 (s, 2H), 3.65 (s, 3H) 3.42 (s, 2H), 2.73-2.60 (m, 4H); LC-MS Rt 1.07 min; MS m/z [M+H]$^+$ 466.1; Method 1.

Example 35: N-(3-cyano-5-(3-fluorobenzyl)-4,5,6,7-tetrahydrothieno[3,2-c]pyridin-2-yl)-2-(3-fluoro-5-methoxyphenyl)acetamide

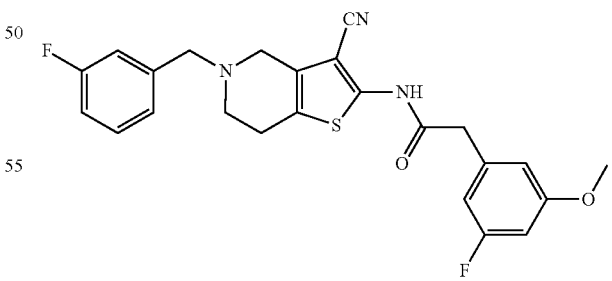

Yield 24%; $^1$H NMR (400 MHz, DMSO-$d_6$) δ 11.83 (s, 1H), 7.45-7.35 (m, 1H), 7.23-7.16 (m, 2H), 7.11 (dt, J=2.4, 8.4 Hz, 1H), 6.77-6.70 (m, 3H), 3.84 (s, 2H), 3.76 (s, 3H), 3.73 (s, 2H), 3.43 (s, 2H), 2.73 (d, J=4.8 Hz, 2H), 2.69 (d, J=4.5 Hz, 2H); LC-MS Rt 1.06 min, MS m/z [M+1]$^+$ 454.1; Method 1.

Example 36: N-(3-cyano-5-(3-fluorobenzyl)-4,5,6,7-tetrahydrothieno[3,2-c]pyridin-2-yl)-2-(1-(methylsulfonyl)-1H-pyrrol-3-yl)acetamide

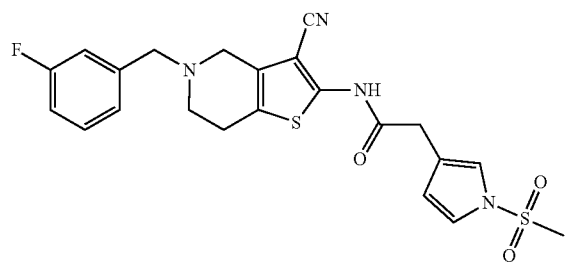 [SMILES: CS(=O)(=O)n1ccc(CC(=O)Nc2sc3c(c2C#N)CN(Cc2cccc(F)c2)CC3)c1]

Yield 22%; $^1$H NMR (400 MHz, DMSO-$d_6$) δ 11.84-11.62 (m, 1H), 7.44-7.35 (m, 1H), 7.24-7.04 (m, 5H), 6.34 (br s, 1H), 3.78-3.64 (m, 4H), 3.44 (s, 2H), 3.42 (s, 3H), 2.79-2.64 (m, 4H); LC-MS Rt 0.97 min; MS m/z [M+H]$^+$ 473.1; Method 1.

Example 37: N-(3-cyano-5-(3-fluorobenzyl)-4,5,6,7-tetrahydrothieno[3,2-c]pyridin-2-yl)-2-(3-ethoxy-4-(methylsulfonyl)phenyl)acetamide

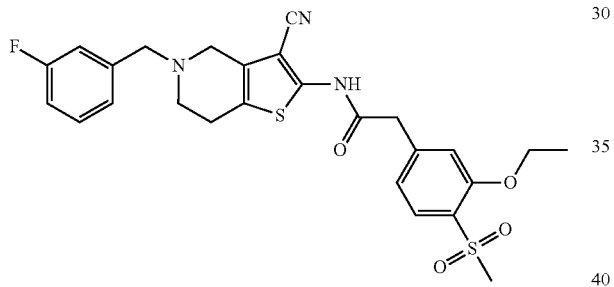

Yield 23%; $^1$H NMR (400 MHz, DMSO-$d_6$) δ 11.93 (s, 1H), 7.75-7.73 (d, J=8.0 Hz, 1H), 7.39-7.38 (m, 1H), 7.25 (s, 1H), 7.21-7.19 (m, 2H), 7.14-7.10 (m, 1H), 7.09-7.04 (m, 1H), 4.28-4.19 (q, J=6.9 Hz, 2H), 3.96 (s, 2H), 3.72 (s, 2H), 3.42 (s, 2H), 3.24 (s, 3H), 2.73-2.67 (m, 4H), 1.42-1.38 (t, J=7.0 Hz, 3H); LC-MS Rt 0.95 min; MS m/z [M+H]$^+$ 528.2; Method 1.

Example 38: N-(3-cyano-5-(3-fluorobenzyl)-4,5,6,7-tetrahydrothieno[3,2-c]pyridin-2-yl)-2-(3-cyano-5-methoxyphenyl)acetamide

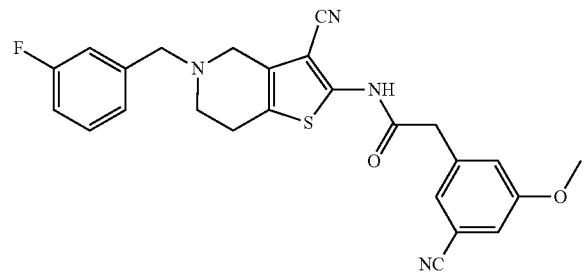 [SMILES: COc1cc(C#N)cc(CC(=O)Nc2sc3c(c2C#N)CN(Cc2cccc(F)c2)CC3)c1]

Yield 10.86%; $^1$H NMR (400 MHz, CDCl$_3$) δ 8.60 (s, 1H), 7.33-7.28 (m, 1H), 7.23 (s, 1H), 7.17-7.06 (m, 4H), 7.02-6.93 (m, 1H), 3.86 (s, 3H), 3.81 (s, 2H), 3.72 (s, 2H), 3.54 (s, 2H), 2.78 (d, J=4.3, 10.2 Hz, 4H); LC-MS Rt 1.01 min; MS m/z [M+1]$^+$ 461.1; Method 1.

Example 39: 2-(3-chloro-5-methoxyphenyl)-N-(3-cyano-5-(3-fluorobenzyl)-4,5,6,7-tetrahydrothieno[3,2-c]pyridin-2-yl)acetamide

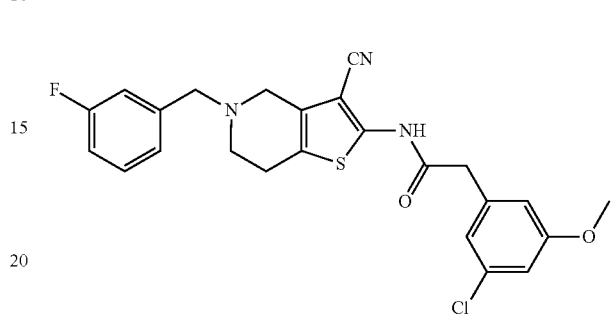

Yield 18%; $^1$H NMR (400 MHz, DMSO-$d_6$) δ 11.92 (s, 1H), 7.38-7.33 (m, 2H), 7.21-7.19 (m, 2H), 7.10 (dt, J=2.1, 8.6 Hz, 1H), 7.02 (d, J=3.0 Hz, 1H), 6.89 (dd, J=3.0, 8.8 Hz, 1H), 3.98 (s, 2H), 3.75 (s, 3H), 3.73 (s, 2H), 3.43 (s, 2H), 2.73 (d, J=5.0 Hz, 2H), 2.68 (d, J=4.9 Hz, 2H). LC-MS Rt 1.07 min; MS m/z [M+1]$^+$ 470.1; Method 1.

Example 40: N-(3-cyano-5-(3-fluorobenzyl)-4,5,6,7-tetrahydrothieno[3,2-c]pyridin-2-yl)-2-(2-fluoro-3-methoxyphenyl)acetamide

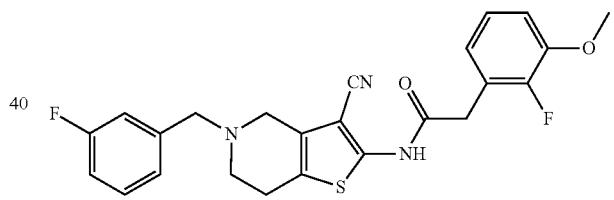

Yield 10.4%; $^1$H NMR (400 MHz, DMSO-$d_6$) δ 11.88 (s, 1H), 7.42-7.35 (m, 1H), 7.22-7.15 (m, 2H), 7.14-7.03 (m, 3H), 6.94-6.84 (m, 1H), 3.88 (s, 2H), 3.82 (s, 3H), 3.72 (s, 2H), 3.42-3.41 (m, 2H), 2.72 (d, J=4.9 Hz, 2H), 2.66 (s, 2H); LC-MS Rt 1.03 min; MS m/z [M+H]$^+$ 454.1; Method 1.

Example 41: 2-(2-chloro-3-methoxyphenyl)-N-(3-cyano-5-(3-fluorobenzyl)-4,5,6,7-tetrahydrothieno[3,2-c]pyridin-2-yl)acetamide

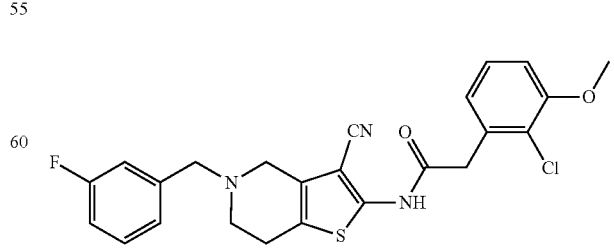

Yield 22.9%; $^1$H NMR (400 MHz, DMSO-$d_6$) δ 11.93 (s, 1H), 7.43-7.35 (m, 1H), 7.31-7.24 (m, 1H), 7.23-7.15 (m, 2H), 7.14-7.05 (m, 2H), 6.97 (d, J=7.6 Hz, 1H), 4.01 (s, 2H), 3.85 (s, 3H), 3.72 (s, 2H), 3.42 (s, 2H), 2.77-2.63 (m, 4H); LC-MS Rt 1.05 min; MS m/z [M+H]+ 470.0; Method 1.

Example 42: N-(3-cyano-5-(3-fluorobenzyl)-4,5,6,7-tetrahydrothieno[3,2-c]pyridin-2-yl)-2-(3,3-dimethyl-1,1-dioxido-2,3-dihydrobenzo[b]thiophen-5-yl)acetamide

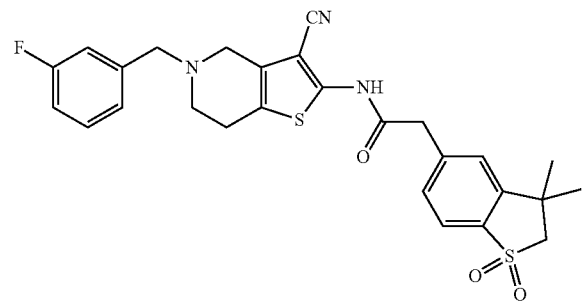 [SMILES: CC1(C)CS(=O)(=O)c2ccc(CC(=O)Nc3sc4c(c3C#N)CN(Cc3cccc(F)c3)CC4)cc21]

Yield 31%; ¹H NMR (400 MHz, DMSO-d₆) δ 7.65-7.59 (m, 2H), 7.47-7.38 (m, 2H), 7.21-7.08 (m, 3H), 3.94 (s, 2H), 3.72 (s, 2H), 3.49 (s, 2H), 3.33 (m, 2H), 2.72-2.65 (m, 4H), 1.46 (s, 6H); LC-MS Rt 0.96 min; MS m/z [M+H]+ 524.2; Method 1.

Example 43: N-(3-cyano-5-(3-fluorobenzyl)-4,5,6,7-tetrahydrothieno[3,2-c]pyridin-2-yl)-2-(3-fluoro-4-sulfamoylphenyl)acetamide

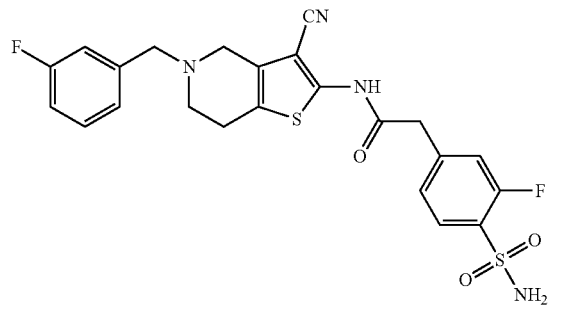 [SMILES: N#Cc1c(NC(=O)Cc2ccc(S(N)(=O)=O)c(F)c2)sc2c1CN(Cc1cccc(F)c1)CC2]

¹H NMR (400 MHz, DMSO-d₆) δ 11.91 (s, 1H), 7.75 (t, J=7.9 Hz, 1H), 7.63 (s, 2H), 7.37 (dd, J=11.2, 1.3 Hz, 3H), 7.28 (dd, J=8.1, 1.5 Hz, 1H), 7.20 (s, 2H), 4.40 (d, J=90.5 Hz, 1H), 3.99 (s, 2H), 3.75 (d, J=20.8 Hz, 2H), 3.42 (s, 1H), 3.10-2.89 (m, 1H), 2.81-2.63 (m, 3H); LC-MS Rt 0.62 min, MS m/z [M+H]+ 503.1; Method 7.

Example 44: Methyl (4-(2-((3-cyano-5-(3-fluorobenzyl)-4,5,6,7-tetrahydrothieno[3,2-c]pyridin-2-yl)amino)-2-oxoethyl)phenyl)(methyl)phosphinate

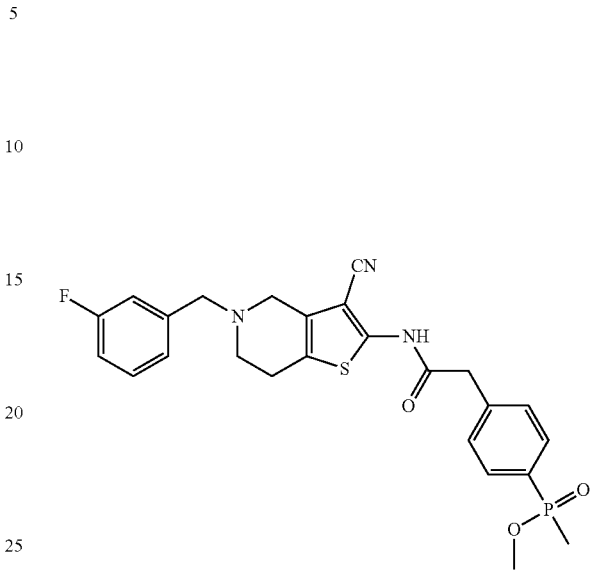

¹H NMR (400 MHz, DMSO-d₆) δ 12.14 (s, 1H), 7.71 (dd, J=11.7, 8.2 Hz, 2H), 7.48 (dd, J=8.2, 2.9 Hz, 6H), 4.39 (d, J=88.4 Hz, 3H), 3.97 (s, 2H), 3.68 (s, 2H), 3.48 (d, J=11.2 Hz, 3H), 3.00 (s, 2H), 1.64 (d, J=14.5 Hz, 3H), 1.24 (s, 1H); LC-MS Rt 0.62 min, MS m/z [M+H]+ 498.1; Method 7.

Example 45: N-(3-cyano-5-(3-fluorobenzyl)-4,5,6,7-tetrahydrothieno[3,2-c]pyridin-2-yl)-2-(4-((difluoromethyl)sulfonyl)phenyl)acetamide

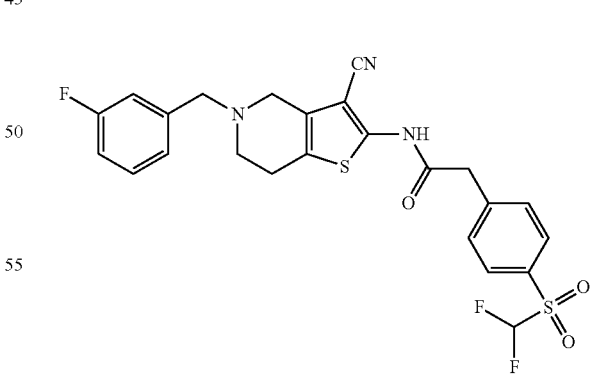

¹H NMR (400 MHz, DMSO-d₆) δ 7.96-7.91 (m, 2H), 7.73-7.68 (m, 2H), 7.43-7.35 (m, 1H), 7.29 (s, 1H), 7.22-7.15 (m, 2H), 7.13-7.06 (m, 1H), 4.01 (s, 2H), 3.72 (s, 2H), 3.41 (d, J=1.9 Hz, 2H), 2.73 (t, J=5.6 Hz, 2H), 2.69-2.62 (m, 2H); LC-MS Rt 0.81 min, MS m/z [M+H]+ 520.1; Method 5.

Example 46: N-(3-cyano-5-(3-fluorobenzyl)-4,5,6,7-tetrahydrothieno[3,2-c]pyridin-2-yl)-2-(4-(methylsulfonamido)phenyl)acetamide

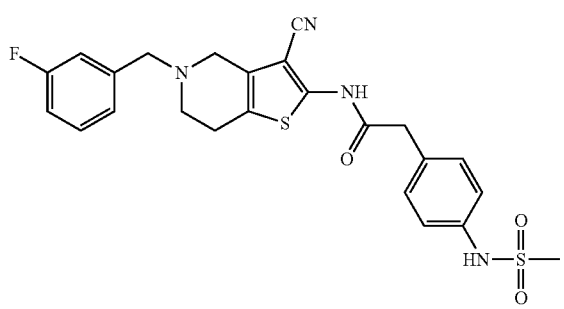 [SMILES: CS(=O)(=O)Nc1ccc(CC(=O)Nc2sc3c(c2C#N)CN(Cc2cccc(F)c2)CC3)cc1]

$^1$H NMR (400 MHz, DMSO-d$_6$) δ 9.67 (s, 1H), 7.43-7.35 (m, 1H), 7.26 (d, J=8.5 Hz, 2H), 7.22-7.14 (m, 4H), 7.10 (td, J=8.6, 2.2 Hz, 1H), 3.80 (s, 2H), 3.72 (s, 2H), 3.42 (s, 2H), 2.96 (s, 3H), 2.73 (t, J=5.3 Hz, 2H), 2.67 (d, J=4.6 Hz, 2H); LC-MS Rt 0.66 min, MS m/z [M+H]$^+$ 499.1; Method 5.

Example 47: N-(3-cyano-5-(3-fluorobenzyl)-4,5,6,7-tetrahydrothieno[3,2-c]pyridin-2-yl)-2-(4-(N,N-dimethylsulfamoyl)phenyl)acetamide

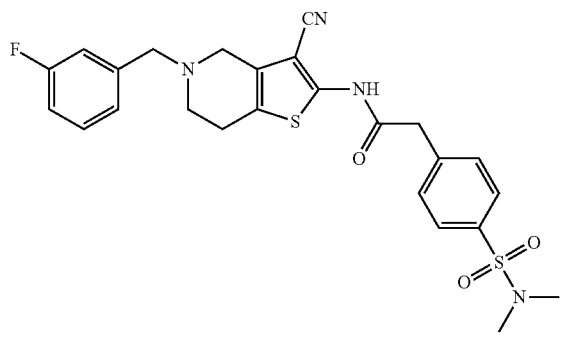 [SMILES: CN(C)S(=O)(=O)c1ccc(CC(=O)Nc2sc3c(c2C#N)CN(Cc2cccc(F)c2)CC3)cc1]

$^1$H NMR (400 MHz, DMSO-d$_6$) δ 11.92 (s, 1H), 7.76-7.68 (m, 2H), 7.57 (d, J=8.4 Hz, 2H), 7.43-7.35 (m, 1H), 7.23-7.15 (m, 2H), 7.13-7.07 (m, 1H), 4.00 (s, 2H), 3.73 (s, 2H), 3.43 (s, 2H), 2.73 (d, J=5.0 Hz, 2H), 2.68 (d, J=4.5 Hz, 2H), 2.61 (s, 6H); LC-MS Rt 0.76 min, MS m/z [M+H]$^+$ 513.2; Method 5.

Example 48: N-(3-cyano-5-(cyclohexylmethyl)-4,5,6,7-tetrahydrothieno[3,2-c]pyridin-2-yl)-2-(3-methoxy-4-sulfamoylphenyl)-N-methylacetamide

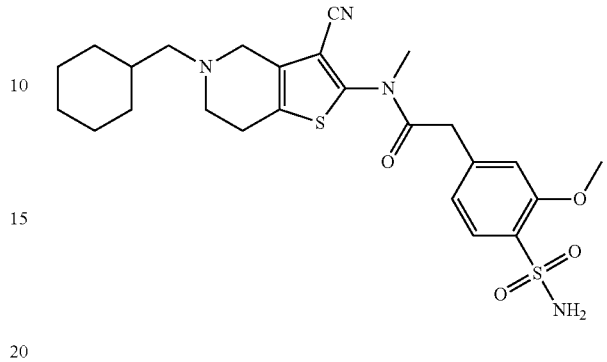

The title compound (18.2 mg, 16.7%) was prepared by a similar method by replacing 5-(cyclohexylmethyl)-2-(methylamino)-4,5,6,7-tetrahydrothieno[3,2-c]pyridine-3-carbonitrile Core-1a_H and Core-1a_E. $^1$H NMR (400 MHz, DMSO-d$_6$) δ 7.63 (d, J=7.5 Hz, 1H), 7.11-6.73 (m, 4H), 3.86 (s, 3H), 3.52-3.39 (m, 3H), 3.23 (s, 3H), 2.86-2.64 (m, 4H), 2.33 (d, J=7.2 Hz, 2H), 1.84-1.49 (m, 6H), 1.33-1.06 (m, 3H), 0.95-0.74 (m, 2H); LC-MS Rt 1.06 min; MS m/z [M+H]$^+$ 517.2; Method 1.

Example 49: N-(5-benzyl-3-cyano-4,4-dimethyl-4,5,6,7-tetrahydrothieno[3,2-c]pyridin-2-yl)-2-(3-methoxy-4-sulfamoylphenyl)acetamide

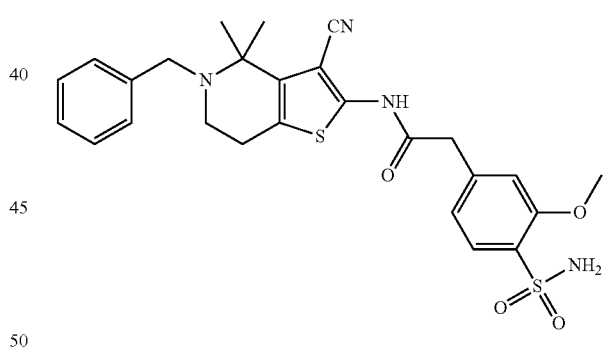

The title compound (18.2 mg, 16.7%) was prepared by a similar method by replacing 2-amino-5-benzyl-4,4-dimethyl-4,5,6,7-tetrahydrothieno[3,2-c]pyridine-3-carbonitrile Core-1a_I and Core-1a_E. $^1$H NMR (400 MHz, DMSO-d$_6$) δ 11.65 (s, 1H), 7.68-7.66 (m, 1H), 7.39-7.37 (m, 2H), 7.34-7.33 (m, 2H), 7.30-7.24 (m, 1H), 7.19 (s, 1H), 7.03-6.92 (m, 3H), 3.94 (s, 2H), 3.91 (s, 3H), 3.68 (s, 2H), 2.68-2.61 (m, 2H), 2.45-2.40 (m, 2H), 1.52 (s, 6H); LC-MS Rt 1.01 min; MS m/z [M+H]$^+$ 525.2; Method 1.

Examples 50 to 52 were prepared by a similar method by using 2-amino-5-((3,3-difluorocyclobutyl)methyl)-4,5,6,7-tetrahydrothieno[3,2-c]pyridine-3-carbonitrile Core-1a_C with the appropriate acid derivatives (either commercially available or preparations described hereinabove).

Example 50: N-(3-cyano-5-((3,3-difluorocyclobutyl)methyl)-4,5,6,7-tetrahydrothieno[3,2-c]pyridin-2-yl)-2-(3-methoxy-4-sulfamoylphenyl)acetamide

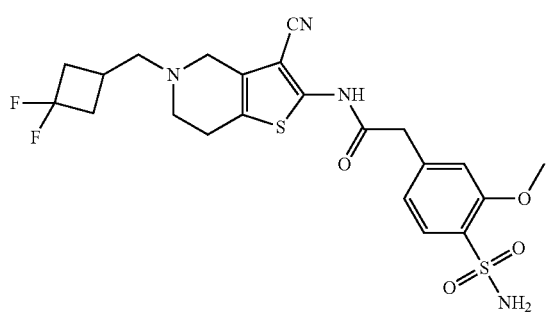 [SMILES: COc1cc(CC(=O)Nc2sc3c(c2C#N)CN(CC2CC(F)(F)C2)CC3)ccc1S(N)(=O)=O]

$^1$H NMR (400 MHz, DMSO-$d_6$) δ 11.86 (s, 1H), 7.67 (d, J=7.91 Hz, 1H), 7.17 (s, 1H), 7.03 (s, 2H), 6.98 (d, J=7.91 Hz, 1H), 3.87-3.96 (m, 5H), 3.43 (s, 1H), 2.69-2.76 (m, 2H), 2.60-2.68 (m, 6H), 2.41 (d, J=7.03 Hz, 1H), 2.18-2.35 (m, 2H), 2.09 (s, 1H); LC-MS Rt 0.85 min; MS m/z [M+H]$^+$ 511.1; Method 1.

Example 51: N-(3-cyano-5-((3,3-difluorocyclobutyl)methyl)-4,5,6,7-tetrahydrothieno[3,2-c]pyridin-2-yl)-2-(3-methoxy-4-(methylsulfonyl)phenyl)acetamide

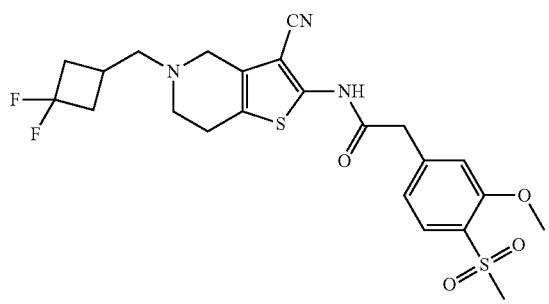 [SMILES: COc1cc(CC(=O)Nc2sc3c(c2C#N)CN(CC2CC(F)(F)C2)CC3)ccc1S(C)(=O)=O]

$^1$H NMR (400 MHz, DMSO-$d_6$) δ 11.89 (s, 1H), 7.74 (d, J=8.0 Hz, 1H), 7.27 (d, J=1.1 Hz, 1H), 7.08 (dd, J=8.0, 1.3 Hz, 1H), 3.95 (d, J=5.3 Hz, 5H), 3.42 (s, 2H), 3.22 (s, 3H), 2.75-2.60 (m, 8H), 2.40 (d, J=7.0 Hz, 1H), 2.35-2.18 (m, 2H); LC-MS Rt 0.55 min, MS m/z [M+H]$^+$ 510.1; Method 5.

Example 52: N-(3-cyano-5-((3,3-difluorocyclobutyl)methyl)-4,5,6,7-tetrahydrothieno[3,2-c]pyridin-2-yl)-2-(1,1-dioxido-2,3-dihydrobenzo[d]isothiazol-5-yl)acetamide

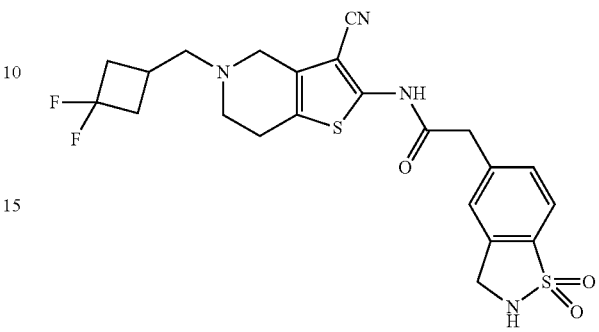

$^1$H NMR (400 MHz, DMSO-$d_6$) δ 11.92 (s, 1H), 7.77 (d, J=7.8 Hz, 2H), 7.52-7.44 (m, 2H), 4.39 (d, J=4.6 Hz, 2H), 4.00 (s, 2H), 3.42 (s, 2H), 2.75-2.60 (m, 8H), 2.40 (d, J=7.3 Hz, 1H), 2.34-2.19 (m, 2H); LC-MS Rt 0.52 min, MS m/z [M+H]$^+$ 493.1; Method 5.

Example 53: N-(3-cyano-5-(3-fluorobenzyl)-6-methyl-4,5,6,7-tetrahydrothieno[3,2-c]pyridin-2-yl)-2-(4-sulfamoylphenyl)acetamide

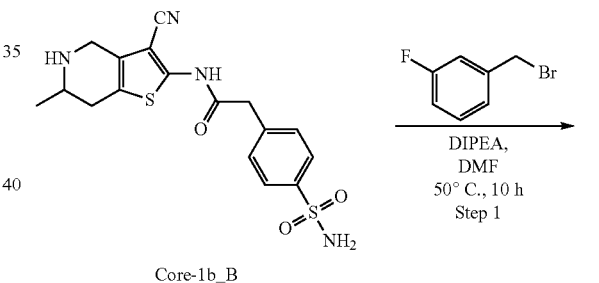

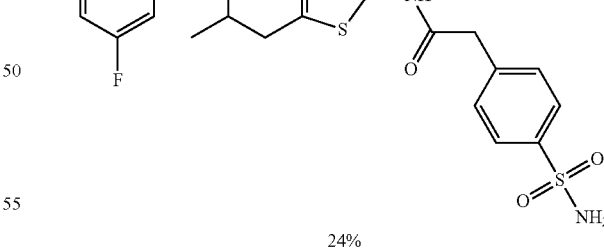

To a solution of N-(3-cyano-6-methyl-4,5,6,7-tetrahydrothieno[3,2-c]pyridin-2-yl)-2-(4-sulfamoylphenyl)acetamide Core-1b_B (318 mg, 0.815 mmol) in DMF (3 mL) was added 1-(bromomethyl)-3-fluorobenzene (154.0 mg, 0.815 mmol) and DIPEA (210.6 mg, 1.63 mmol). The resulting mixture was warmed to 50° C. and stirred at that temperature for 3 h. The reaction mixture was poured into H$_2$O (15 mL) and extracted with EtOAc (15 mL×3), then the organic layer was dried over Na$_2$SO$_4$, and concentrated under reduced pressure to get the crude product. The residue was purified by column chromatography (DCM: MeOH=100:1-10:1), then by reverse chromatography to afford N-(3-cyano-5-(3-fluorobenzyl)-6-methyl-4,5,6,7-tetrahydrothieno[3,2-c]pyridin-2-yl)-2-(4-sulfamoylphenyl)acetamide (95 mg, yield 24%); $^1$H NMR (400 MHz, DMSO-$d_6$) δ 11.9 (s, 1H), 7.98 (d, J=8.4 Hz, 2H), 7.49 (d, J=8.4 Hz, 2H), 7.38-7.09 (m, 6H), 3.95 (s, 2H), 3.70 (s, 2H), 3.45-3.21 (m, 2H), 3.20-3.17 (m, 1H), 2.84 (d, J=8.0 Hz, 1H), 2.45 (d, J=8.0 Hz, 1H), 1.05 (d, J=6.8 Hz, 3H); LC-MS Rt 0.93 min; MS m/z [M+H]$^+$ 499.1; Method 1.

Examples 54 and 55: N-(3-cyano-6-methyl-5-(1-phenylethyl)-4,5,6,7-tetrahydrothieno[3,2-c]pyridin-2-yl)-2-(4-sulfamoylphenyl)acetamide (Enantiomers)

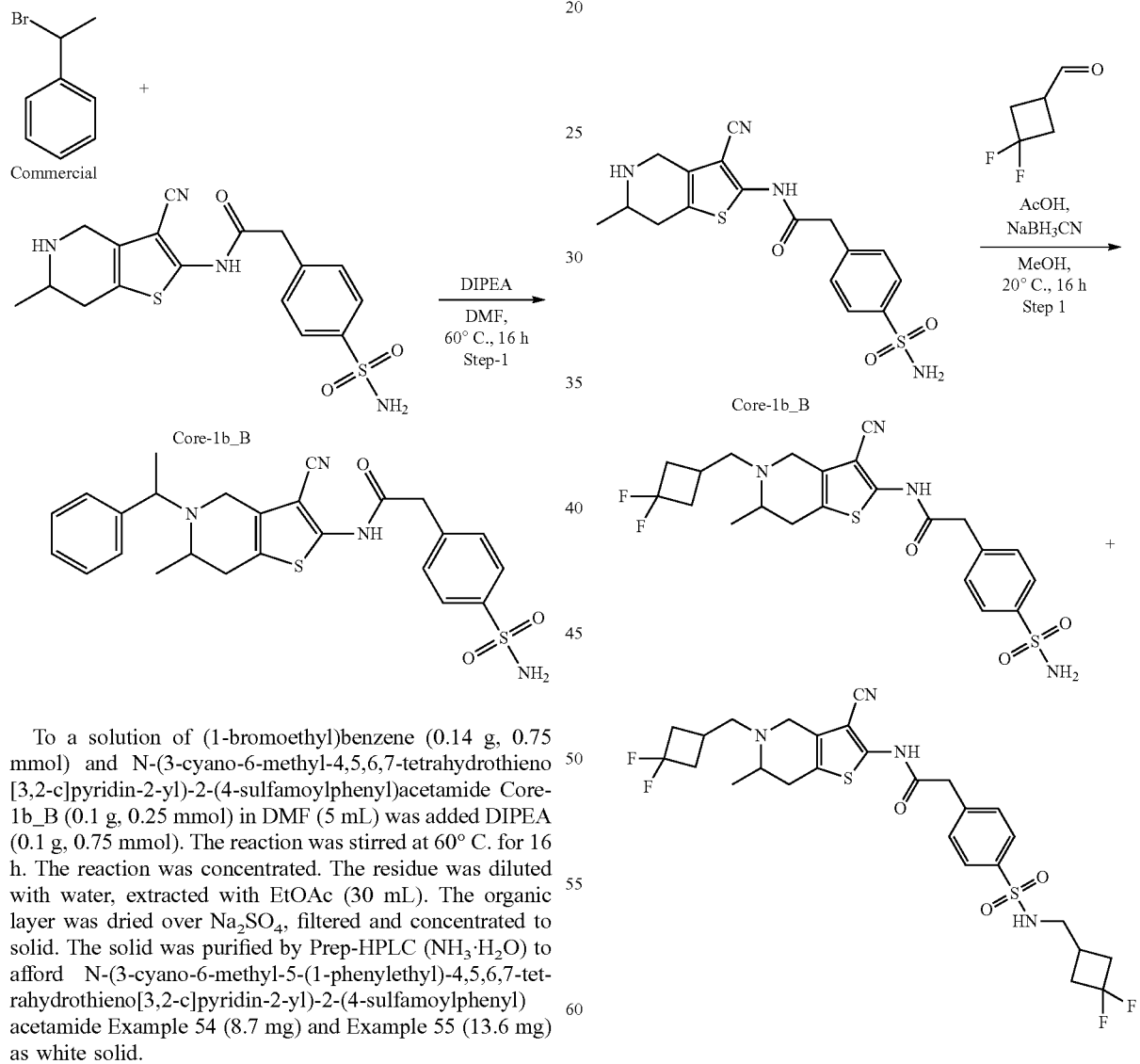

To a solution of (1-bromoethyl)benzene (0.14 g, 0.75 mmol) and N-(3-cyano-6-methyl-4,5,6,7-tetrahydrothieno[3,2-c]pyridin-2-yl)-2-(4-sulfamoylphenyl)acetamide Core-1b_B (0.1 g, 0.25 mmol) in DMF (5 mL) was added DIPEA (0.1 g, 0.75 mmol). The reaction was stirred at 60° C. for 16 h. The reaction was concentrated. The residue was diluted with water, extracted with EtOAc (30 mL). The organic layer was dried over Na$_2$SO$_4$, filtered and concentrated to solid. The solid was purified by Prep-HPLC (NH$_3$·H$_2$O) to afford N-(3-cyano-6-methyl-5-(1-phenylethyl)-4,5,6,7-tetrahydrothieno[3,2-c]pyridin-2-yl)-2-(4-sulfamoylphenyl)acetamide Example 54 (8.7 mg) and Example 55 (13.6 mg) as white solid.

Example 54: 1 H NMR (400 MHz, DMSO-$d_6$) δ 12.02-11.73 (m, 1H), 7.77 (d, J=8.28 Hz, 2H), 7.48 (d, J=8.41 Hz, 2H), 7.37-7.28 (m, 6H), 7.28-7.21 (m, 1H), 4.01-3.86 (m, 2H), 3.83-3.66 (m, 2H), 3.46-3.38 (m, 1H), 3.22-3.10 (m, 1H), 2.78-2.65 (m, 1H), 2.36-2.21 (m, 1H), 1.31 (d, J=6.53 Hz, 3H), 0.85 (d, J=6.53 Hz, 3H); LC-MS Rt 0.65 min, MS m/z [M+H]$^+$ 495.1; Method 3

Example 55: 1H NMR (400 MHz, DMSO-$d_6$) δ 12.15-11.55 (m, 1H), 7.77 (d, J=8.41 Hz, 2H), 7.47 (d, J=8.41 Hz, 2H), 7.41-7.28 (m, 6H), 7.27-7.22 (m, 1H), 3.90 (s, 2H), 3.75 (q, J=6.44 Hz, 1H), 3.55 (d, J=6.40 Hz, 1H), 3.31 (s, 1H), 3.23-3.14 (m, 1H), 2.90 (d, J=10.92 Hz, 1H), 2.43 (d, J=16.31 Hz, 1H), 1.31 (d, J=6.53 Hz, 3H), 0.98 (d, J=6.53 Hz, 3H); LC-MS Rt 0.65 min, MS m/z [M+H]$^+$ 495.1; Method 3.

Examples 56 and 57: N-(3-cyano-5-((3,3-difluorocyclobutyl)methyl)-6-methyl-4,5,6,7-tetrahydrothieno[3,2-c]pyridin-2-yl)-2-(4-sulfamoylphenyl)acetamide & N-(3-cyano-5-((3,3-difluorocyclobutyl)methyl)-6-methyl-4,5,6,7-tetrahydrothieno[3,2-c]pyridin-2-yl)-2-(4-(N-((3,3-difluorocyclobutyl)methyl)sulfamoyl)phenyl)acetamide A mixture of 3,3-difluorocyclobutanecarbaldehyde (4.1 mmol, crude), N-(3-cyano-6-methyl-4,5,6,7-tetrahydrothieno[3,2-c]pyridine-2-yl)-2-(4-sulfamoylphenyl)acetamide Core-1b_B (1.6 g, 4.1 mmol) and AcOH (10 mg) in MeOH (50 mL) was stirred at 20° C. for 4 h. NaBH 3 CN (0.516 g, 8.2 mmol) was added. The mixture was stirred at 20° C. for 12 h then concentrated. The residue was diluted with H₂O (20 mL) and extracted with EtOAc (30 mL×3). The organic layer was washed with brine and concentrated. The crude product was purified by Prep-HPLC (NH₃·H₂O) to afford N-(3-cyano-5-((3,3-difluorocyclobutyl)methyl)-6-methyl-4,5,6,7-tetrahydrothieno[3,2-c]pyridin-2-yl)-2-(4-sulfamoylphenyl)acetamide (238.7 mg, 11%) and the by-product N-(3-cyano-5-((3,3-difluorocyclobutyl)methyl)-6-methyl-4,5,6,7-tetrahydrothieno[3,2-c]pyridin-2-yl)-2-(4-(N-((3,3-difluorocyclobutyl)methyl)sulfamoyl)phenyl)acetamide (34.4 mg).

Example 56: ¹H NMR (400 MHz, DMSO-d₆) δ 11.89 (s, 1H), 7.78 (d, J=8.41 Hz, 2H), 7.48 (d, J=8.41 Hz, 2H), 7.32 (s, 2H), 3.96 (s, 2H), 3.59-3.43 (m, 2H), 3.15-3.05 (m, 1H), 2.80-2.70 (m, 1H), 2.67-2.56 (m, 4H), 2.40-2.32 (m, 2H), 2.27-2.15 (m, 2H), 0.98 (d, J=6.53 Hz, 3H); LC-MS Rt 0.85 min; MS m/z [M+H]⁺ 495.1; Method 1.

Example 57: ¹H NMR (400 MHz, DMSO-d₆) δ 11.90 (s, 1H), 7.86-7.73 (m, 3H), 7.58-7.49 (m, 2H), 4.01-3.95 (m, 2H), 3.58-3.44 (m, 2H), 3.17-3.06 (m, 1H), 2.85 (t, J=6.21 Hz, 2H), 2.80-2.71 (m, 1H), 2.69-2.56 (m, 5H), 2.43-2.13 (m, 7H), 1.10 (s, 1H), 0.98 (d, J=6.53 Hz, 3H); LC-MS Rt 0.71 min; MS m/z [M+H]⁺ 599.1; Method 3.

Example 58: 4-(2-((3-cyano-5-(3-fluorobenzyl)-6-methyl-4,5,6,7-tetrahydrothieno[3,2-c]pyridin-2-yl)amino)-2-oxoethyl)benzamide

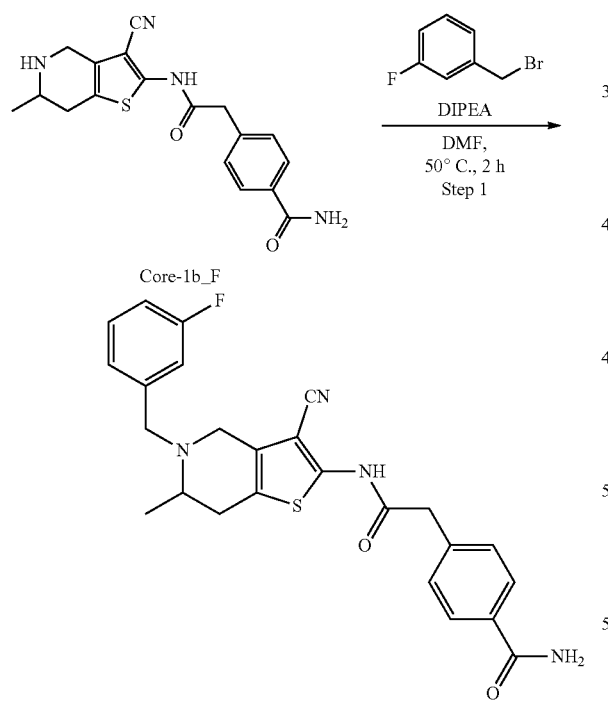

To a solution of 4-(2-((3-cyano-6-methyl-4,5,6,7-tetrahydrothieno[3,2-c]pyridin-2-yl)amino)-2-oxoethyl)benzamide Core-1b_F (78 mg, 0.22 mmol) in DMF was added DIPEA (57 mg, 0.44 mmol) and 1-(bromomethyl)-3-fluorobenzene (62 mg, 0.33 mmol). The mixture was stirred at 50° C. for 2 h. The reaction solution was diluted with water (10 mL) and extracted with EtOAc (10 mL×4). The organic layer was concentrated. The residue was purified by Prep-TLC (9% MeOH in DCM) to afford 4-(2-((3-cyano-5-(3-fluorobenzyl)-6-methyl-4,5,6,7-tetrahydrothieno[3,2-c]pyridin-2-yl)amino)-2-oxoethyl)benzamide (47.5 mg, yield 45%) as yellow solid; ¹H NMR (400 MHz, DMSO-d₆) δ 11.9 (s, 1H), 7.93 (s, 1H), 7.84-7.82 (m, 2H), 7.40-7.32 (m, 4H), 7.19-7.15 (m, 2H), 7.10-7.08 (m, 1H), 3.91 (s, 2H), 3.69 (s, 2H), 3.45-3.40 (m, 2H), 3.19-3.17 (m, 1H), 2.84-2.81 (m, 1H), 2.44-2.39 (m, 1H), 1.04 (d, J=6.4 Hz, 3H); LC-MS Rt 0.66 min; MS m/z [M+H]⁺ 463.0; Method 3.

Examples 59 to 60 were prepared by a similar method by replacing appropriate halide derivative with N-(3-cyano-6-methyl-4,5,6,7-tetrahydrothieno[3,2-c]pyridin-2-yl)-2-(4-sulfamoylphenyl)acetamide Core-1b_B.

Example 59: N-(3-cyano-5-(cyclopentylmethyl)-6-methyl-4,5,6,7-tetrahydrothieno[3,2-c]pyridin-2-yl)-2-(4-sulfamoylphenyl)acetamide hydrochloride

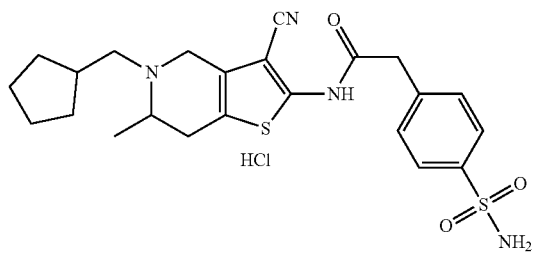 [SMILES: CC1Cc2sc(NC(=O)Cc3ccc(S(N)(=O)=O)cc3)c(C#N)c2CN1CC1CCCC1 ; Cl]

Yield 29%; ¹H NMR (400 MHz, DMSO-d₆) δ 12.15 (s, 1H), 10.62-10.02 (m, 1H), 7.79 (d, J=8.19 Hz, 2H), 7.49 (d, J=8.31 Hz, 2H), 7.33 (s, 2H), 4.51-4.33 (m, 1H), 4.28-4.13 (m, 1H), 4.00 (s, 2H), 3.97-3.80 (m, 1H), 3.18-2.99 (m, 3H), 2.89-2.74 (m, 1H), 2.36-2.22 (m, 1H), 2.01-1.77 (m, 2H), 1.69-1.48 (m, 4H), 1.43-1.33 (m, 1H), 1.32-1.18 (m, 4H); LC-MS Rt 0.95 min; MS m/z [M+H]⁺ 473.1; Method 1.

Example 60: N-(3-cyano-5-(cyclobutylmethyl)-6-methyl-4,5,6,7-tetrahydrothieno[3,2-c]pyridin-2-yl)-2-(4-sulfamoylphenyl)acetamide

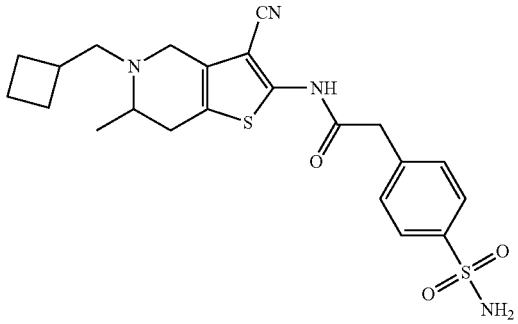 [SMILES: CC1Cc2sc(NC(=O)Cc3ccc(S(N)(=O)=O)cc3)c(C#N)c2CN1CC1CCC1]

Yield 15%; ¹H NMR (400 MHz, DMSO-d₆) δ 12.20-11.66 (m, 1H), 7.77 (d, J=8.3 Hz, 2H), 7.48 (d, J=8.2 Hz, 2H), 7.32 (s, 2H), 3.93 (s, 2H), 3.44 (d, J=6.9 Hz, 2H), 3.30-3.26 (m, 2H), 3.12-3.00 (m, 1H), 2.77-2.66 (m, 1H), 2.47-2.41 (m, 1H), 2.39-2.30 (m, 1H), 2.08-1.94 (m, 2H), 1.94-1.72 (m, 2H), 1.70-1.54 (m, 2H), 0.97 (d, J=6.6 Hz, 3H); LC-MS Rt 0.86 min, MS m/z [M+H]⁺ 459.1; Method 1.

Examples 61 to 63 were prepared by a similar method to that of Example 1.2 by replacing the appropriate aldehyde derivatives with N-(3-cyano-6-methyl-4,5,6,7-tetrahydrothieno[3,2-c]pyridin-2-yl)-2-(4-sulfamoylphenyl)acetamide Core-1b_B.

Example 61: N-(3-cyano-5-(cyclopentylmethyl)-6-methyl-4,5,6,7-tetrahydrothieno[3,2-c]pyridin-2-yl)-2-(4-(N-(cyclopentylmethyl)sulfamoyl)phenyl)acetamide

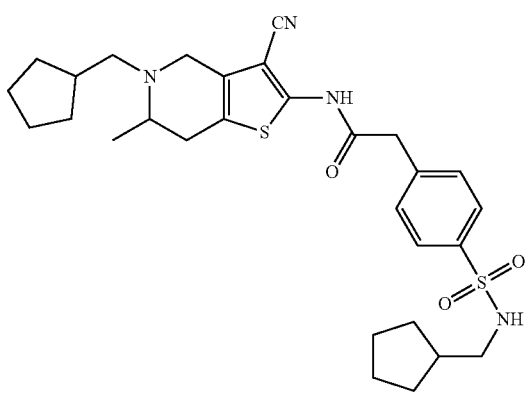 [SMILES: CC1Cc2sc(NC(=O)Cc3ccc(S(=O)(=O)NCC4CCCC4)cc3)c(C#N)c2CN1CC1CCCC1]

Example 61: $^1$H NMR (400 MHz, DMSO-d$_6$) δ 11.88 (s, 1H), 7.74 (d, J=8.41 Hz, 2H), 7.58 (t, J=6.02 Hz, 1H), 7.51 (d, J=8.28 Hz, 2H), 3.96 (s, 2H), 3.50 (q, J=15.73 Hz, 2H), 3.20-3.06 (m, 1H), 2.76-2.72 (m, 1H), 2.63 (t, J=6.65 Hz, 2H), 2.43-2.30 (m, 3H), 2.09-2.05 (m, 1H), 1.96-1.84 (m, 1H), 1.69-1.39 (m, 12H), 1.26-1.09 (m, 4H), 0.96 (d, J=6.53 Hz, 3H); LC-MS Rt 0.75 min; MS m/z [M+H]$^+$ 555.2; Method 3.

Examples 62 and 63: N-(3-cyano-5-(cyclohexylmethyl)-6-methyl-4,5,6,7-tetrahydrothieno[3,2-c]pyridin-2-yl)-2-(4-sulfamoylphenyl)acetamide and N-(3-cyano-5-(cyclohexylmethyl)-6-methyl-4,5,6,7-tetrahydrothieno[3,2-c]pyridin-2-yl)-2-(4-(N-(cyclohexylmethyl)sulfamoyl)phenyl)acetamide

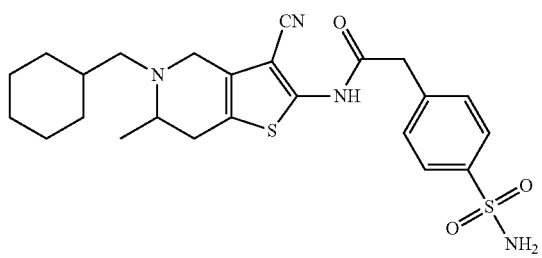

+

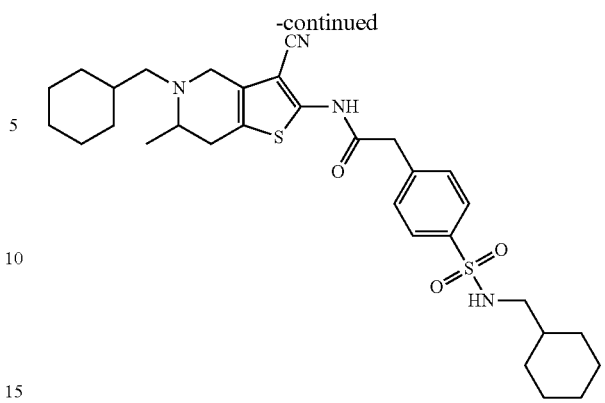

Yield 17%; $^1$H NMR (400 MHz, DMSO-d$_6$) δ 12.14 (s, 1H), 11.06-9.20 (m, 1H), 7.79 (d, J=8.31 Hz, 2H), 7.49 (d, J=8.31 Hz, 2H), 7.33 (s, 2H), 4.34-4.55 (m, 1H), 4.10-4.30 (m, 1H), 4.00 (s, 2H), 3.95-3.77 (m, 1H), 3.19-3.00 (m, 2H), 2.81 (d, J=16.87 Hz, 2H), 2.03-1.56 (m, 6H), 1.42-1.06 (m, 6H), 1.05-0.84 (m, 2H); LC-MS Rt 0.70 min; MS m/z [M+H]$^+$ 487.1; Method 3.

: Yield 26%; $^1$H NMR (400 MHz, CD$_3$OD) δ 7.81 (d, J=7.78 Hz, 2H), 7.54 (d, J=7.78 Hz, 2H), 4.01-3.86 (m, 1H), 3.56 (s, 2H), 2.83 (d, J=14.93 Hz, 1H), 2.66 (d, J=6.40 Hz, 2H), 2.53-2.27 (m, 3H), 1.91-1.47 (m, 10H), 1.44-1.01 (m, 13H), 0.99-0.68 (m, 4H); LC-MS Rt 1.22 min; MS m/z [M+H]$^+$ 583.3; Method 1.

Examples 64 to 69 were prepared by a similar method to that of Core 2a (K$_2$CO$_3$, rt., 16 h) by using N-(3-cyano-6-methyl-4,5,6,7-tetrahydrothieno[3,2-c]pyridin-2-yl)-2-(4-sulfamoylphenyl)acetamide (Core-1b_B) with the appropriate halide derivative (either commercially available or preparations described hereinabove).

Example 64: N-(3-cyano-5-(2,5-dichlorobenzyl)-6-methyl-4,5,6,7-tetrahydrothieno[3,2-c]pyridin-2-yl)-2-(4-sulfamoylphenyl)acetamide

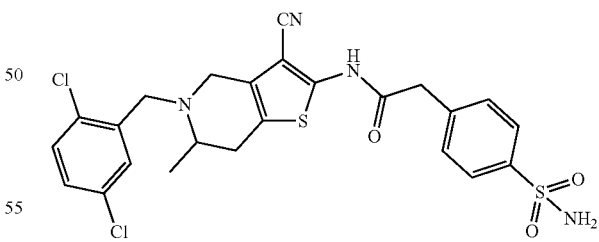

$^1$H NMR (400 MHz, DMSO-d$_6$) δ 7.76 (d, J=8.4 Hz, 2H), 7.57 (d, J=2.6 Hz, 1H), 7.48 (d, J=8.6 Hz, 2H), 7.37 (dd, J=8.5, 2.7 Hz, 1H), 7.29 (s, 1H), 3.89 (s, 2H), 3.74 (d, J=2.7 Hz, 2H), 3.49 (d, J=4.2 Hz, 2H), 3.23-3.20 (m, 1H), 2.81 (d, J=11.3 Hz, 1H), 2.42 (d, J=16.3 Hz, 1H), 1.07 (d, J=6.6 Hz, 3H); LC-MS Rt 0.94 min, MS m/z [M+2H]+552.9; Method 5.

Example 65: N-(3-cyano-5-(3-fluorobenzyl)-6-methyl-4,5,6,7-tetrahydrothieno[3,2-c]pyridin-2-yl)-2-(4-sulfamoylphenyl)acetamide (enantiomers)

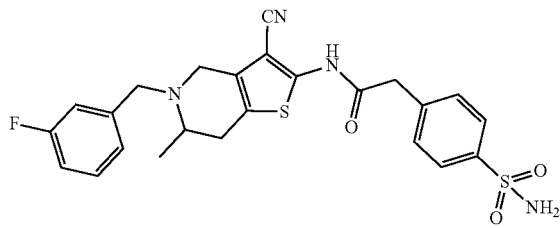 [SMILES: CC1Cc2sc(NC(=O)Cc3ccc(S(N)(=O)=O)cc3)c(C#N)c2CN1Cc1cccc(F)c1]

$^1$H NMR (400 MHz, DMSO-$d_6$) δ 11.89 (s, 1H), 7.78 (d, J=8.1 Hz, 2H), 7.48 (d, J=8.1 Hz, 2H), 7.41-7.28 (m, 3H), 7.17 (t, J=8.9 Hz, 2H), 7.08 (t, J=8.2 Hz, 1H), 3.94 (s, 2H), 3.69 (s, 2H), 3.44 (d, J=6.9 Hz, 2H), 3.21-3.15 (m, 1H), 2.83 (d, J=16.2 Hz, 1H), 2.42 (d, J=15.6 Hz, 1H), 1.05 (d, J=6.5 Hz, 3H); LC-MS Rt 0.62 min, MS m/z [M+H]$^+$ 499.0; Method 5.

Example 66: N-(3-cyano-5-(3-fluorobenzyl)-6-methyl-4,5,6,7-tetrahydrothieno[3,2-c]pyridin-2-yl)-2-(4-sulfamoylphenyl)acetamide (enantiomers)

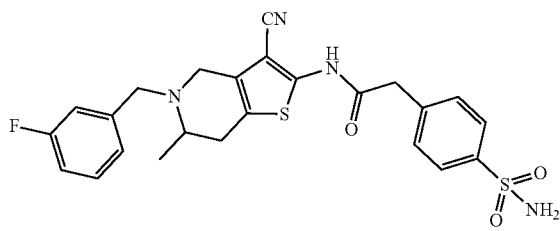 [SMILES: CC1Cc2sc(NC(=O)Cc3ccc(S(N)(=O)=O)cc3)c(C#N)c2CN1Cc1cccc(F)c1]

$^1$H NMR (400 MHz, DMSO-$d_6$) δ 7.77 (d, J=8.4 Hz, 2H), 7.48 (d, J=8.4 Hz, 2H), 7.41-7.34 (m, 1H), 7.31 (s, 2H), 7.22-7.14 (m, 2H), 7.08 (t, J=8.2 Hz, 1H), 3.93 (s, 2H), 3.69 (s, 2H), 3.44 (d, J=6.9 Hz, 2H), 3.23-3.15 (m, 1H), 2.87-2.78 (m, 1H), 2.42 (d, J=16.6 Hz, 1H), 1.05 (d, J=6.6 Hz, 3H); LC-MS Rt 0.62 min, MS m/z [M+H]$^+$ 499.0; Method 5.

Example 67: N-(3-cyano-6-methyl-5-phenethyl-4,5,6,7-tetrahydrothieno[3,2-c]pyridin-2-yl)-2-(4-sulfamoylphenyl)acetamide

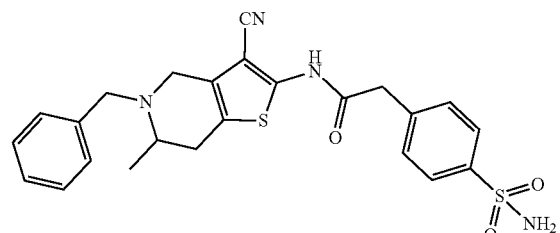

$^1$H NMR (400 MHz, DMSO-$d_6$) δ 7.77 (d, J=8.4 Hz, 2H), 7.48 (d, J=8.4 Hz, 2H), 7.32-7.23 (m, 6H), 7.20-7.15 (m, 1H), 3.93 (s, 2H), 3.69-3.49 (m, 2H), 3.21-3.15 (m, 1H), 2.75 (dt, J=11.2, 5.3 Hz, 5H), 2.35 (d, J=21.6 Hz, 1H), 0.99 (d, J=6.5 Hz, 3H); LC-MS Rt 0.60 min, MS m/z [M+H]$^+$ 495.0; Method 5.

Example 68: N-(3-cyano-5-(2-cyclohexylethyl)-6-methyl-4,5,6,7-tetrahydrothieno[3,2-c]pyridin-2-yl)-2-(4-sulfamoylphenyl)acetamide

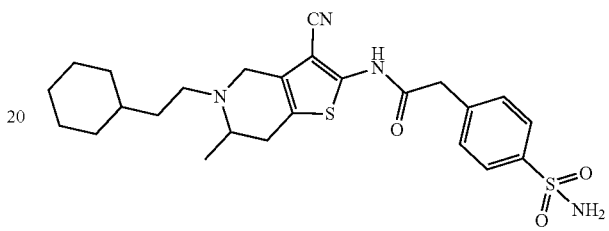

$^1$H NMR (400 MHz, DMSO-$d_6$) δ 7.77 (d, J=8.4 Hz, 2H), 7.48 (d, J=8.4 Hz, 2H), 7.31 (s, 2H), 3.92 (s, 2H), 3.51 (d, J=15.8 Hz, 2H), 3.43 (s, 1H), 3.12-3.06 (m, 1H), 2.74 (d, J=16.2 Hz, 1H), 2.34 (dd, J=14.7, 3.2 Hz, 1H), 1.67 (t, J=14.7 Hz, 5H), 1.39-1.12 (m, 7H), 0.98-0.84 (m, 5H); LC-MS Rt 0.58 min, MS m/z [M+H]$^+$ 501.1; Method 7.

Examples 69 to 70 were prepared by a similar method to that of Example 4 of Core 2a (K$_2$CO$_3$, rt., 16 h) by using N-(3-cyano-6-methyl-4,5,6,7-tetrahydrothieno[3,2-c]pyridin-2-yl)-2-(4-(methylsulfonyl)phenyl)acetamide with the appropriate halide derivative (either commercially available or preparations described hereinabove).

Example 69: N-(3-cyano-5-(3-fluorobenzyl)-6-methyl-4,5,6,7-tetrahydrothieno[3,2-c]pyridin-2-yl)-2-(4-(methylsulfonyl)phenyl)acetamide

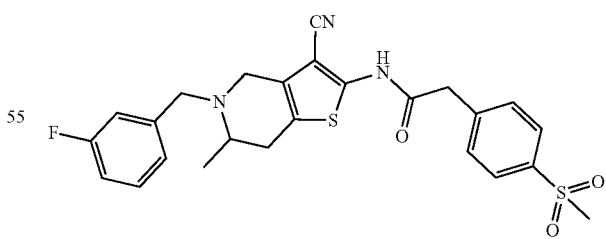

$^1$H NMR (400 MHz, DMSO-$d_6$) δ 11.92 (s, 1H), 7.92-7.85 (m, 2H), 7.58 (d, J=8.4 Hz, 2H), 7.42-7.32 (m, 1H), 7.21-7.12 (m, 2H), 7.11-7.05 (m, 1H), 3.99 (s, 2H), 3.69 (s, 2H), 3.44 (d, J=6.7 Hz, 2H), 3.20 (s, 4H), 2.83 (d, J=16.1 Hz, 1H), 2.41 (dd, J=16.1, 4.3 Hz, 1H), 1.05 (d, J=6.6 Hz, 3H); LC-MS Rt 0.69 min, MS m/z [M+H]$^+$ 498.0; Method 5.

Example 70: N-(3-cyano-5-(2,5-dichlorobenzyl)-6-methyl-4,5,6,7-tetrahydrothieno[3,2-c]pyridin-2-yl)-2-(4-(methylsulfonyl)phenyl)acetamide

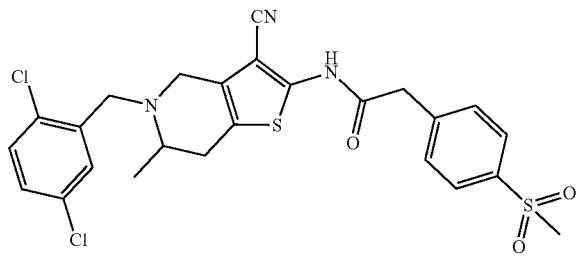 [SMILES: CC1Cc2sc(NC(=O)Cc3ccc(S(C)(=O)=O)cc3)c(C#N)c2CN1Cc1cc(Cl)ccc1Cl]

$^1$H NMR (400 MHz, DMSO-$d_6$) δ 7.87 (d, J=8.3 Hz, 2H), 7.57 (dd, J=5.5, 2.8 Hz, 3H), 7.48 (d, J=8.5 Hz, 1H), 7.37 (dd, J=8.5, 2.6 Hz, 1H), 3.92 (s, 2H), 3.74 (d, J=2.5 Hz, 2H), 3.49 (s, 2H), 3.19 (s, 4H), 2.81 (d, J=16.2 Hz, 1H), 2.41 (d, J=15.5 Hz, 1H), 1.07 (d, J=6.6 Hz, 3H); LC-MS Rt 1.02 min, MS m/z [M+H]$^+$ 548.0; Method 5.

Example 71: N-(3-cyano-5-(cyclohexylmethyl)-6,6-dimethyl-4,5,6,7-tetrahydrothieno[3,2-c]pyridin-2-yl)-2-(4-sulfamoylphenyl)acetamide

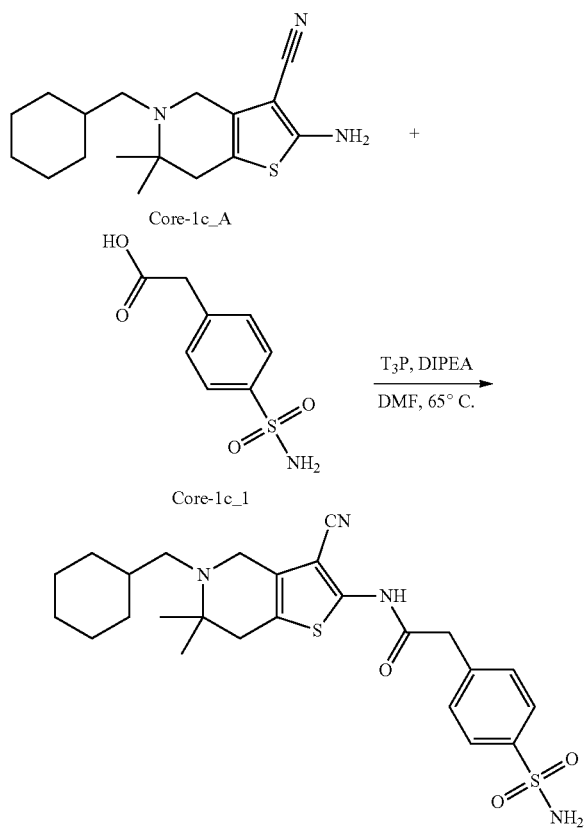

To a solution of 2-amino-5-(cyclohexylmethyl)-6,6-dimethyl-4,5,6,7-tetrahydrothieno[3,2-c]pyridine-3-carbonitrile Core-1c_A (1.15 g, 3.8 mmol) in DMF (12 mL) was added 2-(4-sulfamoylphenyl)acetic acid (1.23 g, 5.7 mmol), DIPEA (982 mg, 7.6 mmol) and a solution of T$_3$P in EtOAc (4.84 g, 50% w/w, 7.6 mmol). The mixture was stirred at 65° C. for 1 h. The reaction mixture was diluted with water (25 mL) and extracted with EtOAc (15 mL×4). The organic layer was concentrated. The residue was purified by column chromatography on silica (PE:EtOAc=10:1-2:1) to afford the desired product (1.15 g, yield 60%) as light yellow solid; LC-MS Rt 1.08 min, MS m/z [M+H]$^+$ 501.3; Method 1; 1 H NMR (400 MHz, DMSO-$d_6$) δ 11.9 (s, 1H), 7.78 (d, J=8.4 Hz, 2H), 7.48 (d, J=8.4 Hz, 2H), 7.33 (s, 2H), 3.96 (s, 2H), 3.49 (s, 2H), 2.46 (s, 2H), 2.24 (d, J=6.8 Hz, 2H), 1.76-1.73 (m, 2H), 1.67-1.64 (m, 3H), 1.39-1.33 (m, 1H), 1.25-1.15 (m, 3H), 1.02 (s, 6H), 0.88-0.75 (m, 2H).

Example 72: N-(3-cyano-5-(cyclohexylmethyl)-6,6-dimethyl-4,5,6,7-tetrahydrothieno[3,2-c]pyridin-2-yl)-2-(3,3-dimethyl-1,1-dioxido-2,3-dihydrobenzo[b]thiophen-5-yl)acetamide

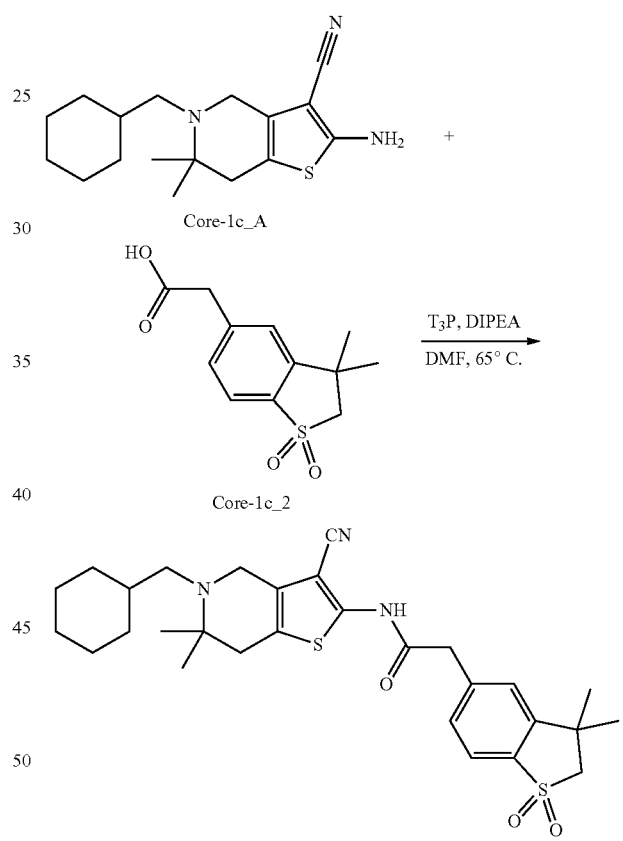

The title compound was prepared by a method similar to that of Example 1.0 by replacing 2-(4-sulfamoylphenyl) acetic acid Core-1c 1 with 2-(3,3-dimethyl-1,1-dioxido-2,3-dihydrobenzo[b]thiophen-5-yl)acetic acid Core-1c_2; Yield 56%; LC-MS Rt 0.76 min, MS m/z [M+H]$^+$ 540.1; Method 3; 1 H NMR (400 MHz, CD$_3$OD) δ 7.64-7.49 (m, 3H), 4.31 (s, 2H), 4.03 (s, 3H), 3.43 (s, 2H), 2.99 (s, 2H), 1.89-0.89 (m, 25H).

Examples 73 to 77 were prepared by a similar method to that of Example 1c.1 by replacing 2-(4-sulfamoylphenyl) acetic acid Core-1c_1 with the appropriate acid derivative.

Example 73: N-(3-cyano-5-(cyclohexylmethyl)-6,6-dimethyl-4,5,6,7-tetrahydrothieno[3,2-c]pyridin-2-yl)-2-phenylacetamide

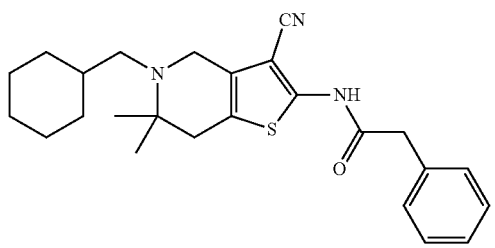 [SMILES: CC1(C)Cc2sc(NC(=O)Cc3ccccc3)c(C#N)c2CN1CC1CCCCC1]

$^1$H NMR (400 MHz, DMSO-d$_6$) δ 11.8 (s, 1H), 7.33-7.25 (m, 5H), 3.85 (s, 2H), 3.48 (s, 2H), 2.49 (s, 2H), 2.23 (d, J=6.8 Hz, 2H), 1.80-1.60 (m, 5H), 1.45-1.35 (m, 1H), 1.20-1.10 (m, 3H), 1.02 (s, 6H), 0.90-0.75 (m, 2H); LC-MS Rt 0.74 min, MS m/z [M+H]$^+$ 422.2; Method 3.

Example 74: 2-(3-(aminomethyl)-1,1-dioxido-2,3-dihydrobenzo[b]thiophen-5-yl)-N-(3-cyano-5-(cyclohexylmethyl)-6,6-dimethyl-4,5,6,7-tetrahydrothieno[3,2-c]pyridin-2-yl)acetamide

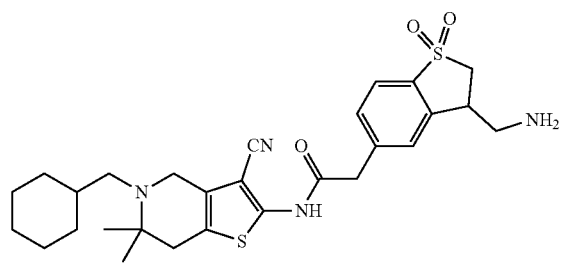 [SMILES: CC1(C)Cc2sc(NC(=O)Cc3ccc4c(c3)C(CN)CS4(=O)=O)c(C#N)c2CN1CC1CCCCC1]

LC-MS Rt 1.03 min, MS m/z [M+H]$^+$ 541.3; Method 3; 1 H NMR (CD$_3$OD) δ 7.68 (d, J=8.0 Hz, 1H), 7.56 (s, 1H), 7.53 (d, J=7.9 Hz, 1H), 3.99 (s, 2H), 3.74-3.64 (m, 2H), 3.62-3.48 (m, 3H), 3.21-3.11 (m, 1H), 3.06-2.92 (m, 1H), 2.53 (s, 2H), 2.32 (d, J=6.8 Hz, 2H), 1.82 (d, J=13.2 Hz, 2H), 1.77-1.64 (m, 3H), 1.46 (ddd, J=3.9, 7.1, 14.1 Hz, 1H), 1.37-1.16 (m, 4H), 1.11 (s, 6H), 0.94-0.83 (m, 2H).

Example 75: N-(3-cyano-5-(cyclohexylmethyl)-6,6-dimethyl-4,5,6,7-tetrahydrothieno[3,2-c]pyridin-2-yl)-N-methyl-2-(4-sulfamoylphenyl)acetamide

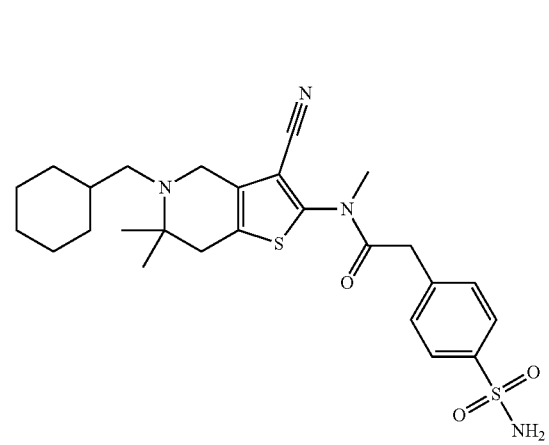 [SMILES: CN(C(=O)Cc1ccc(S(N)(=O)=O)cc1)c1sc2c(c1C#N)CN(CC1CCCCC1)C(C)(C)C2]

LC-MS Rt 1.13 min, MS m/z [M+H]$^+$ 515.4; Method 3; 1 H NMR (400 MHz, CDCl$_3$) δ 7.93-7.79 (m, 2H), 7.37-7.29 (m, 1H), 7.37-7.28 (m, 1H), 4.92 (s, 2H), 3.73 (d, J=1.9 Hz, 2H), 3.63 (s, 2H), 3.34 (s, 3H), 2.62 (s, 2H), 2.32 (d, J=6.8 Hz, 2H), 1.82 (d, J=12.4 Hz, 2H), 1.77-1.66 (m, 3H), 1.46 (dd, J=6.8 Hz, 3.6, 1H), 1.35-1.19 (m, 3H), 1.16 (s, 6H), 0.91-0.78 (m, 2H).

Example 76: N-(3-cyano-5-(cyclohexylmethyl)-6,6-diethyl-4,5,6,7-tetrahydrothieno[3,2-c]pyridin-2-yl)-2-(4-sulfamoylphenyl)acetamide

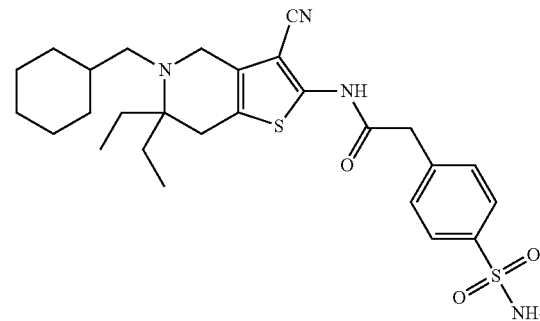

Yield 45%; LC-MS Rt 1.17 min, MS m/z [M+H]$^+$ 529.2; Method 3; 1 H NMR (400 MHz, DMSO-d$^6$) δ 11.86 (s, 1H), 7.78 (d, J=8.4 Hz, 2H), 7.48 (d, J=8.4 Hz, 2H), 7.32 (s, 2H), 3.95 (s, 2H), 3.55 (s, 2H), 2.38 (s, 2H), 2.21 (d, J=6.8 Hz, 2H), 1.57-1.85 (m, 5H), 1.31-1.50 (m, 5H), 1.04-1.27 (m, 3H), 0.55-0.97 (m, 8H).

Example 77: N-(3-cyano-5-((3,3-difluorocyclobutyl)methyl)-6,6-dimethyl-4,5,6,7-tetrahydrothieno[3,2-c]pyridin-2-yl)-2-(4-sulfamoylphenyl)acetamide

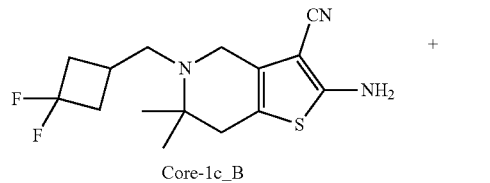

Core-1c_B

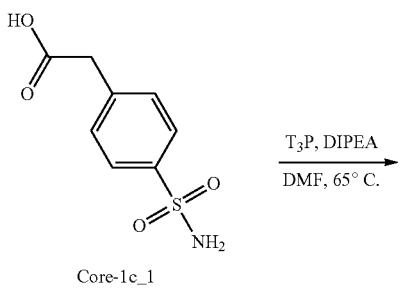

Core-1c_1

T₃P, DIPEA
DMF, 65° C.

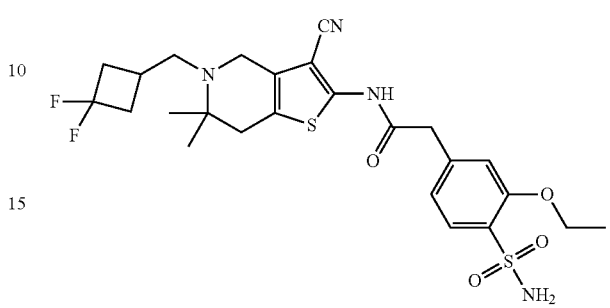

2-Amino-5-((3,3-difluorocyclobutyl)methyl)-6,6-dimethyl-4,5,6,7-tetrahydrothieno[3,2-c]pyridine-3-carbonitrile Core-1c_B (200 mg, 0.64 mmol) in DMF (2 mL) was added 2-(4-sulfamoylphenyl)acetic acid (207 mg, 0.96 mmol), DIPEA (165 mg, 1.28 mmol) and a solution of T₃P in EtOAc (815 mg, 1.28 mmol, w/w 50%). The mixture was stirred at 65° C. for 1 h. The reaction solution was diluted with water (10 mL) and extracted with EtOAc (10 mL×4). The organic layer was concentrated. The residue was purified by prep-TLC (PE:EtOAc=1:1) to afford N-(3-cyano-5-((3,3-difluorocyclobutyl)methyl)-6,6-dimethyl-4,5,6,7-tetrahydrothieno[3,2-c]pyridin-2-yl)-2-(4-sulfamoylphenyl)acetamide (141.5 mg, yield 43%) as off-white solid. LC-MS Rt 0.90 min, MS m/z [M+H]⁺ 509.2; Method 1; 1 H NMR (400 MHz, DMSO-d₆) δ 11.9 (s, 1H), 7.77 (d, J=8.0 Hz, 2H), 7.47 (d, J=8.4 Hz, 2H), 7.32 (s, 2H), 3.95 (s, 2H), 3.50 (s, 2H), 2.70-2.40 (m, 6H), 2.30-2.10 (m, 3H), 1.04 (s, 6H).

Example 78: N-(3-cyano-5-((3,3-difluorocyclobutyl)methyl)-6,6-dimethyl-4,5,6,7-tetrahydrothieno[3,2-c]pyridin-2-yl)-2-(3-ethoxy-4-sulfamoylphenyl)acetamide Example 78 was prepared by a similar method to that of step 3 of 2-amino-5-((3,3-difluorocyclobutyl)methyl)-6,6-dimethyl-4,5,6,7-tetrahydrothieno[3,2-c]pyridine-3-carbonitrile Core-1c_B with 2-(3-ethoxy-4-sulfamoylphenyl)acetic acid. ¹H NMR (400 MHz, DMSO-d₆) δ 7.67 (d, J=8.0 Hz, 1H), 7.17 (s, 1H), 6.96 (d, J=7.7 Hz, 1H), 6.89 (s, 2H), 4.20 (q, J=7.0 Hz, 2H), 3.91 (s, 2H), 3.51 (s, 2H), 2.61-2.54 (m, 3H), 2.29-2.13 (m, 2H), 1.38 (t, J=6.9 Hz, 3H), 1.24 (s, 4H), 1.05 (s, 6H); LC-MS Rt 0.61 min, MS m/z [M+H]⁺ 553.1; Method 5.

Example 79: N-(3-cyano-5-((3,3-difluorocyclobutyl)methyl)-6,6-diethyl-4,5,6,7-tetrahydrothieno[3,2-c]pyridin-2-yl)-2-(4-sulfamoylphenyl)acetamide

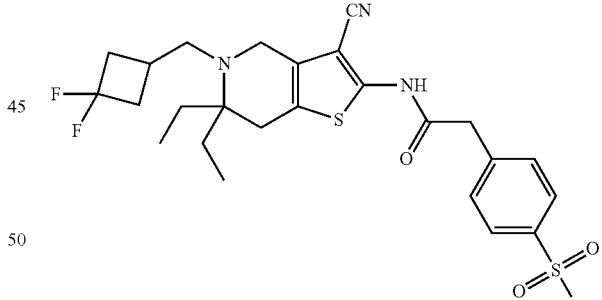

Examples 79 was prepared by a similar method to that of step 3 of Intermediate Core-1c_B by replacing 2-amino-5-(cyclohexylmethyl)-6,6-dimethyl-4,5,6,7-tetrahydrothieno[3,2-c]pyridine-3-carbonitrile Core-1c_A with 2-amino-5-((3,3-difluorocyclobutyl)methyl)-6,6-dimethyl-4,5,6,7-tetrahydrothieno[3,2-c]pyridine-3-carbonitrile Core-1c_B. Yield 12%; LC-MS Rt 1.02 min, MS m/z [M+H]⁺ 537.2; 1 H NMR (400 MHz, CD₃OD) δ 7.89 (d, J=8.4 Hz, 2H), 7.53 (d, J=8.4 Hz, 2H), 3.95 (s, 2H), 3.68 (s, 2H), 2.63-2.66 (m, 3H), 2.45-2.54 (m, 3H), 2.20-2.31 (m, 3H), 1.51-1.66 (m, 4H), 0.91 (t, J=7.6 Hz, 6H).

Example 80: N-(3-cyano-5-(3-fluorobenzyl)-6,6-dimethyl-4,5,6,7-tetrahydrothieno[3,2-c]pyridin-2-yl)-2-(3,3-dimethyl-1,1-dioxido-2,3-dihydrobenzo[b]thiophen-5-yl)acetamide

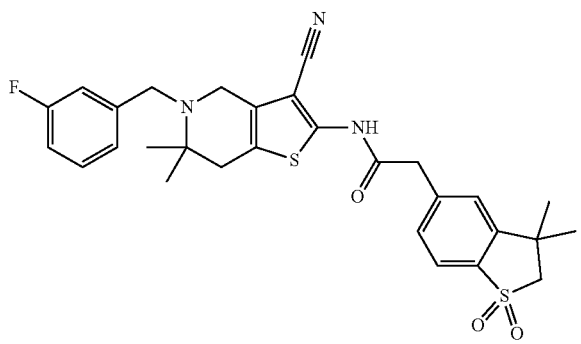 [SMILES: CC1(C)CS(=O)(=O)c2ccc(CC(=O)Nc3sc4c(c3C#N)CN(Cc3cccc(F)c3)C(C)(C)C4)cc21]

Example 80 was prepared by a similar method to that of Example 1c.1 by replacing 2-amino-5-(3-fluorobenzyl)-6,6-dimethyl-4,5,6,7-tetrahydrothieno[3,2-c]pyridine-3-carbonitrile Core-1c_C with 2-(3,3-dimethyl-1,1-dioxido-2,3-dihydrobenzo[b]thiophen-5-yl)acetic acid Core-1c_2. Yield 41%; LC-MS Rt 1.05 min, MS m/z [M+H]$^+$ 552.3; Method 3; 1 H NMR (400 MHz, DMSO-d$_6$) δ 11.9 (s, 1H), 7.69-7.67 (m, 1H), 7.62 (s, 1H), 7.48-7.45 (m, 1H), 7.38-7.32 (m, 1H), 7.18-7.13 (m, 2H), 7.08-7.05 (m, 1H), 3.99 (s, 2H), 3.69 (s, 2H), 3.50 (s, 2H), 3.34-3.32 (m, 2H), 2.59-2.54 (m, 2H), 1.46 (s, 6H), 1.16 (s, 6H).

Example 81: N-(3-cyano-5-(3-fluorobenzyl)-6,6-dimethyl-4,5,6,7-tetrahydrothieno[3,2-c]pyridin-2-yl)-2-(4-sulfamoylphenyl)acetamide

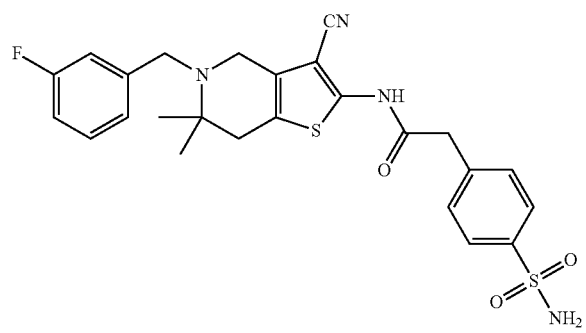 [SMILES: CC1(C)Cc2sc(NC(=O)Cc3ccc(S(N)(=O)=O)cc3)c(C#N)c2CN1Cc1cccc(F)c1]

Example 81 was prepared by a similar method by N-(3-cyano-6,6-dimethyl-4,5,6,7-tetrahydrothieno[3,2-c]pyridin-2-yl)-2-(4-sulfamoylphenyl)acetamide with the appropriate halide derivative (either commercially available or preparations described hereinabove). $^1$H NMR (400 MHz, DMSO-d$_6$) δ 7.81-7.74 (m, 2H), 7.48 (d, J=8.4 Hz, 2H), 7.40-7.29 (m, 3H), 7.22-7.13 (m, 2H), 7.06 (td, J=8.6, 2.0 Hz, 1H), 3.94 (s, 2H), 3.68 (s, 2H), 3.37 (s, 2H), 2.58 (s, 2H), 1.15 (s, 6H); LC-MS Rt 0.65 min, MS m/z [M+H]$^+$ 513.7; Method 5.

Example 82: N-(3-cyano-5-(cyclohexylmethyl)-6,6-dimethyl-4,5,6,7-tetrahydrothieno[3,2-c]pyridin-2-yl)-2-(3-methoxy-4-sulfamoylphenyl)acetamide

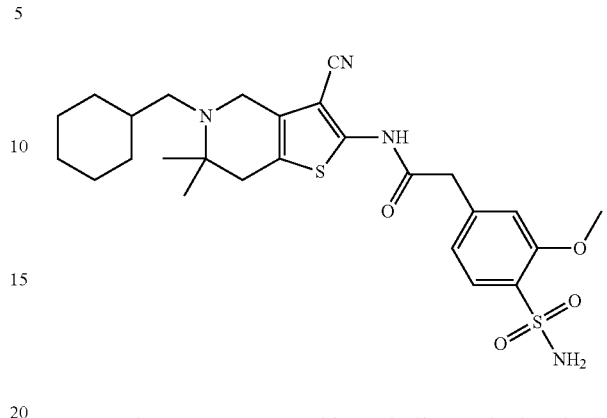

Example 82 were prepared by a similar method to that of Core 2a (K$_2$CO$_3$, rt., 16 h) by using N-(3-cyano-6,6-dimethyl-4,5,6,7-tetrahydrothieno[3,2-c]pyridin-2-yl)-2-(3-methoxy-4-sulfamoylphenyl)acetamide (Core-1c_A14) with the appropriate halide derivative (either commercially available or preparations described hereinabove). $^1$H NMR (400 MHz, DMSO-d$_6$) δ 7.65 (d, J=8.0 Hz, 1H), 7.17 (d, J=1.2 Hz, 1H), 7.04-6.93 (m, 3H), 3.88 (d, J=8.4 Hz, 5H), 3.47 (s, 2H), 2.44 (s, 2H), 2.24 (d, J=7.0 Hz, 2H), 1.74 (d, J=11.3 Hz, 2H), 1.65 (d, J=13.3 Hz, 3H), 1.39 (s, 1H), 1.27-1.10 (m, 3H), 1.02 (s, 6H), 0.81 (q, J=12.0, 10.0 Hz, 2H); LC-MS Rt 0.64 min, MS m/z [M+H]$^+$ 531.2; Method 5.

Example 83 N-(3-cyano-5-(cyclohexylmethyl)-4,5,6,7-tetrahydrothieno[3,2-c]pyridin-2-yl)-2-(3-methoxy-4-sulfamoylphenyl)acetamide

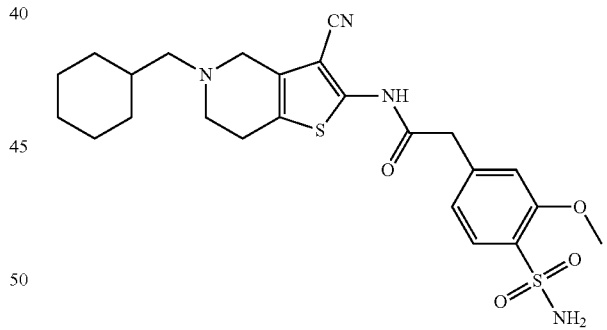

To a solution of 2-amino-5-(cyclohexylmethyl)-4,5,6,7-tetrahydrothieno[3,2-c]pyridine-3-carbonitrile core-1a_B (600 mg, 2.2 mmol) and 2-(3-methoxy-4-sulfamoylphenyl)acetic acid Core-1a_E (809 mg, 3.3 mmol) in DMF (6 mL) were added DIPEA (568 mg, 4.4 mmol) and T$_3$P (2.1 g, 3.3 mmol). The reaction mixture was stirred at 120° C. under microwave for 45 min. Then the reaction mixture was poured into water (60 mL) and Na$_2$CO$_3$ was added to adjusted pH to 8-9. The mixture was extracted with EtOAc (60 mL×3) and the organic layers were combined, dried over Na$_2$SO$_4$, and concentrated. The crude product was washed by MeOH to afford N-(3-cyano-5-(cyclohexylmethyl)-4,5,6,7-tetrahydrothieno[3,2-c]pyridin-2-yl)-2-(3-methoxy-4-sulfamoylphenyl)acetamide Example 83 (315.0 mg, Yield 16%) as white solid, and the mother liquor was purified by pre-HPLC (NH$_3$H$_2$O) to afford another batch of Example 83 (232.0 mg, Yield 12%). $^1$H NMR (400 MHz, DMSO-d$_6$) δ 11.87 (s, 1H), 7.67 (d, J=8.0 Hz, 1H), 7.16 (s, 1H), 7.03 (s, 2H), 6.97 (d, J=8.0 Hz, 1H), 3.93 (s, 2H), 3.89 (s, 3H), 3.34 (s, 2H), 2.65 (s, 4H), 2.29 (d, J=7.0 Hz, 2H), 1.75-1.72 (m, 6H), 1.27-1.09 (m, 3H), 0.90-0.81 (m, 2H); LC-MS Rt 0.67 min; MS m/z [M+H]$^+$ 503.1; Method 3.

Example 84 N-(3-cyano-5-(cyclohexylmethyl)-4,5,6,7-tetrahydrothieno[3,2-c]pyridin-2-yl)-2-(5-sulfamoylthiophen-2-yl)acetamide

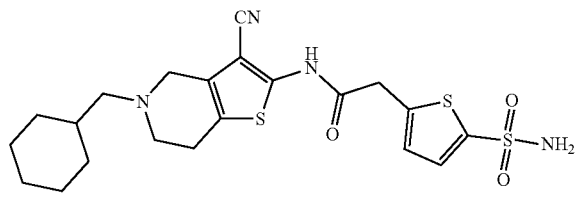 [SMILES: N#Cc1c(NC(=O)Cc2ccc(S(N)(=O)=O)s2)sc2c1CN(CC1CCCCC1)CC2]

Example 84 was prepared by a similar method to that of Example 83 by replacing the appropriate acid derivative. $^1$H NMR (400 MHz, DMSO-d$_6$) δ 8.13 (s, 1H), 7.60 (s, 2H), 7.40 (d, J=3.7 Hz, 1H), 6.99 (d, J=3.7 Hz, 1H), 4.17 (s, 2H), 2.67 (s, 4H), 2.31 (d, J=7.1 Hz, 2H), 1.79-1.71 (m, 2H), 1.70-1.54 (m, 4H), 1.28-1.12 (m, 3H), 0.91-0.79 (m, 2H); LC-MS Rt 0.62 min; MS m/z [M+H]$^+$ 479.0; Method 5.

Example 85 N-(3-cyano-5-(3,5-difluorobenzyl)-6-methyl-4,5,6,7-tetrahydrothieno[3,2-c]pyridin-2-yl)-2-(4-sulfamoylphenyl)acetamide

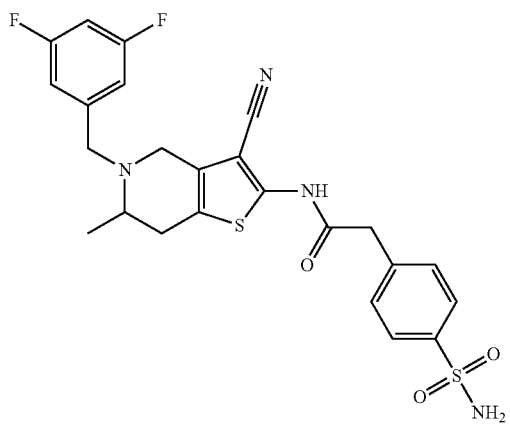 [SMILES: CC1Cc2sc(NC(=O)Cc3ccc(S(N)(=O)=O)cc3)c(C#N)c2CN1Cc1cc(F)cc(F)c1]

Example 85 was prepared by a similar method to that of Core 2a (K$_2$CO$_3$, rt., 15 h) by using N-(3-cyano-6-methyl-4,5,6,7-tetrahydrothieno[3,2-c]pyridin-2-yl)-2-(4-sulfamoylphenyl)acetamide (Core-1b_B) with the appropriate halide derivative (either commercially available or preparations described hereinabove). $^1$H NMR (400 MHz, DMSO-d$_6$) δ 11.90 (s, 1H), 7.77 (d, J=8.4 Hz, 2H), 7.48 (d, J=8.4 Hz, 2H), 7.31 (s, 2H), 7.09-7.07 (m, 3H), 3.94 (s, 2H), 3.70 (s, 2H), 3.46 (ABq, J=16.0 Hz, 2H), 3.20-3.16 (m, 1H), 2.86-2.84 (m, 1H), 2.41 (dd, J=16.4, 4.0 Hz, 1H), 1.05 (s, 3H); LC-MS Rt 0.75 min; MS m/z [M+H]$^+$ 517.0; Method 5.

Example 86 N-(3-cyano-5-(3-fluorobenzyl)-6-methyl-4,5,6,7-tetrahydrothieno[3,2-c]pyridin-2-yl)-2-(3-(2-methoxyethoxy)-4-sulfamoylphenyl)acetamide

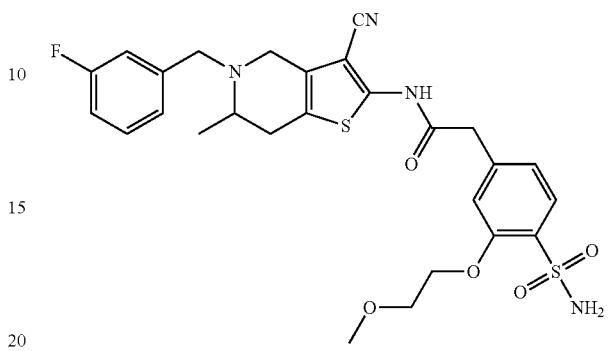

Example 86 was prepared by a similar method to that of Core 2a (K$_2$CO$_3$, rt., 18 h) by using N-(3-cyano-6-methyl-4,5,6,7-tetrahydrothieno[3,2-c]pyridin-2-yl)-2-(3-(2-methoxyethoxy)-4-sulfamoylphenyl)acetamide with the appropriate halide derivative (either commercially available or preparations described hereinabove). $^1$H NMR (400 MHz, DMSO-d$_6$) δ 11.87 (s, 1H), 7.67 (d, J=6.8 Hz, 2H), 7.40 (m, 2H), 7.18 (m, 2H), 7.01 (d, J=6.8 Hz, 2H), 6.83 (s, 2H), 4.27 (d, J=4.4 Hz, 2H), 3.93 (s, 3H), 3.75 (d, J=4.4 Hz, 2H), 3.73 (s, 2H), 3.50-3.30 (m, 2H), 3.44 (s, 3H), 3.20 (m, 1H), 2.89-2.86 (m, 1H), 2.40-2.50 (m, 1H), 1.05 (s, 3H); LC-MS Rt 0.68 min; MS m/z [M+H]$^+$ 573.1; Method 5.

Example 87 N-(3-cyano-6-ethyl-5-(3-fluorobenzyl)-4,5,6,7-tetrahydrothieno[3,2-c]pyridin-2-yl)-2-(4-sulfamoylphenyl)acetamide

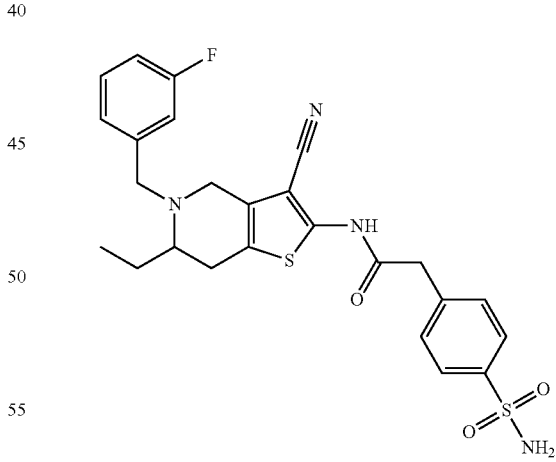

Example 87 was prepared by a similar method to that of (K$_2$CO$_3$, rt., 15 h) by using N-(3-cyano-6-ethyl-4,5,6,7-tetrahydrothieno[3,2-c]pyridin-2-yl)-2-(4-sulfamoylphenyl)acetamide with the appropriate halide derivative (either commercially available or preparations described hereinabove). $^1$H NMR (400 MHz, DMSO-d$_6$) δ 11.90 (s, 1H), 7.77 (d, J=8.4 Hz, 2H), 7.48 (d, J=8.8 Hz, 2H), 7.39-7.36 (m, 1H), 7.31 (s, 2H), 7.19-7.14 (m, 2H), 7.10-7.06 (m, 1H), 3.95 (s, 2H), 3.66 (ABq, J=14.0 Hz, 2H), 3.50 (s, 2H), 2.96-2.92 (m, 1H), 2.78-2.73 (m, 1H), 1.63-1.59 (m, 1H), 1.37-1.31 (m, 1H), 0.92 (t, J=7.6 Hz, 3H); LC-MS Rt 0.72 min; MS m/z [M+H]⁺ 513.0; Method 5.

Example 88 N-(3-cyano-5-(cyclohexylmethyl)-4,5,6,7-tetrahydrothieno[3,2-c]pyridin-2-yl)-2-(1-methyl-4-sulfamoyl-1H-pyrrol-2-yl)acetamide

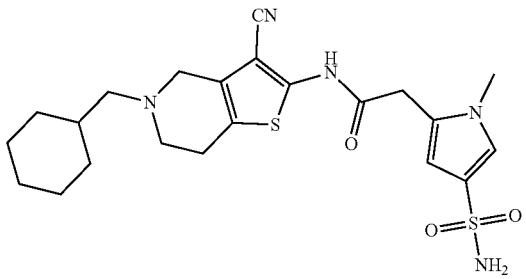 [SMILES: Cn1cc(S(N)(=O)=O)cc1CC(=O)Nc1sc2c(c1C#N)CN(CC1CCCCC1)CC2]

Example 88 was prepared by a similar method to that of Example 83 by replacing the appropriate acid derivative. ¹H NMR (400 MHz, DMSO-d₆) δ 8.15 (s, 1H), 7.19 (d, J=2.0 Hz, 1H), 6.86 (s, 2H), 6.23 (d, J=2.0 Hz, 1H), 3.91 (s, 2H), 3.57 (s, 3H), 2.67 (d, J=3.4 Hz, 4H), 2.31 (d, J=7.1 Hz, 2H), 1.81-1.47 (m, 7H), 1.20 (dtd, J=20.7, 14.9, 13.5, 10.0 Hz, 4H), 0.95-0.77 (m, 2H); LC-MS Rt 0.56 min; MS m/z [M+H]⁺ 476.1; Method 5.

Example 89 4-(2-((3-cyano-5-(3-fluorobenzyl)-4,5,6,7-tetrahydrothieno[3,2-c]pyridin-2-yl)amino)-2-oxoethyl)-2-ethoxybenzamide

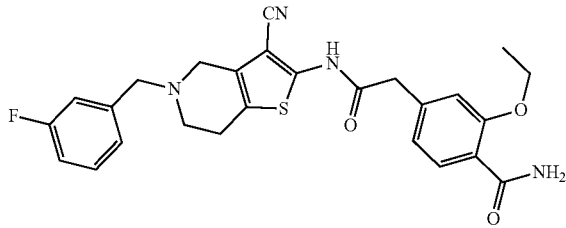 [SMILES: CCOc1cc(CC(=O)Nc2sc3c(c2C#N)CN(Cc2cccc(F)c2)CC3)ccc1C(N)=O]

Step 1: tert-butyl 3-cyano-2-(2-(3-ethoxy-4-(ethoxycarbonyl)phenyl)acetamido)-6,7-dihydrothieno[3,2-c]pyridine-5(4H)-carboxylate To a mixture of Core-1a_A2 (111 mg, 0.396 mmol), and 2-(2-oxoindolin-6-yl)acetic acid (100 mg, 0.396 mmol) in DMF (1.5 mL), was added TEA (138 µL, 0.991 mmol) and T₃P (354 µL, 0.595 mmol) under argon. The reaction was stirred at room temperature for 2 h. The crude mixture was partioned between EtOAc and water. The organic layer was recovered and the aq.layer was further extracted with EtOAc. The combined organic layers were washed with water (×3) and brine, dried over Na₂SO₄, filtered, and concentrated. The residue was purified by normal phase chromatography using silica gel (Solvent: c-Hexane/EtOAc=1:0 to 0:1) to give the product (143 mg, yield 56%). LC-MS Rt 1.26 min; MS m/z [M–H]⁻ 512.4; Method 5.

Step 2: ethyl 4-(2-((3-cyano-5-(3-fluorobenzyl)-4,5,6,7-tetrahydrothieno[3,2-c]pyridin-2-yl)amino)-2-oxoethyl)-2-ethoxybenzoate To a solution of tert-butyl 3-cyano-2-(2-(3-ethoxy-4-(ethoxycarbonyl)phenyl)acetamido)-6,7-dihydrothieno[3,2-c]pyridine-5(4H)-carboxylate (143 mg, 0.223 mmol) in DCM (1 mL) was added TFA (343 µL, 4.45 mmol). The reaction mixture was stirred at room temperature for 2 h. The mixture was then concentrated in vacuo and redissolved in DMF and added 1-(bromomethyl)-3-fluorobenzene (41.0 µL, 0.334 mmol) and Cs₂CO₃ (218 mg, 0.668 mmol). The reaction was stirred at room temperature for 2 h. The crude mixture was partioned between EtOAc and water. The organic layer was recovered and the aq.layer was further extracted with EtOAc. The combined organic layers were washed with water (×3) and brine, dried over Na₂SO₄, filtered, and concentrated. The residue was purified by normal phase chromatography using silica gel (Solvent: c-Hexane/EtOAc=1:0 to 0:1) to give the product (95 mg, yield 79%). LC-MS Rt 0.89 min; MS m/z [M+H]⁺ 522.2; Method 5.

Step 3: 4-(2-((3-cyano-5-(3-fluorobenzyl)-4,5,6,7-tetrahydrothieno[3,2-c]pyridin-2-yl)amino)-2-oxoethyl)-2-ethoxybenzoic acid To a solution of ethyl 4-(2-((3-cyano-5-(3-fluorobenzyl)-4,5,6,7-tetrahydrothieno[3,2-c]pyridin-2-yl)amino)-2-oxoethyl)-2-ethoxybenzoate (72 mg, 0.138 mmol) in THF (1.5 mL)—water (1.5 mL) was added LiOH (13.22 mg, 0.552 mmol). The reaction mixture was stirred at room temperature two overnights. The mixture was concentrated in vacuo. It was redissolved in EtOAc and the solution was washed with aq 1M HCl. The org later was recovered, concentrated to give the product (42 mg, yield 60%). LC-MS Rt 0.72 min; MS m/z [M+H]⁺ 494.1; Method 5.

Step 4: 4-(2-((3-cyano-5-(3-fluorobenzyl)-4,5,6,7-tetrahydrothieno[3,2-c]pyridin-2-yl)amino)-2-oxoethyl)-2-ethoxybenzamide 4-(2-((3-cyano-5-(3-fluorobenzyl)-4,5,6,7-tetrahydrothieno[3,2-c]pyridin-2-yl)amino)-2-oxoethyl)-2-ethoxybenzoic acid (36 mg, 0.073 mmol) and HATU (36.1 mg, 0.095 mmol) were dissolved in DMF (1 mL). Ammonium chloride (19.51 mg, 0.365 mmol) was added along with DIPEA (0.025 mL, 0.146 mmol). The reaction mixture was stirred at room temperature for 1 h. The crude mixture was partioned between EtOAc and water. The organic layer was recovered and the aq.layer was further extracted with EtOAc. The combined organic layers were washed with water (×3) and brine, dried over Na₂SO₄, filtered, and concentrated. The residue was purified by Prep-HPLC to give the product (6 mg, Yield 16%). ¹H NMR (400 MHz, DMSO-d₆) δ 7.77 (s, 1H), 7.75 (s, 1H), 7.54 (s, 1H), 7.50 (s, 1H), 7.42-7.36 (m, 1H), 7.21-7.16 (m, 2H), 7.12-7.08 (m, 2H), 6.94 (d, J=8.0 Hz, 1H), 4.17 (q, J=8.0 Hz, 2H), 3.86 (s, 2H), 3.72 (s, 2H), 3.42 (s, 2H), 2.73 (m, 2H), 2.66 (m, 2H), 1.39 (t, J=8.0 Hz, 3H); LC-MS Rt 0.68 min; MS m/z [M+H]⁺ 493.1; Method 5.

Example 90: N-(3-cyano-6-(1-phenylethyl)-4,5,6,7-tetrahydrothieno[2,3-c]pyridin-2-yl)-2-(4-sulfamoylphenyl)-acetamide hydrochloride

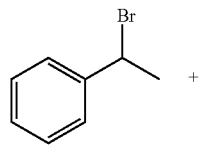

Core-2a_6a
Commercial

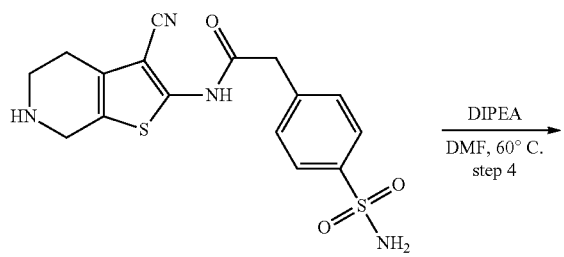

DIPEA
DMF, 60° C.
step 4

To a solution of (1-bromoethyl)benzene Core-2a 6a (63 mg, 0.34 mol) in DMF (10 mL) was added N-(3-cyano-4,5,6,7-tetrahydrothieno[2,3-c]pyridine-2-yl)-2-(4-sulfamoylphenyl)acetamide (Intermediate Core-2a_A) (100 mg, 0.26 mol) and DIPEA (100 mg, 0.78 mmol). The reaction was stirred for 4 h at 60° C. The mixture was quenched by water (20 mL), extracted with EtOAc (20 mL×3), washed with brine (60 mL), dried over Na$_2$SO$_4$, filtered and concentrated. The residue was purified by Prep-HPLC (HCl) to afford N-(3-cyano-6-(1-phenylethyl)-4,5,6,7-tetrahydrothieno[2,3-c]pyridin-2-yl)-2-(4-sulfamoylphenyl)acetamide hydrochloride as a yellow solid (31 mg, yield: 17%); $^1$H NMR (400 MHz, DMSO-d$_6$) δ 12.15 (s, 1H), 11.55 (s, 1H), 7.34-7.79 (m, 11H), 2.82-4.68 (m, 9H), 1.73 (d, J=2 Hz, 3H); LC-MS Rt 0.907 min, MS m/z [M+H]$^+$ 481.1; Method 1.

Example 91: Methyl-2-((3-cyano-2-(2-(4-sulfamoylphenyl)acetamido)-4,5-dihydrothieno[2,3-c]pyridin-6-(71-1)-yl)methyl)benzoate hydrochloride

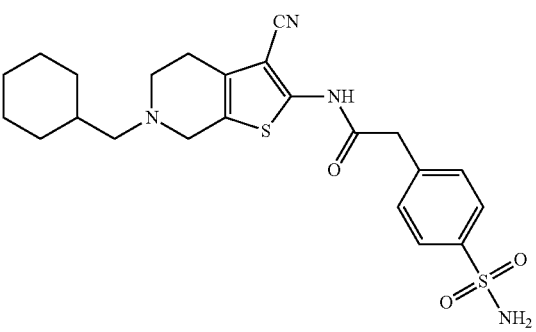 [SMILES: N#Cc1c(NC(=O)Cc2ccc(S(N)(=O)=O)cc2)sc2c1CCN(CC1CCCCC1)C2]

$^1$H NMR: (400 MHz, DMSO-d$_6$) δ 12.21 (br s, 1H), 10.19 (br s, 1H), 8.12-8.11 (br d, J=6.7 Hz, 1H), 7.80-7.67 (m, 6H), 7.51-7.49 (d, J=8.4 Hz, 2H), 7.36 (s, 2H), 4.81-4.71 (m, 2H), 4.38 (br s, 2H), 4.01 (s, 2H), 3.89 (s, 3H), 3.76-3.49 (m, 2H), 3.00 (m, 2H); LC-MS Rt 0.886 min, MS m/z [M+H]$^+$ 525.1, Method 1.

Example 92: N-(3-cyano-6-(cyclohexylmethyl)-4,5,6,7-tetrahydrothieno[2,3-c]pyridin-2-yl)-2-(4-sulfamoylphenyl) acetamide $^1$H NMR: (400 MHz, MeOD) δ 7.88-7.87 (d, J=8.5 Hz, 2H), 7.52-7.50 (d, J=8.4 Hz, 2H), 3.95 (s, 2H), 3.51 (s, 2H), 2.80-2.77 (m, 2H), 2.70-2.69 (br d, J=5.4 Hz, 2H), 2.37-2.36 (d, J=7.0 Hz, 2H), 1.83-1.80 (br d, J=14.1 Hz, 2H), 1.75-1.71 (br d, J=15.1 Hz, 2H), 1.64-1.56 (m, 2H), 1.32-1.29 (br d, J=11.8 Hz, 3H), 0.98-0.89 (m, 2H); LC-MS: Rt 0.987 min, MS m/z [M+H]$^+$ 473.2. Method 1.

Example 93: N-(3-cyano-6-(3,5-difluorobenzyl)-4,5,6,7-tetrahydrothieno[2,3-c]pyridin-2-yl)-2-(4-sulfamoylphenyl) acetamide

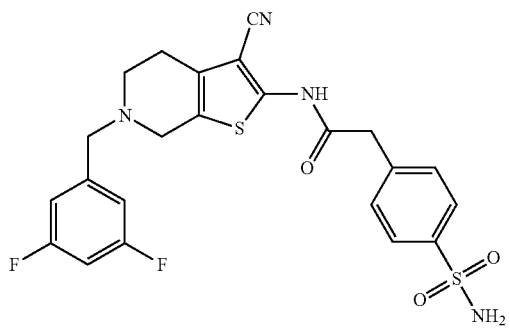 [SMILES: N#Cc1c(NC(=O)Cc2ccc(S(N)(=O)=O)cc2)sc2c1CCN(Cc1cc(F)cc(F)c1)C2]

$^1$H NMR (400 MHz, DMSO-d$_6$) δ 11.91 (s, 1H), 7.77 (d, J=8.0 Hz, 2H), 7.48 (d, J=8.0 Hz, 2H), 7.32 (s, 2H), 7.13-7.06 (m, 3H), 3.96 (s, 2H), 3.70 (s, 2H), 3.51 (s, 2H), 2.76-2.73 (m, 2H), 2.60-2.58 (m, 2H); LC-MS Rt 0.686 min, MS m/z [M+H]$^+$ 503.0. Method 3.

Example 94: N-(3-cyano-6-(2-methoxybenzyl)-4,5,6,7-tetrahydrothieno[2,3-c]pyridin-2-yl)-2-(4-sulfamoylphenyl) acetamide

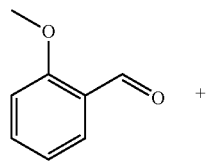

Core-2a_6h

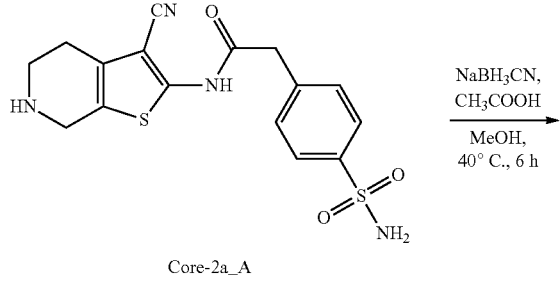

The title compound was prepared by a similar method by replacing 2,5-dichloronicotinaldehyde Core-2a_6g (Example 2 step 4) with N-(3-cyano-4,5,6,7-tetrahydrothieno[2,3-c]pyridine-2-yl)-2-(4-sulfamoylphenyl)acetamide (Intermediate Core-2a_A); $^1$H NMR (400 MHz, DMSO-d$_6$) δ 12.17 (s, 1H), 7.79 (d, J=8.4 Hz, 2H), 7.53-7.48 (m, 4H), 7.35 (s, 2H), 7.14 (d, J=8.4 Hz, 1H), 7.06-7.04 (m, 1H), 4.40-4.36 (m, 4H), 4.01 (s, 2H), 3.84 (s, 3H), 3.43-3.34 (m, 2H), 2.95-2.67 (m, 2H); LC-MS Rt 0.883 min, MS m/z [M+H]$^+$ 497.2, Method 1.

Examples 95 to 97 were prepared by a similar method to that of Example 2 by replacing N-(3-cyano-4,5,6,7-tetrahydrothieno[2,3-c]pyridine-2-yl)-2-(4-sulfamoylphenyl)acetamide (Intermediate A) with the appropriate aldehyde derivatives (either commercially available or preparations described hereinabove).

Example 95: N-(3-cyano-6-(2,3-dimethylbenzyl)-4,5,6,7-tetrahydrothieno[2,3-c]pyridin-2-yl)-2-(4-sulfamoylphenyl) acetamide

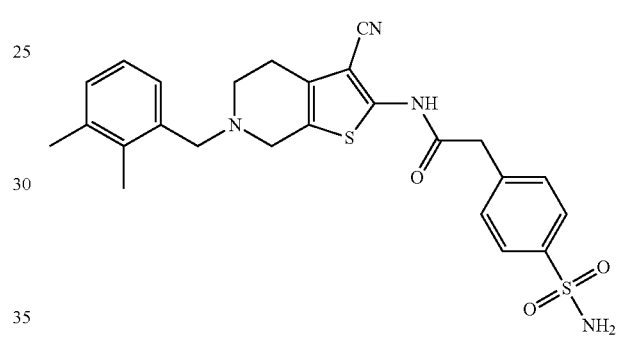

$^1$H NMR (400 MHz, DMSO-d$_6$) δ 12.18 (s, 1H), 10.77 (br, s, 1H), 7.79 (d, J=8.4 Hz, 2H), 7.49 (d, J=8.4 Hz, 2H), 7.47-7.42 (m, 1H), 7.35 (s, 2H), 7.27-7.17 (m, 2H), 4.52-4.31 (m, 4H), 4.00 (s, 2H), 3.66-3.51 (m, 2H), 2.96 (s, 2H), 2.28 (s, 6H); LC-MS Rt 0.961 min, MS m/z [M+H]$^+$ 495.2, Method 1.

Example 96: N-(3-cyano-6-((2-methylpyridin-4-yl)methyl)-4,5,6,7-tetrahydrothieno[2,3-c]pyridin-2-yl)-2-(4-sulfamoylphenyl)acetamide

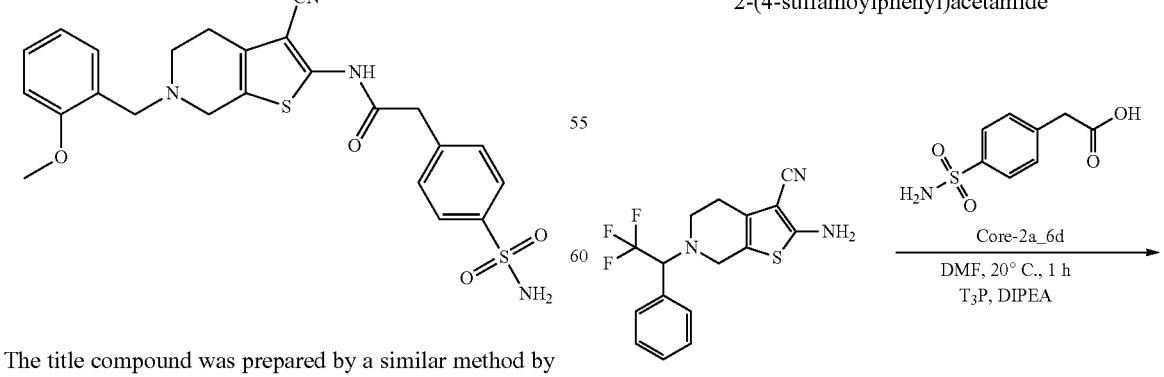

129

-continued

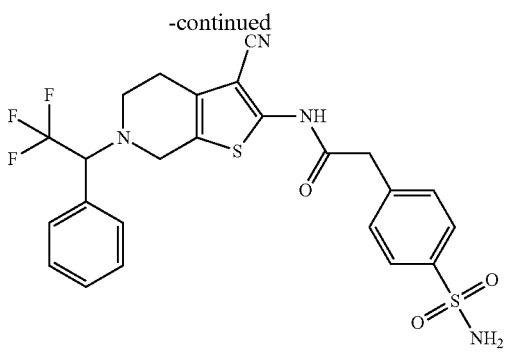

To a solution of 2-amino-6-(2,2,2-trifluoro-1-phenylethyl)-4,5,6,7-tetrahydrothieno[2,3-c]pyridine-3-carbonitrile (Intermediate Core-2a_D) (60 mg, 0.178 mmol), 2-(4-sulfamoylphenyl)acetic acid Core-2a 6d (60 mg, 0.267 mmol), DIPEA (46 mg, 0.356 mmol) in DMF (10 mL) was added aq. T$_3$P (50% in EtOAc) (170 mg, 0.267 mmol) at 20° C. The mixture was stirred at 20° C. for 1 h. The reaction was concentrated to oil and diluted with EtOAc (10 mL), washed with brine, dried over Na$_2$SO$_4$ and filtered. The filtrate was concentrated to a yellow oil, which was purified by prep-HPLC (base) to get N-(3-cyano-6-(2,2,2-trifluoro-1-phenylethyl)-4,5,6,7-tetrahydrothieno[2,3-c]pyridin-2-yl)-2-(4-sulfamoylphenyl)acetamide (18 mg, yield: 18%) as a yellow solid; $^1$H NMR (400 MHz, CD$_3$OD) δ 7.88 (d, J=8.41 Hz, 2H), 7.37-7.59 (m, 7H), 4.51-4.58 (m, 1H), 3.94 (s, 2H), 3.66-3.84 (m, 2H), 3.06-3.19 (m, 1H), 2.78-2.92 (m, 1H), 2.56-2.72 (m, 2H); LC-MS Rt 0.945 min, MS m/z [M+H]$^+$ 535.1, Method 1.

Example 97: N-(3-cyano-6-(2-methylbenzyl)-4,5,6,7-tetrahydrothieno[2,3-c]pyridin-2-yl)-2-(4-sulfamoylphenyl)acetamide

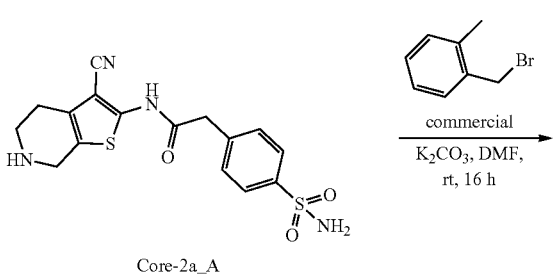

To a solution of 1-(bromomethyl)-2-methylbenzene (23.5 mg, 0.127 mmol) in DMF (2 mL) were added N-(3-cyano-4,5,6,7-tetrahydrothieno[2,3-c]pyridine-2-yl)-2-(4-sulfamoylphenyl)acetamide (Intermediate A) (50 mg, 0.106 mmol) and K$_2$CO$_3$ (58.4 mg, 0.422 mmol). The reaction was stirred for 16 h at rt. The mixture was quenched by water (2×10 mL), extracted with EtOAc (20 mL×3), washed with brine (20 mL), dried over Na$_2$SO$_4$, filtrated and concentrated to a crude solid, which was purified by prep-HPLC to get N-(3-cyano-6-(2-methylbenzyl)-4,5,6,7-tetrahydrothieno[2,3-c]pyridin-2-yl)-2-(4-sulfamoylphenyl)acetamide (20.9 mg, yield: 40%); $^1$H NMR (400 MHz, DMSO-d$_6$) δ 11.88 (s, 1H), 7.78 (d, J=8.4 Hz, 2H), 7.48 (d, J=8.4 Hz, 2H), 7.31 (s, 2H), 7.25 (d, J=6.1 Hz, 1H), 7.18-7.11 (m, 3H), 3.96 (s, 2H), 3.62 (s, 2H), 3.48 (s, 2H), 2.75 (t, J=5.7 Hz, 2H), 2.58 (s, 2H), 2.31 (s, 3H). LC-MS Rt 0.60 min, MS m/z [M+H]$^+$ 481.1

Examples 98 to 116 were prepared by a similar method to that of Example 4.0 by using N-(3-cyano-4,5,6,7-tetrahydrothieno[2,3-c]pyridine-2-yl)-2-(4-sulfamoylphenyl)acetamide (Core-2a_A) with the appropriate halide derivative (either commercially available or preparations described hereinabove).

Example 98: N-(3-cyano-6-(4-methylbenzyl)-4,5,6,7-tetrahydrothieno[2,3-c]pyridin-2-yl)-2-(4-sulfamoylphenyl)acetamide

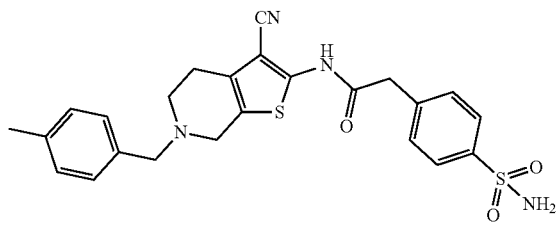 [SMILES: Cc1ccc(CN2CCc3c(sc(NC(=O)Cc4ccc(S(N)(=O)=O)cc4)c3C#N)C2)cc1]

$^1$H NMR (400 MHz, DMSO-d$_6$) δ 8.35 (s, 1H), 7.75 (d, J=8.4 Hz, 2H), 7.47 (d, J=8.4 Hz, 2H), 7.28 (s, 2H), 7.21 (d, J=8.0 Hz, 2H), 7.13 (d, J=7.8 Hz, 2H), 3.83 (s, 2H), 3.60 (s, 3H), 2.70 (t, J=5.6 Hz, 2H), 2.53 (d, J=6.7 Hz, 3H), 2.28 (s, 3H); LC-MS Rt 0.68 min, MS m/z [M+H]$^+$ 481.1.

Example 99: N-(3-cyano-6-(2-fluorobenzyl)-4,5,6,7-tetrahydrothieno[2,3-c]pyridin-2-yl)-2-(4-sulfamoylphenyl)acetamide

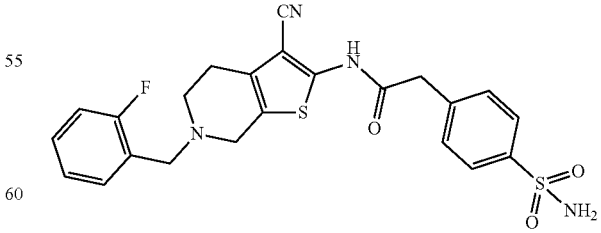

$^1$H NMR (400 MHz, DMSO-d$_6$) δ 11.89 (s, 1H), 7.78 (d, J=8.4 Hz, 2H), 7.54-7.40 (m, 3H), 7.31 (s, 3H), 7.25-7.10 (m, 2H), 3.96 (s, 2H), 3.72 (s, 2H), 3.51 (s, 2H), 2.76 (s, 2H), 2.59 (s, 2H); LC-MS Rt 0.56 min, MS m/z [M+H]$^+$ 485.1

Example 100: N-(3-cyano-6-(3-fluorobenzyl)-4,5,6,7-tetrahydrothieno[2,3-c]pyridin-2-yl)-2-(4-sulfamoylphenyl)acetamide

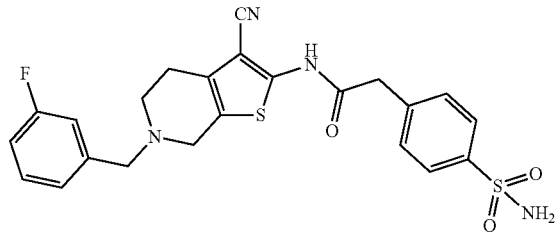 [SMILES: N#Cc1c(NC(=O)Cc2ccc(S(N)(=O)=O)cc2)sc2c1CCN(Cc1cccc(F)c1)C2]

$^{1}$H NMR (400 MHz, DMSO-d$_6$) δ 11.89 (s, 1H), 7.84-7.71 (m, 2H), 7.48 (d, J=8.4 Hz, 2H), 7.42-7.26 (m, 3H), 7.13 (dt, J=30.6, 7.7 Hz, 3H), 3.96 (s, 2H), 3.69 (s, 2H), 3.50 (s, 2H), 2.75 (s, 2H), 2.60 (s, 2H)); LC-MS Rt 0.57 min, MS m/z [M+H]$^+$ 485.1.

Example 101: N-(3-cyano-6-(4-fluorobenzyl)-4,5,6,7-tetrahydrothieno[2,3-c]pyridin-2-yl)-2-(4-sulfamoylphenyl)acetamide

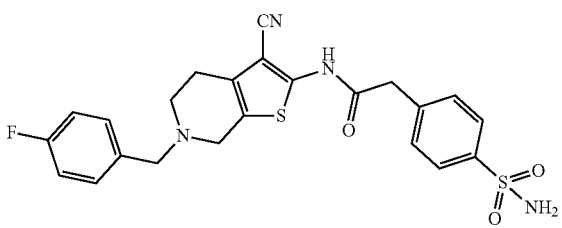 [SMILES: N#Cc1c(NC(=O)Cc2ccc(S(N)(=O)=O)cc2)sc2c1CCN(Cc1ccc(F)cc1)C2]

$^{1}$H NMR (400 MHz, DMSO-d$_6$) δ 11.89 (s, 1H), 7.82-7.74 (m, 2H), 7.48 (d, J=8.5 Hz, 2H), 7.42-7.26 (m, 4H), 7.15 (t, J=8.9 Hz, 2H), 3.96 (s, 2H), 3.66 (s, 2H), 3.47 (s, 2H), 2.73 (d, J=5.3 Hz, 2H), 2.59 (d, J=5.2 Hz, 2H); LC-MS Rt 0.54 min, MS m/z [M+H]$^+$ 485.1.

Example 102: N-(3-cyano-6-(3-methylbenzyl)-4,5,6,7-tetrahydrothieno[2,3-c]pyridin-2-yl)-2-(4-sulfamoylphenyl)acetamide

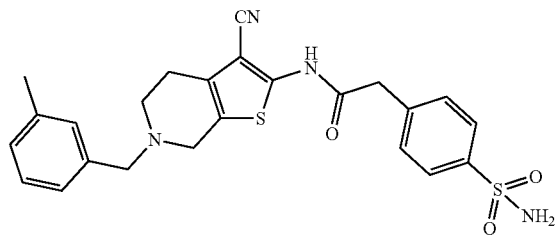 [SMILES: Cc1cccc(CN2CCc3c(sc(NC(=O)Cc4ccc(S(N)(=O)=O)cc4)c3C#N)C2)c1]

$^{1}$H NMR (400 MHz, DMSO-d$_6$) δ 11.88 (s, 1H), 7.78 (d, J=8.4 Hz, 2H), 7.48 (d, J=8.4 Hz, 2H), 7.31 (s, 2H), 7.25-7.03 (m, 4H), 3.96 (s, 2H), 3.62 (s, 2H), 3.46 (s, 2H), 2.73 (s, 2H), 2.58 (s, 2H), 2.29 (s, 3H); LC-MS Rt 0.60 min, MS m/z [M+H]$^+$ 481.1.

Example 103: N-(3-cyano-6-(2-methylbenzyl)-4,5,6,7-tetrahydrothieno[2,3-c]pyridin-2-yl)-2-(4-(methylsulfonyl)phenyl)acetamide

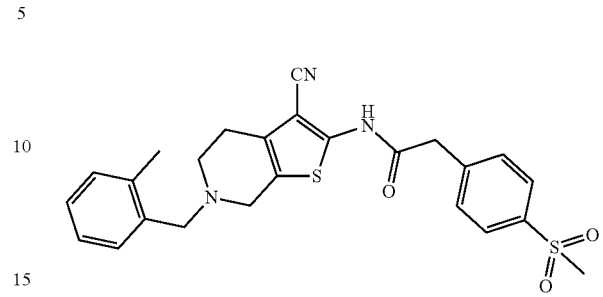

$^{1}$H NMR (400 MHz, DMSO-d$_6$) δ 7.91-7.86 (m, 2H), 7.61-7.54 (m, 2H), 7.27-7.23 (m, 1H), 7.19-7.10 (m, 3H), 3.98 (s, 2H), 3.62 (s, 2H), 3.47 (d, J=1.8 Hz, 2H), 3.19 (s, 3H), 2.75 (t, J=5.7 Hz, 2H), 2.57 (t, J=5.8 Hz, 2H), 2.31 (s, 3H); LC-MS Rt 0.64 min, MS m/z [M+H]$^+$ 481.1.

Example 104: N-(3-cyano-6-(3-methylbenzyl)-4,5,6,7-tetrahydrothieno[2,3-c]pyridin-2-yl)-2-(4-(methylsulfonyl)phenyl)acetamide

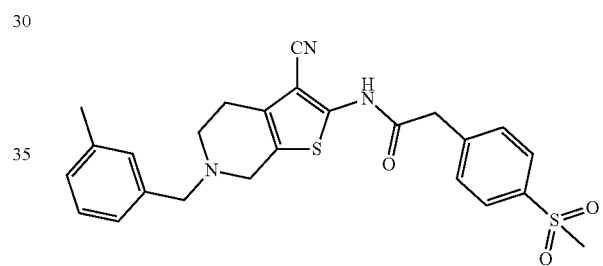

$^{1}$H NMR (400 MHz, DMSO-d$_6$) δ 7.91-7.86 (m, 2H), 7.60-7.55 (m, 2H), 7.21 (t, J=7.5 Hz, 1H), 7.15-7.05 (m, 3H), 3.99 (s, 2H), 3.62 (s, 2H), 3.45 (s, 2H), 3.19 (s, 3H), 2.73 (t, J=5.7 Hz, 2H), 2.58 (s, 2H), 2.29 (s, 3H); LC-MS Rt 0.64 min, MS m/z [M+H]$^+$ 481.1.

Example 105: N-(3-cyano-6-(3,4-difluorobenzyl)-4,5,6,7-tetrahydrothieno[2,3-c]pyridin-2-yl)-2-(4-sulfamoylphenyl)acetamide

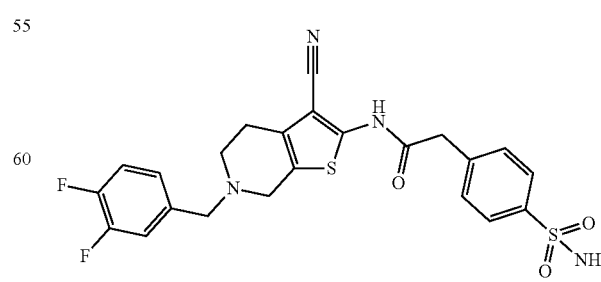

LC-MS Rt 0.67 min, MS m/z [M+H]$^+$ 503.0.

Example 106: N-(3-cyano-6-(2,3-difluorobenzyl)-4,5,6,7-tetrahydrothieno[2,3-c]pyridin-2-yl)-2-(4-sulfamoylphenyl)acetamide

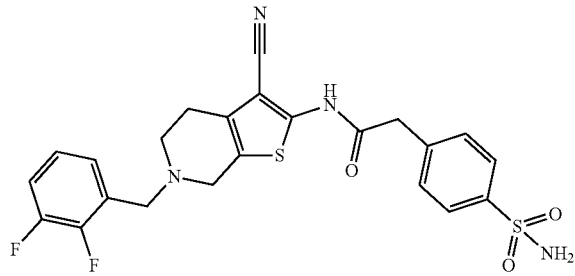 [SMILES: N#Cc1c(NC(=O)Cc2ccc(S(N)(=O)=O)cc2)sc2c1CCN(Cc1cccc(F)c1F)C2]

LC-MS Rt 0.67 min, MS m/z [M+H]+ 503.0.

Example 107: N-(6-(2-chloro-4-fluorobenzyl)-3-cyano-4,5,6,7-tetrahydrothieno[2,3-c]pyridin-2-yl)-2-(4-sulfamoylphenyl)acetamide

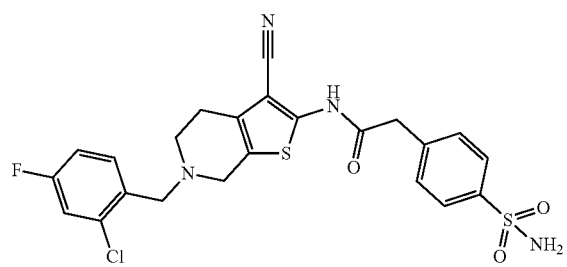 [SMILES: N#Cc1c(NC(=O)Cc2ccc(S(N)(=O)=O)cc2)sc2c1CCN(Cc1ccc(F)cc1Cl)C2]

LC-MS Rt 0.73 min, MS m/z [M+H]+ 520.1.

Example 108: Methyl 3-((3-cyano-2-(2-(4-sulfamoylphenyl)acetamido)-4,7-dihydrothieno[2,3-c]pyridin-6(5H)-yl)methyl)benzoate

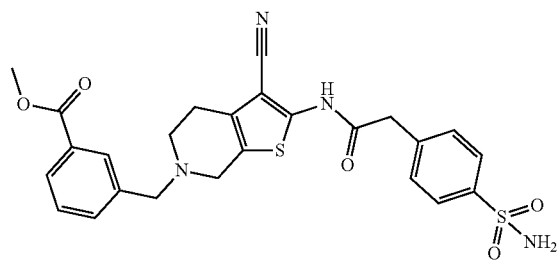 [SMILES: COC(=O)c1cccc(CN2CCc3c(sc(NC(=O)Cc4ccc(S(N)(=O)=O)cc4)c3C#N)C2)c1]

$^1$H NMR (400 MHz, DMSO-$d_6$) δ 7.95 (s, 1H), 7.87 (s, 1H), 7.81-7.74 (m, 2H), 7.62 (s, 1H), 7.55-7.42 (m, 3H), 7.31 (s, 2H), 3.97 (s, 2H), 3.86 (s, 3H), 3.74 (s, 1H), 3.49 (s, 1H), 2.76 (s, 1H), 2.60 (s, 1H), 1.24 (s, 2H). LC-MS Rt 0.58 min, MS m/z [M+H]+ 525.1.

Example 109: N-(3-cyano-6-(2,5-dichlorobenzyl)-4,5,6,7-tetrahydrothieno[2,3-c]pyridin-2-yl)-2-(4-sulfamoylphenyl)acetamide

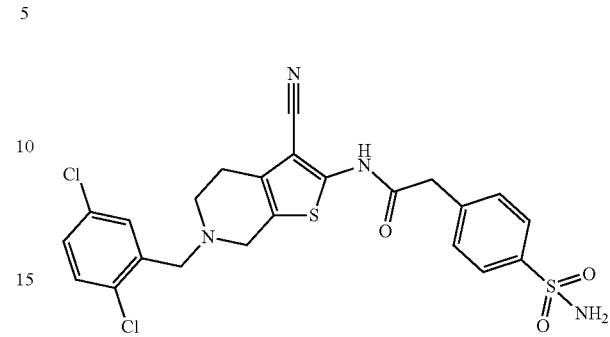

LC-MS Rt 0.91 min, MS m/z [M+H]+ 536.9.

Example 110: N-(3-cyano-6-(3,5-dimethylbenzyl)-4,5,6,7-tetrahydrothieno[2,3-c]pyridin-2-yl)-2-(4-sulfamoylphenyl)acetamide

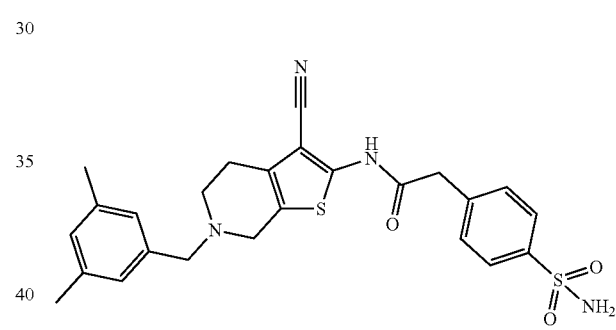

LC-MS Rt 0.66 min, MS m/z [M+H]+ 595.1.

Example 111: N-(6-(2-chloro-6-fluorobenzyl)-3-cyano-4,5,6,7-tetrahydrothieno[2,3-c]pyridin-2-yl)-2-(4-sulfamoylphenyl)acetamide

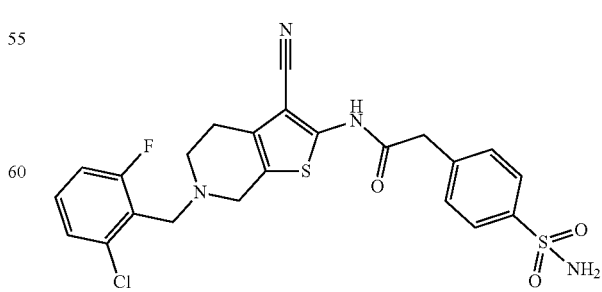

LC-MS Rt 0.75 min, MS m/z [M+H]+ 520.1.

Example 112: N-(3-cyano-6-(2,6-dichlorobenzyl)-4,5,6,7-tetrahydrothieno[2,3-c]pyridin-2-yl)-2-(4-sulfamoylphenyl)acetamide

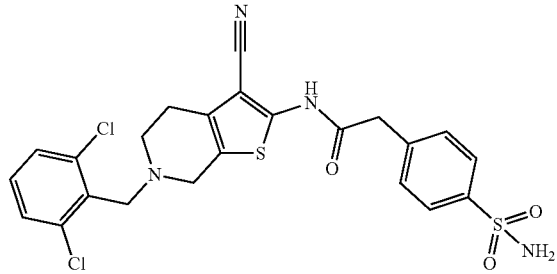 [SMILES: N#Cc1c(NC(=O)Cc2ccc(S(N)(=O)=O)cc2)sc2c1CCN(Cc1c(Cl)cccc1Cl)C2]

LC-MS Rt 0.86 min, MS m/z [M+H]$^+$ 537.1.

Example 113: N-(3-cyano-6-(2,5-difluorobenzyl)-4,5,6,7-tetrahydrothieno[2,3-c]pyridin-2-yl)-2-(4-sulfamoylphenyl)acetamide

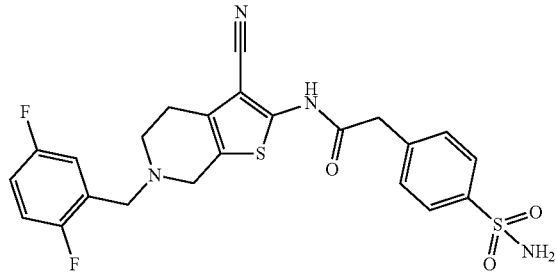 [SMILES: N#Cc1c(NC(=O)Cc2ccc(S(N)(=O)=O)cc2)sc2c1CCN(Cc1cc(F)ccc1F)C2]

LC-MS Rt 0.66 min, MS m/z [M+H]$^+$ 503.1.

Example 114: N-(6-(2-chlorobenzyl)-3-cyano-4,5,6,7-tetrahydrothieno[2,3-c]pyridin-2-yl)-2-(4-sulfamoylphenyl)acetamide

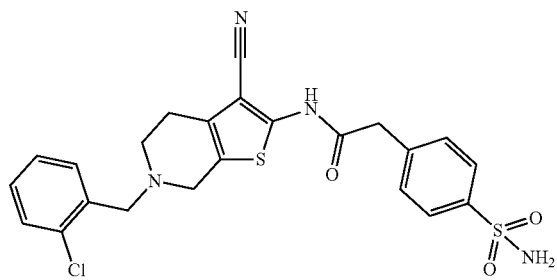 [SMILES: N#Cc1c(NC(=O)Cc2ccc(S(N)(=O)=O)cc2)sc2c1CCN(Cc1ccccc1Cl)C2]

LC-MS Rt 0.67 min, MS m/z [M+H]$^+$ 501.1.

Example 115: N-(3-cyano-6-(2-fluoro-3-methylbenzyl)-4,5,6,7-tetrahydrothieno[2,3-c]pyridin-2-yl)-2-(4-sulfamoylphenyl)acetamide

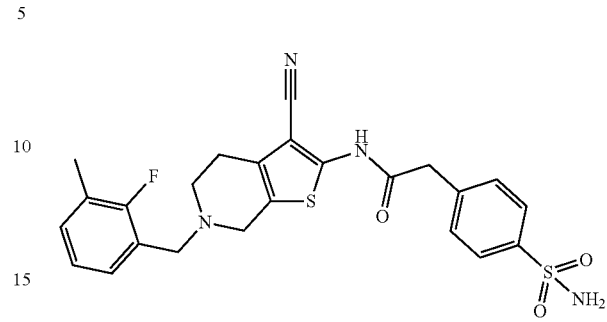

LC-MS Rt 0.62 min, MS m/z [M+H]$^+$ 499.1.

Example 116: N-(3-cyano-6-(2,6-difluorobenzyl)-4,5,6,7-tetrahydrothieno[2,3-c]pyridin-2-yl)-2-(4-sulfamoylphenyl)acetamide

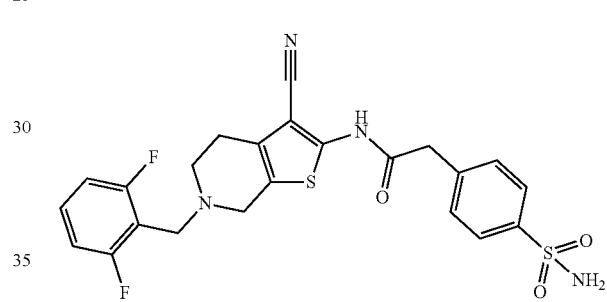

$^1$H NMR (400 MHz, DMSO-d$_6$) δ 11.96 (s, 1H), 7.82-7.73 (m, 2H), 7.56-7.43 (m, 3H), 7.31 (s, 2H), 7.16 (s, 2H), 3.97 (s, 2H), 3.38 (s, 6H), 2.75-2.60 (m, 2H); LC-MS Rt 0.64 min, MS m/z [M+H]$^+$ 503.1.

Examples 117 to 121 were prepared by a similar method to that of Example 4 by using N-(3-cyano-4,5,6,7-tetrahydrothieno[2,3-c]pyridin-2-yl)-2-(4-(methylsulfonyl)phenyl)acetamide with the appropriate halide derivative (either commercially available or preparations described hereinabove).

Example 117: N-(3-cyano-6-(3,4-difluorobenzyl)-4,5,6,7-tetrahydrothieno[2,3-c]pyridin-2-yl)-2-(4-(methylsulfonyl)phenyl)acetamide

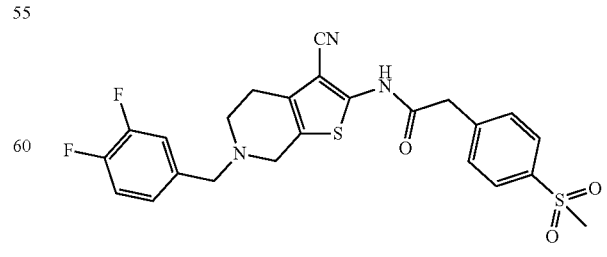

$^1$H NMR (400 MHz, DMSO-d$_6$) δ 11.96 (s, 1H), 7.89 (d, J=8.3 Hz, 2H), 7.58 (d, J=8.3 Hz, 2H), 7.44-7.32 (m, 2H), 7.19 (s, 1H), 4.00 (s, 2H), 3.66 (s, 2H), 3.49 (s, 2H), 3.20 (s, 3H), 2.74 (t, J=5.6 Hz, 2H), 2.59 (s, 2H); LC-MS Rt 0.69 min, MS m/z [M+H]+ 502.0.

Example 118: N-(3-cyano-6-(3,5-dimethylbenzyl)-4,5,6,7-tetrahydrothieno[2,3-c]pyridin-2-yl)-2-(4-(methylsulfonyl)phenyl)acetamide

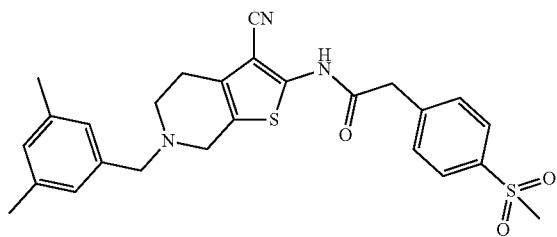 [SMILES: Cc1cc(C)cc(CN2CCc3c(sc(NC(=O)Cc4ccc(S(C)(=O)=O)cc4)c3C#N)C2)c1]

¹H NMR (400 MHz, DMSO-d₆) δ 7.92-7.84 (m, 2H), 7.58 (d, J=8.4 Hz, 2H), 6.90 (d, J=17.4 Hz, 3H), 3.99 (s, 2H), 3.57 (s, 2H), 3.44 (s, 2H), 3.19 (s, 3H), 2.72 (t, J=5.7 Hz, 2H), 2.57 (t, J=6.9 Hz, 2H), 2.25 (s, 6H); LC-MS Rt 0.71 min, MS m/z [M+H]+ 494.0.

Example 119: N-(3-cyano-6-(3-fluorobenzyl)-4,5,6,7-tetrahydrothieno[2,3-c]pyridin-2-yl)-2-(4-(methylsulfonyl)phenyl)acetamide

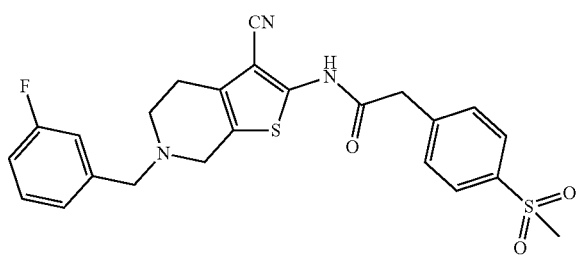 [SMILES: CS(=O)(=O)c1ccc(CC(=O)Nc2sc3c(c2C#N)CCN(Cc2cccc(F)c2)C3)cc1]

¹H NMR (400 MHz, DMSO-d₆) δ 7.92-7.85 (m, 2H), 7.58 (d, J=8.4 Hz, 2H), 7.41-7.31 (m, 1H), 7.21-6.98 (m, 3H), 3.99 (s, 2H), 3.69 (s, 2H), 3.49 (s, 2H), 3.19 (s, 3H), 2.74 (t, J=5.7 Hz, 2H), 2.59 (d, J=5.3 Hz, 2H); LC-MS Rt 0.65 min, MS m/z [M+H]+ 484.0.

Example 120: methyl 3-((3-cyano-2-(2-(4-(methylsulfonyl)phenyl)acetamido)-4,7-dihydrothieno[2,3-c]pyridin-6(51-1)-yl)methyl)benzoate

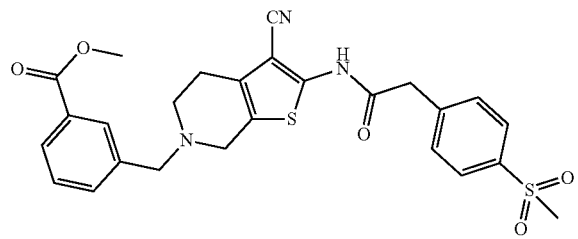 [SMILES: COC(=O)c1cccc(CN2CCc3c(sc(NC(=O)Cc4ccc(S(C)(=O)=O)cc4)c3C#N)C2)c1]

¹H NMR (400 MHz, DMSO-d₆) δ 7.94 (s, 1H), 7.87 (td, J=6.2, 1.6 Hz, 3H), 7.59 (dd, J=15.9, 8.1 Hz, 3H), 7.49 (t, J=7.7 Hz, 1H), 3.98 (s, 2H), 3.85 (s, 3H), 3.74 (s, 2H), 3.48 (s, 2H), 3.19 (s, 3H), 2.75 (t, J=5.7 Hz, 2H), 2.59 (d, J=5.3 Hz, 2H); LC-MS Rt 0.64 min, MS m/z [M+H]+ 524.1.

Example 121: N-(3-cyano-6-(2,5-dichlorobenzyl)-4,5,6,7-tetrahydrothieno[2,3-c]pyridin-2-yl)-2-(4-(methylsulfonyl)phenyl)acetamide

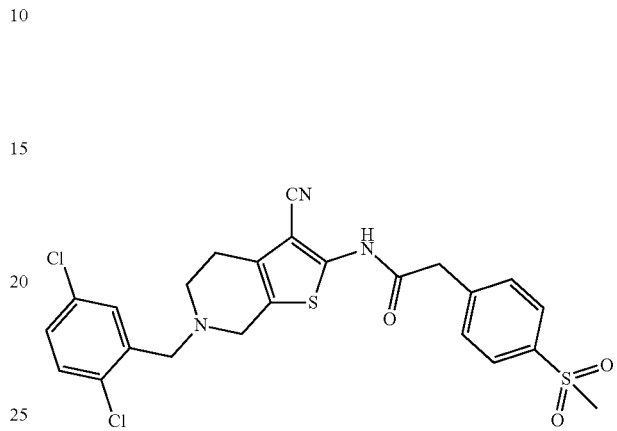

¹H NMR (400 MHz, DMSO-d₆) δ 7.92-7.85 (m, 2H), 7.62-7.54 (m, 3H), 7.48 (d, J=8.5 Hz, 1H), 7.38 (dd, J=8.5, 2.6 Hz, 1H), 3.99 (s, 2H), 3.75 (s, 2H), 3.57 (s, 2H), 3.19 (s, 3H), 2.81 (t, J=5.7 Hz, 2H), 2.62 (d, J=5.3 Hz, 2H); LC-MS Rt 0.98 min, MS m/z [M+H]+ 535.8

Examples 122 to 123 were prepared by a similar method to that of Example 4.0 of Core 2b (K₂CO₃, rt., 16 h) by using N-(3-cyano-5-methyl-4,5,6,7-tetrahydrothieno[2,3-c]pyridin-2-yl)-2-(4-sulfamoylphenyl)acetamide with the appropriate halide derivative (either commercially available or preparations described hereinabove).

Example 122: N-(3-cyano-6-(3-fluorobenzyl)-5-methyl-4,5,6,7-tetrahydrothieno[2,3-c]pyridin-2-yl)-2-(4-sulfamoylphenyl)acetamide

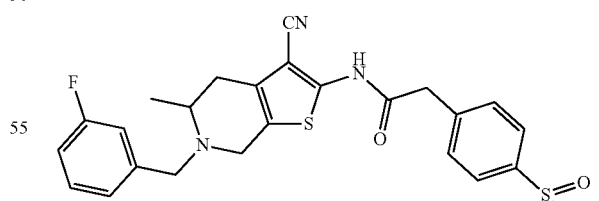

¹H NMR (400 MHz, DMSO-d₆) δ 11.89 (s, 1H), 7.78 (d, J=8.4 Hz, 2H), 7.48 (d, J=8.4 Hz, 2H), 7.31 (s, 3H), 7.21-6.99 (m, 3H), 3.96 (s, 2H), 3.71-3.51 (m, 4H), 3.18 (d, J=5.3 Hz, 1H), 2.74 (d, J=13.8 Hz, 1H), 2.34 (d, J=14.7 Hz, 1H), 1.10 (d, J=6.2 Hz, 3H); LC-MS Rt 0.62 min, MS m/z [M+H]+ 499.0.

Example 123: N-(3-cyano-6-(3-fluorobenzyl)-5-methyl-4,5,6,7-tetrahydrothieno[2,3-c]pyridin-2-yl)-2-(4-sulfamoylphenyl)acetamide

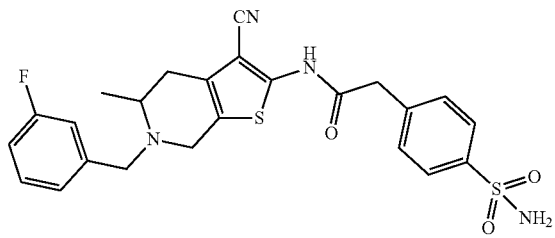 [SMILES: CC1Cc2c(sc(NC(=O)Cc3ccc(S(N)(=O)=O)cc3)c2C#N)CN1Cc1cccc(F)c1]

¹H NMR (400 MHz, DMSO-d₆) δ 11.89 (s, 1H), 7.81-7.73 (m, 2H), 7.48 (d, J=8.4 Hz, 2H), 7.40-7.28 (m, 3H), 7.14 (t, J=8.2 Hz, 2H), 7.06 (t, J=8.3 Hz, 1H), 3.96 (s, 2H), 3.71-3.53 (m, 4H), 3.23-3.12 (m, 1H), 2.79-2.70 (m, 1H), 2.38-2.29 (m, 1H), 1.10 (d, J=6.6 Hz, 3H); LC-MS Rt 0.62 min, MS m/z [M+H]⁺ 499.0.

Example 124: N-(3-cyano-6-(3-fluorobenzyl)-5,6,7,8-tetrahydro-4H-thieno[2,3-d]azepin-2-yl)-2-(4-sulfamoylphenyl)acetamide

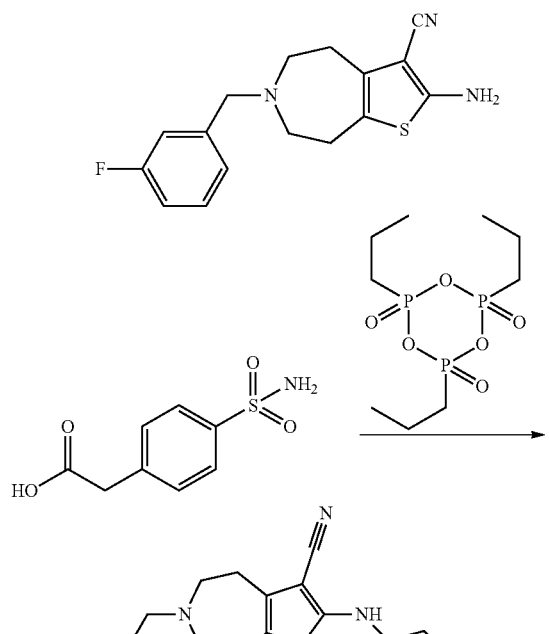

¹H NMR (400 MHz, DMSO-d₆) δ 7.80-7.74 (m, 2H), 7.48 (d, J=8.4 Hz, 2H), 7.41-7.29 (m, 3H), 7.22-7.15 (m, 2H), 7.07 (td, J=8.3, 1.8 Hz, 1H), 3.95 (s, 2H), 3.75 (s, 2H), 2.81-2.64 (m, 8H); LC-MS Rt 0.53 min, MS m/z [M+H]⁺ 499.4

Example 125: N-(3-cyano-6-(cyclohexylmethyl)-5,6,7,8-tetrahydro-4H-thieno[2,3-d]azepin-2-yl)-2-(4-sulfamoylphenyl)acetamide

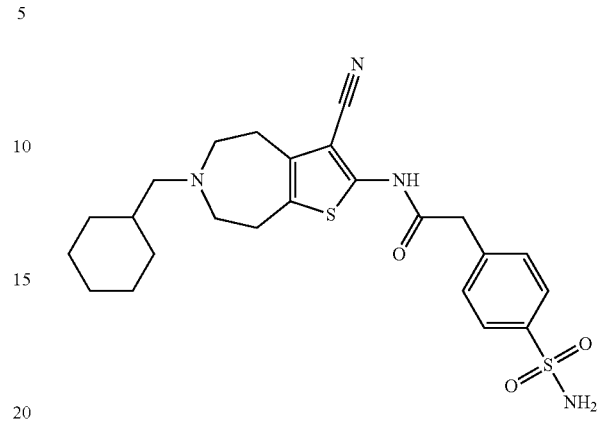

¹H NMR (400 MHz, DMSO-d₆) δ 7.81-7.74 (m, 2H), 7.51-7.45 (m, 2H), 7.31 (s, 2H), 3.93 (s, 2H), 2.77-2.64 (m, 8H), 2.33 (d, J=7.1 Hz, 2H), 1.75 (d, J=13.2 Hz, 2H), 1.66 (d, J=13.0 Hz, 3H), 1.53-1.42 (m, 1H), 1.28-1.11 (m, 3H), 0.84 (q, J=11.8 Hz, 2H); LC-MS Rt 0.62 min, MS m/z [M+H]⁺ 487.1.

Example 126: N-(3-cyano-7-(3-fluorobenzyl)-5,6,7,8-tetrahydro-4H-thieno[2,3-c]azepin-2-yl)-2-(4-sulfamoylphenyl)acetamide

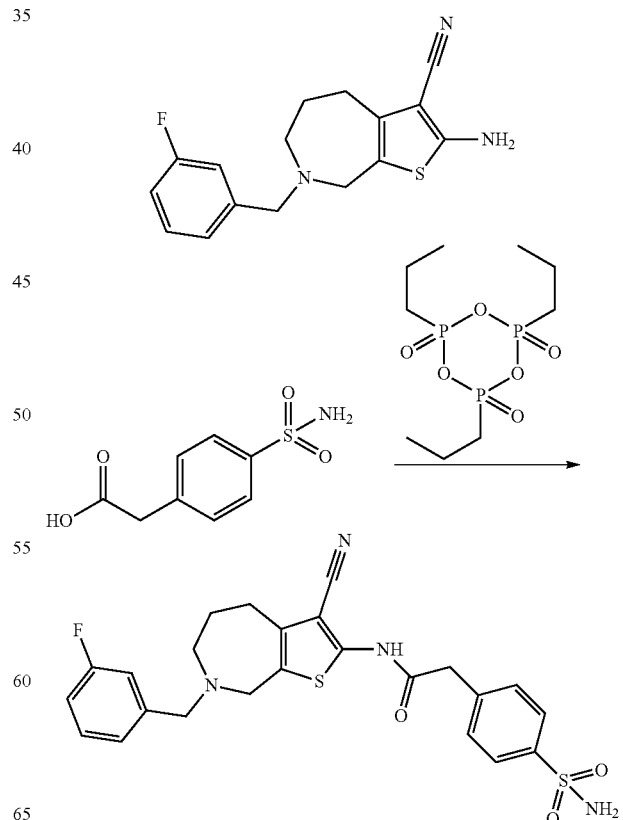

Example 126 was prepared by a similar method by using 2-amino-7-(3-fluorobenzyl)-5,6,7,8-tetrahydro-4H-thieno[2,3-c]azepine-3-carbonitrile with the appropriate acid derivative (either commercially available or preparations described hereinabove). $^1$H NMR (400 MHz, DMSO-$d_6$) δ 7.78 (d, J=8.3 Hz, 2H), 7.49 (d, J=8.3 Hz, 2H), 7.38-7.28 (m, 3H), 7.13-7.00 (m, 3H), 3.96 (s, 2H), 3.75 (s, 2H), 3.57 (s, 2H), 3.11-3.03 (m, 2H), 2.83-2.70 (m, 2H), 1.67 (s, 2H); LC-MS Rt 0.58 min, MS m/z [M+H]$^+$ 499.6.

Example 127: N-(3-cyano-7-(cyclohexylmethyl)-5,6,7,8-tetrahydro-4H-thieno[2,3-c]azepin-2-yl)-2-(4-sulfamoylphenyl)acetamide

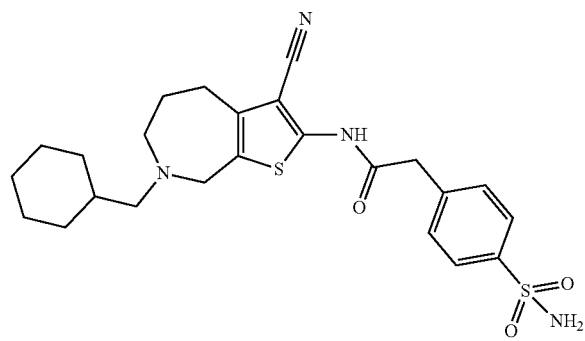 [SMILES: N#Cc1c(NC(=O)Cc2ccc(S(N)(=O)=O)cc2)sc2c1CCCN(CC1CCCCC1)C2]

Example 127 was prepared by a similar method by using 2-amino-7-(cyclohexylmethyl)-5,6,7,8-tetrahydro-4H-thieno[2,3-c]azepine-3-carbo-nitrile with the appropriate acid derivative (either commercially available or preparations described hereinabove). $^1$H NMR (400 MHz, DMSO-$d_6$) δ 7.79-7.74 (m, 2H), 7.51-7.44 (m, 2H), 7.30 (s, 2H), 3.90 (s, 2H), 3.72 (s, 2H), 3.04-3.01 (m, 2H), 2.75-2.70 (m, 2H), 2.13 (d, J=7.1 Hz, 2H), 1.63 (d, J=18.4 Hz, 7H), 1.25-1.13 (m, 4H), 0.79 (t, J=11.6 Hz, 2H); LC-MS Rt 0.63 min, MS m/z [M+H]$^+$ 487.1.

High-Content Imaging Cell-Based Flavivirus Immunodetection (HCI-CFI) Assay

A549 cells (7×10$^3$ cells per well) in a 384-well plate were infected with the DENV-2 (MY97-10340) strain at an MOI of 0.3. The cells were then treated with 3-fold, 10-point serial dilutions of test compound. After 48 h, the cells were fixed with paraformadehyde, and the viral E protein detected with 4G2 antibody labeled with Dylight™ 488 (GenScript). Cell nuclei were stained with Draq5 (Pierce/Thermo), and images were taken on the Opera imaging system (Perkin Elmer). A dose-response curve was plotted to calculate the effective concentration of compound needed to reduce expression of E protein by 50% (EC$_{50}$) using GraphPad Prism.

The resulted EC$_{50}$ values are summarized in Table 1 below: ±≥1 μM; 1 μM>++≥0.1 μM; 0.1 μm>+++

TABLE 1

Dengue IC$_{50}$ Data

| Example No. | Dengue 1 virus MY97-10245 in A549 using HCI [Inhibitor/IC$_{50}$] Qualified AC$_{50}$ | Dengue 2 virus MY97-10340 in A549 using HCI [Inhibitor/IC$_{50}$] Qualified AC$_{50}$ | Dengue 3 virus MY05-34640-WT-C6/36 in A549 using HCI [Inhibitor/IC$_{50}$] Qualified AC$_{50}$ | Dengue 4 virus MY01-22713 in A549 using HCI [Inhibitor/IC$_{50}$] Qualified AC$_{50}$ |
|---|---|---|---|---|
| 1 | + | ++ | ++ | ++ |
| 2 | + | ++ | ++ | ++ |
| 3 | ++ | +++ | +++ | +++ |
| 4 | ++ | +++ | ++ | +++ |
| 5 | ++ | +++ | +++ | +++ |
| 6 | ++ | +++ | +++ | +++ |
| 7 | +++ | +++ | +++ | +++ |
| 8 | + | ++ | ++ | ++ |
| 9 | ++ | +++ | +++ | +++ |
| 10 | ++ | +++ | +++ | +++ |
| 11 | +++ | ++ | +++ | +++ |
| 12 | +++ | +++ | +++ | +++ |
| 13 | ++ | ++ | ++ | ++ |
| 14 | ++ | ++ | ++ | ++ |
| 15 | ++ | ++ | ++ | ++ |
| 16 | ++ | +++ | +++ | +++ |
| 17 | ++ | +++ | +++ | +++ |
| 18 | +++ | +++ | +++ | +++ |
| 19 | +++ | +++ | +++ | +++ |
| 20 | + | ++ | + | + |
| 21 | +++ | +++ | +++ | +++ |
| 22 | ++ | +++ | +++ | +++ |
| 23 | ++ | ++ | +++ | ++ |
| 24 | ++ | ++ | +++ | ++ |
| 25 | ++ | +++ | +++ | +++ |
| 26 | + | + | + | + |
| 27 | ++ | +++ | +++ | +++ |
| 28 | ++ | ++ | +++ | +++ |
| 29 | ++ | +++ | +++ | +++ |
| 30 | ++ | +++ | +++ | +++ |
| 31 | + | ++ | ++ | ++ |
| 32 | ++ | ++ | +++ | +++ |
| 33 | ++ | ++ | +++ | +++ |
| 34 | + | + | ++ | ++ |

TABLE 1-continued

| Example No. | Dengue 1 virus MY97-10245 in A549 using HCl [Inhibitor/$IC_{50}$] Qualified $AC_{50}$ | Dengue 2 virus MY97-10340 in A549 using HCl [Inhibitor/$IC_{50}$] Qualified $AC_{50}$ | Dengue 3 virus MY05-34640-WT-C6/36 in A549 using HCl [Inhibitor/$IC_{50}$] Qualified $AC_{50}$ | Dengue 4 virus MY01-22713 in A549 using HCl [Inhibitor/$IC_{50}$] Qualified $AC_{50}$ |
|---|---|---|---|---|
| | Dengue $IC_{50}$ Data | | | |
| 35 | + | ++ | ++ | ++ |
| 36 | + | ++ | ++ | ++ |
| 37 | ++ | +++ | +++ | +++ |
| 38 | + | ++ | ++ | ++ |
| 39 | + | + | ++ | ++ |
| 40 | + | ++ | ++ | ++ |
| 41 | + | ++ | ++ | ++ |
| 42 | ++ | +++ | +++ | +++ |
| 43 | ++ | +++ | +++ | +++ |
| 44 | + | ++ | ++ | ++ |
| 45 | + | + | ++ | ++ |
| 46 | ++ | ++ | ++ | ++ |
| 47 | ++ | +++ | +++ | ++ |
| 48 | + | + | + | + |
| 49 | + | ++ | ++ | + |
| 50 | ++ | ++ | ++ | ++ |
| 51 | ++ | ++ | ++ | ++ |
| 52 | + | ++ | ++ | ++ |
| 53 | ++ | +++ | +++ | +++ |
| 54 (Peak-1) | ++ | +++ | +++ | +++ |
| 55 (Peak-2) | ++ | +++ | +++ | +++ |
| 56 | + | ++ | ++ | +++ |
| 57 | + | ++ | + | ++ |
| 58 | ++ | +++ | +++ | +++ |
| 59 | + | ++ | ++ | ++ |
| 60 | + | ++ | ++ | ++ |
| 61 | + | ++ | + | + |
| 62 | ++ | +++ | +++ | +++ |
| 63 | + | ++ | ++ | ++ |
| 64 | +++ | +++ | +++ | +++ |
| 65 | ++ | +++ | +++ | +++ |
| 66 | ++ | +++ | +++ | +++ |
| 67 | + | +++ | +++ | +++ |
| 68 | ++ | +++ | +++ | +++ |
| 69 | ++ | +++ | +++ | +++ |
| 70 | ++ | +++ | +++ | +++ |
| 71 | +++ | +++ | +++ | +++ |
| 72 | +++ | +++ | +++ | +++ |
| 73 | ++ | ++ | ++ | ++ |
| 74 | ++ | ++ | ++ | ++ |
| 75 | + | + | + | + |
| 76 | +++ | +++ | +++ | +++ |
| 77 | ++ | +++ | +++ | +++ |
| 78 | ++ | +++ | +++ | +++ |
| 79 | +++ | +++ | +++ | +++ |
| 80 | ++ | +++ | +++ | +++ |
| 81 | ++ | +++ | +++ | +++ |
| 82 | +++ | +++ | +++ | +++ |
| 83 | +++ | +++ | +++ | +++ |
| 84 | +++ | +++ | +++ | +++ |
| 85 | ++ | +++ | +++ | +++ |
| 86 | ++ | +++ | +++ | +++ |
| 87 | ++ | +++ | +++ | +++ |
| 88 | ++ | +++ | +++ | +++ |
| 89 | ++ | ++ | ++ | ++ |
| 90 | + | ++ | ++ | ++ |
| 91 | | + | + | ++ |
| 92 | ++ | +++ | ++ | +++ |
| 93 | ++ | +++ | +++ | +++ |
| 94 | + | + | ++ | ++ |
| 95 | ++ | ++ | +++ | +++ |
| 96 | ++ | +++ | +++ | +++ |
| 97 | ++ | ++ | ++ | ++ |
| 98 | + | ++ | ++ | ++ |
| 99 | + | ++ | ++ | ++ |
| 101 | ++ | ++ | ++ | +++ |
| 102 | + | ++ | ++ | ++ |
| 103 | ++ | ++ | ++ | ++ |
| 104 | + | ++ | ++ | +++ |
| 105 | + | ++ | ++ | ++ |

TABLE 1-continued

Dengue IC$_{50}$ Data

| Example No. | Dengue 1 virus MY97-10245 in A549 using HCl [Inhibitor/IC$_{50}$] Qualified AC$_{50}$ | Dengue 2 virus MY97-10340 in A549 using HCl [Inhibitor/IC$_{50}$] Qualified AC$_{50}$ | Dengue 3 virus MY05-34640-WT-C6/36 in A549 using HCl [Inhibitor/IC$_{50}$] Qualified AC$_{50}$ | Dengue 4 virus MY01-22713 in A549 using HCl [Inhibitor/IC$_{50}$] Qualified AC$_{50}$ |
|---|---|---|---|---|
| 106 | ++ | +++ | +++ | +++ |
| 107 | ++ | ++ | ++ | +++ |
| 108 | ++ | +++ | +++ | +++ |
| 109 | + | ++ | ++ | ++ |
| 110 | ++ | +++ | +++ | +++ |
| 111 | ++ | +++ | +++ | +++ |
| 112 | + | ++ | ++ | +++ |
| 113 | ++ | +++ | +++ | +++ |
| 114 | ++ | ++ | ++ | +++ |
| 115 | ++ | +++ | +++ | +++ |
| 116 | ++ | +++ | +++ | +++ |
| 117 | ++ | ++ | ++ | +++ |
| 118 | + | ++ | ++ | ++ |
| 119 | + | ++ | +++ | +++ |
| 120 | + | ++ | ++ | +++ |
| 121 | + | ++ | + | ++ |
| 122 | + | +++ | ++ | +++ |
| 123 | + | ++ | ++ | ++ |
| 124 | ++ | ++ | +++ | +++ |
| 125 | + | ++ | ++ | ++ |
| 126 | ++ | ++ | ++ | +++ |
| 127 | + | ++ | ++ | ++ |

Antiviral In Vivo Efficacy in Dengue Mouse Model

AG129 mice (lacking IFN-α/β and IFN-γ receptors, (Schul, W. et al. 2007. *J. Infect. Dis.,* 195, 665-74)) was obtained from Biological Resource Center (BRC), Singapore. Male and female AG129 mice aged 8 to 14 weeks (weighed 20-30 grams, n=6 per group) were used. Infection of DENV-2 (strain TSV01) was given intraperitoneally (500 μL, 1.4×107 pfu/mL). The DENV-2 strain TSVO1 was used in the mouse model and was propagated in C6/36 mosquito cells. Compounds were formulated (% w/w) in either 0.5% methylcellulose, 0.5% Tween and 99.0% deionized water or 20% polyethylene glycol (PEG300), 10% Cremophor RH40, and 70% 100 mM pH 3 citrate buffer (% v/v). Compounds were dosed immediately after infection through oral gavage for 3 consecutive days. Terminal blood sample (anticoagulant: K2EDTA) was obtained for viremia read-out by qRT-PCR as previously described (Santiago, G. A., et al. 2013. *PLoS Negl. Trop. Dis.,* 7, e2311).

TABLE 2

Antiviral in vivo efficacy of N-substitued tetrahydrothienopyridine derivatives in dengue mouse model

| Example No. | Dose/regimen | Log DENV-2 viremia reduction |
|---|---|---|
| 53 | 100 mg/kg q.d. | 1.06 |
| 53 | 100 mg/kg b.i.d. | 1.78 |
| 53 | 30 mg/kg b.i.d. | 0.80 |
| 71 | 10 mg/kg b.i.d. | 0.51 |
| 71 | 30 mg/kg b.i.d. | 1.45 |
| 71 | 60 mg/kg q.d. | 1.54 |
| 71 | 180 mg/kg single dose | 1.49 |
| 71 | 100 mg/kg b.i.d. | 3.0 |
| 77 | 30 mg/kg b.i.d. | 0.62 |
| 83 | 30 mg/kg b.i.d. | 0.60 |
| 83 | 100 mg/kg q.d. | 0.94 |
| 100 | 100 mg/kg b.i.d. | 1.50 |
| 109 | 100 mg/kg b.i.d. | 1.60 |

The invention claimed is:

1. A compound of formula (I), or a pharmaceutically acceptable salt thereof:

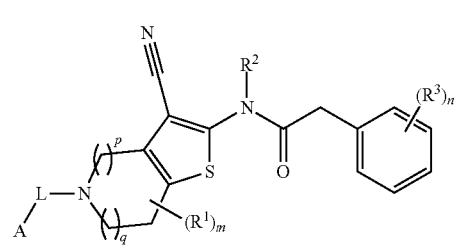

(I)

wherein:

A is phenyl or 3-6 membered cycloalkyl, wherein the 3-6 membered cycloalkyl is optionally substituted with —C$_{1-6}$alkyl, cyano, —C$_{1-4}$aminoalkyl, —C$_{1-4}$alkoxyl, —C$_{1-6}$haloalkyl, —C$_{1-4}$haloalkoxyl, or halogen; and wherein the phenyl is substituted with —C$_{1-6}$alkyl, cyano, —C$_{1-4}$aminoalkyl, —C$_{1-4}$alkoxyl, —C$_{1-6}$haloalkyl, —C$_{1-4}$haloalkoxyl, or halogen;

L is —C$_{1-6}$alkylene-;

each R$^1$ is independently selected from —C$_{1-6}$alkyl, cyano, —C$_{1-4}$aminoalkyl, —C$_{1-4}$alkoxyl, —C$_{1-6}$haloalkyl, —C$_{1-4}$haloalkoxyl, and halogen;

R$^2$ is H or —C$_{1-6}$alkyl;

each R$^3$ is independently selected from —C$_{1-6}$alkyl, —CN, —C$_{1-4}$alkoxyl, —C$_{1-6}$haloalkyl, —C$_{1-4}$haloalkoxyl, halogen, —C(O)R$^{3a}$, —C(O)OR$^{3b}$, —C(O)NR$^{3c}$R$^{3d}$, —P(O)R$^{3e}$R$^{3f}$, —P(O)(OR$^{3g}$)(OR$^{3h}$), —P(O)(OR$^{3i}$)(R$^{3j}$), —S(O)$_2$R$^{3k}$, —S(O)$_2$NR$^{3l}$R$^{3m}$, —S(O)R$^{3n}$, —NR$^{3o}$R$^{3p}$, —NR$^{3q}$C(O)R$^{3r}$, —N(R$^{3s}$)C(O)OR$^{3t}$ and —NR$^{3u}$S(O)$_2$R$^{3v}$, wherein each of the —C$_{1-6}$alkyl, —C$_{1-4}$alkoxyl, —C$_{1-6}$haloalkyl, and —C$_{1-4}$ haloalkoxyl is independently optionally substituted by hydroxyl, —NR$^{3w}$R$^{3x}$, —C$_{1-4}$alkoxyl, —S(O)₂ NR³ʸR³ᶻ, or —S(O)₂R³ᵃ²; wherein each of R³ʷ, R³ˣ, R³ʸ, and R³ᶻ is independently H, —C₁₋₄alkyl or —C₁₋₆haloalkyl and R³ᵃ² is —C₁₋₄alkyl or —C₁₋₆haloalkyl; or any two R³ may combine with one atom to form a 5-6 membered fused heterocycloalkyl, wherein the heterocycloalkyl comprises one or two heteroatoms selected from N and S, and wherein the heterocycloalkyl is independently optionally substituted with one or two groups selected from —C₁₋₆alkyl, —C₁₋₄aminoalkyl —CN, —C₁₋₄alkoxyl, halogen, —C₁₋₆haloalkyl and —C₁₋₄haloalkoxyl;

each of R³ᵃ, R³ᵇ, R³ᶜ, R³ᵈ, R³ᵉ, R^f, R³ᵍ, R³ʰ, R³ⁱ, R³ʲ, R³ᵏ, R³ⁿ, R³ᵒ, R³ᵖ, R³ᑫ, R³ʳ, R³ˢ, R³ᵗ, R³ᵘ, R³ᵛ is independently selected from H, —C₁₋₆alkyl and —C₁₋₆haloalkyl;

each of R³ˡ and R³ᵐ is independently selected from H, —C₁₋₆alkyl, —C₁₋₆haloalkyl, -aminoalkyl, and -hydroxyalkyl, wherein the —C₁₋₆alkyl is optionally further substituted by 3-6 membered cycloalkyl, and wherein the 3-6 membered cycloalkyl substituent is optionally further substituted by 1 or 2 halogens;

p is 1;
q is 1;
m is 0, 1 or 2; and
n is 0, 1 or 2.

2. The compound of claim 1, or a pharmaceutically acceptable salt thereof, wherein the compound of formula (I) is a compound of formula (IA), or a pharmaceutically acceptable salt thereof:

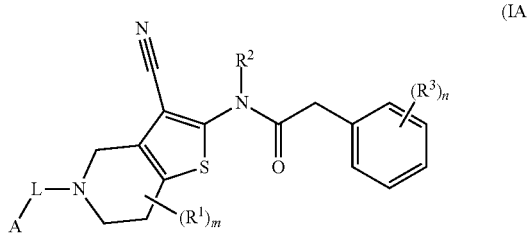

(IA)

wherein:
A is phenyl or 3-6 membered cycloalkyl, wherein the 3-6 membered cycloalkyl is optionally substituted with —C₁₋₆alkyl, cyano, —C₁₋₄aminoalkyl, —C₁₋₄alkoxyl, —C₁₋₆haloalkyl, —C₁₋₄haloalkoxyl, or halogen; and wherein the phenyl is substituted with —C₁₋₆alkyl, cyano, —C₁₋₄aminoalkyl, —C₁₋₄alkoxyl, —C₁₋₆haloalkyl, —C₁₋₄haloalkoxyl, or halogen;

L is —C₁₋₆alkylene-;

each R¹ is independently selected from —C₁₋₆alkyl, cyano, —C₁₋₄aminoalkyl, —C₁₋₄alkoxyl, —C₁₋₆haloalkyl, —C₁₋₄haloalkoxyl, and halogen;

R² is H or —C₁₋₆alkyl;

each R³ is independently selected from —C₁₋₆alkyl, —CN, —C₁₋₄alkoxyl, —C₁₋₆haloalkyl, —C₁₋₄haloalkoxyl, halogen, —C(O)R³ᵃ, —C(O)OR³ᵇ, —C(O)NR³ᶜR³ᵈ, —P(O)R³ᵉR³ᶠ, —P(O)(OR³ᵍ)(OR³ʰ), —P(O)(OR³ⁱ)(R³ʲ), —S(O)₂R³ᵏ, —S(O)₂NR³ˡR³ᵐ, —S(O)R³ⁿ, —NR³ᵒR³ᵖ, —NR³ᑫC(O)R³ʳ, —N(R³ˢ)C(O)OR³ᵗ and —NR³ᵘS(O)₂R³ᵛ, wherein each of the —C₁₋₆alkyl, —C₁₋₄alkoxyl, —C₁₋₆haloalkyl, and —C₁₋₄haloalkoxyl is independently optionally substituted by hydroxyl, —NR³ʷR³ˣ, —C₁₋₄alkoxyl, —S(O)₂ NR³ʸR³ᶻ, or —S(O)₂R³ᵃ²; wherein each of R³ʷ, R³ˣ, R³ʸ, and R³ᶻ is independently H, —C₁₋₄alkyl or —C₁₋₆haloalkyl and R³ᵃ² is —C₁₋₄alkyl or —C₁₋₆haloalkyl; or any two R³ may combine with one atom to form a 5-6 membered fused heterocycloalkyl, wherein the heterocycloalkyl comprises one or two heteroatoms selected from N and S, and wherein the heterocycloalkyl is independently optionally substituted with one or two groups selected from —C₁₋₆alkyl, —C₁₋₄aminoalkyl —CN, —C₁₋₄alkoxyl, halogen, —C₁₋₆haloalkyl and —C₁₋₄haloalkoxyl;

each of R³ᵃ, R³ᵇ, R³ᶜ, R³ᵈ, R³ᵉ, R³ᶠ, R³ᵍ, R³ʰ, R³ⁱ, R³ʲ, R³ᵏ, R³ⁿ, R³ᵒ, R³ᵖ, R³ᑫ, R³ʳ, R³ˢ, R³ᵗ, R³ᵘ, R³ᵛ is independently selected from H, —C₁₋₆alkyl and —C₁₋₆haloalkyl;

each of R³ˡ and R³ᵐ is independently selected from H, —C₁₋₆alkyl, —C₁₋₆haloalkyl, -aminoalkyl, and -hydroxyalkyl, wherein the —C₁₋₆alkyl is optionally further substituted by 3-6 membered cycloalkyl, and wherein the 3-6 membered cycloalkyl substituent is optionally further substituted by 1 or 2 halogens;

m is 0, 1 or 2; and
n is 0, 1 or 2.

3. The compound of claim 1, or a pharmaceutically acceptable salt thereof, wherein R² is H or CH₃.

4. The compound of claim 1, or a pharmaceutically acceptable salt thereof, wherein L is selected from —CH₂—, —CH(CH₃)—, —CH₂—CH₂— and —CH₂CH₂CH₂—.

5. The compound of claim 1, or a pharmaceutically acceptable salt thereof, wherein at least one R³ is —S(O)₂NH₂, —S(O)₂N(CH₃)₂, —S(O)₂NHCH₃, —S(O)₂NH—CH₂-cyclobutyl, —S(O)₂NH—CH₂-cyclopentyl, —S(O)₂NH—CH₂-cyclohexyl, —S(O)₂NH—CH₂-difluorocyclobutyl, —S(O)₂CH₃ or —S(O)₂CHF₂.

6. A compound of Formula (IC), or a pharmaceutically acceptable salt thereof:

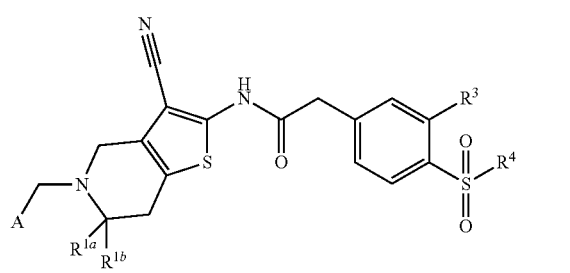

(IC)

wherein:
A is selected from cyclobutyl, cyclopentyl, cyclohexyl and bicyclo[1.1.1]pentanyl, each of which is optionally substituted with F or Cl; or A is phenyl substituted with F or Cl;

R¹ᵃ and R¹ᵇ are independently selected from —H, —CH₃ and —CH₂CH₃;

R³ is H, —OCH₃ or —OCH₂CH₃;

R⁴ is selected from —NH₂, —N(CH₃)₂, —NHCH₃, —NH—CH₂-cyclobutyl, —NH—CH₂-cyclopentyl, —NH—CH₂-cyclohexyl, —NH—CH₂-difluorocyclobutyl, —CH₃ and —CHF₂; or R⁴ is combined with R³ to form a 1,1-dioxido-2,3-dihydrothiophenyl or 1,1-dioxido-2,3-dihydroisothiazolyl ring.

7. The compound of claim 1, wherein the compound is selected from:

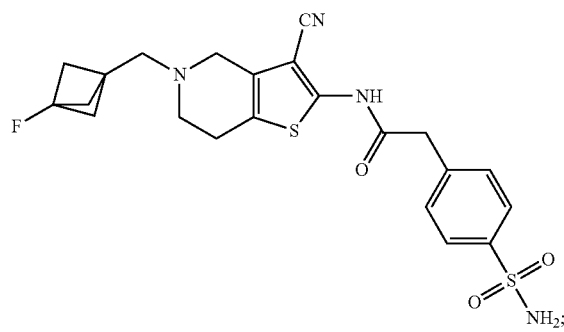

N-(3-cyano-5-((3-fluorobicyclo[1.1.1]pentan-1-yl)methyl)-4,5,6,7-tetrahydrothieno[3,2-c]pyridin-2-yl)-2-(4-sulfamoylphenyl)acetamide

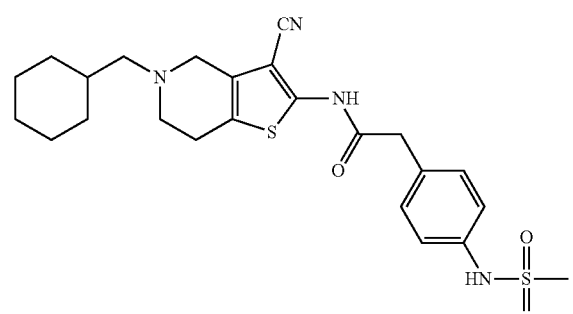

N-(3-cyano-5-(cyclohexylmethyl)-4,5,6,7-tetrahydrothieno[3,2-c]pyridin-2-yl)-2-(4-(methylsulfonamido)phenyl)acetamide

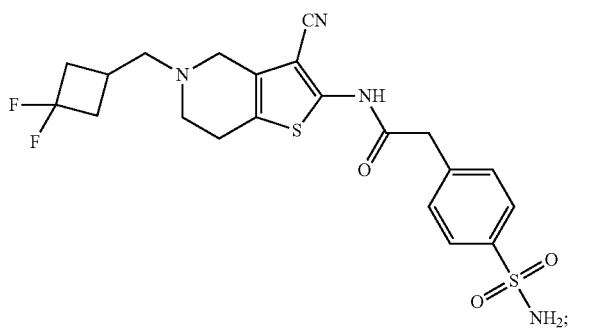

N-(3-cyano-5-((3,3-difluorocyclobutyl)methyl)-4,5,6,7-tetrahydrothieno[3,2-c]pyridin-2-yl)-2-(4-sulfamoylphenyl)acetamide

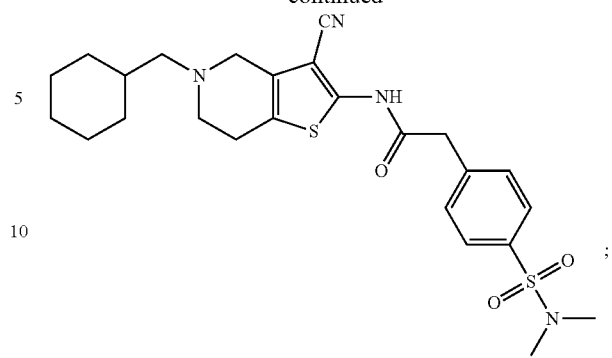

N-(3-cyano-5-(cyclohexylmethyl)-4,5,6,7-tetrahydrothieno[3,2-c]pyridin-2-yl)-2-(4-(N,N-dimethylsulfamoyl)phenyl)acetamide

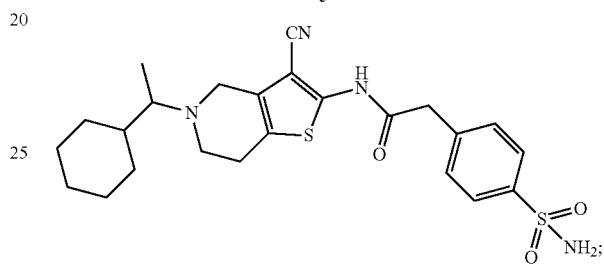

N-(3-cyano-5-(1-cyclohexylethyl)-4,5,6,7-tetrahydrothieno[3,2-c]pyridin-2-yl)-2-(4-sulfamoylphenyl)acetamide

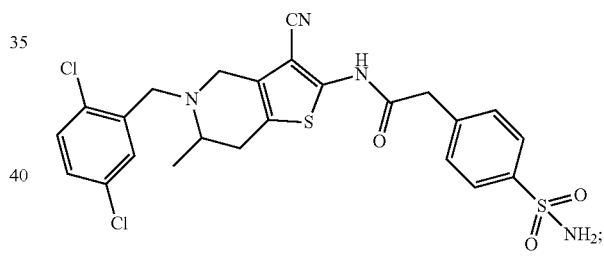

N-(3-cyano-5-(2,5-dichlorobenzyl)-6-methyl-4,5,6,7-tetrahydrothieno[3,2-c]pyridin-2-yl)-2-(4-sulfamoylphenyl)acetamide

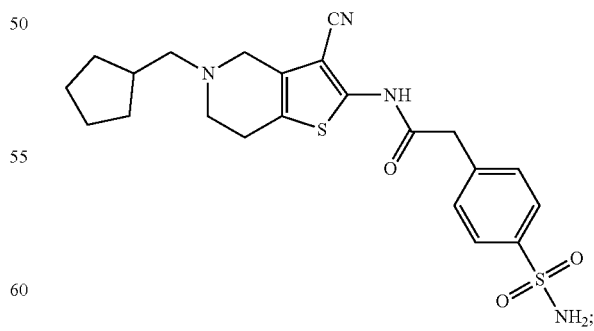

N-(3-cyano-5-(cyclopentylmethyl)-4,5,6,7-tetrahydrothieno[3,2-c]pyridin-2-yl)-2-(4-sulfamoylphenyl)acetamide

151

-continued

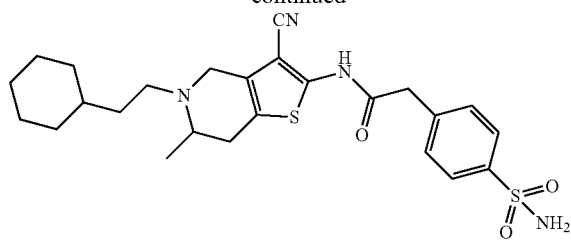

N-(3-cyano-5-(2-cyclohexylethyl)-
6-methyl-4,5,6,7-
tetrahydrothieno[3,2-c]pyridin-2-
yl)-2-(4-sulfamoylphenyl)acetamide

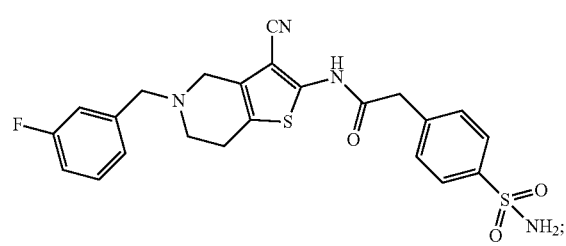

N-(3-cyano-5-(3-fluorobenzyl)-
4,5,6,7-tetrahydrothieno[3,2-
c]pyridin-2-yl)-2-(4-
sulfamoylphenyl)acetamide

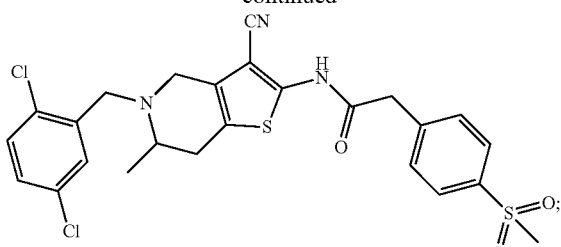

N-(3-cyano-5-(3-fluorobenzyl)-6-
methyl-4,5,6,7-
tetrahydrothieno[3,2-c]pyridin-2-
yl)-2-(4-
(methylsulfonyl)phenyl)acetamide

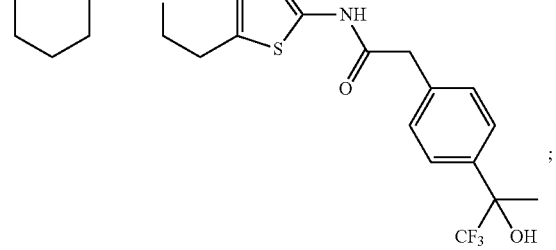

N-(3-cyano-5-(cyclohexylmethyl)-
4,5,6,7-tetrahydrothieno[3,2-
c]pyridin-2-yl)-2-(4-
sulfamoylphenyl)acetamide

152

-continued

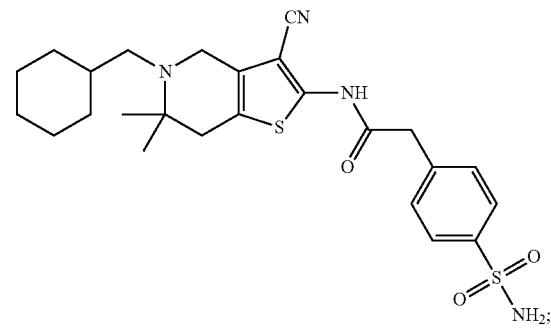

N-(3-cyano-5-(2,5-dichlorobenzyl)-
6-methyl-4,5,6,7-
tetrahydrothieno[3,2-c]pyridin-2-
yl)-2-(4-
(methylsulfonyl)phenyl)acetamide

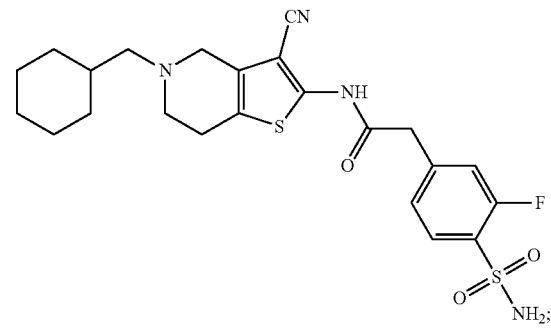

N-(3-cyano-5-(cyclohexylmethyl)-
4,5,6,7-tetrahydrothieno[3,2-
c]pyridin-2-yl)-2-(4-(1,1,1-
trifluoro-2-hydroxypropan-2-
yl)phenyl)acetamide N-(3-cyano-5-(cyclohexylmethyl)-
6,6-dimethyl-4,5,6,7-
tetrahydrothieno[3,2-c]pyridin-2-
yl)-2-(4-sulfamoylphenyl)acetamide N-(3-cyano-5-(cyclohexylmethyl)-
4,5,6,7-tetrahydrothieno[3,2-
c]pyridin-2-yl)-2-(3-fluoro-4-
sulfamoylphenyl)acetamide

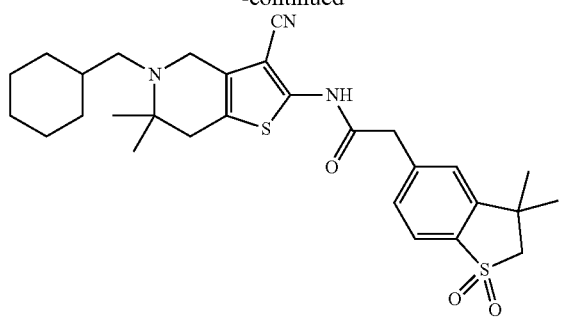

N-(3-cyano-5-(cyclohexylmethyl)-
6,6-dimethyl-4,5,6,7-
tetrahydrothieno[3,2-c]pyridin-2-
yl)-2-(3,3-dimethyl-1,1-dioxido-2,3-
dihydrobenzo[b]thiophen-5-
yl)acetamide

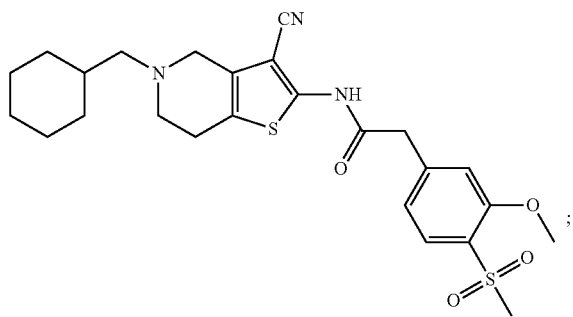

N-(3-cyano-5-(cyclohexylmethyl)-
4,5,6,7-tetrahydrothieno[3,2-
c]pyridin-2-yl)-2-(3-methoxy-4-
(methylsulfonyl)phenyl)acetamide

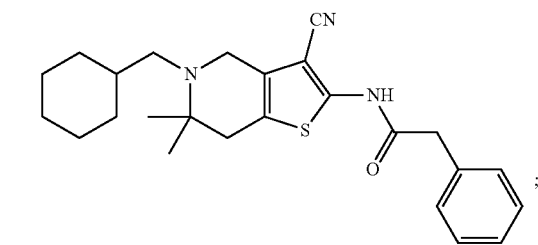

N-(3-cyano-5-(cyclohexylmethyl)-
6,6-dimethyl-4,5,6,7-
tetrahydrothieno[3,2-c]pyridin-2-
yl)-2-phenylacetamide

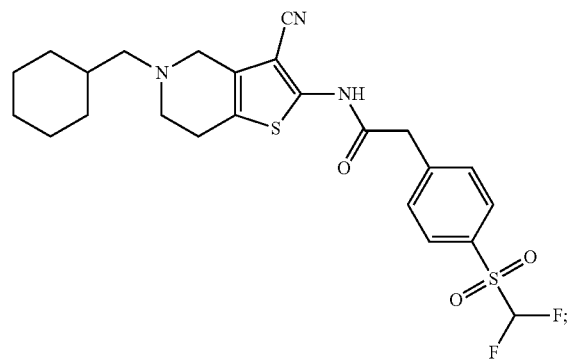

N-(3-cyano-5-(cyclohexylmethyl)-
4,5,6,7-tetrahydrothieno[3,2-
c]pyridin-2-yl)-2-(4-
((difluoromethyl)sulfonyl)phenyl)
acetamide

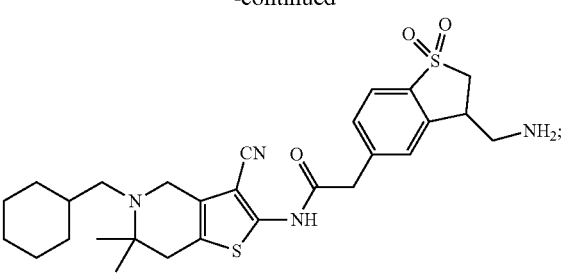

2-(3-(aminomethyl)-1,1-dioxido-
2,3-dihydrobenzo[b]thiophen-5-yl)-
N-(3-cyano-5-(cyclohexylmethyl)-
6,6-dimethyl-4,5,6,7-
tetrahydrothieno[3,2-c]pyridin-2-
yl)acetamide

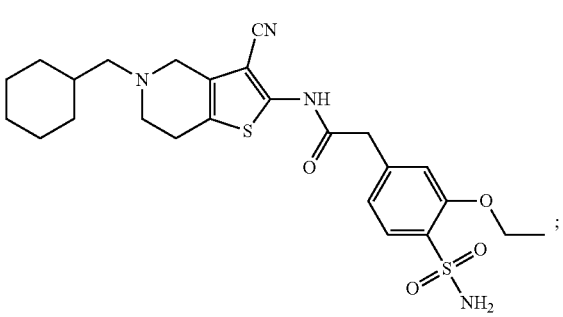

N-(3-cyano-5-(cyclohexylmethyl)-
4,5,6,7-tetrahydrothieno[3,2-
c]pyridin-2-yl)-2-(3-ethoxy-4-
sulfamoylphenyl)acetamide

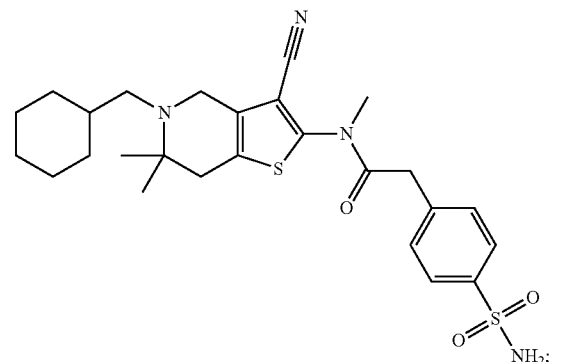

N-(3-cyano-5-(cyclohexylmethyl)-
6,6-dimethyl-4,5,6,7-
tetrahydrothieno[3,2-c]pyridin-2-
yl)-N-methyl-2-(4-
sulfamoylphenyl)acetamide

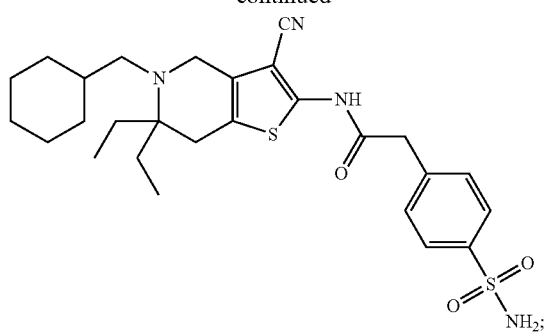

N-(3-cyano-5-(cyclohexylmethyl)-
6,6-diethyl-4,5,6,7-
tetrahydrothieno[3,2-c]pyridin-2-
yl)-2-(4-sulfamoylphenyl)acetamide

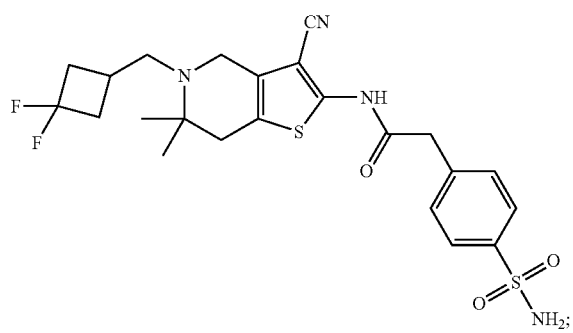

N-(3-cyano-5-((3,3-
difluorocyclobutyl)methyl)-6,6-
dimethyl-4,5,6,7-
tetrahydrothieno[3,2-c]pyridin-2-
yl)-2-(4-sulfamoylphenyl)acetamide

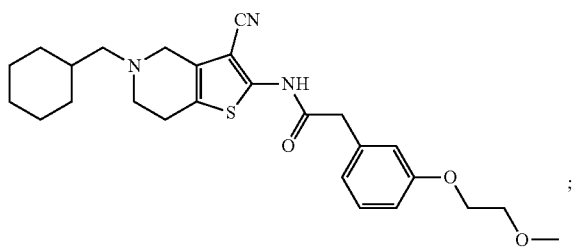

N-(3-cyano-5-(cyclohexylmethyl)-
4,5,6,7-tetrahydrothieno[3,2-
c]pyridin-2-yl)-2-(3-(2-
methoxyethoxy)phenyl)acetamide

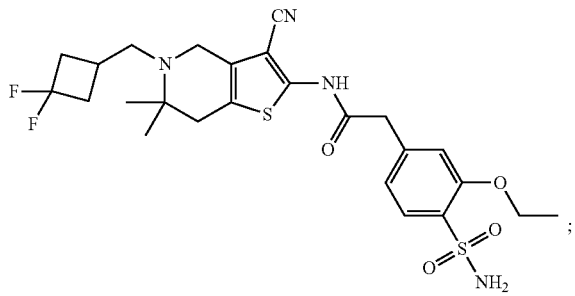

N-(3-cyano-5-((3,3-
difluorocyclobutyl)methyl)-6,6-
dimethyl-4,5,6,7-
tetrahydrothieno[3,2-c]pyridin-2-
yl)-2-(3-ethoxy-4-
sulfamoylphenyl)acetamide

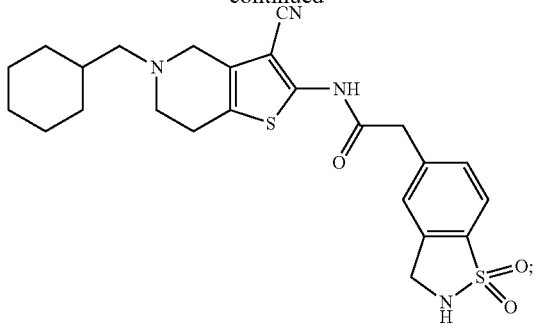

N-(3-cyano-5-(cyclohexylmethyl)-
4,5,6,7-tetrahydrothieno[3,2-
c]pyridin-2-yl)-2-(1,1-dioxido-2,3-
dihydrobenzo[d]isothiazol-5-
yl)acetamide

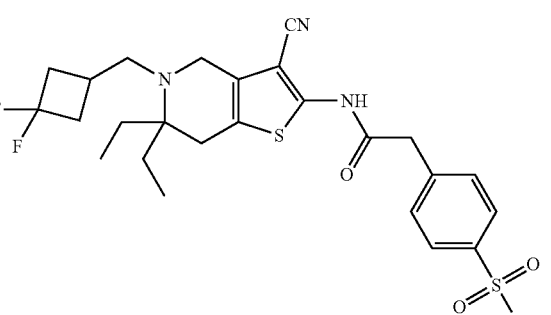

N-(3-cyano-5-((3,3-
difluorocyclobutyl)methyl)-6,6-
diethyl-4,5,6,7-
tetrahydrothieno[3,2-c]pyridin-2-
yl)-2-(4-sulfamoylphenyl)acetamide

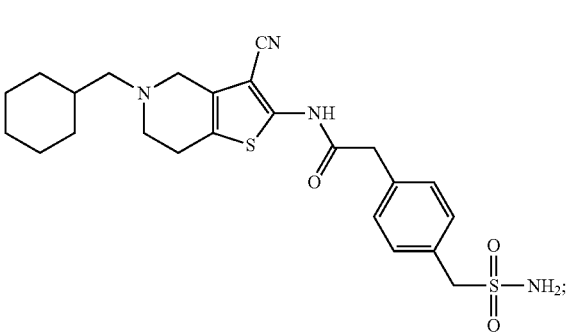

N-(3-cyano-5-(cyclohexylmethyl)-
4,5,6,7-tetrahydrothieno[3,2-
c]pyridin-2-yl)-2-(4-
(sulfamoylmethyl)phenyl)acetamide -continued

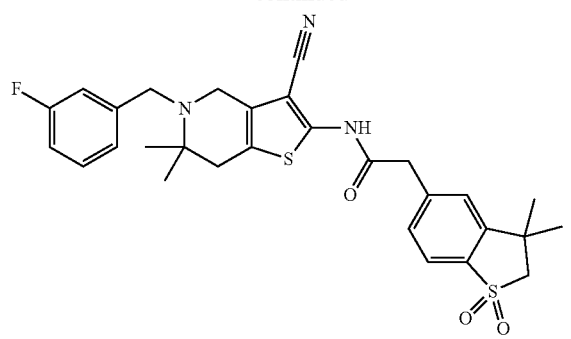

N-(3-cyano-5-(3-fluorobenzyl)-6,6-dimethyl-4,5,6,7-tetrahydrothieno[3,2-c]pyridin-2-yl)-2-(3,3-dimethyl-1,1-dioxido-2,3-dihydrobenzo[b]thiophen-5-yl)acetamide

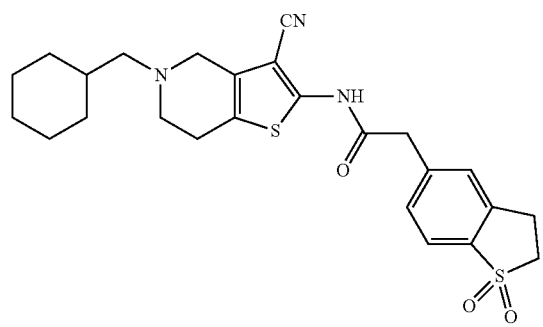

N-(3-cyano-5-(cyclohexylmethyl)-4,5,6,7-tetrahydrothieno[3,2-c]pyridin-2-yl)-2-(1,1-dioxido-2,3-dihydrobenzo[b]thiophen-5-yl)acetamide

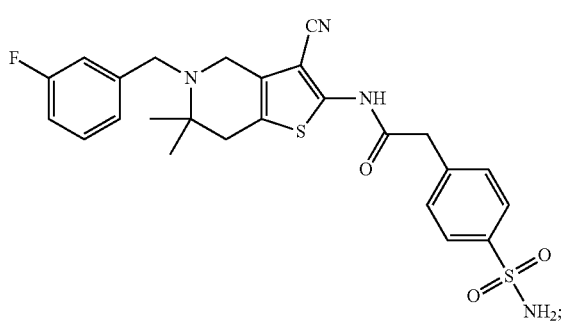

N-(3-cyano-5-(3-fluorobenzyl)-6,6-dimethyl-4,5,6,7-tetrahydrothieno[3,2-c]pyridin-2-yl)-2-(4-sulfamoylphenyl)acetamide -continued

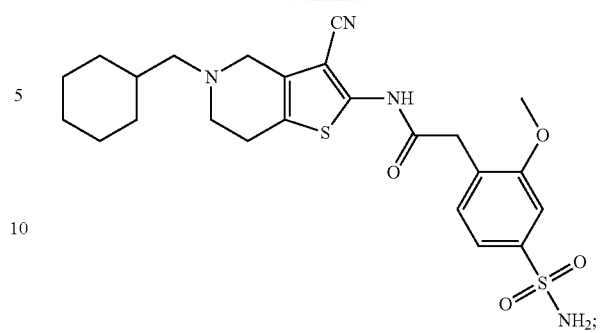

N-(3-cyano-5-(cyclohexylmethyl)-4,5,6,7-tetrahydrothieno[3,2-c]pyridin-2-yl)-2-(2-methoxy-4-sulfamoylphenyl)acetamide

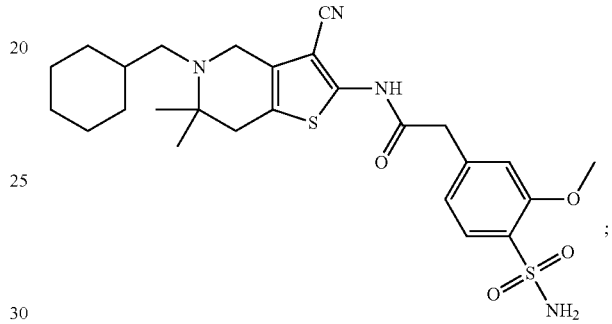

N-(3-cyano-5-(cyclohexylmethyl)-6,6-dimethyl-4,5,6,7-tetrahydrothieno[3,2-c]pyridin-2-yl)-2-(3-methoxy-4-sulfamoylphenyl)acetamide

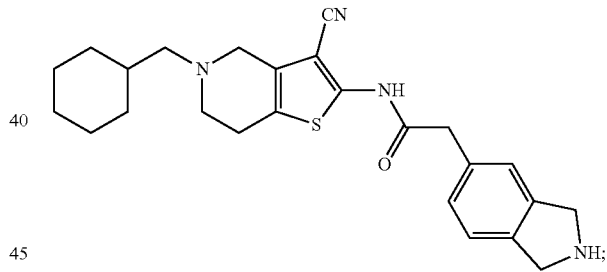

N-(3-cyano-5-(cyclohexylmethyl)-4,5,6,7-tetrahydrothieno[3,2-c]pyridin-2-yl)-2-(isoindolin-5-yl)acetamide

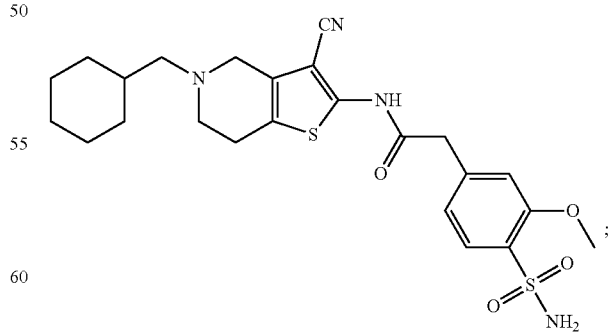

N-(3-cyano-5-(cyclohexylmethyl)-4,5,6,7-tetrahydrothieno[3,2-c]pyridin-2-yl)-2-(3-methoxy-4-sulfamoylphenyl)acetamide

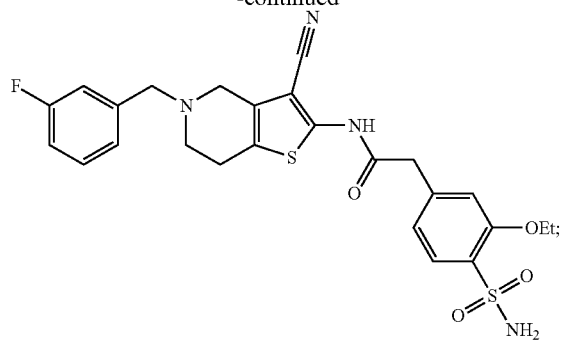

N-(3-cyano-5-(3-fluorobenzyl)-
4,5,6,7-tetrahydrothieno[3,2-
c]pyridin-2-yl)-2-(3-ethoxy-4-
sulfamoylphenyl)acetamide

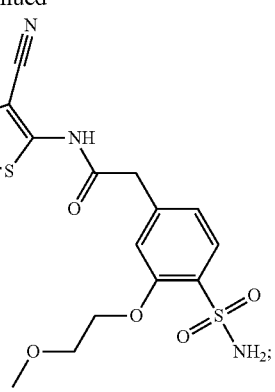

N-(3-cyano-5-(3-fluorobenzyl)-6-
methyl-4,5,6,7-
tetrahydrothieno[3,2-c]pyridin-2-
yl)-2-(3-(2-methoxyethoxy)-4-
sulfamoylphenyl)acetamide

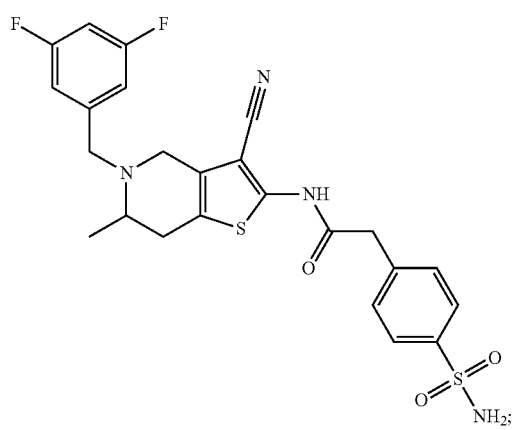

N-(3-cyano-5-(3,5-difluorobenzyl)-
6-methyl-4,5,6,7-
tetrahydrothieno[3,2-c]pyridin-2-
yl)-2-(4-sulfamoylphenyl)acetamide

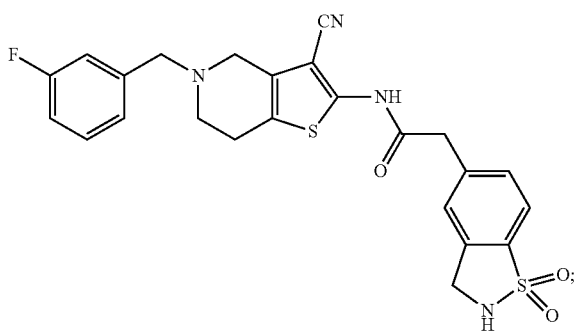

N-(3-cyano-5-(3-fluorobenzyl)-
4,5,6,7-tetrahydrothieno[3,2-
c]pyridin-2-yl)-2-(1,1-dioxido-2,3-
dihydrobenzo[d]isothiazol-5-
yl)acetamide

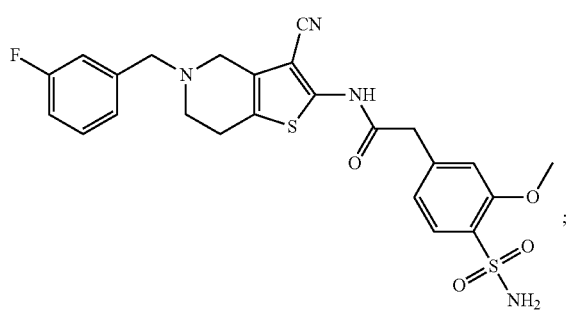

N-(3-cyano-5-(3-fluorobenzyl)-
4,5,6,7-tetrahydrothieno[3,2-
c]pyridin-2-yl)-2-(3-methoxy-4-
sulfamoylphenyl)acetamide

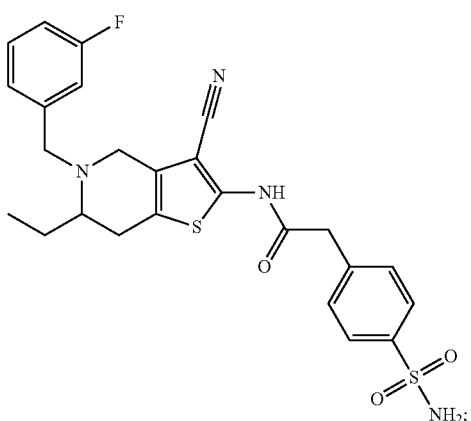

N-(3-cyano-6-ethyl-5-(3-
fluorobenzyl)-4,5,6,7-
tetrahydrothieno[3,2-c]pyridin-2-
yl)-2-(4-sulfamoylphenyl)acetamide -continued

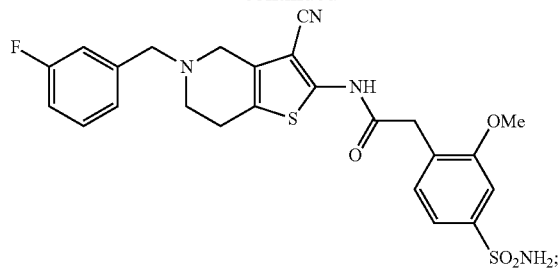

N-(3-cyano-5-(3-fluorobenzyl)-
4,5,6,7-tetrahydrothieno[3,2-
c]pyridin-2-yl)-2-(2-methoxy-4-
sulfamoylphenyl)acetamide

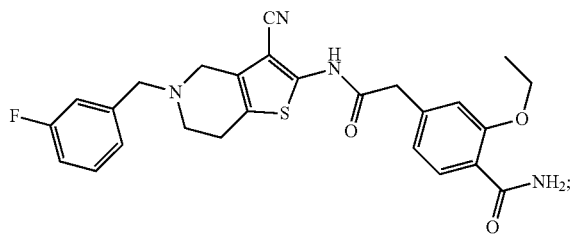

4-(2-((3-cyano-5-(3-fluorobenzyl)-
4,5,6,7-tetrahydrothieno[3,2-
c]pyridin-2-yl)amino)-2-oxoethyl)-
2-ethoxybenzamide

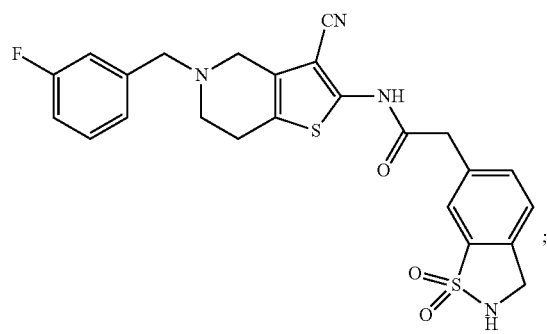

N-(3-cyano-5-(3-fluorobenzyl)-
4,5,6,7-tetrahydrothieno[3,2-
c]pyridin-2-yl)-2-(1,1-dioxido-2,3-
dihydrobenzo[d]isothiazol-6-
yl)acetamide

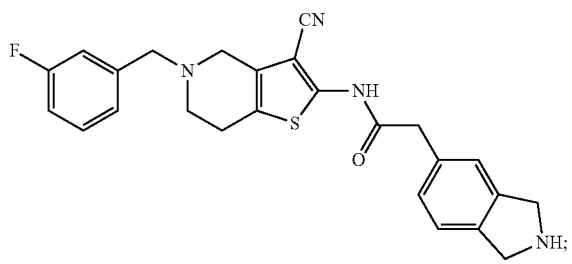

N-(3-cyano-5-(3-fluorobenzyl)-
4,5,6,7-tetrahydrothieno[3,2-
c]pyridin-2-yl)-2-(isoindolin-5-
yl)acetamide -continued

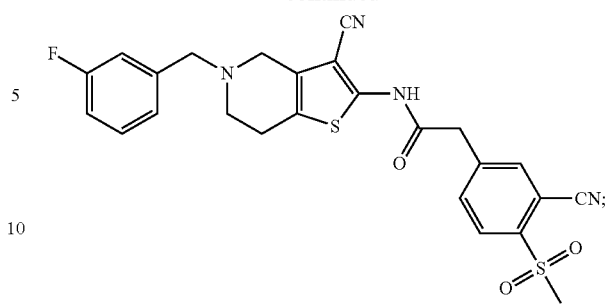

2-(3-cyano-4-
(methylsulfonyl)phenyl)-N-(3-
cyano-5-(3-fluorobenzyl)-4,5,6,7-
tetrahydrothieno[3,2-c]pyridin-2-
yl)acetamide

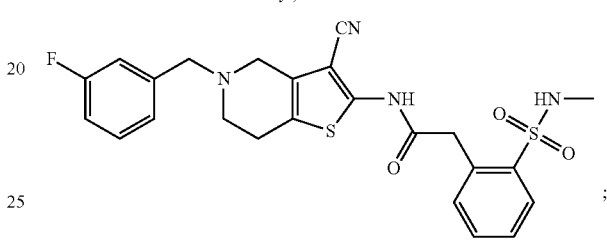

N-(3-cyano-5-(3-fluorobenzyl)-
4,5,6,7-tetrahydrothieno[3,2-
c]pyridin-2-yl)-2-(2-(N-
methylsulfamoyl)phenyl)acetamide

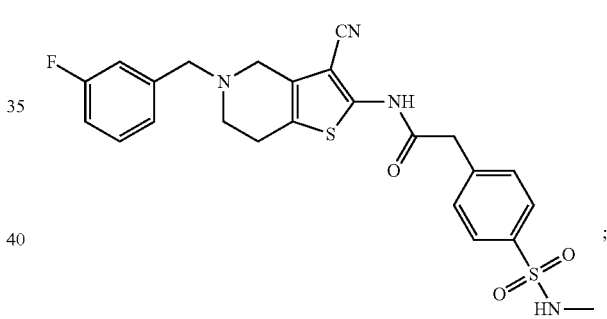

N-(3-cyano-5-(3-fluorobenzyl)-
4,5,6,7-tetrahydrothieno[3,2-
c]pyridin-2-yl)-2-(4-(N-
methylsulfamoyl)phenyl)acetamide

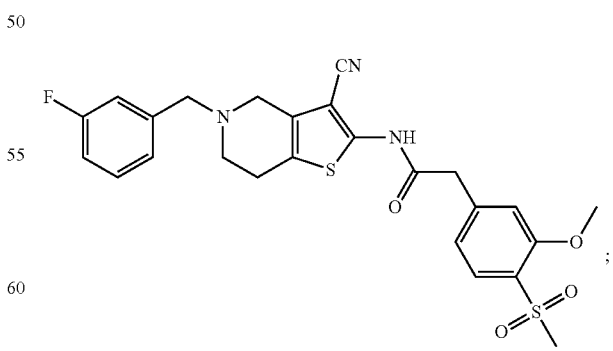

N-(3-cyano-5-(3-fluorobenzyl)-
4,5,6,7-tetrahydrothieno[3,2-
c]pyridin-2-yl)-2-(3-methoxy-4-
(methylsulfonyl)phenyl)acetamide

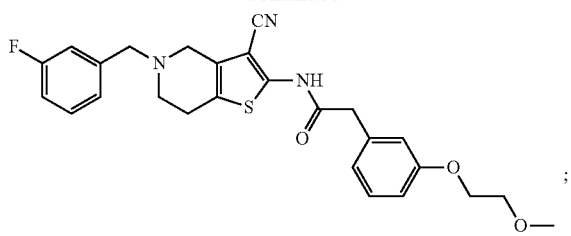

N-(3-cyano-5-(3-fluorobenzyl)-
4,5,6,7-tetrahydrothieno[3,2-
c]pyridin-2-yl)-2-(3-(2-
methoxyethoxy)phenyl)acetamide

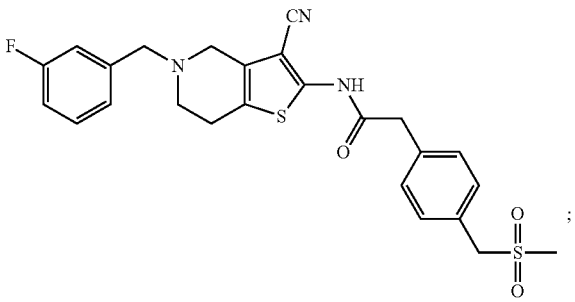

N-(3-cyano-5-(3-fluorobenzyl)-
4,5,6,7-tetrahydrothieno[3,2-
c]pyridin-2-yl)-2-(4-
((methylsulfonyl)methyl)phenyl)a
cetamide

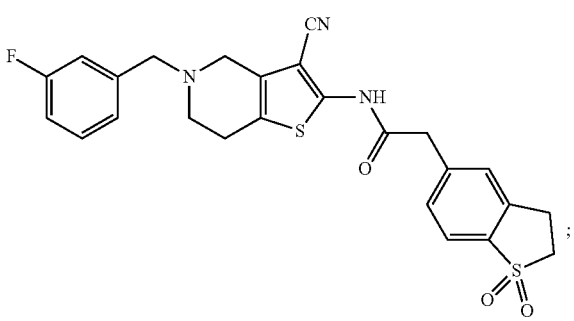

N-(3-cyano-5-(3-fluorobenzyl)-
4,5,6,7-tetrahydrothieno[3,2-
c]pyridin-2-yl)-2-(1,1-dioxido-2,3-
dihydrobenzo[b]thiophen-5-
yl)acetamide

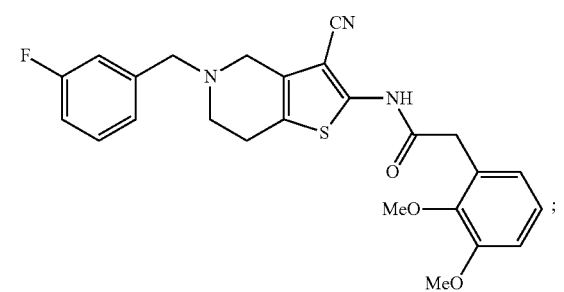
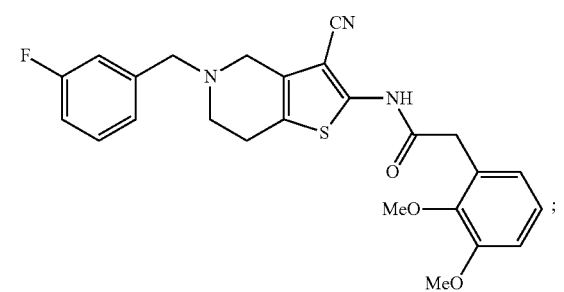
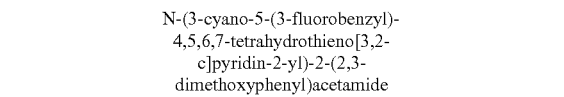

N-(3-cyano-5-(3-fluorobenzyl)-
4,5,6,7-tetrahydrothieno[3,2-
c]pyridin-2-yl)-2-(2,3-
dimethoxyphenyl)acetamide

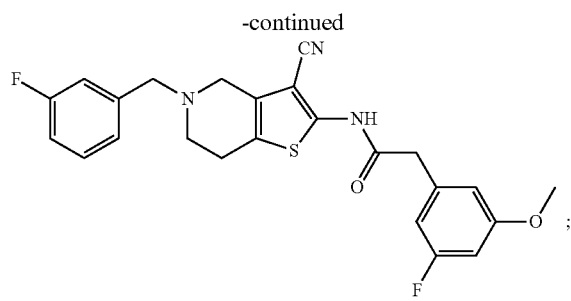

N-(3-cyano-5-(3-fluorobenzyl)-
4,5,6,7-tetrahydrothieno[3,2-
c]pyridin-2-yl)-2-(3-fluoro-5-
methoxyphenyl)acetamide

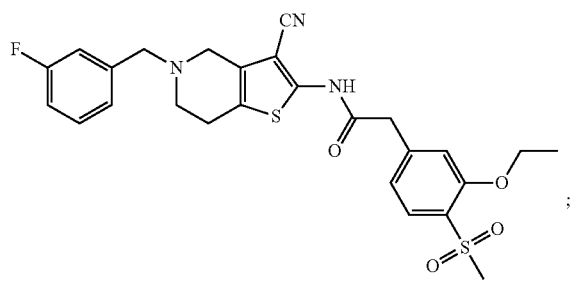

N-(3-cyano-5-(3-fluorobenzyl)-
4,5,6,7-tetrahydrothieno[3,2-
c]pyridin-2-yl)-2-(3-ethoxy-4-
(methylsulfonyl)phenyl)acetamide

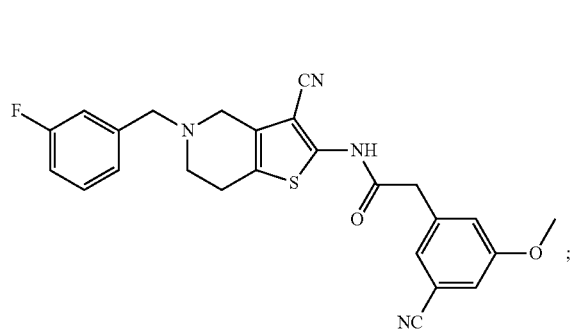

N-(3-cyano-5-(3-fluorobenzyl)-
4,5,6,7-tetrahydrothieno[3,2-
c]pyridin-2-yl)-2-(3-cyano-5-
methoxyphenyl)acetamide

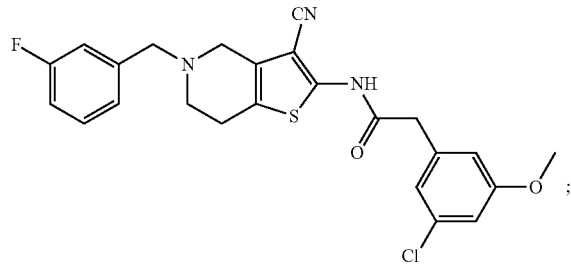

2-(3-chloro-5-methoxyphenyl)-N-
(3-cyano-5-(3-fluorobenzyl)-
4,5,6,7-tetrahydrothieno[3,2-
c]pyridin-2-yl)acetamide -continued

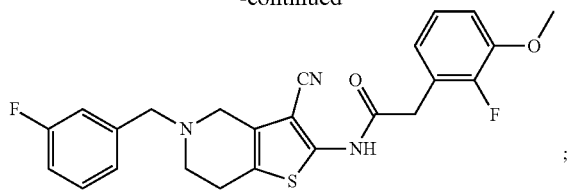

N-(3-cyano-5-(3-fluorobenzyl)-
4,5,6,7-tetrahydrothieno[3,2-
c]pyridin-2-yl)-2-(2-fluoro-3-
methoxyphenyl)acetamide

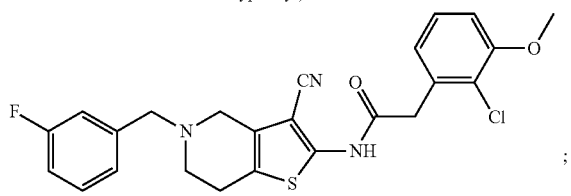

2-(2-chloro-3-methoxyphenyl)-N-
(3-cyano-5-(3-fluorobenzyl)-
4,5,6,7-tetrahydrothieno[3,2-
c]pyridin-2-yl)acetamide

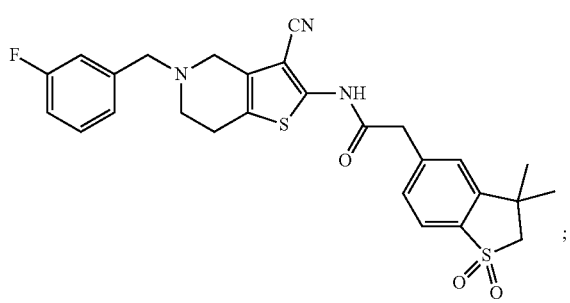

N-(3-cyano-5-(3-fluorobenzyl)-
4,5,6,7-tetrahydrothieno[3,2-
c]pyridin-2-yl)-2-(3,3-dimethyl-
1,1-dioxido-2,3-
dihydrobenzo[b]thiophen-5-
yl)acetamide

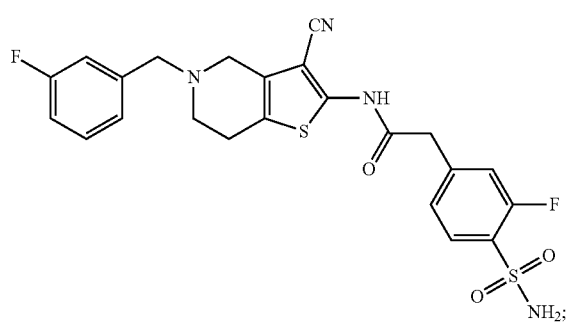

N-(3-cyano-5-(3-fluorobenzyl)-
4,5,6,7-tetrahydrothieno[3,2-
c]pyridin-2-yl)-2-(3-fluoro-4-
sulfamoylphenyl)acetamide -continued

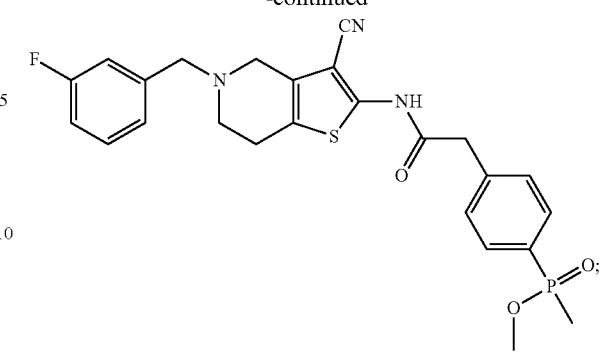

Methyl (4-(2-((3-cyano-5-(3-
fluorobenzyl)-4,5,6,7-
tetrahydrothieno[3,2-c]pyridin-2-
yl)amino)-2-
oxoethyl)phenyl(methyl)phosphin
ate

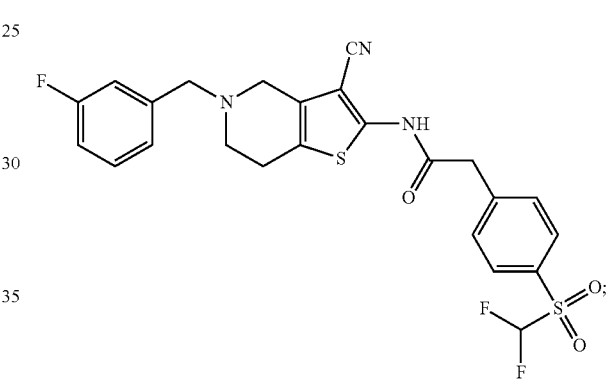

N-(3-cyano-5-(3-fluorobenzyl)-
4,5,6,7-tetrahydrothieno[3,2-
c]pyridin-2-yl)-2-(4-
((difluoromethyl)sulfonyl)phenyl)
acetamide

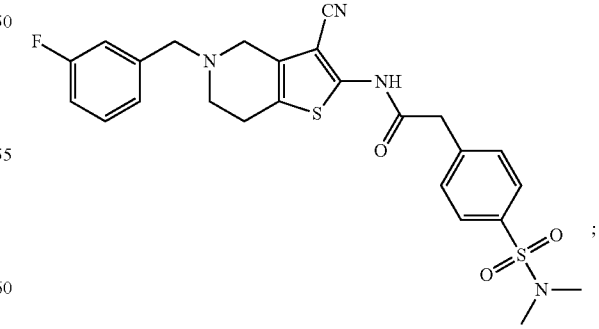

N-(3-cyano-5-(3-fluorobenzyl)-
4,5,6,7-tetrahydrothieno[3,2-
c]pyridin-2-yl)-2-(4-(N,N-
dimethylsulfamoyl)phenyl)acetami
de 167
-continued

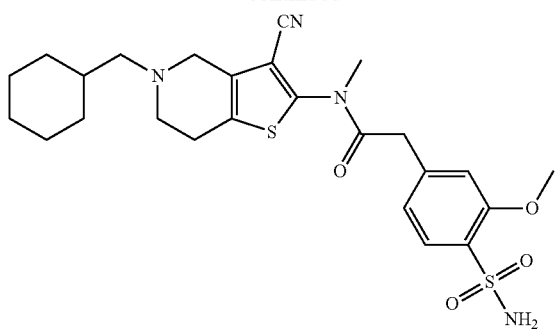

N-(3-cyano-5-(cyclohexylmethyl)-
4,5,6,7-tetrahydrothieno[3,2-
c]pyridin-2-yl)-2-(3-methoxy-4-
sulfamoylphenyl)-N-
methylacetamide

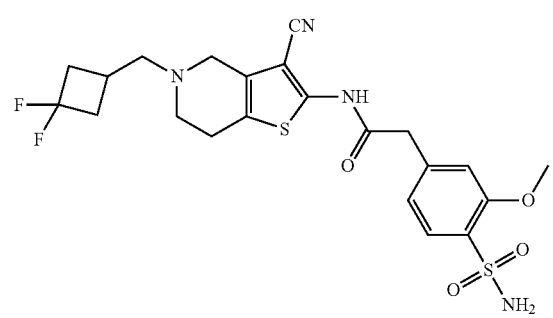

N-(3-cyano-5-((3,3-
difluorocyclobutyl)methyl)-
4,5,6,7-tetrahydrothieno[3,2-
c]pyridin-2-yl)-2-(3-methoxy-4-
sulfamoylphenyl)acetamide

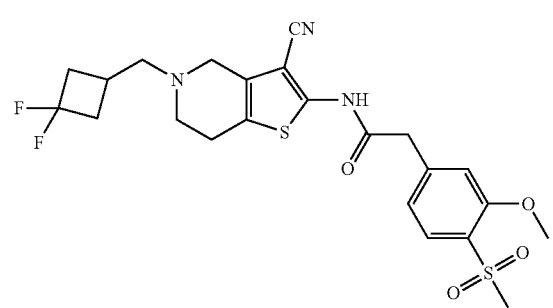

N-(3-cyano-5-((3,3-
difluorocyclobutyl)methyl)-
4,5,6,7-tetrahydrothieno[3,2-
c]pyridin-2-yl)-2-(3-methoxy-4-
(methylsulfonyl)phenyl)acetamide 168
-continued

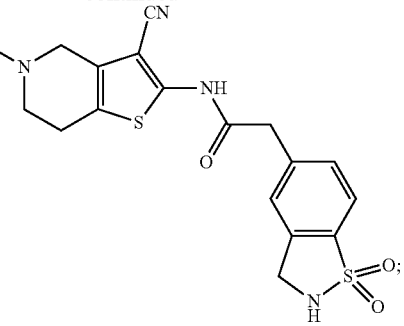

N-(3-cyano-5-((3,3-
difluorocyclobutyl)methyl)-
4,5,6,7-tetrahydrothieno[3,2-
c]pyridin-2-yl)-2-(1,1-dioxido-2,3-
dihydrobenzo[d]isothiazol-5-
yl)acetamide N-(3-cyano-5-(3-fluorobenzyl)-6-
methyl-4,5,6,7-
tetrahydrothieno[3,2-c]pyridin-2-
yl)-2-(4-
sulfamoylphenyl)acetamide N-(3-cyano-5-((3,3-
difluorocyclobutyl)methyl)-6-
methyl-4,5,6,7-
tetrahydrothieno[3,2-c]pyridin-2-
yl)-2-(4-
sulfamoylphenyl)acetamide or a pharmaceutically acceptable salt thereof.

8. A pharmaceutical composition comprising a compound of claim 1, and a pharmaceutically acceptable carrier or excipient.

9. The pharmaceutical composition of claim 8 further comprising at least one additional pharmaceutical agent.

10. A method for treating a disease caused by a viral infection comprising the step of administering to a subject in need thereof a therapeutically effective amount of a compound according to claim 1, wherein the viral infection is caused by dengue virus.

11. The compound of claim 1, wherein the compound is selected from:

169

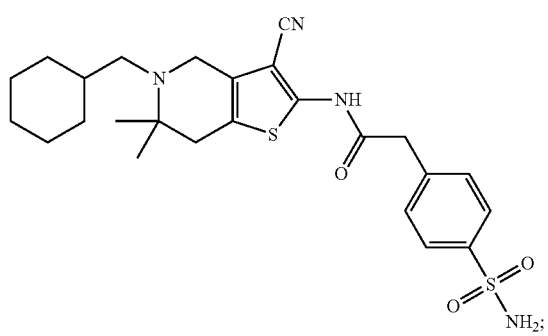

N-(3-cyano-5-(cyclohexylmethyl)-6,6-dimethyl-4,5,6,7-tetrahydrothieno[3,2-c]pyridin-2-yl)-2-(4-sulfamoylphenyl)acetamide

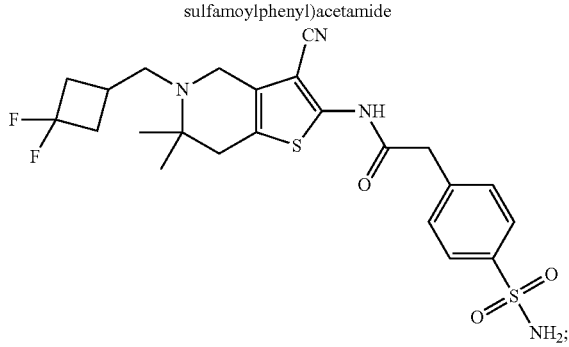

N-(3-cyano-5-((3,3-difluorobicyclobutyl)methyl)-6,6-dimethyl-4,5,6,7-tetrahydrothieno[3,2-c]pyridin-2-yl)-2-(4-sulfamoylphenyl)acetamide

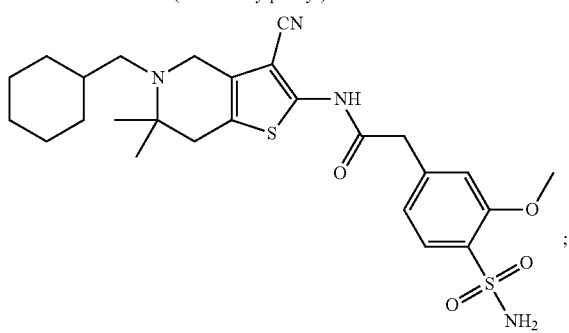

N-(3-cyano-5-(cyclohexylmethyl)-6,6-dimethyl-4,5,6,7-tetrahydrothieno[3,2-c]pyridin-2-yl)-2-(3-methoxy-4-sulfamoylphenyl)acetamide

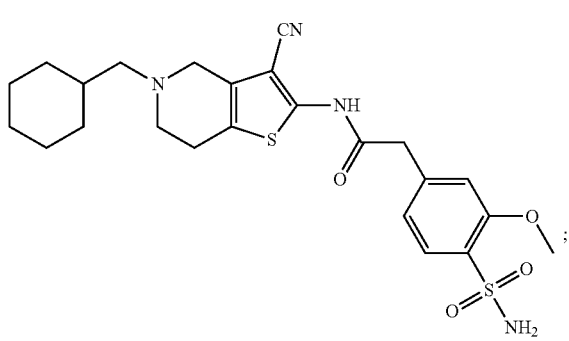

N-(3-cyano-5-(cyclohexylmethyl)-4,5,6,7-tetrahydrothieno[3,2-c]pyridin-2-yl)-2-(3-methoxy-4-sulfamoylphenyl)acetamide

170

-continued

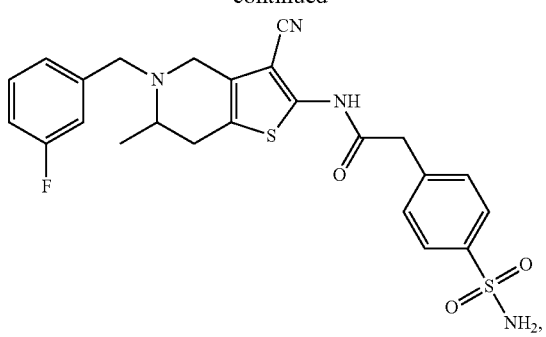

N-(3-cyano-5-(3-fluorobenzyl)-6-methyl-4,5,6,7-tetrahydrothieno[3,2-c]pyridin-2-yl)-2-(4-sulfamoylphenyl)acetamide or a pharmaceutically acceptable salt thereof.

12. A compound selected from:

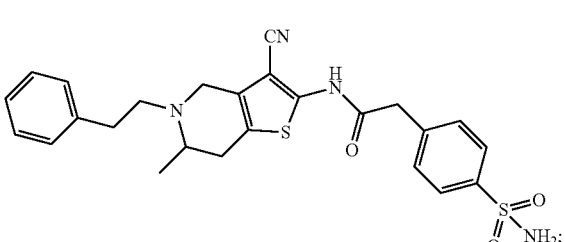

N-(3-cyano-6-methyl-5-phenethyl-4,5,6,7-tetrahydrothieno[3,2-c]pyridin-2-yl)-2-(4-sulfamoylphenyl)acetamide

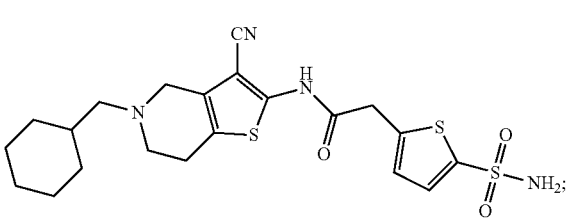

N-(3-cyano-5-(cyclohexylmethyl)-4,5,6,7-tetrahydrothieno[3,2-c]pyridin-2-yl)-2-(5-sulfamoylthiophen-2-yl)acetamide -continued

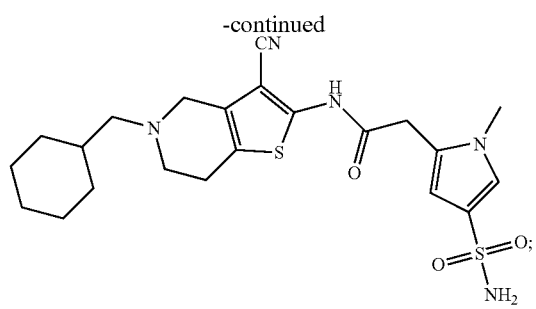

N-(3-cyano-5-(cyclohexylmethyl)-
4,5,6,7-tetrahydrothieno[3,2-
c]pyridin-2-yl)-2-(1-methyl-4-
sulfamoyl-1H-pyrrol-2-yl)acetamide

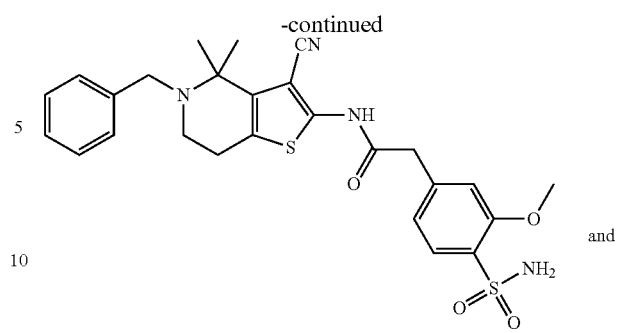

N-(5-benzyl-3-cyano-4,4-dimethyl-
4,5,6,7-tetrahydrothieno[3,2-
c]pyridin-2-yl)-2-(3-methoxy-4-
sulfamoyl)phenyl)acetamide

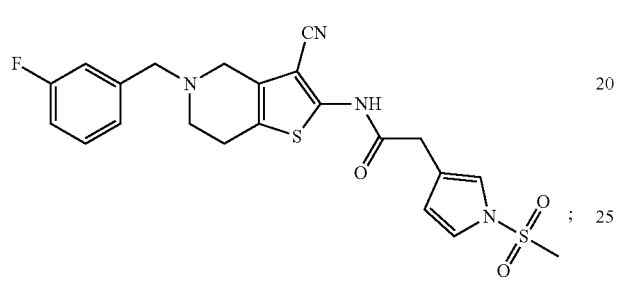

N-(3-cyano-5-(3-fluorobenzyl)-
4,5,6,7-tetrahydrothieno[3,2-
c]pyridin-2-yl)-2-(1-
(methylsulfonyl)-1H-pyrrol-3-
yl)acetamide

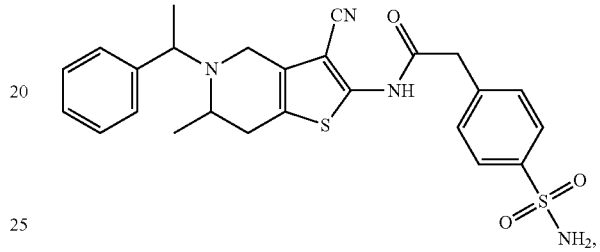

N-(3-cyano-6-methyl-5-(1-
phenylethyl)-4,5,6,7-
tetrahydrothieno[3,2-c]pyridin-2-
yl)-2-(4-(sulfamoylphenyl)acetamide or a pharmaceutically acceptable salt thereof.

\* \* \* \* \*